United States Patent
Ando et al.

(10) Patent No.: US 12,421,191 B2
(45) Date of Patent: Sep. 23, 2025

(54) 3-HYDROXYOXINDOLE DERIVATIVES AS CRHR2 ANTAGONIST

(71) Applicant: RaQualia Pharma Inc., Aichi (JP)

(72) Inventors: Kazuo Ando, Aichi (JP); Masashi Ohmi, Aichi (JP); Ryohei Magara, Aichi (JP)

(73) Assignee: RaQualia Pharma Inc., Aichi (JP)

( * ) Notice: Subject to any disclaimer, the term of this patent is extended or adjusted under 35 U.S.C. 154(b) by 438 days.

(21) Appl. No.: 18/028,062

(22) PCT Filed: Sep. 30, 2021

(86) PCT No.: PCT/JP2021/036112
§ 371 (c)(1),
(2) Date: Mar. 23, 2023

(87) PCT Pub. No.: WO2022/071484
PCT Pub. Date: Apr. 7, 2022

(65) Prior Publication Data
US 2024/0018103 A1 Jan. 18, 2024

Related U.S. Application Data

(60) Provisional application No. 63/085,346, filed on Sep. 30, 2020.

(51) Int. Cl.
*C07D 209/38* (2006.01)

(52) U.S. Cl.
CPC .................. *C07D 209/38* (2013.01)

(58) Field of Classification Search
CPC .................................. C07D 209/38
See application file for complete search history.

(56) References Cited

U.S. PATENT DOCUMENTS

2009/0131398 A1   5/2009   Tokunaga et al.

FOREIGN PATENT DOCUMENTS

| WO | 2006/113864 | 10/2006 |
|----|-------------|---------|
| WO | 2007/032371 | 3/2007 |
| WO | 2008/046083 | 4/2008 |
| WO | 2010/015655 | 2/2010 |
| WO | 2011/092293 | 8/2011 |
| WO | 2011/095450 | 8/2011 |
| WO | 2019/198692 | 10/2019 |

OTHER PUBLICATIONS

International Search Report issued Dec. 7, 2021 in corresponding International Application No. PCT/JP2021/036112.
Written Opinion of the International Searching Authority issued Dec. 7, 2021 in corresponding International Application No. PCT/JP2021/036112.
Richard Hauger et al., "International Union of Pharmacology. XXXVI. Current Status of the Nomenclature for Receptors for Corticotropin-Releasing Factor and Their Ligands", Pharmacol. Rev., vol. 55, No. 1, pp. 21-26, 2003.
Dimitris K. Grammatopoulos et al., "Functional characteristics of CRH receptors and potential clinical applications of CRH-receptor antagonists", Trends Endocrinol. Metab., vol. 13, No. 10, pp. 436-444, Dec. 2002.
Greti Aguilera et al., "Receptor-Mediated Actions of Corticotropin-Releasing Factor in Pituitary Gland and Nervous System", Neuroendocrinology, vol. 43, No. 1, pp. 79-88, 1986.
Takuma Tsuda et al., "Corticotropin releasing hormone receptor 2 exacerbates chronic cardiac dysfunction", J. Experimental Medicine, vol. 214, No. 7, pp. 1877-1888, 2017.
International Preliminary Report on Patentability issued Mar. 28, 2023 in corresponding International (PCT) Application No. PCT/JP2021/036112.

*Primary Examiner* — Golam M Shameem
(74) *Attorney, Agent, or Firm* — Wenderoth, Lind & Ponack, L.L.P.

(57) ABSTRACT

The present invention relates to 3-hydroxyoxindole derivatives which have antagonistic activities against CRHR2, and which are useful in the treatment or prevention of disorders and diseases in which CRHR2 is involved. The invention also relates to pharmaceutical compositions comprising these compounds and the use of these compounds and compositions in the prevention or treatment of such diseases in which CRHR2 is involved.

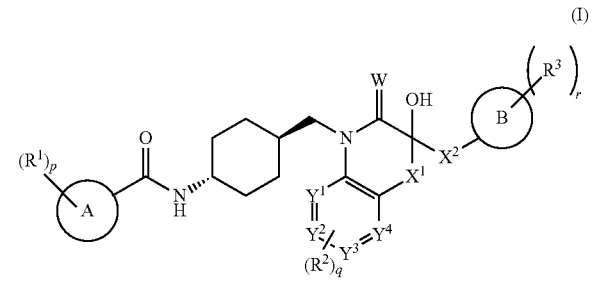

14 Claims, No Drawings

3-HYDROXYOXINDOLE DERIVATIVES AS CRHR2 ANTAGONIST

TECHNICAL FIELD

The present invention relates to 3-hydroxyoxindole derivatives which have antagonistic activities against corticotropin releasing hormone receptor 2 (CRHR2), and which is useful in the treatment or prevention of disorders and diseases in which CRHR2 is involved. The invention also relates to their preparation, pharmaceutical compositions comprising these compounds, and the use of these compounds and compositions in the prevention or treatment of such diseases in which CRHR2 is involved.

BACKGROUND ART

Corticotropin-releasing hormone receptors (CRHRs), also known as corticotropin-releasing factor receptors (CRFRs), are a G protein-coupled receptor (GPCR) family that binds corticotropin-releasing hormone (CRH) (NPL 1). There are two receptors in the family, designated as type 1 and type 2, each encoded by a separate gene (CRHR1 and CRHR2 respectively). CRHRs are important mediators in the stress response. (NPL 2). Cells in the anterior lobe of the pituitary gland known as corticotropes express the receptors and will secrete adrenocorticotropic hormone (ACTH) when stimulated. This binding of corticotropin releasing-hormone (CRH) activates the hypothalamic-pituitary-adrenal (HPA) axis, one of the two parts of the fight-or-flight response to stress. (NPL 3). CRHRs are also present in other brain areas such as the amygdala, locus coeruleus and hippocampus. Chronic activation of CRHRs by CRH induced by early life stress has been shown to underlie memory deficits and learning impairments and anxiety in adulthood.

Recently, Tsuda T, Takefuji M, et al., reported that the GPCR corticotropin releasing hormone receptor 2 (CRHR2) is highly expressed in the heart and facilitates heart failure (NPL 4). The results indicate that CRHR2 may be a promising therapeutic target for chronic heart failure.

Novartis discloses corticotropin releasing factor (CRF) receptor antagonists in WO2011/092293 (PL 1) and WO2011/095450 (PL 2). RaQualia discloses fused cyclic urea derivatives as CRHR1 and/or CRHR2 antagonists in WO2019/198692 (PL 3).

The 3-hydroxyoxindole derivatives of the present invention show excellent CRHR2 antagonistic activities and have a number of therapeutic applications.

CITATION LIST

Non Patent Literature

{NPL 1} Hauger R L, et al., Pharmacol. Rev. 55 (1): 21-6, 2003.
{NPL 2} Grammatopoulos D K, et al., Trends Endocrinol. Metab. 13 (10): 436-44, 2002.
{NPL 3} Aguilera G, et al., Neuroendocrinology. 43 (1): 79-88, 1986.
{NPL 4} Tsuda T, Takefuji M, et al., J. Experimental Medicine, 214, 1877-1888, 2017.

PATENT LITERATURE

{PL 1} WO2011/092293
{PL 2} WO2011/095450
{PL 3} WO2019/198692

SUMMARY OF INVENTION

Technical Problem

It is an objective of the invention to provide new CRHR2 antagonists that are good drug. They possess preferable pharmacokinetic properties such as absorption, distribution, metabolism, and excretion. They are non-toxic and demonstrate few side-effects. Furthermore, the ideal drug exists in a physical form that is stable, non-hygroscopic and easily formulated.

Solution to Problem

With respect to other compounds disclosed in the art, the compounds of the present invention may show less toxicity, preferable absorption and distribution, preferable solubility, preferable plasma protein binding, less drug-drug interaction, preferable metabolic stability, reduced inhibitory activity at human ether-a-go-go related gene (hERG) channel, and/or reduced QT prolongation.

This invention provides as follows.

[1] A compound of the following formula (I):

[Chem. 1]

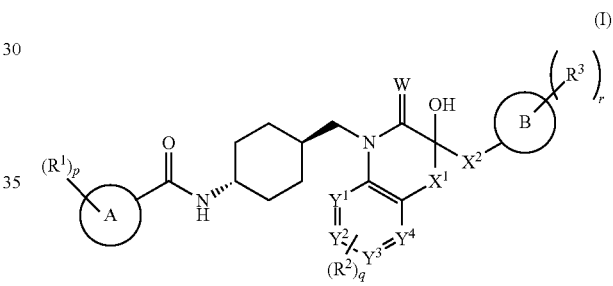

(I)

wherein:

A is aryl or heteroaryl; preferably A is phenyl, naphthyl, or 5 to 10-membered heteroaryl with 1-4 heteroatoms independently selected from O, N, and S; more preferably A is phenyl, naphthyl, 5 to 6-membered heteroaryl with 1-4 heteroatoms independently selected from O, N, and S, or 9 to 10-membered heteroaryl with 1-4 heteroatoms independently selected from O, N, and S; further more preferably A is selected from the group consisting of: phenyl, naphthyl, pyridyl, pyridazinyl, pyrazinyl, pyrimidinyl, triazinyl, imidazolyl, pyrazolyl, pyrrolyl, furanyl, thiophenyl, oxazolyl, isoxazolyl, thiazolyl, isothiazolyl, indolyl, indazolyl, benzoimidazolyl, benzofuranyl, benzothiophenyl, quinolinyl, isoquinolinyl, and quinazolinyl;

W is S or O; preferably W is O;

$R^1$ is independently selected from the group consisting of: (1) hydrogen, (2) halogen, (3) $C_{1-6}$ alkyl, (4) —O—$C_{1-6}$ alkyl, and (5) —$NR^aR^b$; wherein the $C_{1-6}$ alkyl or the —O—$C_{1-6}$ alkyl is unsubstituted or substituted with one or more substituents independently selected from the group consisting of: halogen and hydroxyl; preferably $R^1$ is independently selected from the group consisting of: (1) hydrogen, (2) halogen, and (3) $C_{1-6}$ alkyl; wherein the $C_{1-6}$ alkyl is unsubstituted or substituted with one or more halogens;

$R^a$ and $R^b$ are independently selected from the group consisting of: (1) hydrogen, (2) $C_{1-6}$ alkyl, and (3) $C_{3-7}$ cycloalkyl; or $R^a$ may form a 4 to 7 membered ring with $R^b$ which may contain one or more selected from N, O, S, and carbonyl;

p is 1, 2, or 3;

$Y^1$, $Y^2$, $Y^3$, and $Y^4$ are independently selected from the group consisting of CH, $CR^2$, and N; wherein the number of nitrogen atom(s) in the $Y^1$, $Y^2$, $Y^3$, and $Y^4$ is 0, 1, or 2; preferably $Y^1$ and $Y^3$ are independently selected from the group consisting of CH, $CR^2$, and N; $Y^2$ and $Y^4$ are independently selected from the group consisting of: CH and $CR^2$;

$R^2$ is independently selected from the group consisting of: (1) hydrogen, (2) halogen, (3) hydroxyl, (4) $C_{1-6}$ alkyl, (5) —O—$C_{1-6}$ alkyl, and (6) —CN; wherein the $C_{1-6}$ alkyl or the —O—$C_{1-6}$ alkyl is unsubstituted or substituted with one or more substituents independently selected from the group consisting of: halogen and hydroxyl;

q is 1, 2, 3, or 4; preferably q is 1 or 2;

$X^1$ is selected from the group consisting of: a chemical bond, $CH_2$, $CH(C_{1-6}$ alkyl), and $C(C_{1-6}$ alkyl)($C_{1-6}$ alkyl); preferably $X^1$ is a chemical bond;

$X^2$ is selected from the group consisting of: a chemical bond, $C_{1-6}$ alkylene, and $C_{1-6}$ alkylene-(C=O)—, preferably $C_{1-6}$ alkylene is $C_{1-3}$ alkylene; wherein the $C_{1-6}$ alkylene or the $C_{1-6}$ alkylene-(C=O)— is unsubstituted or substituted with one or more substituents independently selected from the group consisting of: halogen, hydroxyl, and $C_{1-6}$ alkyl; preferably $X^2$ is selected from the group consisting of: a chemical bond, —$CH_2$—, —$CH_2CH_2$—, —CH(OH)$CH_2$—, —$CH_2$CH(OH)—, and —$CH_2$—(C=O)—; B is aryl, heteroaryl, or $C_{3-7}$ cycloalkyl; preferably B is phenyl, naphthyl, 5 to 10-membered heteroaryl with 1-4 heteroatoms independently selected from O, N, and S, or $C_{3-7}$ cycloalkyl; more preferably B is phenyl, naphthyl, 5 to 6-membered heteroaryl with 1-4 heteroatoms independently selected from O, N, and S, 9 to 10-membered heteroaryl with 1-4 heteroatoms independently selected from O, N, and S, or $C_{3-7}$ cycloalkyl; further more preferably B is selected from the group consisting of: phenyl, naphthyl, pyridyl, pyridazinyl, pyrazinyl, pyrimidinyl, triazinyl, imidazolyl, pyrazolyl, pyrrolyl, furanyl, thiophenyl, triazolyl, oxazolyl, isoxazolyl, thiazolyl, isothiazolyl, indolyl, indazolyl, benzimidazolyl, benzofuranyl, benzothiophenyl, quinolinyl, isoquinolinyl, and quinazolinyl;

$R^3$ is independently selected from the group consisting of: (1) hydrogen, (2) halogen, (3) hydroxyl, (4) $C_{1-6}$ alkyl, (5) $C_{2-6}$ alkenyl, (6) $C_{3-7}$ cycloalkyl, (7) —O—$C_{1-6}$ alkyl, (8) —O—$C_{3-7}$ cycloalkyl, (9) heterocyclyl, (10) aryl, (11) heteroaryl, (12) —(C=O)—$R^4$, (13) —(C=O)—$NR^5R^6$, (14) —$NR^5$(C=O)$R^4$, (15) —$NR^5R^6$, (16) —S(O)$_2$—$R^4$, (17) —$NR^5$—S(O)$_2R^4$, (18) —S(O)$_2$—$NR^5R^6$, (19) —CN, and (20) —S—$C_{1-6}$ alkyl; wherein the $C_{1-6}$ alkyl, the $C_{2-6}$ alkenyl, the $C_{3-7}$cycloalkyl, the —O—$C_{1-6}$ alkyl, the —O—$C_{3-7}$ cycloalkyl, the heterocyclyl, or the —S—$C_{1-6}$ alkyl is unsubstituted or substituted with one or more substituents independently selected from halogen and hydroxyl; preferably $R^3$ is hydrogen, methyl, methoxyl, fluoro, chloro, trifluoromethyl, and trifluoromethoxyl;

r is 0, 1, 2, 3, or 4; preferably when B is aryl or heteroaryl, r is 0, 1, 2, 3, or 4, or when B is $C_{3-7}$ cycloalkyl, r is 0;

$R^4$ is selected from the group consisting of: (1) hydroxyl, (2) $C_{1-6}$ alkyl, (3) —O—$C_{1-6}$ alkyl, (4) $C_{3-7}$ cycloalkyl, (5) —O—$C_{3-7}$ cycloalkyl, (6) $C_{2-6}$ alkenyl, (7) aryl, (8) heteroaryl, and (9) heterocyclyl; wherein the $C_{1-6}$ alkyl, the —O—$C_{1-6}$ alkyl, the $C_{3-7}$ cycloalkyl, the —O—$C_{3-7}$ cycloalkyl, the $C_{2-6}$ alkenyl, or the heterocyclyl is unsubstituted or substituted with one or more substituents independently selected from halogen and hydroxyl; wherein the aryl or the heteroaryl is unsubstituted or substituted with one or more substituents independently selected from halogen, hydroxyl, $C_{1-6}$ alkyl, —O—$C_{1-6}$ alkyl, and —CN;

$R^5$ and $R^6$ are independently selected from the group consisting of: (1) hydrogen, (2) $C_{1-6}$ alkyl, (3) $C_{3-7}$ cycloalkyl, (4) heterocyclyl, (5) aryl, and (6) heteroaryl; wherein the $C_{1-6}$ alkyl, the $C_{3-7}$ cycloalkyl, or the heterocyclyl is unsubstituted or substituted with one or more substituents independently selected from the group consisting of: halogen and hydroxyl; wherein the aryl or the heteroaryl is unsubstituted or substituted with one or more substituents independently selected from halogen, hydroxyl, $C_{1-6}$ alkyl, —O—$C_{1-6}$ alkyl, and —CN;

or a pharmaceutically acceptable salt thereof or a prodrug thereof.

[2] The compound according to [1]:

wherein:

A is phenyl, naphthyl, or 5 to 10-membered heteroaryl with 1-4 heteroatoms independently selected from O, N, and S;

W is O;

$Y^1$ and $Y^3$ are independently selected from the group consisting of: CH, $CR^2$, and N;

$Y^2$ and $Y^4$ are independently selected from the group consisting of: CH and $CR^2$;

$R^2$ is independently selected from the group consisting of: (1) hydrogen, (2) halogen, (3) hydroxyl, (4) $C_{1-6}$ alkyl, (5) —O—$C_{1-6}$ alkyl, and (6) —CN; wherein the $C_{1-6}$ alkyl or the —O—$C_{1-6}$ alkyl is unsubstituted or substituted with one or more substituents independently selected from the group consisting of: halogen and hydroxyl;

q is 1, 2, 3, or 4; preferably q is 1 or 2;

$X^1$ is a chemical bond;

$X^2$ is selected from the group consisting of: a chemical bond, —$CH_2$—, —$CH_2CH_2$—, —CH(OH)$CH_2$—, —$CH_2$CH(OH)—, and —$CH_2$—(C=O)—;

B is phenyl, naphthyl, 5 to 10-membered heteroaryl with 1-4 heteroatoms independently selected from O, N, and S, or $C_{3-7}$ cycloalkyl;

or a pharmaceutically acceptable salt thereof or a prodrug thereof.

[3] The compound according to [1] or [2]:

wherein:

A is selected from the group consisting of: phenyl, naphthyl, pyridyl, pyridazinyl, pyrazinyl, pyrimidinyl, triazinyl, imidazolyl, pyrazolyl, pyrrolyl, furanyl, thiophenyl, oxazolyl, isoxazolyl, thiazolyl, isothiazolyl, indolyl, indazolyl, benzoimidazolyl, benzofuranyl, benzothiophenyl, quinolinyl, isoquinolinyl, and quinazolinyl;

B is selected from the group consisting of: phenyl, naphthyl, pyridyl, pyridazinyl, pyrazinyl, pyrimidinyl, triazinyl, imidazolyl, pyrazolyl, pyrrolyl, furanyl, thiophenyl, triazolyl, oxazolyl, isoxazolyl, thiazolyl, isothiazolyl, indolyl, indazolyl, benzimidazolyl, benzofuranyl, benzothiophenyl, quinolinyl, isoquinolinyl, and quinazolinyl;

or a pharmaceutically acceptable salt thereof or a prodrug thereof.

[4] A compound of the following formula (II):

[Chem. 2]

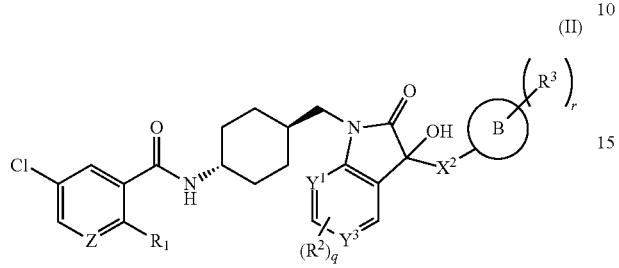

(II)

wherein:

Z is CH or N;

$R^1$ is independently selected from the group consisting of: (1) hydrogen, (2) halogen, (3) $C_{1-6}$ alkyl, (4) —O—$C_{1-6}$ alkyl, and (5) —$NR^aR^b$; wherein the $C_{1-6}$ alkyl or the —O—$C_{1-6}$ alkyl is unsubstituted or substituted with one or more substituents independently selected from the group consisting of: halogen and hydroxyl;

$R^a$ and $R^b$ are independently selected from the group consisting of: (1) hydrogen, (2) $C_{1-6}$ alkyl, and (3) $C_{3-7}$ cycloalkyl; or $R^a$ may form a 4 to 7 membered ring with $R^b$ which may contain one or more selected from N, O, S, and carbonyl; $Y^1$ and $Y^3$ are independently selected from the group consisting of: CH, $CR^2$, and N;

$R^2$ is independently selected from the group consisting of: (1) hydrogen, (2) halogen, (3) hydroxyl, (4) $C_{1-6}$ alkyl, (5) —O—$C_{1-6}$ alkyl, and (6) —CN; wherein the $C_{1-6}$ alkyl or the —O—$C_{1-6}$ alkyl is unsubstituted or substituted with one or more substituents independently selected from the group consisting of: halogen and hydroxyl;

q is 1, 2, 3, or 4;

$X^2$ is selected from the group consisting of: a chemical bond, $C_{1-6}$ alkylene, and $C_{1-6}$ alkylene-(C=O)—; wherein the $C_{1-6}$ alkylene or the $C_{1-6}$ alkylene-(C=O)— is unsubstituted or substituted with one or more substituents independently selected from the group consisting of: halogen, hydroxyl, and $C_{1-6}$ alkyl;

B is aryl, heteroaryl, or $C_{3-7}$ cycloalkyl;

$R^3$ is independently selected from the group consisting of: (1) hydrogen, (2) halogen, (3) hydroxyl, (4) $C_{1-6}$ alkyl, (5) $C_{2-6}$ alkenyl, (6) $C_{3-7}$ cycloalkyl, (7) —O—$C_{1-6}$ alkyl, (8) —O—$C_{3-7}$ cycloalkyl, (9) heterocyclyl, (10) aryl, (11) heteroaryl, (12) —(C=O)—$R^4$, (13) —(C=O)—$NR^5R^6$, (14) —$NR^5$(C=O)$R^4$, (15) —$NR^5R^6$, (16) —$S(O)_2$—$R^4$, (17) —$NR^5$—$S(O)_2R^4$, (18) —$S(O)_2$—$NR^5R^6$, (19) —CN, and (20) —S—$C_{1-6}$ alkyl; wherein the $C_{1-6}$ alkyl, the $C_{2-6}$alkenyl, the $C_{3-7}$cycloalkyl, the —O—$C_{1-6}$ alkyl, the —O—$C_{3-7}$ cycloalkyl, the heterocyclyl, or the —S—$C_{1-6}$ alkyl is unsubstituted or substituted with one or more substituents independently selected from halogen and hydroxyl;

r is 0, 1, 2, 3, or 4; when B is aryl or heteroaryl, r is 0, 1, 2, 3, or 4; or when B is $C_3$_7 cycloalkyl, r is 0;

$R^4$ is selected from the group consisting of: (1) hydroxyl, (2) $C_{1-6}$ alkyl, (3) —O—$C_{1-6}$ alkyl, (4) $C_{3-7}$ cycloalkyl, (5) —O—$C_{3-7}$ cycloalkyl, (6) $C_{2-6}$ alkenyl, (7) aryl, (8) heteroaryl, and (9) heterocyclyl; wherein the $C_{1-6}$ alkyl, the —O—$C_{1-6}$ alkyl, the $C_{3-7}$ cycloalkyl, the —O—$C_{3-7}$ cycloalkyl, the $C_{2-6}$ alkenyl, or the heterocyclyl is unsubstituted or substituted with one or more substituents independently selected from halogen or hydroxyl; wherein the aryl or the heteroaryl is unsubstituted or substituted with one or more substituents independently selected from halogen, hydroxyl, $C_{1-6}$ alkyl, —O—$C_{1-6}$ alkyl, and —CN;

$R^5$ and $R^6$ are independently selected from the group consisting of: (1) hydrogen, (2) $C_{1-6}$ alkyl, (3) $C_{3-7}$ cycloalkyl, (4) heterocyclyl, (5) aryl, and (6) heteroaryl; wherein the $C_{1-6}$ alkyl, the $C_{3-7}$ cycloalkyl, or the heterocyclyl is unsubstituted or substituted with one or more substituents independently selected from the group consisting of: halogen and hydroxyl; wherein the aryl or the heteroaryl is unsubstituted or substituted with one or more substituents independently selected from halogen, hydroxyl, $C_{1-6}$ alkyl, —O—$C_{1-6}$ alkyl, and —CN;

or a pharmaceutically acceptable salt thereof or a prodrug thereof.

[5] The compound according to [4]:

wherein:

$X^2$ is selected from the group consisting of: a chemical bond, —$CH_2$—, —$CH_2CH_2$—, —CH(OH)$CH_2$—, —$CH_2$CH(OH)—, and —$CH_2$—(C=O)—;

B is phenyl, 5 to 10-membered heteroaryl with 1-4 heteroatoms independently selected from O, N, and S, or $C_{3-}$, cycloalkyl;

r is 0, 1, 2, 3, or 4; when B is phenyl or 5 to 10-membered heteroaryl, r is 0, 1, 2, 3, or 4; or when B is $C_{3-7}$ cycloalkyl, r is 0;

or a pharmaceutically acceptable salt thereof or a prodrug thereof.

[6] The compound according to [5]:

wherein:

B is selected from the group consisting of: phenyl, naphthyl, pyridyl, pyridazinyl, pyrazinyl, pyrimidinyl, triazinyl, imidazolyl, pyrazolyl, pyrrolyl, furanyl, thiophenyl, triazolyl, oxazolyl, isoxazolyl, thiazolyl, isothiazolyl, indolyl, indazolyl, benzimidazolyl, benzofuranyl, benzothiophenyl, quinolinyl, isoquinolinyl, and quinazolinyl;

$R^3$ is hydrogen, methyl, methoxyl, fluoro, chloro, trifluoromethyl, and trifluoromethoxyl;

or a pharmaceutically acceptable salt thereof or a prodrug thereof.

[7] A compound which is selected from the group consisting of:

5-chloro-N-((1r,4r)-4-((3-hydroxy-2-oxo-3-phenylindolin-1-yl)methyl)cyclohexyl)-2-methylnicotinamide;

5-chloro-2-(difluoromethyl)-N-((1r,4r)-4-((3-hydroxy-3-(4-methoxyphenyl)-2-oxoindolin-1-yl)methyl)cyclohexyl) nicotinamide;

5-chloro-2-(difluoromethyl)-N-((1r,4r)-4-((3-hydroxy-2-oxo-3-phenylindolin-1-yl)methyl)cyclohexyl)nicotinamide;

5-chloro-2-(difluoromethyl)-N-((1r,4r)-4-((3-hydroxy-2-oxo-3-(pyridin-2-yl)indolin-1-yl)methyl)cyclohexyl) nicotinamide;

5-chloro-2-(difluoromethyl)-N-((1r,4r)-4-((3-hydroxy-3-(6-methoxypyridin-3-yl)-2-oxoindolin-1-yl)methyl)cyclohexyl)nicotinamide;

5-chloro-2-(difluoromethyl)-N-((1r,4r)-4-((3-hydroxy-3-(5-methylpyridin-2-yl)-2-oxoindolin-1-yl)methyl)cyclohexyl)nicotinamide;

5-chloro-2-(difluoromethyl)-N-((1r,4r)-4-((3-(5-fluoro-6-methylpyridin-2-yl)-3-hydroxy-2-oxoindolin-1-yl)methyl)cyclohexyl)nicotinamide;

5-chloro-2-(difluoromethyl)-N-((1r,4r)-4-((3-hydroxy-3-(6-methylpyridin-2-yl)-2-oxoindolin-1-yl)methyl)cyclohexyl)nicotinamide;

5-chloro-2-(difluoromethyl)-N-((1r,4r)-4-((3-hydroxy-3-(6-methoxypyridin-2-yl)-2-oxoindolin-1-yl)methyl)cyclohexyl)nicotinamide;

5-chloro-2-(difluoromethyl)-N-((1r,4r)-4-((3-(3-fluoropyridin-4-yl)-3-hydroxy-2-oxoindolin-1-yl)methyl)cyclohexyl)nicotinamide;

5-chloro-2-(difluoromethyl)-N-((1r,4r)-4-((3-hydroxy-3-(5-methoxypyridin-2-yl)-2-oxoindolin-1-yl)methyl)cyclohexyl)nicotinamide;

5-chloro-2-(difluoromethyl)-N-((1r,4r)-4-((3-hydroxy-2-oxo-3-(5-(trifluoromethyl)pyridin-2-yl)indolin-1-yl)methyl)cyclohexyl)nicotinamide;

5-chloro-N-((1r,4r)-4-((3-(5-chloropyridin-2-yl)-3-hydroxy-2-oxoindolin-1-yl)methyl) cyclohexyl)-2-(difluoromethyl)nicotinamide;

5-chloro-2-(difluoromethyl)-N-((1r,4r)-4-((3-hydroxy-2-oxo-3-(thiazol-2-yl)indolin-1-yl)methyl)cyclohexyl)nicotinamide;

5-chloro-2-(difluoromethyl)-N-((1r,4r)-4-((3-hydroxy-2-oxo-3-(4-(trifluoromethyl)pyridin-2-yl)indolin-1-yl)methyl)cyclohexyl)nicotinamide;

5-chloro-2-(difluoromethyl)-N-((1r,4r)-4-((3-hydroxy-2-oxo-3-phenyl-2,3-dihydro-1H-pyrrolo[2,3-b]pyridin-1-yl)methyl)cyclohexyl)nicotinamide;

5-chloro-2-(difluoromethyl)-N-((1r,4r)-4-((3-(4-fluorophenyl)-3-hydroxy-2-oxoindolin-1-yl)methyl)cyclohexyl)nicotinamide;

5-chloro-2-(difluoromethyl)-N-((1r,4r)-4-((3-(5-fluoropyridin-2-yl)-3-hydroxy-2-oxoindolin-1-yl)methyl)cyclohexyl)nicotinamide;

5-chloro-2-(difluoromethyl)-N-((1r,4r)-4-((3-(3-fluoropyridin-2-yl)-3-hydroxy-2-oxoindolin-1-yl)methyl)cyclohexyl)nicotinamide;

5-chloro-2-(difluoromethyl)-N-((1r,4r)-4-((3-(3-fluorophenyl)-3-hydroxy-2-oxoindolin-1-yl)methyl)cyclohexyl)nicotinamide;

5-chloro-2-(difluoromethyl)-N-((1r,4r)-4-((3-(5-fluoropyridin-3-yl)-3-hydroxy-2-oxoindolin-1-yl)methyl)cyclohexyl)nicotinamide;

5-chloro-N-((1r,4r)-4-((3-(3-chloropyridin-4-yl)-3-hydroxy-2-oxoindolin-1-yl)methyl) cyclohexyl)-2-(difluoromethyl)nicotinamide;

5-chloro-2-(difluoromethyl)-N-((1r,4r)-4-((3-hydroxy-2-oxo-3-(2-oxo-2-phenylethyl)indolin-1-yl)methyl)cyclohexyl)nicotinamide;

5-chloro-N-((1r,4r)-4-((3-(3-chloropyridin-2-yl)-3-hydroxy-2-oxoindolin-1-yl)methyl) cyclohexyl)-2-(difluoromethyl)nicotinamide;

5-chloro-2-(difluoromethyl)-N-((1r,4r)-4-((3-(3,5-difluoropyridin-2-yl)-3-hydroxy-2-oxoindolin-1-yl)methyl)cyclohexyl)nicotinamide;

5-chloro-N-((1r,4r)-4-((3-(5-chloropyridin-3-yl)-3-hydroxy-2-oxoindolin-1-yl)methyl) cyclohexyl)-2-(difluoromethyl)nicotinamide;

5-chloro-2-(difluoromethyl)-N-((1r,4r)-4-((3-(5-fluoro-2-methoxypyridin-4-yl)-3-hydroxy-2-oxoindolin-1-yl)methyl)cyclohexyl)nicotinamide;

5-chloro-N-((1r,4r)-4-((3-(5-chloro-3-fluoropyridin-2-yl)-3-hydroxy-2-oxoindolin-1-yl)methyl)cyclohexyl)-2-(difluoromethyl)nicotinamide;

5-chloro-N-((1r,4r)-4-((5-chloro-3-hydroxy-2-oxo-3-phenylindolin-1-yl)methyl)cyclohexyl)-2-(difluoromethyl)nicotinamide;

5-chloro-N-((1r,4r)-4-((6-chloro-3-hydroxy-2-oxo-3-phenylindolin-1-yl)methyl)cyclohexyl)-2-(difluoromethyl)nicotinamide;

5-chloro-2-(difluoromethyl)-N-((1r,4r)-4-((5-fluoro-3-hydroxy-2-oxo-3-phenylindolin-1-yl)methyl)cyclohexyl)nicotinamide;

5-chloro-2-(difluoromethyl)-N-((1r,4r)-4-((6-fluoro-3-hydroxy-2-oxo-3-phenylindolin-1-yl)methyl)cyclohexyl)nicotinamide;

5-chloro-2-(difluoromethyl)-N-((1r,4r)-4-((3-(2-fluorophenyl)-3-hydroxy-2-oxoindolin-1-yl)methyl)cyclohexyl)nicotinamide;

5-chloro-2-(difluoromethyl)-N-((1r,4r)-4-((3-hydroxy-3-(2-hydroxy-2-phenylethyl)-2-oxoindolin-1-yl)methyl)cyclohexyl)nicotinamide;

5-chloro-2-(difluoromethyl)-N-((1r,4r)-4-((3-hydroxy-2-oxo-3-(thiazol-4-yl)indolin-1-yl)methyl)cyclohexyl)nicotinamide;

5-chloro-2-(difluoromethyl)-N-((1r,4r)-4-((3-hydroxy-3-(2-methoxythiazol-5-yl)-2-oxoindolin-1-yl)methyl)cyclohexyl)nicotinamide;

5-chloro-N-((1r,4r)-4-((3-cyclopentyl-3-hydroxy-2-oxoindolin-1-yl)methyl)cyclohexyl)-2-(difluoromethyl)nicotinamide;

5-chloro-2-(difluoromethyl)-N-((1r,4r)-4-((3-hydroxy-2-oxo-3-phenethylindolin-1-yl) methyl)cyclohexyl)nicotinamide;

5-chloro-2-(difluoromethyl)-N-((1r,4r)-4-((3-hydroxy-3-(1-methyl-1H-indazol-5-yl)-2-oxoindolin-1-yl)methyl)cyclohexyl)nicotinamide;

5-chloro-2-(difluoromethyl)-N-((1r,4r)-4-((3-(2,3-difluorophenyl)-3-hydroxy-2-oxoindolin-1-yl)methyl)cyclohexyl)nicotinamide;

5-chloro-2-(difluoromethyl)-N-((1r,4r)-4-((3-(2-fluoro-6-methoxyphenyl)-3-hydroxy-2-oxoindolin-1-yl)methyl)cyclohexyl)nicotinamide;

5-chloro-N-((1r,4r)-4-((3-(4-chlorophenyl)-3-hydroxy-2-oxoindolin-1-yl)methyl)cyclohexyl)-2-(difluoromethyl)nicotinamide;

5-chloro-2-(difluoromethyl)-N-((1r,4r)-4-((3-hydroxy-2-oxo-3-(o-tolyl)indolin-1-yl)methyl)cyclohexyl)nicotinamide;

5-chloro-2-(difluoromethyl)-N-((1r,4r)-4-((3-(3,5-difluorophenyl)-3-hydroxy-2-oxoindolin-1-yl)methyl)cyclohexyl)nicotinamide;

5-chloro-N-((1r,4r)-4-((3-(3-chloro-4-fluorophenyl)-3-hydroxy-2-oxoindolin-1-yl)methyl)cyclohexyl)-2-(difluoromethyl)nicotinamide;

5-chloro-N-((1r,4r)-4-((3-(3-cyanophenyl)-3-hydroxy-2-oxoindolin-1-yl)methyl)cyclohexyl)-2-(difluoromethyl)nicotinamide;

5-chloro-2-(difluoromethyl)-N-((1r,4r)-4-((3-hydroxy-3-(3-methoxyphenyl)-2-oxoindolin-1-yl)methyl)cyclohexyl)nicotinamide;

5-chloro-N-((1r,4r)-4-((3-(3-chlorophenyl)-3-hydroxy-2-oxoindolin-1-yl)methyl)cyclohexyl)-2-(difluoromethyl)nicotinamide;

5-chloro-2-(difluoromethyl)-N-((1r,4r)-4-((3-hydroxy-2-oxo-3-(m-tolyl)indolin-1-yl)methyl)cyclohexyl)nicotinamide;

5-chloro-2-(difluoromethyl)-N-((1r,4r)-4-((3-hydroxy-2-oxo-3-(3-(trifluoromethyl)phenyl)indolin-1-yl)methyl)cyclohexyl)nicotinamide;

5-chloro-2-(difluoromethyl)-N-((1r,4r)-4-((3-hydroxy-2-oxo-3-(3-(trifluoromethoxy)phenyl)indolin-1-yl)methyl)cyclohexyl)nicotinamide;

N-((1r,4r)-4-((3-(5-amino-3-methyl-1-(pyridin-2-yl)-1H-pyrazol-4-yl)-3-hydroxy-2-oxoindolin-1-yl)methyl)cyclohexyl)-5-chloro-2-(difluoromethyl)nicotinamide;

5-chloro-2-(difluoromethyl)-N-((1r,4r)-4-((3-(2,4-difluorophenyl)-3-hydroxy-2-oxoindolin-1-yl)methyl)cyclohexyl)nicotinamide;

5-chloro-2-(difluoromethyl)-N-((1r,4r)-4-((3-(2-fluoro-4-methoxyphenyl)-3-hydroxy-2-oxoindolin-1-yl)methyl)cyclohexyl)nicotinamide;

5-chloro-N-((1r,4r)-4-((3-(5-chloro-6-methoxypyridin-2-yl)-3-hydroxy-2-oxoindolin-1-yl)methyl)cyclohexyl)-2-(difluoromethyl)nicotinamide;

5-chloro-2-(difluoromethyl)-N-((1r,4r)-4-((3-hydroxy-2-oxo-3-(p-tolyl)indolin-1-yl)methyl)cyclohexyl)nicotinamide;

5-chloro-2-(difluoromethyl)-N-((1r,4r)-4-((3-hydroxy-3-(4-methylthiazol-2-yl)-2-oxoindolin-1-yl)methyl)cyclohexyl)nicotinamide;

5-chloro-2-(difluoromethyl)-N-((1r,4r)-4-((3-(2,5-difluorophenyl)-3-hydroxy-2-oxoindolin-1-yl)methyl)cyclohexyl)nicotinamide;

5-chloro-N-((1r,4r)-4-((3-(5-cyano-2-fluorophenyl)-3-hydroxy-2-oxoindolin-1-yl)methyl)cyclohexyl)-2-(difluoromethyl)nicotinamide;

5-chloro-2-(difluoromethyl)-N-((1r,4r)-4-((3-hydroxy-3-(1-hydroxy-2-phenylethyl)-2-oxoindolin-1-yl)methyl)cyclohexyl)nicotinamide;

5-chloro-2-(difluoromethyl)-N-((1r,4r)-4-((3-(2,6-difluorophenyl)-3-hydroxy-2-oxoindolin-1-yl)methyl)cyclohexyl)nicotinamide;

5-chloro-2-(difluoromethyl)-N-((1r,4r)-4-((3-(3-fluoro-2-methoxy-6-methylpyridin-4-yl)-3-hydroxy-2-oxoindolin-1-yl)methyl)cyclohexyl)nicotinamide;

5-chloro-2-(difluoromethyl)-N-((1r,4r)-4-((3-(2-fluoro-3-methylphenyl)-3-hydroxy-2-oxoindolin-1-yl)methyl)cyclohexyl)nicotinamide;

5-chloro-2-(difluoromethyl)-N-((1r,4r)-4-((3-(3-fluoro-2-methoxypyridin-4-yl)-3-hydroxy-2-oxoindolin-1-yl)methyl)cyclohexyl)nicotinamide;

5-chloro-N-((1r,4r)-4-((3-(2-chlorophenyl)-3-hydroxy-2-oxoindolin-1-yl)methyl)cyclohexyl)-2-(difluoromethyl)nicotinamide;

5-chloro-2-(difluoromethyl)-N-((1r,4r)-4-((3-(2-fluoro-3-methoxyphenyl)-3-hydroxy-2-oxoindolin-1-yl)methyl)cyclohexyl)nicotinamide;

5-chloro-N-((1r,4r)-4-((3-(3-chloro-2-fluorophenyl)-3-hydroxy-2-oxoindolin-1-yl)methyl)cyclohexyl)-2-(difluoromethyl)nicotinamide;

5-chloro-2-(difluoromethyl)-N-((1r,4r)-4-((3-(3,4-difluorophenyl)-3-hydroxy-2-oxoindolin-1-yl)methyl)cyclohexyl)nicotinamide;

5-chloro-2-(difluoromethyl)-N-((1r,4r)-4-((3-(3-(difluoromethyl)phenyl)-3-hydroxy-2-oxoindolin-1-yl)methyl)cyclohexyl)nicotinamide;

5-chloro-2-(difluoromethyl)-N-((1r,4r)-4-((3-(2-fluoro-3-(trifluoromethyl)phenyl)-3-hydroxy-2-oxoindolin-1-yl)methyl)cyclohexyl)nicotinamide;

5-chloro-N-((1r,4r)-4-((3-(3-cyano-2-fluorophenyl)-3-hydroxy-2-oxoindolin-1-yl)methyl)cyclohexyl)-2-(difluoromethyl)nicotinamide;

5-chloro-N-((1r,4r)-4-((3-(3-(1,1-difluoroethyl)phenyl)-3-hydroxy-2-oxoindolin-1-yl) methyl)cyclohexyl)-2-(difluoromethyl)nicotinamide;

5-chloro-2-(difluoromethyl)-N-((1r,4r)-4-((3-hydroxy-3-(3-(methylthio)phenyl)-2-oxoindolin-1-yl)methyl)cyclohexyl)nicotinamide;

5-chloro-2-(difluoromethyl)-N-((1r,4r)-4-((3-(2-fluoro-5-methoxyphenyl)-3-hydroxy-2-oxoindolin-1-yl)methyl)cyclohexyl)nicotinamide;

5-chloro-2-(difluoromethyl)-N-((1r,4r)-4-((3-(3-fluoro-4-methoxypyridin-2-yl)-3-hydroxy-2-oxoindolin-1-yl)methyl)cyclohexyl)nicotinamide;

5-chloro-2-(difluoromethyl)-N-((1r,4r)-4-((3-hydroxy-2-oxo-3-(quinolin-2-yl)indolin-1-yl)methyl)cyclohexyl)nicotinamide;

5-chloro-2-(difluoromethyl)-N-((1r,4r)-4-((3-hydroxy-3-(isoquinolin-1-yl)-2-oxoindolin-1-yl)methyl)cyclohexyl)nicotinamide;

5-chloro-2-(difluoromethyl)-N-((1r,4r)-4-((7-fluoro-3-(5-fluoropyridin-2-yl)-3-hydroxy-2-oxoindolin-1-yl)methyl)cyclohexyl)nicotinamide;

5-chloro-2-(difluoromethyl)-N-((1r,4r)-4-((6-fluoro-3-(5-fluoropyridin-2-yl)-3-hydroxy-2-oxoindolin-1-yl)methyl)cyclohexyl)nicotinamide;

5-chloro-2-(difluoromethyl)-N-((1r,4r)-4-((5-fluoro-3-(5-fluoropyridin-2-yl)-3-hydroxy-2-oxoindolin-1-yl)methyl)cyclohexyl)nicotinamide;

5-chloro-2-(difluoromethyl)-N-((1r,4r)-4-((4-fluoro-3-(5-fluoropyridin-2-yl)-3-hydroxy-2-oxoindolin-1-yl)methyl)cyclohexyl)nicotinamide;

5-chloro-2-(difluoromethyl)-N-((1r,4r)-4-((7-fluoro-3-(2-fluorophenyl)-3-hydroxy-2-oxoindolin-1-yl)methyl)cyclohexyl)nicotinamide;

5-chloro-2-(difluoromethyl)-N-((1r,4r)-4-((6-fluoro-3-(2-fluorophenyl)-3-hydroxy-2-oxoindolin-1-yl)methyl)cyclohexyl)nicotinamide;

5-chloro-2-(difluoromethyl)-N-((1r,4r)-4-((7-fluoro-3-(3-fluoropyridin-4-yl)-3-hydroxy-2-oxoindolin-1-yl)methyl)cyclohexyl)nicotinamide;

5-chloro-2-(difluoromethyl)-N-((1r,4r)-4-((6-fluoro-3-(3-fluoropyridin-4-yl)-3-hydroxy-2-oxoindolin-1-yl)methyl)cyclohexyl)nicotinamide;

5-chloro-2-(difluoromethyl)-N-((1r,4r)-4-((5-fluoro-3-(3-fluoropyridin-4-yl)-3-hydroxy-2-oxoindolin-1-yl)methyl)cyclohexyl)nicotinamide;

5-chloro-2-(difluoromethyl)-N-((1r,4r)-4-((4-fluoro-3-(3-fluoropyridin-4-yl)-3-hydroxy-2-oxoindolin-1-yl)methyl)cyclohexyl)nicotinamide;

5-chloro-2-(difluoromethyl)-N-((1r,4r)-4-((3-(5-fluoropyridin-2-yl)-3-hydroxy-2-oxo-6-(trifluoromethyl)indolin-1-yl)methyl)cyclohexyl)nicotinamide;

5-chloro-2-(difluoromethyl)-N-((1r,4r)-4-((3-(5-fluoropyridin-2-yl)-3-hydroxy-2-oxo-6-(trifluoromethoxy)indolin-1-yl)methyl)cyclohexyl)nicotinamide;

5-chloro-2-(difluoromethyl)-N-((1r,4r)-4-((3-(2-fluorophenyl)-3-hydroxy-2-oxo-6-(trifluoromethyl)indolin-1-yl)methyl)cyclohexyl)nicotinamide;

5-chloro-2-(difluoromethyl)-N-((1r,4r)-4-((3-hydroxy-2-oxo-3-(thiophen-2-yl)indolin-1-yl)methyl)cyclohexyl)nicotinamide;

5-chloro-2-(difluoromethyl)-N-((1r,4r)-4-((3-hydroxy-2-oxo-3-(thiophen-3-yl)indolin-1-yl)methyl)cyclohexyl)nicotinamide;

5-chloro-2-(difluoromethyl)-N-((1r,4r)-4-((5-fluoro-3-(2-fluorophenyl)-3-hydroxy-2-oxoindolin-1-yl)methyl)cyclohexyl)nicotinamide;

5-chloro-2-(difluoromethyl)-N-((1r,4r)-4-((3-(2-fluorophenyl)-3-hydroxy-2-oxo-2,3-dihydro-1H-pyrrolo[2,3-b]pyridin-1-yl)methyl)cyclohexyl)nicotinamide;

5-chloro-2-(difluoromethyl)-N-((1r,4r)-4-((3-(3-fluorothiophen-2-yl)-3-hydroxy-2-oxoindolin-1-yl)methyl)cyclohexyl)nicotinamide;

5-chloro-2-(difluoromethyl)-N-((1r,4r)-4-((3-hydroxy-3-(4-methoxythiophen-2-yl)-2-oxoindolin-1-yl)methyl)cyclohexyl)nicotinamide;

N-((1r,4r)-4-((3-(benzo[d]thiazol-2-yl)-3-hydroxy-2-oxoindolin-1-yl)methyl)cyclohexyl)-5-chloro-2-(difluoromethyl)nicotinamide;

5-chloro-2-(difluoromethyl)-N-((1r,4r)-4-((3-(4-fluorothiophen-2-yl)-3-hydroxy-2-oxoindolin-1-yl)methyl)cyclohexyl)nicotinamide;

5-chloro-2-(difluoromethyl)-N-((1r,4r)-4-((3-hydroxy-3-(5-methoxythiophen-2-yl)-2-oxoindolin-1-yl)methyl)cyclohexyl)nicotinamide;

5-chloro-N-((1r,4r)-4-((3-(5-chlorothiophen-2-yl)-3-hydroxy-2-oxoindolin-1-yl)methyl)cyclohexyl)-2-(difluoromethyl)nicotinamide;

5-chloro-2-(difluoromethyl)-N-((1r,4r)-4-((3-(3-fluoropyridin-4-yl)-3-hydroxy-2-oxo-2,3-dihydro-1H-pyrrolo[2,3-b]pyridin-1-yl)methyl)cyclohexyl)nicotinamide;

5-chloro-N-((1r,4r)-4-((6-fluoro-3-(2-fluorophenyl)-3-hydroxy-2-oxoindolin-1-yl)methyl)cyclohexyl)-2-methylnicotinamide;

5-chloro-N-((1r,4r)-4-((5-fluoro-3-(2-fluorophenyl)-3-hydroxy-2-oxoindolin-1-yl)methyl)cyclohexyl)-2-methylnicotinamide;

5-chloro-2-(difluoromethyl)-N-((1r,4r)-4-((3-(2-fluorophenyl)-3-hydroxy-2-oxo-2,3-dihydro-1H-pyrrolo[3,2-c]pyridin-1-yl)methyl)cyclohexyl)nicotinamide;

5-chloro-2-(difluoromethyl)-N-((1r,4r)-4-((3-(2-fluorophenyl)-3-hydroxy-6-methoxy-2-oxoindolin-1-yl)methyl)cyclohexyl)nicotinamide;

5-chloro-2-(difluoromethyl)-N-((1r,4r)-4-((3-(3-fluoropyridin-4-yl)-3-hydroxy-6-methoxy-2-oxoindolin-1-yl)methyl)cyclohexyl)nicotinamide;

5-chloro-2-(difluoromethyl)-N-((1r,4r)-4-((3-(2-fluorophenyl)-3-hydroxy-5-methoxy-2-oxoindolin-1-yl)methyl)cyclohexyl)nicotinamide;

5-chloro-2-(difluoromethyl)-N-((1r,4r)-4-((3-(2-fluorophenyl)-3-hydroxy-7-methoxy-2-oxoindolin-1-yl)methyl)cyclohexyl)nicotinamide;

5-chloro-2-(difluoromethyl)-N-((1r,4r)-4-((3-(3-fluoropyridin-4-yl)-3-hydroxy-7-methoxy-2-oxoindolin-1-yl)methyl)cyclohexyl)nicotinamide;

5-chloro-2-(difluoromethyl)-N-((1r,4r)-4-((3-(furan-3-yl)-3-hydroxy-2-oxoindolin-1-yl)methyl)cyclohexyl)nicotinamide;

5-chloro-N-((1r,4r)-4-((3-hydroxy-3-(3-methoxyphenyl)-2-oxoindolin-1-yl)methyl)cyclohexyl)-2-(trifluoromethyl)nicotinamide;

5-chloro-N-((1r,4r)-4-((3-(5-chloropyridin-2-yl)-3-hydroxy-2-oxoindolin-1-yl)methyl) cyclohexyl)-2-(trifluoromethyl)nicotinamide;

5-chloro-N-((1r,4r)-4-((3-(2,3-difluorophenyl)-3-hydroxy-2-oxoindolin-1-yl)methyl)cyclohexyl)-2-(trifluoromethyl)nicotinamide;

5-chloro-2-(difluoromethyl)-N-((1r,4r)-4-((3-(3,5-dimethoxyphenyl)-3-hydroxy-2-oxoindolin-1-yl)methyl)cyclohexyl)nicotinamide;

5-chloro-2-(difluoromethyl)-N-((1r,4r)-4-((6-fluoro-3-(5-fluoro-2-methoxypyridin-4-yl)-3-hydroxy-2-oxoindolin-1-yl)methyl)cyclohexyl)nicotinamide;

5-chloro-2-(difluoromethyl)-N-((1r,4r)-4-((3-(2,3-difluorophenyl)-6-fluoro-3-hydroxy-2-oxoindolin-1-yl)methyl)cyclohexyl)nicotinamide;

5-chloro-N-((1r,4r)-4-((3-(3-chloro-2-fluorophenyl)-6-fluoro-3-hydroxy-2-oxoindolin-1-yl)methyl)cyclohexyl)-2-(difluoromethyl)nicotinamide;

5-chloro-2-(difluoromethyl)-N-((1r,4r)-4-((3-(2,5-difluorophenyl)-6-fluoro-3-hydroxy-2-oxoindolin-1-yl)methyl)cyclohexyl)nicotinamide;

5-chloro-N-((1r,4r)-4-((3-(5-chloropyridin-2-yl)-6-fluoro-3-hydroxy-2-oxoindolin-1-yl)methyl)cyclohexyl)-2-(difluoromethyl)nicotinamide;

5-chloro-2-(difluoromethyl)-N-((1r,4r)-4-((3-(2-fluorophenyl)-3-hydroxy-4-methoxy-2-oxoindolin-1-yl)methyl)cyclohexyl)nicotinamide;

5-chloro-2-(difluoromethyl)-N-((1r,4r)-4-((3-(2,3-difluorophenyl)-3-hydroxy-2-oxo-2, 3-dihydro-1H-pyrrolo[2,3-b]pyridin-1-yl)methyl)cyclohexyl)nicotinamide;

5-chloro-2-(difluoromethyl)-N-((1r,4r)-4-((3-(2,5-difluorophenyl)-3-hydroxy-2-oxo-2, 3-dihydro-1H-pyrrolo[2,3-b]pyridin-1-yl)methyl)cyclohexyl)nicotinamide;

5-chloro-2-(difluoromethyl)-N-((1r,4r)-4-((3-(2,3-difluorophenyl)-5-fluoro-3-hydroxy-2-oxoindolin-1-yl)methyl)cyclohexyl)nicotinamide;

5-chloro-2-(difluoromethyl)-N-((1r,4r)-4-((5-fluoro-3-(5-fluoro-2-methoxypyridin-4-yl)-3-hydroxy-2-oxoindolin-1-yl)methyl)cyclohexyl)nicotinamide;

5-chloro-N-((1r,4r)-4-((3-(5-chloropyridin-2-yl)-5-fluoro-3-hydroxy-2-oxoindolin-1-yl)methyl)cyclohexyl)-2-(difluoromethyl)nicotinamide;

5-chloro-2-(difluoromethyl)-N-((1r,4r)-4-((3-(2,5-difluorophenyl)-5-fluoro-3-hydroxy-2-oxoindolin-1-yl)methyl)cyclohexyl)nicotinamide;

5-chloro-N-((1r,4r)-4-((3-(2,5-difluorophenyl)-3-hydroxy-2-oxoindolin-1-yl)methyl)cyclohexyl)-2-methylnicotinamide;

5-chloro-N-((1r,4r)-4-((3-(2-fluoro-5-methoxyphenyl)-3-hydroxy-2-oxoindolin-1-yl)methyl)cyclohexyl)-2-methylnicotinamide;

5-chloro-N-((1r,4r)-4-((3-(2-fluoro-5-(trifluoromethyl)phenyl)-3-hydroxy-2-oxoindolin-1-yl)methyl)cyclohexyl)-2-methylnicotinamide;

5-chloro-N-((1r,4r)-4-((3-(3-hydroxy-3-(5-methylthiophen-3-yl)-2-oxoindolin-1-yl)methyl)cyclohexyl)nicotinamide;

5-chloro-N-((1r,4r)-4-((3-(5-chlorothiophen-3-yl)-3-hydroxy-2-oxoindolin-1-yl)methyl)cyclohexyl)-2-(difluoromethyl)nicotinamide;

5-chloro-N-((1r,4r)-4-((3-hydroxy-2-oxo-3-(2,3,5-trifluorophenyl)indolin-1-yl)methyl) cyclohexyl)-2-methylnicotinamide;

5-chloro-2-(difluoromethyl)-N-((1r,4r)-4-((3-hydroxy-2-oxo-3-(2,3,5-trifluorophenyl)indolin-1-yl)methyl)cyclohexyl)nicotinamide;

5-chloro-N-((1r,4r)-4-((3-(5-chloro-2-fluorophenyl)-3-hydroxy-2-oxoindolin-1-yl)methyl)cyclohexyl)-2-(difluoromethyl)nicotinamide;

5-chloro-2-(difluoromethyl)-N-((1r,4r)-4-((3-hydroxy-2-oxo-3-(2,3,4-trifluorophenyl)indolin-1-yl)methyl)cyclohexyl)nicotinamide;

5-chloro-2-(difluoromethyl)-N-((1r,4r)-4-((3-(2-fluoro-5-(trifluoromethyl)phenyl)-3-hydroxy-2-oxoindolin-1-yl)methyl)cyclohexyl)nicotinamide;

5-chloro-N-((1r,4r)-4-((3-(5-chloro-2-fluorophenyl)-3-hydroxy-2-oxoindolin-1-yl)methyl)cyclohexyl)-2-methylnicotinamide;

5-chloro-N-((1r,4r)-4-((3-hydroxy-2-oxo-3-(2,3,4-trifluorophenyl)indolin-1-yl)methyl) cyclohexyl)-2-methylnicotinamide;

5-chloro-N-((1r,4r)-4-((3-(2,3-difluoro-4-methoxyphenyl)-3-hydroxy-2-oxoindolin-1-yl)methyl)cyclohexyl)-2-methylnicotinamide;

5-chloro-N-((1r,4r)-4-((3-(5-chloropyridin-2-yl)-4-fluoro-3-hydroxy-2-oxoindolin-1-yl)methyl)cyclohexyl)-2-(difluoromethyl)nicotinamide;

5-chloro-N-((1r,4r)-4-((7-chloro-3-(2-fluorophenyl)-3-hydroxy-2-oxoindolin-1-yl)methyl)cyclohexyl)-2-(difluoromethyl)nicotinamide;

5-chloro-2-(difluoromethyl)-N-((1r,4r)-4-((3-(2-fluorophenyl)-3-hydroxy-5-methyl-2-oxoindolin-1-yl)methyl)cyclohexyl)nicotinamide;

5-chloro-N-((1r,4r)-4-((3-(2,3-difluorophenyl)-6-fluoro-3-hydroxy-2-oxoindolin-1-yl) methyl)cyclohexyl)-2-methylnicotinamide;

5-chloro-N-((1r,4r)-4-((6-fluoro-3-(5-fluoro-2-methoxypyridin-4-yl)-3-hydroxy-2-oxoindolin-1-yl)methyl)cyclohexyl)-2-methylnicotinamide;

5-chloro-N-((1r,4r)-4-((3-(5-chloropyridin-2-yl)-6-fluoro-3-hydroxy-2-oxoindolin-1-yl)methyl)cyclohexyl)-2-methylnicotinamide;

5-chloro-N-((1r,4r)-4-((3-(2-fluorophenyl)-3-hydroxy-6-methoxy-2-oxoindolin-1-yl)methyl)cyclohexyl)-2-methylnicotinamide;

5-chloro-2-(difluoromethyl)-N-((1r,4r)-4-((3-(5-fluoropyridin-2-yl)-3-hydroxy-6-methyl-2-oxoindolin-1-yl)methyl) cyclohexyl)nicotinamide;

5-chloro-2-(difluoromethyl)-N-((1r,4r)-4-((3-(2-fluorophenyl)-3-hydroxy-6-methyl-2-oxoindolin-1-yl)methyl)cyclohexyl)nicotinamide;

5-chloro-2-(difluoromethyl)-N-((1r,4r)-4-((3-(3-fluoropyridin-4-yl)-3-hydroxy-6-methyl-2-oxoindolin-1-yl)methyl) cyclohexyl)nicotinamide;

5-chloro-N-((1r,4r)-4-((3-(2,5-difluorophenyl)-3-hydroxy-2-oxoindolin-1-yl)methyl)cyclohexyl)-2-methylbenzamide;

N-((1r,4r)-4-((3-(2,5-difluorophenyl)-3-hydroxy-2-oxoindolin-1-yl)methyl)cyclohexyl)-2-methyl-2H-indazole-3-carboxamide;

5-chloro-N-((1r,4r)-4-((3-(2,5-difluorophenyl)-3-hydroxy-2-oxoindolin-1-yl)methyl)cyclohexyl)-2-(trifluoromethoxy)benzamide;

5-chloro-N-((1r,4r)-4-((3-(2,3-difluoro-4-methoxyphenyl)-3-hydroxy-2-oxoindolin-1-yl)methyl)cyclohexyl)-2-(difluoromethyl)nicotinamide;

5-chloro-2-(cyclobutylamino)-N-((1r,4r)-4-((3-(2,5-difluorophenyl)-3-hydroxy-2-oxoindolin-1-yl)methyl)cyclohexyl)nicotinamide;

5-chloro-2-(difluoromethyl)-N-((1r,4r)-4-((6-fluoro-3-(3-fluoro-2-methoxypyridin-4-yl)-3-hydroxy-2-oxoindolin-1-yl)methyl)cyclohexyl)nicotinamide;

5-chloro-2-(difluoromethyl)-N-((1r,4r)-4-((6-fluoro-3-(2-fluoro-5-methoxyphenyl)-3-hydroxy-2-oxoindolin-1-yl) methyl)cyclohexyl)nicotinamide;

5-chloro-N-((1r,4r)-4-((3-(5-chloropyridin-2-yl)-3-hydroxy-4-methoxy-2-oxoindolin-1-yl)methyl)cyclohexyl)-2-(difluoromethyl)nicotinamide;

5-chloro-2-(difluoromethyl)-N-((1r,4r)-4-((3-(2,3-difluorophenyl)-3-hydroxy-4-methoxy-2-oxoindolin-1-yl) methyl)cyclohexyl)nicotinamide;

5-chloro-N-((1r,4r)-4-((3-(2,3-difluorophenyl)-3-hydroxy-2-oxo-2,3-dihydro-1H-pyrrolo[2,3-b]pyridin-1-yl) methyl)cyclohexyl)-2-methylnicotinamide;

5-chloro-N-((1r,4r)-4-((3-(5-chloropyridin-2-yl)-5-fluoro-3-hydroxy-2-oxoindolin-1-yl)methyl)cyclohexyl)-2-methylnicotinamide;

5-chloro-N-((1r,4r)-4-((5-fluoro-3-(5-fluoro-2-methoxypyridin-4-yl)-3-hydroxy-2-oxoindolin-1-yl)methyl)cyclohexyl)-2-methylnicotinamide;

5-chloro-N-((1r,4r)-4-((3-(2,3-difluorophenyl)-5-fluoro-3-hydroxy-2-oxoindolin-1-yl) methyl)cyclohexyl)-2-methylnicotinamide;

5-chloro-N-((1r,4r)-4-((3-(5-cyano-2-fluorophenyl)-3-hydroxy-2-oxoindolin-1-yl)methyl)cyclohexyl)-2-(trifluoromethyl)nicotinamide;

5-chloro-N-((1r,4r)-4-((3-(2-fluoro-4-methoxyphenyl)-3-hydroxy-2-oxoindolin-1-yl)methyl)cyclohexyl)-2-(trifluoromethyl)nicotinamide;

5-chloro-N-((1r,4r)-4-((3-(5-fluoro-2-methoxypyridin-4-yl)-3-hydroxy-2-oxoindolin-1-yl)methyl)cyclohexyl)-2-(trifluoromethyl)nicotinamide;

5-chloro-N-((1r,4r)-4-((3-(2,3-difluorophenyl)-3-hydroxy-2-oxoindolin-1-yl)methyl)cyclohexyl)-2-methylbenzamide;

2,5-dichloro-N-((1r,4r)-4-((3-(2,3-difluorophenyl)-3-hydroxy-2-oxoindolin-1-yl)methyl)cyclohexyl)nicotinamide;

5-chloro-2-(difluoromethyl)-N-((1r,4r)-4-((5-fluoro-3-(2-fluoro-5-methoxyphenyl)-3-hydroxy-2-oxoindolin-1-yl) methyl)cyclohexyl)nicotinamide;

5-chloro-2-(difluoromethyl)-N-((1r,4r)-4-((5-fluoro-3-(3-fluoro-2-methoxypyridin-4-yl)-3-hydroxy-2-oxoindolin-1-yl)methyl)cyclohexyl)nicotinamide;

5-chloro-N-((1r,4r)-4-((6-chloro-3-(2-fluorophenyl)-3-hydroxy-2-oxoindolin-1-yl)methyl)cyclohexyl)-2-(difluoromethyl)nicotinamide;

5-chloro-2-(cyclopropylamino)-N-((1r,4r)-4-((3-(2,3-difluorophenyl)-3-hydroxy-2-oxoindolin-1-yl)methyl)cyclohexyl)nicotinamide;

5-chloro-N-((1r,4r)-4-((3-(5-cyano-2,3-difluorophenyl)-3-hydroxy-2-oxoindolin-1-yl) methyl)cyclohexyl)-2-methylnicotinamide;

5-chloro-N-((1r,4r)-4-((3-(2,3-difluorophenyl)-3-hydroxy-2-oxoindolin-1-yl)methyl)cyclohexyl)-2-methylnicotinamide;

5-chloro-2-(difluoromethyl)-N-((1r,4r)-4-((3-(5-fluoropyridin-2-yl)-3-hydroxy-7-methyl-2-oxoindolin-1-yl)methyl) cyclohexyl)nicotinamide;

5-chloro-2-(difluoromethyl)-N-((1r,4r)-4-((3-(2-fluorophenyl)-3-hydroxy-7-methyl-2-oxoindolin-1-yl)methyl)cyclohexyl)nicotinamide;

5-chloro-2-(difluoromethyl)-N-((1r,4r)-4-((3-(3-fluoropyridin-4-yl)-3-hydroxy-7-methyl-2-oxoindolin-1-yl)methyl) cyclohexyl)nicotinamide;

5-chloro-N-((1r,4r)-4-((4,6-difluoro-3-(2-fluorophenyl)-3-hydroxy-2-oxoindolin-1-yl) methyl)cyclohexyl)-2-(difluoromethyl)nicotinamide;

5-chloro-2-(difluoromethyl)-N-((1r,4r)-4-((3-(5-fluoropyridin-2-yl)-3-hydroxy-4-methyl-2-oxoindolin-1-yl)methyl) cyclohexyl)nicotinamide;

5-chloro-2-(difluoromethyl)-N-((1r,4r)-4-((3-(2-fluorophenyl)-3-hydroxy-4-methyl-2-oxoindolin-1-yl)methyl)cyclohexyl)nicotinamide;

5-chloro-2-(difluoromethyl)-N-((1r,4r)-4-((3-(3-fluoropyridin-4-yl)-3-hydroxy-4-methyl-2-oxoindolin-1-yl)methyl) cyclohexyl)nicotinamide;

5-chloro-N-((1r,4r)-4-((7-fluoro-3-(2-fluorophenyl)-3-hydroxy-2-oxoindolin-1-yl)methyl)cyclohexyl)-2-methylnicotinamide;

5-chloro-N-((1r,4r)-4-((4-fluoro-3-(5-fluoropyridin-2-yl)-3-hydroxy-2-oxoindolin-1-yl)methyl)cyclohexyl)-2-(trifluoromethyl)nicotinamide;
5-chloro-N-((1r,4r)-4-((3-(5-chloropyridin-2-yl)-4-fluoro-3-hydroxy-2-oxoindolin-1-yl)methyl)cyclohexyl)-2-(trifluoromethyl)nicotinamide;
5-chloro-N-((1r,4r)-4-((3-(5-fluoropyridin-2-yl)-3-hydroxy-2-oxoindolin-1-yl)methyl)cyclohexyl)-2-(trifluoromethyl)nicotinamide;
5-chloro-N-((1r,4r)-4-((3-(2-fluoro-5-methoxyphenyl)-3-hydroxy-2-oxoindolin-1-yl)methyl)cyclohexyl)-2-(trifluoromethyl)nicotinamide;
5-chloro-N-((1r,4r)-4-((3-(3-chloro-2-fluorophenyl)-3-hydroxy-2-oxoindolin-1-yl)methyl)cyclohexyl)-2-(trifluoromethyl)nicotinamide;
5-chloro-N-((1r,4r)-4-((3-hydroxy-2-oxo-3-phenylindolin-1-yl)methyl)cyclohexyl)-2-(trifluoromethyl)nicotinamide;
5-chloro-N-((1r,4r)-4-((3-(2,5-difluorophenyl)-3-hydroxy-2-oxoindolin-1-yl)methyl)cyclohexyl)-2-(trifluoromethyl)nicotinamide;
5-chloro-2-(difluoromethyl)-N-((1r,4r)-4-((4-fluoro-3-(2-fluoro-5-methoxyphenyl)-3-hydroxy-2-oxoindolin-1-yl)methyl)cyclohexyl)nicotinamide;
5-chloro-N-((1r,4r)-4-((3-(3-chloro-2-fluorophenyl)-4-fluoro-3-hydroxy-2-oxoindolin-1-yl)methyl)cyclohexyl)-2-(difluoromethyl)nicotinamide;
5-chloro-2-(difluoromethyl)-N-((1r,4r)-4-((4-fluoro-3-(2-fluorophenyl)-3-hydroxy-2-oxoindolin-1-yl)methyl)cyclohexyl)nicotinamide; and
5-chloro-2-(difluoromethyl)-N-((1r,4r)-4-((3-(2,3-difluorophenyl)-4-fluoro-3-hydroxy-2-oxoindolin-1-yl)methyl)cyclohexyl)nicotinamide;

or a pharmaceutically acceptable salt thereof or a prodrug thereof.

[8] The compound according to [7], which is selected from the group consisting of:
5-chloro-2-(difluoromethyl)-N-((1r,4r)-4-((3-hydroxy-3-(4-methoxyphenyl)-2-oxoindolin-1-yl)methyl)cyclohexyl)nicotinamide;
5-chloro-2-(difluoromethyl)-N-((1r,4r)-4-((3-hydroxy-2-oxo-3-phenylindolin-1-yl)methyl)cyclohexyl)nicotinamide;
5-chloro-2-(difluoromethyl)-N-((1r,4r)-4-((3-(3-fluoropyridin-4-yl)-3-hydroxy-2-oxoindolin-1-yl)methyl)cyclohexyl)nicotinamide;
5-chloro-N-((1r,4r)-4-((3-(5-chloropyridin-2-yl)-3-hydroxy-2-oxoindolin-1-yl)methyl)cyclohexyl)-2-(difluoromethyl)nicotinamide;
5-chloro-2-(difluoromethyl)-N-((1r,4r)-4-((3-(4-fluorophenyl)-3-hydroxy-2-oxoindolin-1-yl)methyl)cyclohexyl)nicotinamide;
5-chloro-2-(difluoromethyl)-N-((1r,4r)-4-((3-(5-fluoropyridin-2-yl)-3-hydroxy-2-oxoindolin-1-yl)methyl)cyclohexyl)nicotinamide;
5-chloro-2-(difluoromethyl)-N-((1r,4r)-4-((3-(3-fluorophenyl)-3-hydroxy-2-oxoindolin-1-yl)methyl)cyclohexyl)nicotinamide;
5-chloro-2-(difluoromethyl)-N-((1r,4r)-4-((3-(5-fluoro-2-methoxypyridin-4-yl)-3-hydroxy-2-oxoindolin-1-yl)methyl)cyclohexyl)nicotinamide;
5-chloro-N-((1r,4r)-4-((6-chloro-3-hydroxy-2-oxo-3-phenylindolin-1-yl)methyl)cyclohexyl)-2-(difluoromethyl)nicotinamide;
5-chloro-2-(difluoromethyl)-N-((1r,4r)-4-((3-(2-fluorophenyl)-3-hydroxy-2-oxoindolin-1-yl)methyl)cyclohexyl)nicotinamide;
5-chloro-2-(difluoromethyl)-N-((1r,4r)-4-((3-(2,3-difluorophenyl)-3-hydroxy-2-oxoindolin-1-yl)methyl)cyclohexyl)nicotinamide;
5-chloro-2-(difluoromethyl)-N-((1r,4r)-4-((3-hydroxy-3-(3-methoxyphenyl)-2-oxoindolin-1-yl)methyl)cyclohexyl)nicotinamide;
5-chloro-N-((1r,4r)-4-((3-(3-chlorophenyl)-3-hydroxy-2-oxoindolin-1-yl)methyl)cyclohexyl)-2-(difluoromethyl)nicotinamide;
5-chloro-2-(difluoromethyl)-N-((1r,4r)-4-((3-hydroxy-2-oxo-3-(m-tolyl)indolin-1-yl) methyl)cyclohexyl)nicotinamide;
5-chloro-2-(difluoromethyl)-N-((1r,4r)-4-((3-(2,4-difluorophenyl)-3-hydroxy-2-oxoindolin-1-yl)methyl)cyclohexyl)nicotinamide;
5-chloro-2-(difluoromethyl)-N-((1r,4r)-4-((3-(2-fluoro-4-methoxyphenyl)-3-hydroxy-2-oxoindolin-1-yl)methyl)cyclohexyl)nicotinamide;
5-chloro-2-(difluoromethyl)-N-((1r,4r)-4-((3-hydroxy-2-oxo-3-(p-tolyl)indolin-1-yl)methyl)cyclohexyl)nicotinamide;
5-chloro-2-(difluoromethyl)-N-((1r,4r)-4-((3-(2,5-difluorophenyl)-3-hydroxy-2-oxoindolin-1-yl)methyl)cyclohexyl)nicotinamide;
5-chloro-N-((1r,4r)-4-((3-(5-cyano-2-fluorophenyl)-3-hydroxy-2-oxoindolin-1-yl)methyl)cyclohexyl)-2-(difluoromethyl)nicotinamide;
5-chloro-2-(difluoromethyl)-N-((1r,4r)-4-((3-(2-fluoro-3-methylphenyl)-3-hydroxy-2-oxoindolin-1-yl)methyl)cyclohexyl)nicotinamide;
5-chloro-2-(difluoromethyl)-N-((1r,4r)-4-((3-(2-fluoro-3-methoxyphenyl)-3-hydroxy-2-oxoindolin-1-yl)methyl)cyclohexyl)nicotinamide;
5-chloro-N-((1r,4r)-4-((3-(3-chloro-2-fluorophenyl)-3-hydroxy-2-oxoindolin-1-yl)methyl)cyclohexyl)-2-(difluoromethyl)nicotinamide;
5-chloro-2-(difluoromethyl)-N-((1r,4r)-4-((3-(2-fluoro-5-methoxyphenyl)-3-hydroxy-2-oxoindolin-1-yl)methyl)cyclohexyl)nicotinamide;
5-chloro-2-(difluoromethyl)-N-((1r,4r)-4-((6-fluoro-3-(5-fluoropyridin-2-yl)-3-hydroxy-2-oxoindolin-1-yl)methyl)cyclohexyl)nicotinamide;
5-chloro-2-(difluoromethyl)-N-((1r,4r)-4-((7-fluoro-3-(2-fluorophenyl)-3-hydroxy-2-oxoindolin-1-yl)methyl)cyclohexyl)nicotinamide;
5-chloro-2-(difluoromethyl)-N-((1r,4r)-4-((6-fluoro-3-(2-fluorophenyl)-3-hydroxy-2-oxoindolin-1-yl)methyl)cyclohexyl)nicotinamide;
5-chloro-2-(difluoromethyl)-N-((1r,4r)-4-((6-fluoro-3-(3-fluoropyridin-4-yl)-3-hydroxy-2-oxoindolin-1-yl)methyl)cyclohexyl)nicotinamide;
5-chloro-2-(difluoromethyl)-N-((1r,4r)-4-((3-hydroxy-2-oxo-3-(thiophen-3-yl)indolin-1-yl)methyl)cyclohexyl)nicotinamide;
5-chloro-2-(difluoromethyl)-N-((1r,4r)-4-((5-fluoro-3-(2-fluorophenyl)-3-hydroxy-2-oxoindolin-1-yl)methyl)cyclohexyl)nicotinamide;
5-chloro-2-(difluoromethyl)-N-((1r,4r)-4-((3-(2-fluorophenyl)-3-hydroxy-2-oxo-2,3-dihydro-1H-pyrrolo[2,3-b]pyridin-1-yl)methyl)cyclohexyl)nicotinamide;
5-chloro-2-(difluoromethyl)-N-((1r,4r)-4-((3-(3-fluorothiophen-2-yl)-3-hydroxy-2-oxoindolin-1-yl)methyl)cyclohexyl)nicotinamide;
5-chloro-2-(difluoromethyl)-N-((1r,4r)-4-((3-(4-fluorothiophen-2-yl)-3-hydroxy-2-oxoindolin-1-yl)methyl)cyclohexyl)nicotinamide;

5-chloro-2-(difluoromethyl)-N-((1r,4r)-4-((3-hydroxy-3-(5-methoxythiophen-2-yl)-2-oxoindolin-1-yl)methyl)cyclohexyl)nicotinamide;

5-chloro-2-(difluoromethyl)-N-((1r,4r)-4-((3-(2-fluorophenyl)-3-hydroxy-6-methoxy-2-oxoindolin-1-yl)methyl)cyclohexyl)nicotinamide;

5-chloro-N-((1r,4r)-4-((3-(2,3-difluorophenyl)-3-hydroxy-2-oxoindolin-1-yl)methyl)cyclohexyl)-2-(trifluoromethyl)nicotinamide;

5-chloro-2-(difluoromethyl)-N-((1r,4r)-4-((6-fluoro-3-(5-fluoro-2-methoxypyridin-4-yl)-3-hydroxy-2-oxoindolin-1-yl)methyl)cyclohexyl)nicotinamide;

5-chloro-2-(difluoromethyl)-N-((1r,4r)-4-((3-(2,3-difluorophenyl)-6-fluoro-3-hydroxy-2-oxoindolin-1-yl)methyl)cyclohexyl)nicotinamide;

5-chloro-N-((1r,4r)-4-((3-(3-chloro-2-fluorophenyl)-6-fluoro-3-hydroxy-2-oxoindolin-1-yl)methyl)cyclohexyl)-2-(difluoromethyl)nicotinamide;

5-chloro-2-(difluoromethyl)-N-((1r,4r)-4-((3-(2,5-difluorophenyl)-6-fluoro-3-hydroxy-2-oxoindolin-1-yl)methyl)cyclohexyl)nicotinamide;

5-chloro-N-((1r,4r)-4-((3-(5-chloropyridin-2-yl)-6-fluoro-3-hydroxy-2-oxoindolin-1-yl)methyl)cyclohexyl)-2-(difluoromethyl)nicotinamide;

5-chloro-2-(difluoromethyl)-N-((1r,4r)-4-((3-(2,3-difluorophenyl)-5-fluoro-3-hydroxy-2-oxoindolin-1-yl)methyl)cyclohexyl)nicotinamide;

5-chloro-2-(difluoromethyl)-N-((1r,4r)-4-((5-fluoro-3-(5-fluoro-2-methoxypyridin-4-yl)-3-hydroxy-2-oxoindolin-1-yl)methyl)cyclohexyl)nicotinamide;

5-chloro-N-((1r,4r)-4-((3-(5-chloropyridin-2-yl)-5-fluoro-3-hydroxy-2-oxoindolin-1-yl)methyl)cyclohexyl)-2-(difluoromethyl)nicotinamide;

5-chloro-N-((1r,4r)-4-((3-(2-fluoro-5-methoxyphenyl)-3-hydroxy-2-oxoindolin-1-yl)methyl)cyclohexyl)-2-methylnicotinamide;

5-chloro-2-(difluoromethyl)-N-((1r,4r)-4-((3-hydroxy-3-(5-methylthiophen-3-yl)-2-oxoindolin-1-yl)methyl)cyclohexyl)nicotinamide;

5-chloro-N-((1r,4r)-4-((3-hydroxy-2-oxo-3-(2,3,5-trifluorophenyl)indolin-1-yl)methyl) cyclohexyl)-2-methylnicotinamide;

5-chloro-2-(difluoromethyl)-N-((1r,4r)-4-((3-hydroxy-2-oxo-3-(2,3,5-trifluorophenyl)indolin-1-yl)methyl)cyclohexyl)nicotinamide;

5-chloro-2-(difluoromethyl)-N-((1r,4r)-4-((3-hydroxy-2-oxo-3-(2,3,4-trifluorophenyl)indolin-1-yl)methyl)cyclohexyl)nicotinamide;

5-chloro-N-((1r,4r)-4-((3-(2,3-difluoro-4-methoxyphenyl)-3-hydroxy-2-oxoindolin-1-yl)methyl)cyclohexyl)-2-methylnicotinamide;

5-chloro-N-((1r,4r)-4-((3-(5-chloropyridin-2-yl)-4-fluoro-3-hydroxy-2-oxoindolin-1-yl)methyl)cyclohexyl)-2-(difluoromethyl)nicotinamide;

5-chloro-N-((1r,4r)-4-((3-(2,3-difluorophenyl)-6-fluoro-3-hydroxy-2-oxoindolin-1-yl) methyl)cyclohexyl)-2-methylnicotinamide;

5-chloro-2-(difluoromethyl)-N-((1r,4r)-4-((3-(2-fluorophenyl)-3-hydroxy-6-methyl-2-oxoindolin-1-yl)methyl)cyclohexyl)nicotinamide;

5-chloro-2-(difluoromethyl)-N-((1r,4r)-4-((3-(3-fluoropyridin-4-yl)-3-hydroxy-6-methyl-2-oxoindolin-1-yl)methyl)cyclohexyl)nicotinamide;

5-chloro-N-((1r,4r)-4-((3-(2,3-difluoro-4-methoxyphenyl)-3-hydroxy-2-oxoindolin-1-yl)methyl)cyclohexyl)-2-(difluoromethyl)nicotinamide;

5-chloro-2-(difluoromethyl)-N-((1r,4r)-4-((6-fluoro-3-(3-fluoro-2-methoxypyridin-4-yl)-3-hydroxy-2-oxoindolin-1-yl)methyl)cyclohexyl)nicotinamide;

5-chloro-2-(difluoromethyl)-N-((1r,4r)-4-((6-fluoro-3-(2-fluoro-5-methoxyphenyl)-3-hydroxy-2-oxoindolin-1-yl)methyl)cyclohexyl)nicotinamide;

5-chloro-2-(difluoromethyl)-N-((1r,4r)-4-((3-(2,3-difluorophenyl)-3-hydroxy-4-methoxy-2-oxoindolin-1-yl)methyl)cyclohexyl)nicotinamide;

5-chloro-N-((1r,4r)-4-((3-(2,3-difluorophenyl)-5-fluoro-3-hydroxy-2-oxoindolin-1-yl) methyl)cyclohexyl)-2-methylnicotinamide;

5-chloro-N-((1r,4r)-4-((3-(2-fluoro-4-methoxyphenyl)-3-hydroxy-2-oxoindolin-1-yl)methyl)cyclohexyl)-2-(trifluoromethyl)nicotinamide;

2,5-dichloro-N-((1r,4r)-4-((3-(2,3-difluorophenyl)-3-hydroxy-2-oxoindolin-1-yl)methyl)cyclohexyl)nicotinamide;

5-chloro-2-(difluoromethyl)-N-((1r,4r)-4-((5-fluoro-3-(2-fluoro-5-methoxyphenyl)-3-hydroxy-2-oxoindolin-1-yl)methyl)cyclohexyl)nicotinamide;

5-chloro-N-((1r,4r)-4-((6-chloro-3-(2-fluorophenyl)-3-hydroxy-2-oxoindolin-1-yl)methyl)cyclohexyl)-2-(difluoromethyl)nicotinamide;

5-chloro-N-((1r,4r)-4-((3-(2,3-difluorophenyl)-3-hydroxy-2-oxoindolin-1-yl)methyl)cyclohexyl)-2-methylnicotinamide;

5-chloro-N-((1r,4r)-4-((4,6-difluoro-3-(2-fluorophenyl)-3-hydroxy-2-oxoindolin-1-yl) methyl)cyclohexyl)-2-(difluoromethyl)nicotinamide;

5-chloro-2-(difluoromethyl)-N-((1r,4r)-4-((4-fluoro-3-(5-fluoropyridin-2-yl)-3-hydroxy-2-oxoindolin-1-yl)methyl)cyclohexyl)nicotinamide;

5-chloro-2-(difluoromethyl)-N-((1r,4r)-4-((3-(5-fluoropyridin-2-yl)-3-hydroxy-4-methyl-2-oxoindolin-1-yl)methyl)cyclohexyl)nicotinamide;

5-chloro-2-(difluoromethyl)-N-((1r,4r)-4-((3-(2-fluorophenyl)-3-hydroxy-4-methyl-2-oxoindolin-1-yl)methyl)cyclohexyl)nicotinamide;

5-chloro-N-((1r,4r)-4-((3-(2-fluoro-5-methoxyphenyl)-3-hydroxy-2-oxoindolin-1-yl)methyl)cyclohexyl)-2-(trifluoromethyl)nicotinamide;

5-chloro-2-(difluoromethyl)-N-((1r,4r)-4-((4-fluoro-3-(2-fluoro-5-methoxyphenyl)-3-hydroxy-2-oxoindolin-1-yl)methyl)cyclohexyl)nicotinamide;

5-chloro-N-((1r,4r)-4-((3-(3-chloro-2-fluorophenyl)-4-fluoro-3-hydroxy-2-oxoindolin-1-yl)methyl)cyclohexyl)-2-(difluoromethyl)nicotinamide;

5-chloro-2-(difluoromethyl)-N-((1r,4r)-4-((4-fluoro-3-(2-fluorophenyl)-3-hydroxy-2-oxoindolin-1-yl)methyl)cyclohexyl)nicotinamide; and 5-chloro-2-(difluoromethyl)-N-((1r,4r)-4-((3-(2,3-difluorophenyl)-4-fluoro-3-hydroxy-2-oxoindolin-1-yl)methyl)cyclohexyl)nicotinamide;

or a pharmaceutically acceptable salt thereof or a prodrug thereof.

[9] A use of a compound according to any one of [1] to [8] or a pharmaceutically acceptable salt, prodrug, solvate or composition thereof for the manufacture of a medicament for the treatment of a condition or disorder in which CRHR2 is involved.

[10] The use according to [9], wherein said condition or disorder is selected from the group consisting of: gastrointestinal disorders, major depressive disorders, schizophrenic disorders, neurodegenerative diseases, pain, dysfunction of appetite and food intake, sleep disorders, cognitive disorders, tolerance to and dependence on a number of substances, inflammation, fertility problems, sexual dysfunctions and pre-term birth and non-inflammatory urogenital disorders, allergic disorders, mast cell activation disorders, Cushing's syndrome, emesis, gastrointestinal disorders, neurotoxic injury, loss of hair, heart disease, and combinations thereof.

[11] The use according to [10], wherein the heart disease is selected from the group consisting of: acute and chronic heart failure, cardiovascular disease, hyper tension, myocardial infarction, coronary artery disease, and abdominal aortic aneurysm.

[12] A method for the treatment of a condition or disorder in which CRHR2 is involved, in an animal, including a human, which comprises administering to the animal in need of such treatment a therapeutically effective amount of a compound or a prodrug thereof or a pharmaceutically acceptable salt thereof, according to any one of [1] to [8].

[13] The method according to [12], wherein said condition or disorder is selected from the group consisting of: gastrointestinal disorders, major depressive disorders, schizophrenic disorders, neurodegenerative diseases, pain, dysfunction of appetite and food intake, sleep disorders, cognitive disorders, tolerance to and dependence on a number of substances, inflammation, fertility problems, sexual dysfunctions and pre-term birth and non-inflammatory urogenital disorders, allergic disorders, mast cell activation disorders, Cushing's syndrome, emesis, gastrointestinal disorders, neurotoxic injury, loss of hair, heart disease, and combinations thereof.

[14] The method according to [13], wherein the heart disease is selected from the group consisting of: acute and chronic heart failure, cardiovascular disease, hyper tension, myocardial infarction, coronary artery disease, and abdominal aortic aneurysm.

[15] A pharmaceutical composition comprising a compound or a pharmaceutically acceptable salt thereof or a prodrug thereof, according to any one of [1] to [8], and a pharmaceutically acceptable carrier.

[16] The pharmaceutical composition according to [15], further comprising another pharmacologically active agent.

[17] A compound according to any one of [1] to [8] or a prodrug thereof or a pharmaceutically acceptable salt for use in the treatment of a condition or disorder in which CRHR2 is involved.

[18] A process for preparing a pharmaceutical composition, wherein the process comprises mixing a compound according to any one of [1] to [8] or a pharmaceutically acceptable salt thereof or a prodrug thereof and a pharmaceutically acceptable carrier or excipient.

The compounds of formulae (I) and (II) are racemic with one chiral center, and the description of formulae (I) and (II) in this application is one example. The giometric position with respect to the bond on both sides of the cyclohexane ring is trans. That is, when the bond to the portion containing the A ring may be a wedged line or a dashed line, the bond to the portion containing the B ring is a dashed line or a wedged line, respectively. For example, in the case of formula (I), it is as follows.

[Chem. 3]

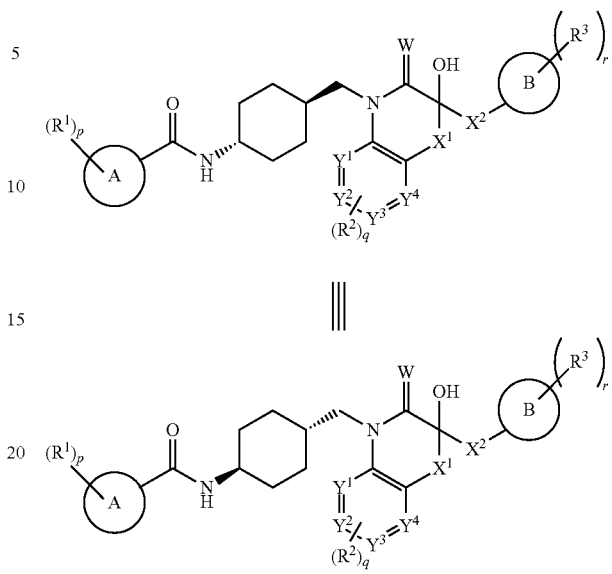

Advantageous Effects of Invention

The compounds showed activities against CRHR2. In particular, the 3-hydroxyoxindole derivatives of the present invention show excellent antagonistic activities against the CRHR2 over the compounds with close chemical structure, leading to better pharmacological profiles, preferable absorption and distribution, preferable solubility, preferable plasma protein binding, and preferable metabolic stability, leading to improvements in the side-effect profile such as reducing inhibitory activity at hERG channel and/or QT prolongation. The 3-hydroxyoxindole derivatives of the present invention are therefore useful in the treatment of a wide range of disorders.

Therefore, according to a further aspect of the invention, we provide a compound of formulae (I) and (II), or a salt thereof, for the treatment or alleviation of treatment of any state with increased endogenous level of CRH and urocortins or in which the HPA (hypothalamic pituitary axis) is dysregulated, or of various diseases induced or facilitated by CRH and urocortins.

Compounds of the invention are in particular useful for the treatment or prevention of gastrointestinal disorders including irritable bowel syndrome with or without diarrhea, inflammatory bowel diseases, post-operative ileus, reflux disease and infectious diarrhea.

Compounds of the invention are also in particular useful for the treatment or prevention of major depressive disorders including bipolar depression, unipolar depression, single or recurrent major depressive episodes with or without psychotic features, catatonic features, melancholic features, atypical features or postpartum onset, the treatment of anxiety and the treatment of panic disorders. Other mood disorders encompassed within the term major depressive disorders include fatigue syndrome and dysthymic disorder with early or late onset and with or without atypical features, neurotic depression, post traumatic stress disorders, post operative stress and social phobia; dementia of the Alzheimer type, with early or late onset, with depressed mood; vascular dementia with depressed mood; mood disorders induced by alcohol, amphetamines, cocaine, hallucinogens, inhalants, opioids, phencyclidine, sedatives, hypnotics, anxiolytics and other substances; schizoaffective disorder of the depressed type; and adjustment disorder with depressed mood. Major depressive disorders may also result from a general medical condition including, but not limited to, myocardial infarction, diabetes, miscarriage or abortion, etc.

Compounds of the invention are also useful in the treatment or prevention of schizophrenic disorders including paranoid schizophrenia, disorganized schizophrenia, catatonic schizophrenia, undifferentiated schizophrenia, residual schizophrenia.

Compounds of the invention are also useful in the treatment or prevention of neurodegenerative diseases such as Alzheimer's disease, Parkinson's disease, Huntington's disease, senile dementia of the Alzheimer's type, and multi-infarct dementia.

Compounds of the invention are useful as analgesics. In particular, they are useful in the treatment of traumatic pain such as postoperative pain; traumatic avulsion pain such as brachial plexus; chronic pain such as arthritic pain such as occurring in osteo-, rheumatoid or psoriatic arthritis; neuropathic pain such as post-herpetic neuralgia, trigeminal neuralgia, segmental or intercostal neuralgia, fibromyalgia, causalgia, peripheral neuropathy, diabetic neuropathy, chemotherapy-induced neuropathy, AIDS related neuropathy, occipital neuralgia, geniculate neuralgia, glossopharyngeal neuralgia, reflex sympathetic dystrophy, phantom limb pain; various forms of headache such as migraine, acute or chronic tension headache, temporomandibular pain, maxillary sinus pain, cluster headache; odontalgia; cancer pain; pain of visceral origin; gastrointestinal pain; nerve entrapment pain; sport's injury pain; dysmenorrhea; menstrual pain; meningitis; arachnoiditis; musculoskeletal pain; low back pain e.g. spinal stenosis; prolapsed disc; sciatica; angina; ankylosing spondylitis; gout; burns; scar pain; itch; and thalamic pain such as post stroke thalamic pain.

Compounds of the invention are also useful for the treatment of dysfunction of appetite and food intake and in circumstances such as anorexia, anorexia nervosa, bulimia, obesity and metabolic syndrome.

Compounds of the invention are also useful in the treatment of sleep disorders including dyssomnia, insomnia, sleep apnea, narcolepsy, and circadian rhythmic disorders.

Compounds of the invention are also useful in the treatment or prevention of cognitive disorders. Cognitive disorders include dementia, amnestic disorders and cognitive disorders not otherwise specified.

Furthermore compounds of the invention are also useful as memory and/or cognition enhancers in healthy humans with no cognitive and/or memory deficit.

Compounds of the invention are also useful in the treatment of tolerance to and dependence on a number of substances. For example, they are useful in the treatment of dependence on nicotine, alcohol, caffeine, phencyclidine (phencyclidine like compounds), or in the treatment of tolerance to and dependence on opiates (e.g. *Cannabis*, heroin, morphine) or benzodiazepines; in the treatment of cocaine, sedative hypnotic, amphetamine or amphetamine-related drugs (e.g. dextroamphetamine, methylamphetamine) addiction or a combination thereof.

Compounds of the invention are also useful as anti-inflammatory agents. In particular, they are useful in the treatment of inflammation in asthma, influenza, chronic bronchitis and rheumatoid arthritis; in the treatment of inflammatory diseases of the gastrointestinal tract such as Crohn's disease, ulcerative colitis, post-operative gastric ileus (POI), inflammatory bowel disease (IBD) and non-steroidal anti-inflammatory drug induced damage; inflammatory diseases of the skin such as herpes and eczema; inflammatory diseases of the bladder such as cystitis and urge incontinence; and eye and dental inflammation.

Compounds of the invention are also useful in the treatment of fertility problems, sexual dysfunctions and pre-term birth and non-inflammatory urogenital disorders such as overactive bladder and related urinary incontinence.

Compounds of the invention are also useful in the treatment of allergic disorders, in particular allergic disorders of the skin such as urticaria, and allergic disorders of the airways such as rhinitis.

Compounds of the invention are also useful in the treatment of mast cell activation disorders such as mastocytosis.

Compounds of the invention are also useful the treatment of Cushing's syndrome induced by drugs such as steroids or cancer such as pituitary adenoma.

Compounds of the invention are also useful in the treatment of emesis, i.e. nausea, retching and vomiting. Emesis includes acute emesis, delayed emesis and anticipatory emesis. The compounds of the invention are useful in the treatment of emesis however induced. For example, emesis may be induced by drugs such as cancer chemotherapeutic agents such as alkylating agents, e.g. cyclophosphamide, carmustine, lomustine and chlorambucil; cytotoxic antibiotics, e.g. dactinomycin, doxorubicin, mitomycin-C and bleomycin; anti-metabolites, e.g. cytarabine, methotrexate and 5-fluorouracil; vinca alkaloids, e.g. etoposide, vinblastine and vincristine; and others such as cisplatin, dacarbazine, procarbazine and hydroxyurea; and combinations thereof; radiation sickness; radiation therapy, e.g. irradiation of the thorax or abdomen, such as in the treatment of cancer; poisons; toxins such as toxins caused by metabolic disorders or by infection, e.g. gastritis, or released during bacterial or viral gastrointestinal infection; pregnancy; vestibular disorders, such as motion sickness, vertigo, dizziness and Meniere's disease; post-operative sickness; gastrointestinal obstruction; reduced gastrointestinal motility; visceral pain, e.g. myocardial infarction or peritonitis; migraine; increased intracranial pressure; decreased intracranial pressure (e.g. altitude sickness); opioid analgesics, such as morphine; and gastro-oesophageal reflux disease, acid indigestion, over-indulgence of food or drink, acid stomach, sour stomach, regurgitation, heartburn, such as episodic heartburn, nocturnal heartburn, and meal-induced heartburn and dyspepsia.

Compounds of the invention are of particular use in the treatment of gastrointestinal disorders such as irritable bowel syndrome; skin disorders such as psoriasis, pruritus and sunburn; vasospastic diseases such as angina, vascular headache and Reynaud's disease; cerebral ischemia such as cerebral vasospasm following subarachnoid haemorrhage; fibrosing and collagen diseases such as scleroderma and eosinophilic fascioliasis; disorders related to immune enhancement or suppression such as systemic lupus erythematosus and rheumatic diseases such as fibrositis; and cough.

Compounds of the invention are useful for the treatment of neurotoxic injury which follows cerebral stroke, thromboembolic stroke, hemorrhagic stroke, cerebral ischemia, cerebral vasospasm, hypoglycemia, hypoxia, anoxia, perinatal asphyxia, and cardiac arrest.

Compounds of the invention are useful for hair growth.

Compounds of the invention are useful for heart disease including acute and chronic heart failure, cardiovascular disease, hyper tension, myocardial infarction, coronary artery disease, and abdominal aortic aneurysm.

The utility of the agents of the invention in the above indicated diseases can be confirmed in a range of standard tests. Examples of such tests may include, but are not limited to, the following:

(1) The anxiolytic activity of the agents of the invention can be confirmed in the mouse elevated plus-maze [see, for example, Rodgers R. J., Behavioural Pharmacology 8:477-496 (1997) where the relevance of the elevated plus-maze is discussed on p. 486; for the method, see Rodgers R. J. et al. Ethology and Psychopharmacology (Eds S J Cooper and CA Hendrie), pp 9-44 (1994), J. Wiley, Chichester]. (2) The analgesic activity of the agents of the invention can be confirmed in rat visceral hyperalgesia models following colorectal distension [see for example Schwetz I, Am J Physiology 286: G683-G691 (2004); for the method, see Ness T. J., Brain Research 450:153-169 (1988)]. (3) The anti-diarrheal activity of the agents of the invention can be confirmed in rat defecation models during stress or CRF challenge [see for example, Maillot C., Gastroenterology 119:1569-1579 (2002)]. (4) The hair growth activity of the agents of the invention can be confirmed in the method described in WO 2007/149938. (5) The anti-heart disease activity of the agents of the invention can be confirmed in the method described in this specification and the literature, e.g. Drug Discovery Today Volume 20, Number 7, 906-914 (2015). (6) Other activities of the agents of the invention can be confirmed in the method described in literatures known by a person skilled in the art including well-known art and commonly used art.

Novartis discloses corticotropin releasing factor (CRF) receptor antagonists in WO2011/092293 (PL 1) and WO2011/095450 (PL 2). RaQualia discloses fused cyclic urea derivatives as CRHR1 and/or CRHR2 antagonists in WO2019/198692 (PL 3).

The present invention is characterized by 3-hydroxyoxindole ring in the above formulae (I) and (II). Namely the core structure of the present invention is quite different from those of the invention in WO2011/092293 (PL 1), WO2011/095450 (PL 2) and WO2019/198692 (PL 3).

The present invention is characterized by 3-hydroxyoxindole ring has showed favorable aqueous solubility.

DESCRIPTION OF EMBODIMENTS

As appreciated by those of skill in the art, "halogen" as used herein is intended to include fluoro, chloro, bromo, and iodo. Similarly, 1-6, as in $C_{1-6}$ is defined to identify the number as having 1, 2, 3, 4, 5, or 6. According to the definition, for example, $C_{1-6}$, as in $C_{1-6}$ alkyl is defined to identify the alkyl group as having 1, 2, 3, 4, 5, or 6 carbons. Similarly, $C_{2-6}$ alkenyl is defined to identify the alkenyl group as having 2, 3, 4, 5, or 6 carbons. A group which is designated as being independently substituted with substituents may be independently substituted with multiple numbers of such substituents.

The term "alkyl", as used herein, means a linear saturated monovalent hydrocarbon radical of one to six carbon atoms or a branched saturated monovalent hydrocarbon radical of three to six carbon atoms, e.g., methyl, ethyl, propyl, 2-propyl, butyl (including all isomeric forms), pentyl (including all isomeric forms), and the like.

The term "lower alkyl", as used herein, means $C_{1-6}$ alkyl, such as, but not limited to, methyl, ethyl, n-propyl, i-propyl, n-butyl, i-butyl, sec-butyl, t-butyl, and the like.

The term "alkoxy", as used herein, means an —O-alkyl such as, but not limited to, methoxy, ethoxy, propoxy, 2-propoxy, butoxy (including all isomeric forms), and the like.

The term "cycloalkyl", as used herein, means a mono- or bi-cyclic ring such as, but not limited to, cyclopropyl, cyclobutyl, cyclopentyl, cyclohexyl, cycloheptyl, norbornyl, adamantyl groups, and the like. In this specification, preferable cycloalkyl is $C_{3-7}$ mono cycloalkyl, more preferable cycloalkyl is $C_{3-6}$ mono cycloalkyl, further more preferable cycloalkyl is $C_{3-5}$ mono cycloalkyl.

The term "aryl", as used herein, means unsaturated or partially saturated mono- or bi-cyclic 5-15 membered ring which consists of carbon atoms. Examples of such aryl include, but are not limited to, phenyl, naphthyl, indanyl, indenyl, 1,2,3,4-tetrahydronaphthyl, 1,2-dihydronaphthyl, 2,3-dihydro-1H-indenyl, cyclohexenyl, cyclopentenyl, (1S,4S)-bicyclo[2.2.2]oct-2-enyl, and (1R,4S)-bicyclo[2.2.1]hept-2-enyl and the like. In this specification, preferable aryl is 6-10 membered unsaturated aryl, more preferable aryl is phenyl or naphthyl.

The term "heteroaryl" as used herein, means unsaturated or partially saturated mono- or bi-cyclic 5-15 membered ring with 1-4 heteroatoms independently selected from O, N, S, and carbonyl, preferably unsaturated or partially saturated mono- or bi-cyclic 5-10 membered ring with 1-4 heteroatoms independently selected from O, N, S, and carbonyl, more preferably unsaturated 5-6 membered ring with 1-4 heteroatoms independently selected from O, N, and S, or unsaturated or partially saturated 9-10 membered ring with 1-4 heteroatoms independently selected from O, N, S, and carbonyl.

Examples of such heteroaryl include, but are not limited to, thiophenyl, thiazolyl, isoxazolyl, pyrazolyl, pyrazyl, tetrazolyl, furanyl, pyrrolyl, imidazolyl, oxazolyl, isothiazolyl, triazolyl, thiadiazolyl, pyridyl, pyrimidyl, pyridazinyl, pyrazinyl, pyranyl, triazinyl, 3,6-dihydro-2H-pyran, 1,2,3,6-tetrahydropyridyl, benzofuranyl, benzothiophenyl, benzotriazolyl, benzoxazolyl, indolyl, indazolyl, benzoimidazolyl, pyrrolopyridyl, 2,3-dihydro-pyrrolo[2,3-b]pyridyl, 2,3-dihydro-1H-pyrrolo[2,3-c]pyridyl, pyrrolopyrimidinyl, pyrazolopyridyl, pyrazolopyrimidinyl, imidazopyridinyl, furopyridyl, benzoisoxazolyl, imidazopyrazinyl, imidazopyridazinyl, imidazopyrimidinyl, quinolyl, isoquinolyl, quinoxalyl, quinazolinyl, phthalazinyl, quinoxalinyl, naphthyridinyl, pyridopyrimidinyl, 2,3-dihydro-[1,4]dioxino[2,3-b]pyridyl, 2,3-dihydro-[1,4]dioxino[2,3-c]pyridyl, 1H-indolyl, 1H-pyrrolo[2,3-b]pyridyl, 1H-pyrrolo[2,3-c]pyridyl, 1H-pyrrolo[3,2-c]pyridyl, 1H-pyrrolo[3,2-b]pyridyl, 7H-pyrrolo[2,3-d]pyrimidyl, 7H-pyrrolo[2,3-c]pyridazinyl, 1H-indazolyl, 2H-indazolyl, 1H-pyrazolo[3,4-b]pyridyl, 1H-pyrazolo[3,4-c]pyridyl, 1H-pyrazolo[4,3-c]pyridyl, 1H-pyrazolo[4,3-b]pyridyl, 1H-pyrazolo[3,4-d]pyrimidyl, 1H-benzo[d]imidazolyl, 3H-imidazo[4,5-b]pyridyl, 1H-imidazo[4,5-b]pyridyl, 9H-purinyl, 1H-imidazo[4,5-d]pyridazinyl, 1H-imidazo[4,5-b]pyrazinyl, imidazo[1,2-a]pyridyl, imidazo[1,5-a]pyridyl, imidazo[1,2-a]pyrazinyl, imidazo[1,2-b]pyridazinyl, pyrazolo[1,5-a]pyridyl, pyrazolo[1,5-a]pyrimidyl, furo[3,2-c]pyridyl, benzo[d]isoxazolyl, 2,3-dihydro-1H-indenyl, indolinyl, isoindolinyl, indolin-2-one-yl, isoindolin-1-one-yl, 1H-benzo[d]imidazol-2(3H)-one-yl, benzo[d]oxazol-2(3H)-one-yl, 1H-pyrrolo[2,3-b]pyridin-2(3H)-one-yl, 1H-imidazo[4,5-b]pyridin-2(3H)-one-yl, quinolyl, isoquinolyl, quinazolinyl, phthalazinyl, 2,6-naphthyridinyl, 2,7-naphthyridinyl, quinoxalinyl, pyrido[3,4-d]pyrimidyl, pyrido[2,3-d]pyrimidyl, 1,2,3,4-tetrahydroquinolyl, 1,2,3,4- tetrahydroisoquinolyl, 3,4-dihydro-2H-benzo[b][1,4]oxazinyl, 2,3-dihydro-[1,4]dioxino[2,3-b]pyridyl, 3,4-dihydroquinolin-2(1H)-one-yl, 2H-benzo[b][1,4]oxazin-3(4H)-one-yl, quinolin-2(1H)-one-yl, or 4,5-dihydro-1H-benzo[b]azepin-2(3H)-one-yl, and N-oxides thereof and S-oxides thereof and the like.

In this specification, preferable heteroaryl is 5 to 6-membered heteroaromatic ring with 1-4 heteroatoms independently selected from O, N, and S, or 9 to 10-membered heteroaromatic ring with 1-4 heteroatoms independently selected from O, N, and S, more preferable heteroaryl is 5-6 membered N-containing heteroaromatic ring, further more preferable heteroaryl is benzoimidazolyl, dihydroisoquinolyl, indolyl, indazolyl, pyrazolyl, pyrazinyl, pyridazinyl, pyridyl, quinolyl, isoquinolyl, and thiazolyl.

The term "heterocyclyl" as used herein includes both unsaturated and saturated heterocyclic moieties, wherein the unsaturated heterocyclic moieties (i.e. "heteroaryl") include, but not limited to, benzofuranyl, benzofurazanyl, benzimidazolonyl, benzoimidazolyl, benzoisothiazolyl, benzoisoxazolyl, benzothiadiazolyl, benzothiazolyl, benzoxadiazolyl, benzoxazolonyl, benzoxazolyl, benzothiophenyl, benzotriazolyl, carbazolyl, carbolinyl, chromanyl, cinnolinyl, 2,3-dioxoindolyl, furanyl, furazanyl, furopyridyl, furopyrrolyl, imidazolyl, imidazopyrazinyl, imidazopyridinyl, imidazopyrimidinyl, imidazothiazolyl, indazolyl, indolazinyl, indolinyl, indolyl, isobenzofuranyl, isochromanyl, isoindolyl, isoquinolyl, isoxazolopyridyl, isoxazolinyl, isoxazolyl, isothiazolyl, naphthyridinyl, oxazolinyl, oxadiazolyl, oxazolyl, oxetanyl, 2-oxoindolyl, oxoisoindolyl, phthalazyl, pyrazolyl, pyrazolopyridyl, pyrazolopyrimidinyl, pyrazinyl, pyridyl, pyrimidyl, pyridazinyl, pyridopyrimidinyl, pyrrolopyridyl, pyrrolyl, quinazolinyl, quinolyl, quinoxalinyl, tetrazolopyridyl, tetrazolyl, thiadiazolyl, thiazolyl, thiophenyl, thienopyrazinyl, thienopyrazolyl, thienopyridyl, thienopyrrolyl, triazolopyrimidinyl, triazolyl, 4-oxo-1,4-dihydroquinolyl, 2-oxo-1,2-dihydropyridyl, 4-oxo-1,4-dihydropyrimidyl, 2-oxo-1,2-dihydroquinolyl, 4-oxo-4H-pyrido[1,2-a]pyrimidyl, 4-oxo-1,4-dihydro-1,8-naphthyridyl, 3,6-dihydro-2H-pyranyl, 1,2,3,6-tetrahydropyridinyl, tetrahydro-2H-thiopyran 1,1-dioxide, and N-oxides thereof, and wherein the saturated heterocyclic moieties include, but not limited to, azetidinyl, 1,4-dioxanyl, hexahydroazepinyl, piperazinyl, piperidinyl, pyridin-2-onyl, pyrrolidinyl, morpholinyl, tetrahydrofuranyl, tetrahydropyranyl, thiomorpholinyl, triazolopyrimidyl, tetrahydrothienyl, pyrrolidinonyl, 3,4-dihydro-2H-pyrido[3,2-b][1,4]oxazinyl, 2-oxo-2,5,6,7-tetrahydro-1H-cyclopentapyridyl, 4,5,6,7-tetrahydroindazolyl, 5,6,7,8-tetrahydro-1,6-naphthyridyl, 1,4-oxazepanyl, and N-oxides thereof and S-oxides thereof. In this specification, preferable heterocyclyl is 3 to 8-membered heterocyclyl with 1-4 heteroatoms independently selected from O, N, S, and carbonyl, more preferable heterocyclyl is 4-6 membered saturated mono heterocyclyl with 1-4 heteroatoms selected from O, N, S, and carbonyl, further more preferable heterocyclyl is 5-6 membered saturated mono heterocyclyl with 1-3 heteroatoms selected from O, N, S, and carbonyl.

The term "protecting group", as used herein, means a hydroxy or amino protecting group which is selected from typical hydroxy or amino protecting groups described in Protective Groups in Organic Synthesis edited by T. W. Greene et al. (John Wiley & Sons, 2007).

The term "treating" or "treatment", as used herein, includes prohibiting, restraining, slowing, stopping, or reversing the progression or severity of an existing symptom or disorder. As used herein, the term "preventing" or "to prevent" includes prohibiting, restraining, or inhibiting the incidence or occurrence of a symptom or disorder.

As used herein, the article "a" or "an" refers to both the singular and plural form of the object to which it refers unless indicated otherwise.

Included within the scope of the "compounds of the invention" are all salts, solvates, hydrates, complexes, polymorphs, prodrugs, radiolabeled derivatives, stereoisomers and optical isomers of the compounds of formulae (I) and (II).

Compounds of formulae (I) and (II) can form acid addition salts thereof. It will be appreciated that for use in medicine the salts of the compounds of formulae (I) and (II) should be pharmaceutically acceptable. Suitable pharmaceutically acceptable salts will be apparent to those skilled in the art and include those described in J. Pharm. Sci, 1977, 66, 1-19, such as acid addition salts formed with inorganic acids e.g., but not limited to, hydrochloric, hydrobromic, sulfuric, nitric or phosphoric acid; and organic acids e.g., but not limited to, succinic, maleic, formic, acetic, trifluoroacetic, propionic, fumaric, citric, tartaric, benzoic, p-toluenesulfonic, methanesulfonic or naphthalenesulfonic acid. Certain of the compounds of formulae (I) and (II) may form acid addition salts with one or more equivalents of the acid. The present invention includes within its scope all possible stoichiometric and non-stoichiometric forms. In addition, certain compounds containing an acidic function such as a carboxy can be isolated in the form of their inorganic salt in which the counter ion can be selected from sodium, potassium, lithium, calcium, magnesium and the like, as well as from organic bases such as choline, arginine, benzathine, diethylamine, glycine, lysine, meglumine, olamine, 2-amino-2-methylpropan-1-ol, benethamine, tert-butylamine, epolamine, ethylenediamine, hydrabamine, morpholine, piperazine, procaine, triethanolamine, diethanolamine, monoethanolamine, triisopropanolamine, and tromethamine.

Also within the scope of the invention are so-called "prodrugs" of the compounds of formulae (I) and (II). Thus certain derivatives of compounds of formulae (I) and (II) which may have little or no pharmacological activity themselves can, when administered into or onto the body, be converted into compounds of formulae (I) and (II) having the desired activity, for example, by hydrolytic cleavage. Such derivatives are referred to as "prodrugs". Further information on the use of prodrugs may be found in Pro-drugs as Novel Delivery Systems, Vol. 14, ACS Symposium Series (T Higuchi and W Stella) and Bioreversible Carriers in Drug Design, Pergamon Press, 1987 (ed. E B Roche, American Pharmaceutical Association).

The term "animal," as used herein, includes a mammalian subject or a non-mammalian subject. Examples of suitable mammalian subject may include, without limit, human, rodents, companion animals, livestock, and primates. Suitable rodents may include, but are not limited to, mice, rats, hamsters, gerbils, and guinea pigs. Suitable companion animals may include, but are not limited to, cats, dogs, rabbits, and ferrets. Suitable livestock may include, but are not limited to, horses, goats, sheep, swine, cattle, llamas, and alpacas. Suitable primates may include, but are not limited to, chimpanzees, lemurs, macaques, marmosets, spider monkeys, squirrel monkeys, and vervet monkeys. Examples of suitable non-mammalian subject may include, without limit, birds, reptiles, amphibians, and fish. Non-limiting examples of birds include chickens, turkeys, ducks, and geese. The preferred mammalian subject is a human.

The term "CRHR2 agonist", as used herein, includes but are not limited to, urocortin 2, urocortin 1, urocortin 3, sauvagine, CRF, and CRF peptide family containing CRF analogs.

Prodrugs in accordance with the invention can, for example, be produced by replacing appropriate functionalities present in the compounds of formulae (I) and (II) with certain moieties known to those skilled in the art as 'pro-moieties' as described, for example, in Design of Prodrugs by H Bundgaard (Elsevier, 1985). Some examples of prodrugs in accordance with the invention include:

(i) where the compound of formulae (I) and (II) contains an alcohol functionality (—OH), compounds wherein the hydroxy group is replaced with a moiety convertible in vivo into the hydroxy group. Said moiety convertible in vivo into the hydroxy group means a moiety transformable in vivo into a hydroxy group by e.g. hydrolysis and/or by an enzyme, e.g. an esterase. Examples of said moiety include, but are not limited to, ester and ether groups which may be hydrolyzed easily in vivo. Preferred are the moieties replaced the hydrogen of hydroxy group with acyloxyalkyl, 1-(alkoxycarbonyloxy)alkyl, phthalidyl and acyloxyalkyloxycarbonyl such as pivaloyloxymethyloxycarbonyl; and (ii) where the compound of the formulae (I) and (II) contains an amino group, a 3-hydroxyoxindole derivative prepared by reacting with a suitable acid halide or a suitable acid anhydride is exemplified as a prodrug. A particularly preferred 3-hydroxyoxindole derivative as a prodrug is —NHCO(CH$_2$)$_2$OCH$_3$, —NHCOCH (NH$_2$)CH$_3$ or the like.

Further examples of replacement groups in accordance with the foregoing examples and examples of other prodrug types may be found in the aforementioned references.

Salts and solvates having non-pharmaceutically acceptable counter-ions or associated solvents are within the scope of the present invention, for example, for use as intermediates in the preparation of other compounds of formulae (I) and (II) and their pharmaceutically acceptable salts.

Compounds of formulae (I) and (II) may have crystalline forms including polymorph forms, which are within the scope of the present invention.

Additionally, compounds of formulae (I) and (II) may be administered as prodrugs. As used herein, a "prodrug" of a compound of formulae (I) and (II) is a functional derivative of the compound which, upon administration to a patient, eventually liberates the compound of formulae (I) and (II) in vivo. Administration of a compound of formulae (I) and (II) as a prodrug may enable the skilled artisan to do one or more of the following: (a) modify the onset of action of the compound in vivo; (b) modify the duration of action of the compound in vivo; (c) modify the transportation or distribution of the compound in vivo; (d) modify the solubility of the compound in vivo; and (e) overcome a side effect or other difficulty encountered with the compound. Typical functional derivatives used to prepare prodrugs include modifications of the compound that are chemically or enzymatically cleaved in vivo. Such modifications, which include the preparation of phosphates, amides, esters, thioesters, carbonates, and carbamates, are well known to those skilled in the art.

In certain of the compounds of formulae (I) and (II), there may be one or more chiral carbon atoms. In such cases, compounds of formulae (I) and (II) exist as racemates or stereoisomers. The invention includes racemates and all optical isomers such as stereoisomeric forms of the compounds of formulae (I) and (II) including enantiomers, diastereoisomers and mixtures thereof. The different stereoisomeric forms may be separated or resolved one from the other by conventional methods or any given isomer may be obtained by conventional stereoselective or asymmetric syntheses.

Certain of the compounds herein can exist in various tautomeric forms and it is to be understood that the invention encompasses all such tautomeric forms.

The invention also includes isotopically-labeled compounds, which are identical to those described herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine, iodine, and chlorine, such as $^2$H, $^3$H, $^{11}$C, $^{13}$C, $^{14}$C, $^{18}$F, $^{123}$I and $^{125}$I. Compounds of the invention that contain the aforementioned isotopes and/or other isotopes of other atoms are within the scope of the present invention. Isotopically-labeled compounds of the present invention, for example those into which radioactive isotopes such as $^3$H, $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. $^{11}$C and $^{18}$F isotopes are particularly useful in PET (positron emission tomography), and $^{123}$I isotopes are particularly useful in SPECT (single photon emission computerized tomography), all useful in brain imaging. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of the invention can generally be prepared by carrying out the procedures disclosed in the Schemes and/or in the Examples below, then substituting a readily available isotopically labeled reagent for a non-isotopically labeled reagent.

With respect to other compounds disclosed in the art, certain compounds exhibit unexpected properties, such as with respect to duration of action and/or metabolism, such as preferable metabolic stability, preferable oral bioavailability or absorption, and/or decreased drug-drug interactions.

A skilled physician will be able to determine the appropriate situation in which subjects are susceptible to or at risk of, for example, stroke as well as suffering from stroke for administration by methods of the present invention.

CRHR2 have been implicated in a wide range of biological functions. This has suggested a potential role for these receptors in a variety of disease processes in humans or other species. The compounds of the present invention have utility in treating, preventing, ameliorating, controlling or reducing the risk of a variety of disorders associated with CRHR2, including one or more of the following conditions or diseases: gastrointestinal disorders, major depressive disorders, schizophrenic disorders, neurodegenerative diseases, pain, dysfunction of appetite and food intake, sleep disorders, cognitive disorders, tolerance to and dependence on a number of substances, inflammation, fertility problems, sexual dysfunctions and pre-term birth and non-inflammatory urogenital disorders, allergic disorders, mast cell activation disorders, Cushing's syndrome, emesis, gastrointestinal disorders, neurotoxic injury, loss of hair, heart failure, and the like.

The dosage of active ingredient in the compositions of this invention may be varied, however, it is necessary that the amount of the active ingredient be such that a suitable dosage form is obtained. The active ingredient may be administered to patients (animals and human) in need of such treatment in dosages that will provide optimal pharmaceutical efficacy.

The selected dosage depends upon the desired therapeutic effect, on the route of administration, and on the duration of the treatment. The dose will vary from patient to patient depending upon the nature and severity of disease, the patient's weight, special diets then being followed by a patient, concurrent medication, and other factors which those skilled in the art will recognize.

For administration to human patients, the total daily dose of the compounds of the invention is typically in the range of 0.1 mg to 1000 mg depending, of course, on the mode of administration. For example, oral administration may require a total daily dose of from 1 mg to 1000 mg, while an intravenous dose may only require from 0.1 mg to 100 mg. The total daily dose may be administered in single or divided doses and may at the physician's discretion, fall outside of the typical range given herein.

These dosages are based on an average human subject having a weight of about 60 kg to 70 kg. The physician will readily be able to determine doses for subjects whose weight falls outside this range, such as infants and the elderly.

In one embodiment, the dosage range will be about 0.5 mg to 500 mg per patient per day; in another embodiment about 0.5 mg to 200 mg per patient per day; in another embodiment about 1 mg to 100 mg per patient per day; and in another embodiment about 5 mg to 50 mg per patient per day; in yet another embodiment about 1 mg to 30 mg per patient per day. Pharmaceutical compositions of the present invention may be provided in a solid dosage formulation such as comprising about 0.5 mg to 500 mg active ingredient, or comprising about 1 mg to 250 mg active ingredient. The pharmaceutical composition may be provided in a solid dosage formulation comprising about 1 mg, 5 mg, 10 mg, 25 mg, 50 mg, 100 mg, 200 mg or 250 mg active ingredient. For oral administration, the compositions may be provided in the form of tablets containing 1.0 to 1000 milligrams of the active ingredient, such as 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, such as once or twice per day.

Compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefore, contemporaneously or sequentially with a compound of the present invention. When a compound of the present invention is used contemporaneously with one or more other drugs, a pharmaceutical composition in unit dosage form containing such other drugs and the compound of the present invention is envisioned. However, the combination therapy may also include therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly.

Accordingly, the pharmaceutical compositions of the present invention include those that contain one or more other active ingredients, in addition to a compound of the present invention. The above combinations include combinations of a compound of the present invention not only with one other active compound, but also with two or more other active compounds.

Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is envisioned. Accordingly, the pharmaceutical compositions of the present invention include those that also contain one or more other active ingredients, in addition to a compound of the present invention.

The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, including about 200:1 to about 1:200. Combinations of a compound of the present invention and other active ingredients will generally also be within the aforementioned range, but in each case, an effective dose of each active ingredient should be used. In such combinations the compound of the present invention and other active agents may be administered separately or in conjunction. In addition, the administration of one element may be prior to, concurrent to, or subsequent to the administration of other agent(s).

A CRHR2 antagonist may be usefully combined with another pharmacologically active compound, or with two or more other pharmacologically active compounds, particularly in the treatment of inflammatory, pain and urological diseases or disorders. For example, a CRHR2 antagonist, particularly a compound of formulae (I) and (II), or a prodrug thereof or a pharmaceutically acceptable salt or solvate thereof, as defined above, may be administered simultaneously, sequentially or separately in combination with one or more agents selected from:

an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine, or pentazocine;

a nonsteroidal antiinflammatory drug (NSAID), e.g. aspirin, diclofenac, diflunisal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin, or zomepirac;

a barbiturate sedative, e.g. amobarbital, aprobarbital, butabarbital, butalbital, mephobarbital, metharbital, methohexital, pentobarbital, phenobarbital, secobarbital, talbutal, thiamylal, or thiopental;

a benzodiazepine having a sedative action, e.g. chlordiazepoxide, clorazepate, diazepam, flurazepam, lorazepam, oxazepam, temazepam, or triazolam;

an H1 antagonist having a sedative action, e.g. diphenhydramine, pyrilamine, promethazine, chlorpheniramine, or chlorcyclizine;

a sedative such as glutethimide, meprobamate, methaqualone, or dichloralphenazone;

a skeletal muscle relaxant, e.g. baclofen, carisoprodol, chlorzoxazone, cyclobenzaprine, methocarbamol, or orphenadrine;

an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinone, cis-4-(phosphonomethyl)-2-piperidinecarboxylic acid, budipine, EN-3231 (MorphiDex (registered trademark), a combination formulation of morphine and dextromethorphan), topiramate, neramexane or perzinfotel including an NR2B antagonist, e.g. ifenprodil, traxoprodil, or (−)-(R)-6-{2-[4-(3-fluorophenyl)-4-hydroxy-1-piperidinyl]-1-hydroxyethyl-3,4-dihydro-2 (1H)-quinolinone;

an alpha-adrenergic, e.g. doxazosin, tamsulosin, clonidine, guanfacine, dexmedetomidine, modafinil, or 4-amino-6,7-dimethoxy-2-(5-methane-sulfonamido-1,2,3,4-tetrahydroisoquinol-2-yl)-5-(2-pyridyl)quinazoline;

a tricyclic antidepressant, e.g. desipramine, imipramine, amitriptyline, or nortriptyline;

an anticonvulsant, e.g. carbamazepine, lamotrigine, topiramate, or valproate;

a tachykinin (NK) antagonist, particularly an NK-3, NK-2 or NK-1 antagonist, e.g. (alphaR,9R)-7-[3,5-bis(trifluoromethyl)benzyl]-8,9,10,11-tetrahydro-9-methyl-5-(4-methylphenyl)-7H-[1,4]diazocino[2,1-g][1,7]-naphthyridine-6, 13-dione (TAK-637), 5-[[(2R,3S)-2-[(1R)-1-[3,5-bis(trifluoromethyl)phenyl]ethoxy-3-(4-fluorophenyl)-4-morpholinyl]-methyl]-1,2-dihydro-3H-1,2,4-triazol-3-one (MK-869), aprepitant, lanepitant, dapitant, or 3-[[2-methoxy-5-(trifluoromethoxy)phenyl]-methylamino]-2-phenylpiperidine (2S,3S);

a muscarinic antagonist, e.g. oxybutynin, tolterodine, propiverine, trospium chloride, darifenacin, solifenacin, temiverine, or ipratropium;

a COX-2 selective inhibitor, e.g. celecoxib, rofecoxib, parecoxib, valdecoxib, deracoxib, etoricoxib, or lumiracoxib;

a coal-tar analgesic, e.g. paracetamol;

a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion (registered trademark), or sarizotan;

a vanilloid receptor agonist (e.g. resiniferatoxin) or antagonist (e.g. capsazepine);

a transient receptor potential cation channel subtype (V1, V2, V3, V4, M8, M2, A1) agonist or antagonist;

a beta-adrenergic such as propranolol;

a local anaesthetic such as mexiletine;

a corticosteroid such as dexamethasone;

a 5-HT receptor agonist or antagonist, particularly a 5-HT1B/1D agonist such as eletriptan, sumatriptan, naratriptan, zolmitriptan, or rizatriptan;

a 5-HT2A receptor antagonist such as R(+)-alpha-(2,3-dimethoxy-phenyl)-1-[2-(4-fluorophenylethyl)]-4-piperidinemethanol (MDL-100907);

a cholinergic (nicotinic) analgesic, such as ispronicline (TC-1734), (E)-N-methyl-4-(3-pyridinyl)-3-buten-1-amine (RJR-2403), (R)-5-(2-azetidinylmethoxy)-2-chloropyridine (ABT-594), or nicotine;

Tramadol (registered trademark);

a PDEV inhibitor, such as

5-[2-ethoxy-5-(4-methyl-1-piperazinylsulphonyl)phenyl]-1-methyl-3-n-propyl-1,6-dihydro-7H-pyrazolo[4,3-d]pyrimidin-7-one (sildenafil), (6R,12aR)-2,3,6,7,12,12a-hexahydro-2-methyl-6-(3,4-methylenedioxyphenyl)pyrazino [2',1':6,1]pyrido[3,4-b]indole-1,4-dione (IC-351 or tadalafil), 2-[2-ethoxy-5-(4-ethyl-piperazin-1-yl-sulphonyl)phenyl]-5-methyl-7-propyl-3H-imidazo[5,1-f][1,2,4]triazin-4-one (vardenafil), 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one, 5-(5-acetyl-2-propoxy-3-pyridinyl)-3-ethyl-2-(1-isopropyl-3-azetidinyl)-2,6-dihydro-7H-pyrazolo[4,3-d]pyrimidin-7-one, 5-[2-ethoxy-5-(4-ethylpiperazin-1-ylsulphonyl)pyridin-3-yl]-3-ethyl-2-[2-methoxyethyl]-2,6-dihydro-7H-pyrazolo [4,3-d]pyrimidin-7-one, 4-[(3-chloro-4-methoxybenzyl)amino]-2-[(2S)-2-(hydroxymethyl)pyrrolidin-1-yl]-N-(pyrimidin-2-ylmethyl) pyrimidine-5-carboxamide, or 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide;

an alpha-2-delta ligand such as gabapentin, pregabalin, 3-methylgabapentin, (3-(aminomethyl)bicyclo[3.2.0] hept-3-yl)acetic acid, (3S,5R)-3-(aminomethyl)-5-methylheptanoic acid, (3S,5R)-3-amino-5-methylheptanoic acid, (3S,5R)-3-amino-5-methyloctanoic acid, (2S,4S)-4-(3-chlorophenoxy)proline, (2S,4S)-4-(3-fluorobenzyl)proline, [(1R,5R,6S)-6-(aminomethyl)bicyclo[3.2.0]hept-6-yl]acetic acid, 3-((1-(aminomethyl) cyclohexyl)methyl)-4H-[1,2,4]oxadiazol-5-one, C-[1-((1H-tetrazol-5-yl)methyl)cycloheptyl]methylamine, (3S,4S)-(1-(aminomethyl)-3,4-dimethylcyclopentyl) acetic acid, (3S,5R)-3-(aminomethyl)-5-methyloctanoic acid, (3S,5R)-3-amino-5-methylnonanoic acid, (3S,5R)-3-amino-5-methyloctanoic acid, (3R,4R,5R)-3-amino-4,5-dimethylheptanoic acid, or (3R,4R,5R)-3-amino-4,5-dimethyloctanoic acid;

a cannabinoid;

a metabotropic glutamate subtype 1 receptor (mGluR1) antagonist;

a serotonin reuptake inhibitor such as sertraline, sertraline metabolite desmethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine, or trazodone;

a noradrenaline (norepinephrine) reuptake inhibitor, such as maprotiline, lofepramine, mirtazapine, oxaprotiline, fezolamine, tomoxetine, mianserin, bupropion, bupropion metabolite hydroxybupropion, nomifensine, or viloxazine (Vivalan (registered trademark)), especially a selective noradrenaline reuptake inhibitor such as reboxetine, in particular (S,S)-reboxetine;

a dual serotonin-noradrenaline reuptake inhibitor, such as venlafaxine, venlafaxine metabolite O-desmethylvenlafaxine, clomipramine, clomipramine metabolite desmethylclomipramine, duloxetine, milnacipran, or imipramine;

an inducible nitric oxide synthase (iNOS) inhibitor such as S-[2-1[(1-iminoethyl)amino]ethyl]-L-homocysteine, S-[2-1[(1-iminoethyl)-amino]ethyl]-4,4-dioxo-L-cysteine, S-[2-1[(1-iminoethyl)amino]ethyl]-2-methyl-L-cysteine, (2S,5Z)-2-amino-2-methyl-7-[(1-iminoethyl)amino]-5-heptenoic acid, 2-[[(1R,3S)-3-amino-4-hydroxy-1-(5-thiazolyl)-butyl]thio]-5-chloro-3-pyridinecarbonitrile; 2-[[(1R,3S)-3-amino-4-hydroxy-1-(5-thiazolyl)butyl]thio]-4-chlorobenzonitrile, (2S, 4R)-2-amino-4-[[2-chloro-5-(trifluoromethyl)phenyl] thio]-5-thiazolebutanol, 2-[[(1R,3S)-3-amino-4-hydroxy-1-(5-thiazolyl)butyl]thio]-6-(trifluoromethyl)-3-pyridinecarbonitrile, 2-[[(1R,3S)-3-amino-4-hydroxy-1-(5-thiazolyl)butyl]thio]-5-chlorobenzonitrile, N-[4-[2-(3-chlorobenzylamino)ethyl]phenyl]thiophene-2-carboxamidine, or guanidinoethyldisulfide;

an acetylcholinesterase inhibitor such as donepezil;

a prostaglandin E2 subtype 4 (EP4) antagonist such as N-[({2-[4-(2-ethyl-4,6-dimethyl-1H-imidazo[4,5-c] pyridin-1-yl)phenyl]ethyl}amino)-carbonyl]-4-methylbenzenesulfonamide, or 4-[(1S)-1-({[5-chloro-2-(3-fluorophenoxy)pyridin-3-yl]carbonyl}amino)ethyl] benzoic acid;

a leukotriene B4 antagonist; such as 1-(3-biphenyl-4-ylmethyl-4-hydroxy-chroman-7-yl)-cyclopentanecarboxylic acid (CP-105696), 5-[2-(2-Carboxyethyl)-3-[6-(4-methoxyphenyl)-5E-hexenyl]oxyphenoxy]-valeric acid (ONO-4057), or DPC-11870;

a 5-lipoxygenase inhibitor, such as zileuton, 6-[(3-fluoro-5-[4-methoxy-3,4,5,6-tetrahydro-2H-pyran-4-yl])phenoxy-methyl]-1-methyl-2-quinolone (ZD-2138), or 2,3,5-trimethyl-6-(3-pyridylmethyl)-1,4-benzoquinone (CV-6504);

a sodium channel blocker, such as lidocaine;

a calcium channel blocker, such as ziconotide, zonisamide, or mibefradil;

a 5-HT3 antagonist, such as ondansetron;

a chemotherapy drug such as oxaliplatin, 5-fluorouracil, leucovorin, or paclitaxel;

a calcitonin gene related peptide (CGRP) antagonist;

a bradykinin (BK1 and BK2) antagonist;

a voltage gated sodium dependent channel blocker ($Na_{v1.7}$, $Na_{v1.8}$);

a voltage dependent calcium channel blocker (N-type, T-type);

a P2X (ion channel type ATP receptor) antagonist;

an acid-sensing ion channel (ASIC1a, ASIC3) antagonist;

an angiotensin-converting enzyme (ACE) inhibitors, such as AT2 antagonist;

an Angiotensin receptor blockers (ARBs);

a direct renin inhibitors (DRIs);

mineralocorticoid receptor antagonists (MRAs);

funny channel (If channel) inhibitor, such as ivabradine;

a Chemokine CCR2B receptor antagonist;

a Cathepsin (B, S, K) inhibitor;

a sigma1 receptor agonist or antagonist;

cardiac sarcomere modulators, such as omecamtiv mecarbil (OM), or MYK-491, Mavacamten;

soluble guanylate cyclase (sGC) stimulators, such as vericiguat;

apelin receptor agonists;

sodium/glucose cotransporter protein 2 (SGLT2) inhibitors, such as dapagliflozin, empagliflozin;

a drugs for heart failure, such as Entresto (registered trademark) which is a combination of sacubitril and valsartan;

or the pharmaceutically acceptable salts, or the solvates thereof.

Such combinations offer significant advantages, including synergistic activity, in therapy.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrated compositions are generally preferred. Tablets and capsules for oral administration may be in unit dose form, and may contain conventional excipients, such as binding agents (e.g. pregelatinised maize starch, polyvinylpyrrolidone or hydroxypropyl methylcellulose); fillers (e.g. lactose, microcrystalline cellulose or calcium hydrogen phosphate); tabletting lubricants (e.g. magnesium stearate, talc or silica); disintegrants (e.g. potato starch or sodium starch glycollate); and acceptable wetting agents (e.g. sodium lauryl sulphate). The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents (e.g. sorbitol syrup, cellulose derivatives or hydrogenated edible fats), emulsifying agents (e.g. lecithin or acacia), non-aqueous vehicles (which may include edible oils e.g. almond oil, oily esters, ethyl alcohol or fractionated vegetable oils), preservatives (e.g. methyl or propyl-p-hydroxybenzoates or sorbic acid), and, if desired, conventional flavourings or colorants, buffer salts and sweetening agents as appropriate. Preparations for oral administration may be suitably formulated to give controlled release of the active compound or pharmaceutically acceptable salt thereof.

For parenteral administration, fluid unit dosage forms are prepared utilising a compound of formulae (I) and (II) or pharmaceutically acceptable salt thereof and a sterile vehicle. Formulations for injection may be presented in unit dosage form e.g. in ampoules or in multi-dose, utilising a compound of formulae (I) and (II) or pharmaceutically acceptable salt thereof and a sterile vehicle, optionally with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspension in a sterile vehicle. Advantageously, a surfactant or wetting agent is included in the composition to facilitate uniform distribution of the compound.

Lotions may be formulated with an aqueous or oily base and will in general also contain one or more emulsifying agents, stabilising agents, dispersing agents, suspending agents, thickening agents, or colouring agents. Drops may be formulated with an aqueous or non-aqueous base also comprising one or more dispersing agents, stabilising agents, solubilising agents or suspending agents. They may also contain a preservative.

Compounds of formulae (I) and (II) or pharmaceutically acceptable salts thereof may also be formulated in rectal compositions such as suppositories or retention enemas, e.g. containing conventional suppository bases such as cocoa butter or other glycerides.

Compounds of formulae (I) and (II) or pharmaceutically acceptable salts may also be formulated as depot preparations. Such long acting formulations may be administered by implantation (for example subcutaneously or intramuscularly) or by intramuscular injection. Thus, for example, the compounds of formulae (I) and (II) or pharmaceutically acceptable salts may be formulated with suitable polymeric or hydrophobic materials (for example as an emulsion in an acceptable oil) or ion exchange resins, or as sparingly soluble derivatives, for example, as a sparingly soluble salt.

For intranasal administration, compounds formulae (I) and (II) or pharmaceutically acceptable salts thereof may be formulated as solutions for administration via a suitable metered or unitary dose device or alternatively as a powder mix with a suitable carrier for administration using a suitable delivery device. Thus compounds of formulae (I) and (II) or pharmaceutically acceptable salts thereof may be formulated for oral, buccal, parenteral, topical (including ophthalmic and nasal), depot or rectal administration or in a form suitable for administration by inhalation or insufflation (either through the mouth or nose). The compounds of formulae (I) and (II) and pharmaceutically acceptable salts thereof may be formulated for topical administration in the form of ointments, creams, gels, lotions, pack, tape, pessaries, aerosols or drops (e.g. eye, ear or nose drops). Ointments and creams may, for example, be formulated with an aqueous or oily base with the addition of suitable thickening and/or gelling agents. Ointments for administration to the eye may be manufactured in a sterile manner using sterilized components.

General Synthesis

Throughout the instant application, the following abbreviations are used with the following meanings:

BINAP 2,2'-Bis(diphenylphosphino)-1,1'-binaphthyl
Boc tert-Butoxycarbonyl
JohnPhos 2-(Di-tert-butylphosphino)biphenyl
CyJohnPhos 2-(Dichlorohexylphosphino)biphenyl
DABCO 1,4-Diazabicyclo[2.2.2]octane
DavePhos 2-(Dicyclohexylphosphino)-2'-(dimethylamino)biphenyl
DBN 1,5-Diazabicyclo[4.3.0]non-5-ene
DBU 1,8-Diazabicyclo[5.4.0]undec-7-ene
DCM Dichloromethane
DIEA N,N-Diisopropylethylamine
DME 1,2-Dimethoxyethane
DMF N,N-Dimethylformamide
DMA N,N-Dimethylacetamide
DMAP N,N-Dimethyl-4-aminopyridine
DMSO Dimethyl sulfoxide
EDC 1-Ethyl-3-(3-dimethylaminopropyl)carbodiimide Hydrochloride
ESI Electrospray ionization
EtOAc Ethyl acetate
EtOH Ethanol
Ex Example
HOBT 1-Hydroxybenzotriazole
HATU O-(7-Aza-1H-benzotriazol-1-yl)-N,N,N',N'-tetramethyluronium hexafluorophosphate
HBTU O-(Benzotriazol-1-yl)-N,N,N',N'-tetramethyluronium hexafluorophosphate
HPLC High-Performance liquid chromatography
LC Liquid chromatography
LDA Lithium diisopropylamide
LG Leaving group
tR Retention time
MeCN Acetonitrile
MeOH Methanol
MHz Megahertz
Ms Methanesulfonyl
MS Mass spectrometry
NMP N-methylpyrrolidone
NMR Nuclear magnetic resonance
rt Room temperature
SFC Supercritical fluid chromatography
SPhos 2-Dicyclohexylphosphino-2',6'-dimethoxybiphenyl
tBuXPhos 2-Di-tert-butylphosphino-2',4',6'-triisopropylbiphenyl
T3P (registered trademark) Propylphosphonic acid anhydride (Cyclic Trimer)
TEA Triethylamine
Tf Trifluoromethanesulfonyl
TFA Trifluoroacetic Acid
THF Tetrahydrofuran
TLC Thin layer chromatography
Ts 4-Toluenesulfonyl
UV Ultraviolet
XPhos 2-Dicyclohexylphosphino-2',4',6'-triisopropylbiphenyl
Xantphos 4,5-Bis(diphenylphosphino)-9,9-dimethylxanthene The term of "base" is likewise no particular restriction on the nature of the bases used, and any base commonly used in reactions of this type may equally be used here. Examples of such bases include, but not limited to: alkali metal hydroxides, such as lithium hydroxide, sodium hydroxide, potassium hydroxide, potassium phosphate, and barium hydroxide; alkali metal hydrides, such as lithium hydride, sodium hydride, and potassium hydride; alkali metal alkoxides, such as sodium methoxide, sodium ethoxide, and potassium tert-butoxide; alkali metal carbonates, such as lithium carbonate, sodium carbonate, potassium carbonate, and cesium carbonate; alkali metal hydrogencarbonates, such as lithium hydrogencarbonate, sodium hydrogencarbonate, and potassium hydrogencarbonate; amines, such as N-methylmorpholine, triethylamine, tripropylamine, tributylamine, diisopropylethylamine, N-methylpiperidine, pyridine, 4-pyrrolidinopyridine, picoline, 2,6-di(tert-butyl)-4-methylpyridine, quinoline, N,N-dimethylaniline, N,N-diethylaniline, N,N-dimethyl-4-aminopyridine (DMAP), 1,5-diazabicyclo[4.3.0]non-5-ene (DBN), 1,4-diazabicyclo

[2.2.2]octane (DABCO), 1,8-diazabicyclo[5.4.0]undec-7-ene (DBU), lutidine, and colidine; alkali metal amides, such as lithium amide, sodium amide, potassium amide, lithium diisopropyl amide, potassium diisopropyl amide, sodium diisopropyl amide, lithium bis(trimethylsilyl)amide and potassium bis(trimethylsilyl)amide. Of these, triethylamine, diisopropylethylamine, DMAP, DBU, DBN, DABCO, pyridine, lutidine, colidine, sodium carbonate, sodium hydrogencarbonate, sodium hydroxide, potassium carbonate, potassium hydrogencarbonate, potassium hydroxide, potassium phosphate, barium hydroxide, and cesium carbonate are preferred.

The reactions are normally and preferably effected in the presence of inert solvent. There is no particular restriction on the nature of the solvent to be employed, provided that it has no adverse effect on the reaction or the reagents involved and that it can dissolve reagents, at least to some extent. Examples of suitable solvents include, but not limited to: halogenated hydrocarbons, such as DCM, chloroform, carbon tetrachloride, and dichloroethane; ethers, such as diethyl ether, diisopropyl ether, THF, and 1,4-dioxane; aromatic hydrocarbons, such as benzene, toluene and nitrobenzene; amides, such as, DMF, DMA, and hexamethylphosphoric triamide; amines, such as N-methylmorpholine, triethylamine, tripropylamine, tributylamine, diisopropylethylamine, N-methylpiperidine, pyridine, 4-pyrrolidinopyridine, N,N-dimethylaniline, and N,N-diethylaniline; alcohols, such as methanol, ethanol, propanol, isopropanol, and butanol; nitriles, such as acetonitrile and benzonitrile; sulfoxides, such as dimethyl sulfoxide (DMSO) and sulfolane; ketones, such as acetone and diethylketone. Of these solvents, including but not limited to DMF, DMA, DMSO, THF, diethylether, diisopropylether, dimethoxyethane, acetonitrile, DCM, dichloroethane, and chloroform are preferred.

The invention is illustrated in the following non-limiting examples in which, unless stated otherwise: all reagents are commercially available, all operations are carried out at room or ambient temperature, that is, in the range of about 18-25° C.; microwave reactions are carried out using Biotage Initiator or Biotage Initiator+; evaporation of solvent is carried out using a rotary evaporator under reduced pressure with a bath temperature of up to about 60° C.; reactions are monitored by thin layer chromatography (TLC) and reaction times are given for illustration only; the structure and purity of all isolated compounds are assured by at least one of the following techniques: TLC (Merck silica gel 60 $F_{254}$ precoated TLC plates or Merck $NH_2$ $F_{254}$ precoated HPTLC plates), mass spectrometry or NMR. Yields are given for illustrative purposes only. Flash column chromatography is carried out using Biotage SNAP KP-Sil, Biotage SNAP Isolute NH2, Merck silica gel 60 (230-400 mesh ASTM), Fuji Silysia Chromatorex (registered trademark) NH-DM1020 and NH-DM2035. The pre-purification for the HPLC (preparative LC-MS) is carried out using a strong cation exchange cartridge (ISOLUTE (registered trademark) SCX-2, 1 g/6 mL, Biotage), or strong anion exchange cartridge (ISOLUTE (registered trademark) PE-AX, 1 g/6 mL, Biotage). The purification of compounds using HPLC (preparative LC-MS) or SFC (preparative SFC-MS) is performed by the following apparatus and conditions.

HPLC:
  Apparatus: Waters MS-trigger AutoPurification (registered trademark) system
  Column: Waters XBridge C8, 19 mm×50 mm, 5 micrometer particle or Waters XBridge C18, 19 mm×50 mm, 5 micrometer particle
  Mobile phase 1: (A) 0.05% (v/v) ammonia aqueous solution, (B) MeOH or MeCN
  Mobile phase 2: (A) 0.05% (v/v) formic acid aqueous solution, (B) MeOH or MeCN
  Mobile phase 3: (A) 10 mM ammonium formate aqueous solution, (B) MeCN/water=90/10(v/v)
  Flow rate: 20 mL/min
  Gradient: A/B (95/5) to A/B (5/95) in 5, 7 or 10 min SFC:
  Apparatus: Waters Prep15 SFC system with ACQUITY QDa Detector
  Column: Waters Torus 2-PIC, 10 mm×150 mm, 5 micrometer particle; Waters Torus DEA, 10 mm×150 mm, 5 micrometer particle; Waters Torus DIOL, 10 mm×150 mm, 5 micrometer particle; Waters Torus 1-AA, 10 mm×150 mm, 5 micrometer particle
  Mobile phase: (A) Carbon dioxide ($CO_2$), (B) MeOH or 10 mM ammonia in MeOH
  Flow rate: 15 mL/min
  Gradient: A/B (95/5) to A/B (60/40) in 7 or 10 min
  Temperature: 40° C.
  Pressure: 120 bar (1740 psi)

Mass spectral data (ESI) are obtained by Waters Alliance HPLC system with ZQ mass spectrometer and UV detector. NMR data are determined by 400 MHz (JEOL JNM-ECZ400S) using deuterated chloroform (99.8% D) or dimethylsulfoxide (99.9% D) as solvent unless indicated otherwise, relative to tetramethylsilane (TMS) as internal standard in parts per million (ppm); conventional abbreviations used are: s=singlet, d=doublet, t=triplet, q=quartet, m=multiplet, br=broad, etc. Chemical symbols have their usual meanings; M (mol(s) per liter), L (liter(s)), mL (milliliter(s)), g (gram(s)), mg (milligram(s)), mol (moles), mmol (millimoles). Each prepared compound is generally named by ChemDraw (version 18.2, PerkinElmer Informatics).

Conditions for Determining HPLC Retention Time:
QC Method:
  Apparatus: Waters Acquity Ultra Performance LC with PDA Detector and ZQ mass spectrometer
  Column: YMC Triart C18, 2.1×100 mm, 1.9 micrometer particle
  Column Temperature: 60° C.
  PDA detection: 200-400 nm scan
  MS detection: ESI positive/negative mode
  Mobile phase:
    A: 10 mM ammonium acetate aqueous solution
    B: acetonitrile

| Time(min) | A (%) | B (%) |
|---|---|---|
| 0 | 90 | 10 |
| 0.05 | 90 | 10 |
| 1.9 | 5 | 95 |
| 2.5 | 5 | 95 |
| 2.51 | 90 | 10 |
| run time | | 3 min |
| Flow rate | | 0.75 mL/min |

All of the compounds of the formula (I) and (II) can be prepared by the procedures described in the general methods presented below or by the specific methods described in the Example synthesis part and the Intermediate synthesis part, or by routine modifications thereof. The present invention also encompasses any one or more of these processes for preparing the compound of formula (I) and (II), in addition to any novel intermediates used therein.

In the following general methods, descriptors ($R^1$, $R^2$, $R^3$, $R^4$, $R^5$, $R^6$, A, B, W, $X^1$, $X^2$, p, q, r, $Y^1$, $Y^2$, $Y^3$, and $Y^4$) are as previously defined for the compound of the formula (I) unless otherwise stated. All starting materials in the following general syntheses may be commercially available or obtained by the conventional methods known to those skilled in the art, otherwise noted in the Intermediate synthesis part.

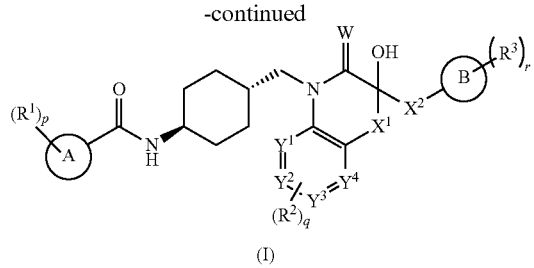

(I)

<Scheme 1>

[Chem.4]

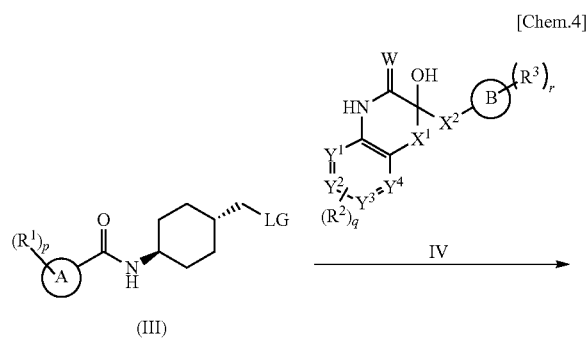

In Scheme 1, a compound of formula (I) can be prepared by the substitution reaction of a compound of formula (III) with a compound of formula (IV) in the presence of a suitable base in an inert solvent. LG is a suitable leaving group such as OTf, OTs, OMs, iodide, bromide, and chloride. Examples of a suitable base include, but not limited to, such as sodium hydride, potassium carbonate, cesium carbonate, potassium tert-butoxide, triethylamine, pyridine, and N,N-diisopropylethylamine. Examples of a suitable organic solvent include such as THF, 1,4-dioxane, DMF, DMSO, MeCN, DMA, NMP, and toluene. The reaction can be carried out at a temperature from about −20 to 200° C., more preferably from about 0 to 100° C. Reaction times are, in general, from about 30 minutes to 48 hours, more preferably from about 1 hour to 24 hours.

<Scheme 2>

[Chem.5]

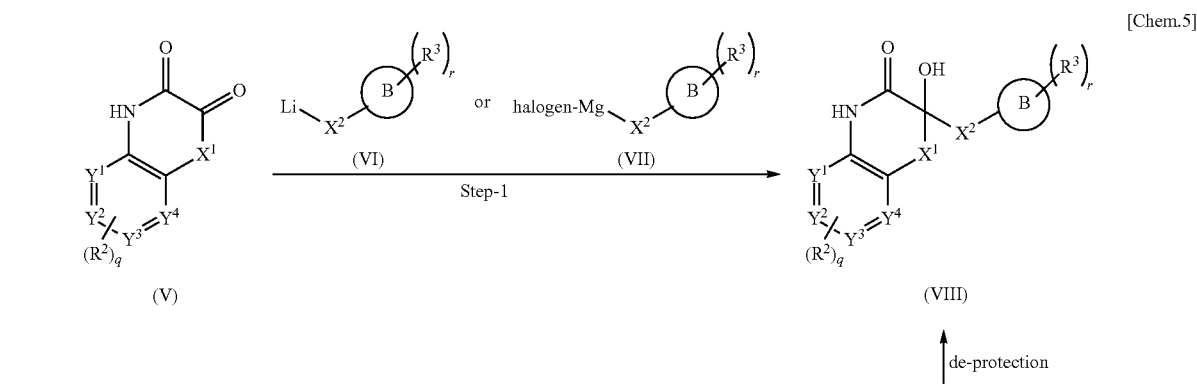

↑ de-protection

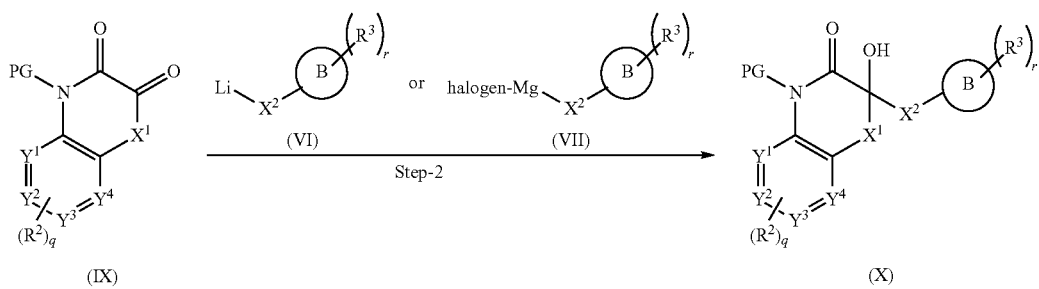

In Step-1 of Scheme 2, a compound of formula (VIII) can be prepared by reacting a compound of formula (V) with a compound of formula (VI) or (VII) in an inert solvent. Examples of a suitable solvent include such as THF, DME, 1,4-dioxane, DMF, DMA, toluene, and diethylether. This reaction can be carried out at a temperature in the range from about −100 to 80° C. Reaction times are, in general, from about 5 minutes to 48 hours. Compounds formula (VI) and (VII) can be prepared as usual manners for example described in Organic Process Research&Development (13, 144-151, 2009) and Chemistry A European Journal (25, 2659-2703, 2019), respectively.

In Step-2 of Scheme 2, a compound of formula (X) can be prepared from a compound of formula (IX) and a compound of formula (VI) or (VII) by the similar manner described in Step-1 of Scheme 2.

A compound of formula (X) can be converted to a compound of formula (VIII) by a usual deprotection manner described in Protecting Groups in Organic Synthesis Forth Edition (John Wiley & Sons, 2007).

<Scheme 3>

[Chem.6]

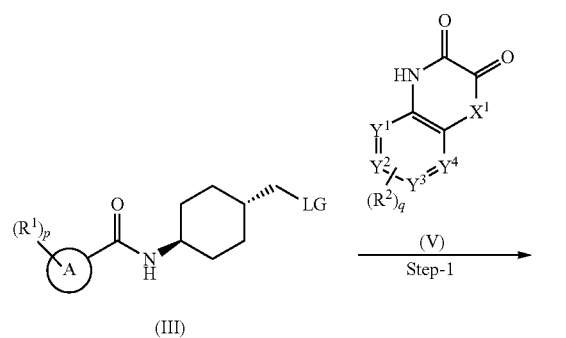

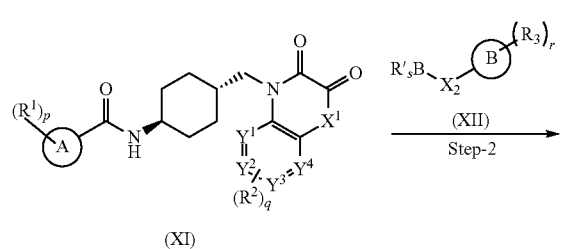

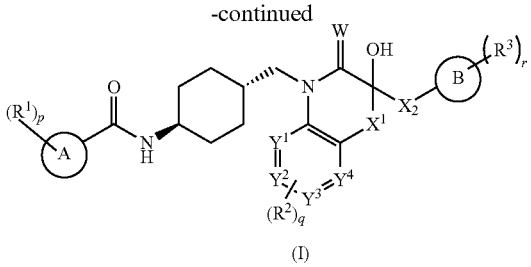

In Step-1 of Scheme 3, a compound of formula (XI) can be prepared from a compound of formula (III) and a compound of formula (V) by the similar general protocol in Scheme 1.

In Step-2 of Scheme 3, when W is O, a compound of formula (I) can be prepared from a compound of formula (XI) and a compound of formula (XII) in the presence of rhodium catalyst, a suitable base, a suitable ligand, in suitable solvents. Examples of a rhodium catalyst include such as chloro(1,5-cyclooctadiene)rhodium(I) dimer, bis(1,5-cyclooctadiene)rhodium(I) tetrafluoroborate, rhodium(III) acetylacetonate, rhodium(II) acetate dimer, rhodium(II) octanoate dimer, rhodium(II) trifluoroacetate dimer, and rhodium(II) heptafluorobutyrate dimer. Examples of a suitable base include: tripotassium phosphate, sodium bicarbonate, sodium carbonate, cesium carbonate, and potassium carbonate. Examples of a suitable ligand include: 4,5-bis (diphenylphosphino)-9,9-dimethylxanthene (Xantphos), triphenylphosphine, tritert-butylphosphine, 1,1'-bis(diphenylphosphino)ferrocene, tri-2-furylphosphine, trio-tolylphosphine, triphenylarsine, 2,2'-bis(diphenylphosphino)-1,1'-binaphthyl (BINAP), 2-(dichlorohexylphosphino)biphenyl (CyJohnPhos), 2-(dicyclohexylphosphino)-2'-(dimethylamino)biphenyl (DavePhos), 2-dicyclohexylphosphino-2',4',6'-triisopropylbiphenyl (XPhos), 2-dicyclohexylphosphino-2',6'-dimethoxybiphenyl (SPhos), 2-di-tert-butylphosphino-2',4',6'-triisopropylbiphenyl (tBuXPhos), and 2-(di-tert-butylphosphino)biphenyl (JohnPhos). Examples of suitable solvents include: DME, THF, 1,4-dioxane, DMF, MeCN, DMSO, DMA, water, methanol, ethanol, toluene, and diethyl ether. The reaction can be carried out at a temperature from about 50 to 200° C., more preferably from about 60 to 120° C. Reaction times are, in general, from about 5 minutes to 48 hours, more preferably from about 30 minutes to 24 hours.

In a representation of BR'$_s$, R' means OH, O-lower alkyl or fluorine, and s is 2 or 3, B is boron atom. As the concrete representation of substituent, $B(OH)_2$, $B(O\text{-lower alkyl})_2$, $B(\text{lower alkyl})_2$, and potassium trifluoroborate $(BF_3)(BF_3K)$ are described, but when $B(O\text{-lower alkyl})_2$ may form the cyclic ring between the lower alkyl groups.

<Scheme 4>

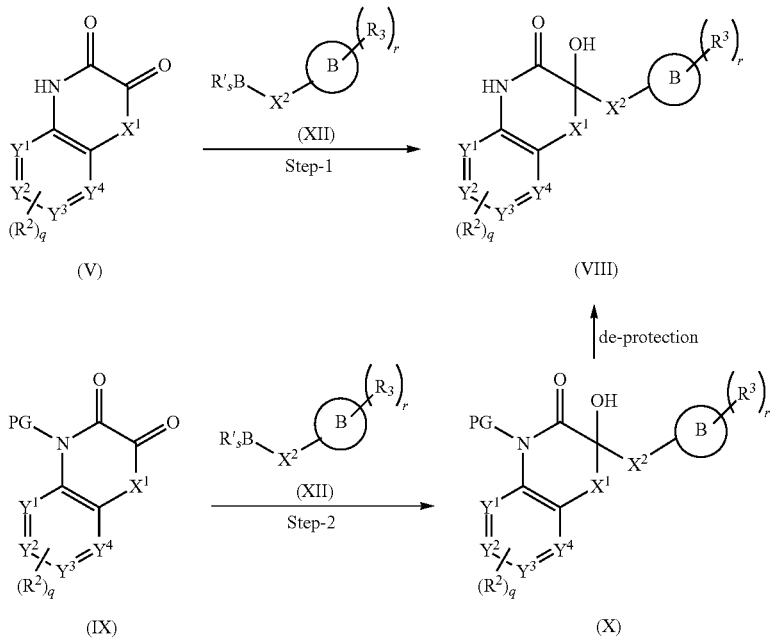

In Step-1 of Scheme 4, a compound of formula (VIII) can be prepared by the similar general protocol in Step-2 of Scheme 3 from a compound of formula (V) or (XII).

In Step-2 of Scheme 4, a compound of formula (X) can be prepared by the similar general protocol in Step-2 of Scheme 3 from a compound of formula (IX) or (XII).

A compound of formula (X) converted to a compound of formula (VIII) by a usual deprotection manner described in Protecting Groups in Organic Synthesis Forth Edition (John Wiley & Sons, 2007).

<Scheme 5>

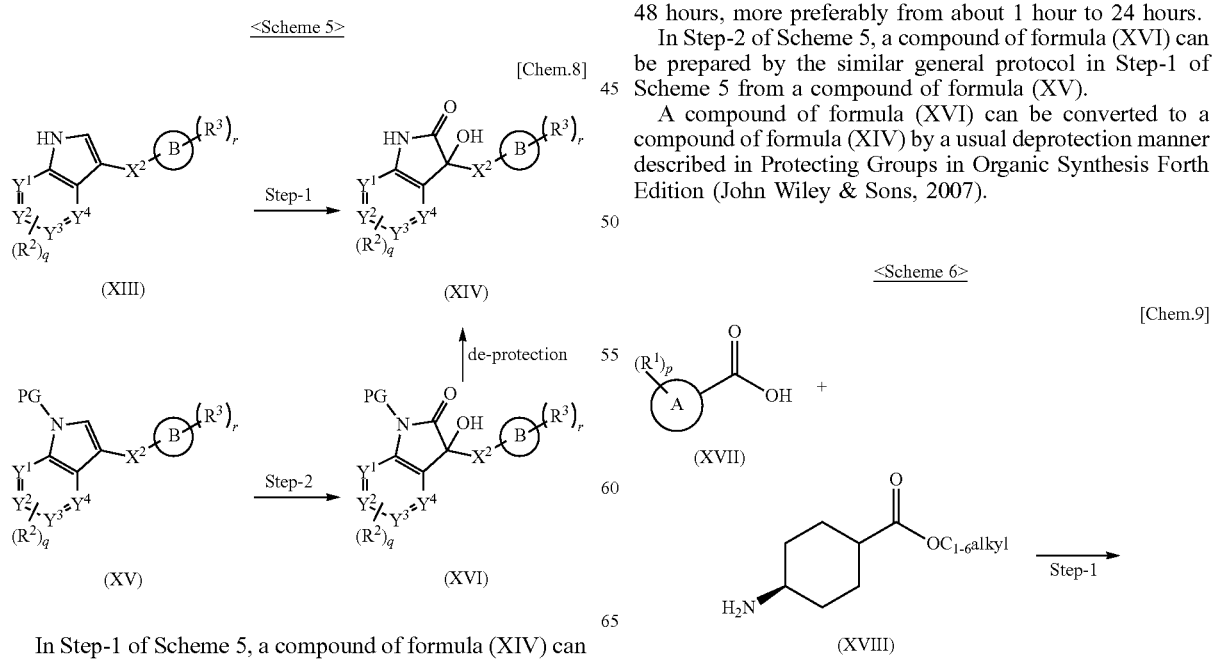

In Step-1 of Scheme 5, a compound of formula (XIV) can be prepared from a compound of formula (XIII) in the presence of an oxidant, a suitable Lewis acid, in suitable solvents. Examples of an oxidant such as [bis(trifluoroacetoxy)iodo]benzene, (diacetoxyiodo)benzene, [bis(trifluoroacetoxy)iodo]pentafluorobenzene, 2-iodoxybenzoic acid, and tert-butyl hypochlorite. Examples of a suitable Lewis acid such as $CeCl_3$, $Ce(OTf)_3$, $InCl_3$, $In(OTf)_3$, $Yb(OTf)_3$, $FeCl_3$, and $Sc(OTf)_3$. Examples of suitable solvents include such as DCM, THF, 1,4-dioxane, DMF, DMSO, MeCN, DMA, toluene, MeOH, EtOH, $CF_3CH_2OH$, water, and DME. The reaction can be carried out at a temperature from about −20 to 100° C., more preferably from about 0 to 40° C. Reaction times are, in general, from about 5 minutes to 48 hours, more preferably from about 1 hour to 24 hours.

In Step-2 of Scheme 5, a compound of formula (XVI) can be prepared by the similar general protocol in Step-1 of Scheme 5 from a compound of formula (XV).

A compound of formula (XVI) can be converted to a compound of formula (XIV) by a usual deprotection manner described in Protecting Groups in Organic Synthesis Forth Edition (John Wiley & Sons, 2007).

-continued

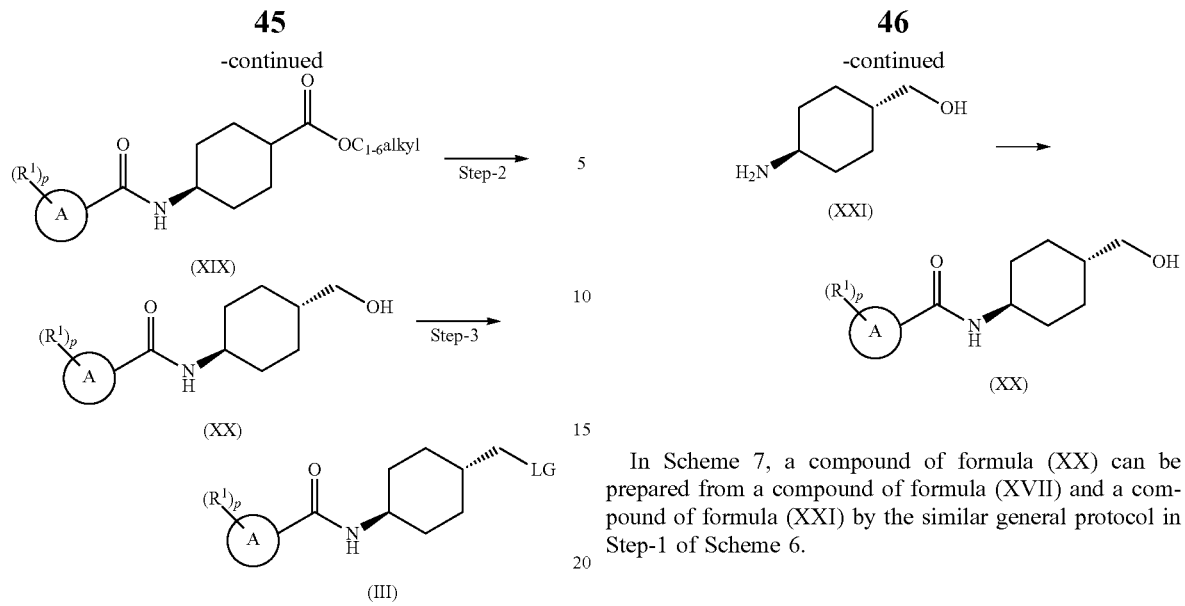

In Scheme 7, a compound of formula (XX) can be prepared from a compound of formula (XVII) and a compound of formula (XXI) by the similar general protocol in Step-1 of Scheme 6.

In Step-1 of Scheme 6, a compound of formula (XIX) can be prepared from a compound of formula (XVII) by condensation with a compound of formula (XVIII) using a suitable condensation reagent such as HBTU, HATU, T3P (registered trademark), EDC, and EDC-HOBT, preferably under the presence of a base such as triethylamine, N,N-diisopropylethylamine, DMAP, DABCO, and DBU in a suitable solvent such as THF, DME, 1,4-dioxane, DMF, DMA, and DCM. This reaction can be carried out at a temperature in the range from about 5 to 60° C. Reaction times are, in general, from about 1 hour to 48 hours.

In Step-2 of Scheme 6, a compound of formula (XX) can be prepared by the reduction of a compound of formula (XIX). In a typical procedure, the reduction is conducted by using a reducing agent such as lithium aluminum hydride, borane, lithium borohydride or sodium borohydride in suitable solvents. Suitable solvents include, such as THF, DME, and 1,4-dioxane. This reaction can be carried out at a temperature in the range of from about −80 to 100° C. Reaction times are, in general, from about 5 minutes to 24 hours.

In Step-3 of Scheme 6, when LG is OMs, a compound of formula (III) can be prepared by mesylation of a compound of formula (XX) with Ms$_2$O or MsCl in suitable organic solvents in the presence of a base. Examples of a suitable base include, but not limited to, such as sodium hydride, potassium carbonate, cesium carbonate, potassium tert-butoxide, triethyl amine, pyridine, and N,N-diisopropylethylamine. Examples of suitable organic solvents include such as DCM, THF, 1,4-dioxane, DMF, DMSO, MeCN, DMA, and toluene. The reaction can be carried out at a temperature from about −20 to 100° C., more preferably from about 0 to 50° C. Reaction times are, in general, from about 5 minutes to 48 hours, more preferably from about 1 hour to 24 hours.

<Scheme 7>

[Chem.10]

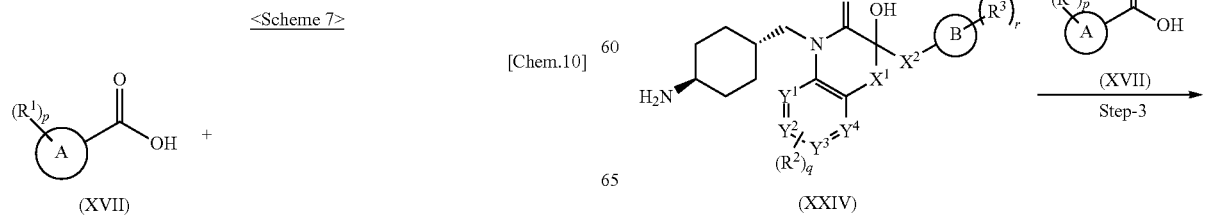

<Scheme 8>

[Chem. 11]

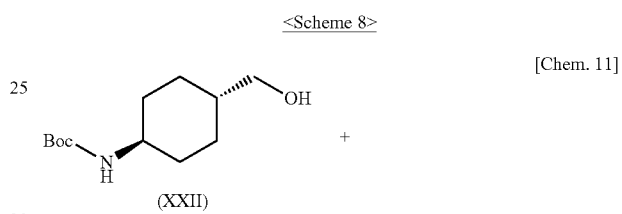

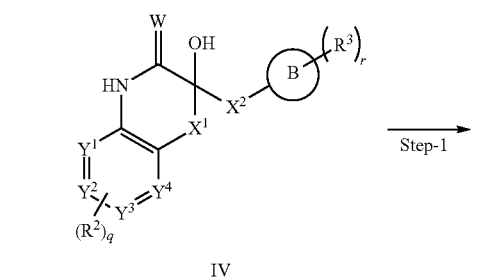

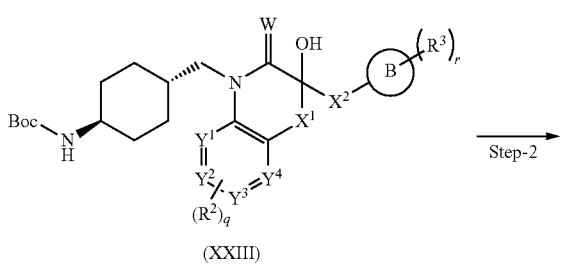

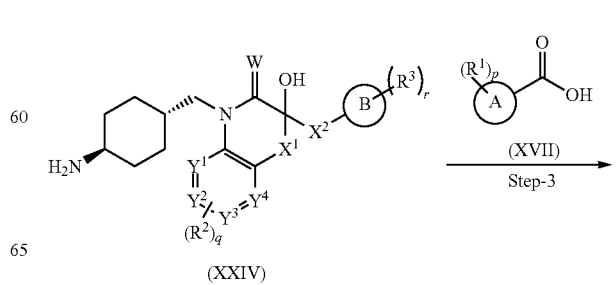

-continued

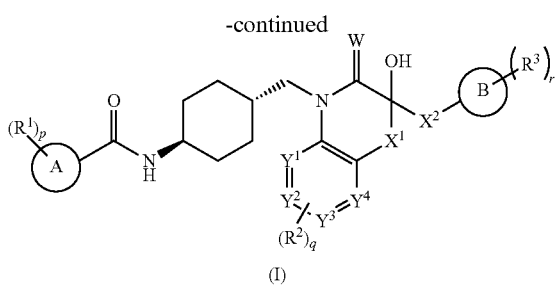

(I)

In Step-1 of Scheme 8, a compound of formula (XXIII) can be prepared from a compound of formula (XXII) and a compound of formula (IV) by the similar general protocol in Scheme 1.

In Step-2 of Scheme 8, a deprotection of Boc group by a usual acidic treatment (for example, hydrogen chloride in 1,4-dioxane, TFA-DCM) to afford a compound of formula (XXIV).

In Step-3 of Scheme 8, a compound of formula (I) can be prepared from a compound of formula (XXIV) and a compound of formula (XVII) by the similar general protocol in Step-1 of Scheme 6.

INTERMEDIATE SYNTHESIS PART

Unless otherwise noted, a compound with a chiral center is synthesized as a racemate in the Intermediate synthesis part.

Intermediate-A ((1r,4r)-4-(5-chloro-2-methylnicotinamido)cyclohexyl)methyl methanesulfonate

[Chem. 12]

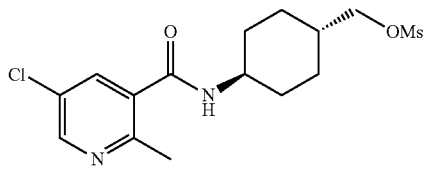

<Step-1>: (1r,4r)-methyl 4-(5-chloro-2-methylnicotinamido)cyclohexanecarboxylate A mixture of 5-chloro-2-methylnicotinic acid (5.23 g, 30.5 mmol), (1r,4r)-methyl 4-aminocyclohexanecarboxylate hydrochloride (5.90 g, 30.5 mmol), HOBt (9.34 g, 61.0 mmol), EDC (11.7 g, 61.0 mmol), and TEA (17 mL, 122 mmol) in DCM (200 mL) is stirred at room temperature overnight. To the mixture is added saturated aqueous sodium bicarbonate. The resultant mixture is extracted with EtOAc. The organic phase is washed with water and brine, dried over MgSO$_4$, filtered and concentrated in vacuo. The resultant residue is purified by column chromatography on silica-gel eluting with 0-70% EtOAc in n-hexane to give 8.55 g (90% yield) of the title compound as a white solid.

MS (ESI) m/z: 311.2 (M+H)$^+$.

$^1$H-NMR (400 MHz, CDCl$_3$) delta 8.50 (1H, d, J=2.3 Hz), 7.62 (1H, d, J=2.7 Hz), 5.57 (1H, d, J=8.2 Hz), 4.00-3.91 (1H, m), 3.69 (3H, s), 2.62 (3H, s), 2.29 (1H, tt, J=12.3, 3.6 Hz), 2.21-2.18 (2H, m), 2.11-2.07 (2H, m), 1.68-1.56 (2H, m), 1.28-1.22 (2H, m).

<Step-2>: 5-chloro-N-((1r,4r)-4-(hydroxymethyl)cyclohexyl)-2-methylnicotinamide

To a solution of (1r,4r)-methyl 4-(5-chloro-2-methylnicotinamido)cyclohexanecarboxylate (8.55 g, 27.5 mmol, Step-1 of Intermediate-A) in THF (180 mL) is added lithium aluminum hydride (1.57 g, 41.3 mmol) portion wise at 0° C. The reaction mixture is stirred at 0° C. After 1 hour, the reaction is quenched with water (150 mL) and Rochelle salt (75 g). The resultant mixture is stirred at room temperature for 1 day. The resultant mixture is extracted with EtOAc, dried over MgSO$_4$, filtered and concentrated in vacuo to give 7.49 g (96% yield) of the title compound as a white solid.

MS (ESI) m/z: 283.2 (M+H)$^+$.

$^1$H-NMR (400 MHz, CDCl$_3$) delta 8.50 (1H, d, J=2.3 Hz), 7.62 (1H, d, J=2.3 Hz), 5.58 (1H, d, J=7.8 Hz), 4.03-3.85 (1H, m), 3.54-3.46 (2H, m), 2.62 (3H, s), 2.22-2.11 (2H, m), 1.96-1.86 (2H, m), 1.60-1.44 (1H, m), 1.35 (1H, brs), 1.31-1.08 (4H, m).

<Step-3>: ((1r,4r)-4-(5-chloro-2-methylnicotinamido)cyclohexyl)methyl methanesulfonate To a mixture of 5-chloro-N-((1r,4r)-4-(hydroxymethyl)cyclohexyl)-2-methylnicotinamide (10.2 g, 35.9 mmol, Step-2 of Intermediate-A) and TEA (15 mL) in DCM (120 mL)/THF (60 mL) is added portionwise methanesulfonic anhydride (14.1 g, 81 mmol) at room temperature. The mixture is stirred at room temperature for 18 hours. To the resultant mixture is added methanesulfonic anhydride (3.13 g, 18.0 mmol) and stirred at room temperature. After 1 hour, to the mixture is added methanesulfonic anhydride (3.13 g, 18.0 mmol) and stirred at room temperature. After 1.5 hours, the reaction is quenched with saturated aqueous sodium bicarbonate (100 mL) and extracted with DCM (3×150 mL). The combined organic phase is dried over sodium sulfate, filtered and concentrated in vacuo. The residual solid is purified by column chromatography on silica-gel eluting with 0-100% EtOAc in DCM to give 10.5 g (81% yield) of the title compound as a white solid.

MS (ESI) m/z: 361.1 (M+H)$^+$.

$^1$H-NMR (400 MHz, CDCl$_3$) delta 8.50 (1H, d, J=2.3 Hz), 7.62 (1H, d, J=2.3 Hz), 5.61 (1H, d, J=7.8 Hz), 4.07 (2H, d, J=6.6 Hz), 4.01-3.85 (1H, m), 3.02 (3H, s), 2.62 (3H, s), 2.24-2.15 (2H, m), 1.98-1.89 (2H, m), 1.85-1.71 (1H, m), 1.32-1.18 (4H, m).

Intermediate-B ((1r,4r)-4-(5-chloro-2-(difluoromethyl)nicotinamido)cyclohexyl)methyl methanesulfonate

[Chem. 13]

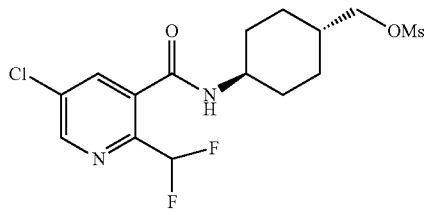

<Step-1>: 5-chloro-2-(difluoromethyl)-N-((1r,4r)-4-(hydroxymethyl)cyclohexyl)nicotinamide A mixture of 5-chloro-2-(difluoromethyl)nicotinic acid (500 mg, 2.41 mmol), ((1r,4r)-4-aminocyclohexyl)methanol hydrochloride (599 mg, 3.61 mmol), HBTU (1.37 g, 3.61 mmol), and TEA (1.68 mL, 12.0 mmol) in DCM (10 mL) is stirred at room temperature overnight. To the mixture is added saturated aqueous sodium bicarbonate. The resultant mixture is extracted with EtOAc. The organic layer is dried over sodium sulfate, filtered and concentrated. The resultant residue is purified by column chromatography on silica-gel eluting with 0-70% EtOAc in n-hexane to give 768 mg (quantitative yield) of the title compound as a pale yellow solid.

MS (ESI) m/z: 319.3 (M+H)+.
1H-NMR (400 MHz, DMSO-$d_6$) delta 8.83 (1H, d, J=2.3 Hz), 8.64 (1H, d, J=7.8 Hz), 8.15 (1H, d, J=2.3 Hz), 7.15 (1H, t, J=54.0 Hz), 4.40 (1H, t, J=5.5 Hz), 3.70-3.60 (1H, m), 3.22 (2H, t, J=5.5 Hz), 1.99-1.88 (2H, m), 1.82-1.72 (2H, m), 1.40-1.13 (3H, m), 1.17-0.90 (2H, m).

<Step-2>: ((1r,4r)-4-(5-chloro-2-(difluoromethyl)nicotinamido)cyclohexyl)methyl methanesulfonate To a mixture of 5-chloro-2-(difluoromethyl)-N-((1r,4r)-4-(hydroxymethyl)cyclohexyl)nicotinamide (768 mg, 2.41 mmol, Step-1 of Intermediate-B) and TEA (1.00 mL, 7.23 mmol) in DCM (4 mL)/THF (4 mL) is added portionwise methanesulfonic anhydride (630 mg, 3.61 mmol) at 0° C. The mixture is stirred at room temperature for 1 hour. The mixture is diluted with saturated aqueous sodium bicarbonate, followed by extraction with DCM. The organic layer is dried over sodium sulfate, filtered and concentrated. The residual solid is purified by column chromatography on silica-gel eluting with 0-60% EtOAc in n-hexane to give 777 mg (81% yield) of the title compound as a pale yellow solid.

MS (ESI) m/z: 397.2 (M+H)+.
1H-NMR (400 MHz, DMSO-$d_6$) delta 8.84 (1H, d, J=2.3 Hz), 8.67 (1H, d, J=7.8 Hz), 8.16 (1H, d, J=2.3 Hz), 7.15 (1H, t, J=54.0 Hz), 4.04 (2H, d, J=6.4 Hz), 3.75-3.62 (1H, m), 3.17 (3H, s), 1.95 (2H, brd, J=11.4 Hz), 1.80 (2H, brd, J=11.4 Hz), 1.72-1.61 (1H, m), 1.36-1.22 (2H, m), 1.18-1.14 (2H, m).

Intermediate-C ((1r,4r)-4-(5-chloro-2-(trifluoromethyl)nicotinamido)cyclohexyl)methyl methanesulfonate

[Chem. 14]

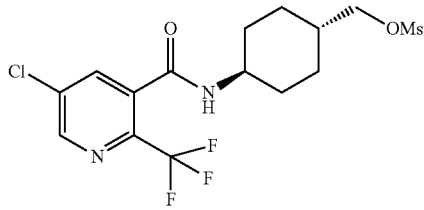

<Step-1>: 5-chloro-N-((1r,4r)-4-(hydroxymethyl)cyclohexyl)-2-(trifluoromethyl)nicotinamide A mixture of 5-chloro-2-(trifluoromethyl)nicotinic acid (2.28 g, 6.84 mmol), ((1r,4r)-4-aminocyclohexyl)methanol hydrochloride (1.47 g, 8.89 mmol), HBTU (3.89 g, 10.3 mmol), and TEA (3.81 mL, 27.4 mmol) in DMF (35 mL) is stirred at room temperature overnight. To the mixture is added water. The resultant mixture is extracted with EtOAc (×2). The organic phase is washed with 0.5 M HCl, water, then saturated aqueous sodium bicarbonate. The organic layer is dried over MgSO4, filtered and concentrated. The resultant residue is purified by column chromatography on silica-gel eluting with 30-75% EtOAc in n-hexane to give 1.62 g (70% yield) of the title compound as a pale yellow solid.

MS (ESI) m/z: 337.4 (M+H)+.
1H-NMR (400 MHz, DMSO-$d_6$) delta 8.87 (1H, d, J=2.3 Hz), 8.57 (1H, d, J=7.8 Hz), 8.22 (1H, d, J=2.3 Hz), 4.40 (1H, t, J=5.5 Hz), 3.69-3.57 (1H, m), 3.22 (2H, t, J=5.5 Hz), 1.91 (2H, brd, J=11.9 Hz), 1.77 (2H, brd, J=11.9 Hz), 1.38-1.26 (1H, m), 1.29-1.14 (2H, m), 1.03-0.99 (2H, m).

<Step-2>: ((1r,4r)-4-(5-chloro-2-(trifluoromethyl)nicotinamido)cyclohexyl)methyl methanesulfonate To a mixture of 5-chloro-N-((1r,4r)-4-(hydroxymethyl)cyclohexyl)-2-(trifluoromethyl)nicotinamide (1.62 g, 4.81 mmol, Step-1 of Intermediate-C) and TEA (2.34 mL, 16.9 mmol) in DCM (10 mL)/THF (20 mL) is added portionwise methanesulfonic anhydride (1.26 g, 7.22 mmol) at 0° C. The mixture is stirred at room temperature for 1.5 hours. The mixture is diluted with saturated aqueous sodium bicarbonate, followed by extraction with DCM (×2). The combined organic phase is dried over MgSO4, filtered and concentrated. The residual solid is purified by column chromatography on silica-gel eluting with 10-80% EtOAc in n-hexane to give 1.89 g (95% yield) of the title compound as an off-white solid.

MS (ESI) m/z: 415.4 (M+H)+.
1H-NMR (400 MHz, CDCl3) delta 8.69 (1H, d, J=2.3 Hz), 7.89 (1H, d, J=2.3 Hz), 5.64 (1H, d, J=7.8 Hz), 4.07 (2H, d, J=6.4 Hz), 4.00-3.89 (1H, m), 3.02 (3H, s), 2.23-2.14 (2H, m), 1.99-1.88 (2H, m), 1.85-1.68 (1H, m), 1.33-1.15 (4H, m).

Intermediate-1

3-hydroxy-3-(pyridin-2-yl)indolin-2-one

[Chem. 15]

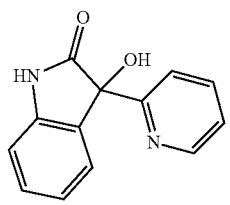

To a solution of 2-iodopyridine (557 mg, 2.72 mmol) in THF (2 mL) is added isopropylmagnesium chloride lithium chloride complex solution 1.3 M in THF (2.09 mL, 2.72 mmol) at 0° C. The mixture is stirred at rt for 2 hours. Then, to the mixture is added indoline-2,3-dione (100 mg, 0.68 mmol) at rt and stirred at rt for 1 hour. The reaction mixture is diluted with saturated aqueous ammonium chloride solution. The mixture is extracted with EtOAc. The organic layer is concentrated. The resultant residue is purified by column chromatography on silica-gel eluting with 0-75% EtOAc in n-hexane to give 142 mg (92% yield) of the title compound as a pale yellow solid.

MS (ESI) m/z: 227.4 (M+H)+.

1H-NMR (400 MHz, DMSO-d6) delta 10.36 (1H, s), 8.35-8.32 (1H, m), 7.88-7.80 (2H, m), 7.25 (1H, ddd, J=8.7, 5.0, 1.8 Hz), 7.19 (1H, td, J=7.8, 1.4 Hz), 6.96 (1H, d, J=6.9 Hz), 6.90-6.83 (2H, m), 6.80 (1H, s).

Intermediate-2

3-hydroxy-3-(6-methoxypyridin-3-yl)indolin-2-one

[Chem. 16]

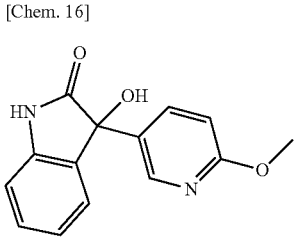 [SMILES: COc1ccc(C2(O)C(=O)Nc3ccccc32)cn1]

To a solution of 5-bromo-2-methoxypyridine (57.5 mg, 0.306 mmol) in THF (0.34 mL) is added n-BuLi solution 1.6 M in hexane (0.21 mL, 0.336 mmol) at −78° C., stirred for 1 hour. To the mixture is added indoline-2,3-dione (15 mg, 0.102 mmol) at −78° C. After stirred for 2 hours, the reaction is diluted with cooled water, followed by extraction with EtOAc, and the extract is dried over sodium sulfate, filtered through a short column of amino-functional silica gel to give 30 mg (quantitative yield) of the title compound as a brown solid.

MS (ESI) m/z: 257.1 (M+H)+.

Intermediate-3

3-hydroxy-3-(5-methylpyridin-2-yl)indolin-2-one

[Chem. 17]

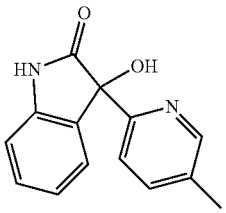

To a cooled solution (−78° C.) of 2-bromo-5-methylpyridine (0.234 g, 1.36 mmol) in THF (3 mL) is added n-BuLi solution 2.6 M in hexane (0.52 mL, 1.36 mmol) dropwise. The mixture is stirred at −78° C. for 30 min. A solution of indoline-2,3-dione (0.10 g, 0.68 mmol) in THF (2 mL) is added and the resulting mixture is slowly warmed to 0° C. during a period of 2 hours. The mixture is diluted with saturated aqueous ammonium chloride solution (20 mL) and the residue is extracted with EtOAc (20 mL×2). The combined organic layers are washed with brine (10 mL), dried over Na2SO4, filtered and concentrated in vacuo. The crude material is purified by silica gel column chromatography (n-hexane/EtOAc) to give 3-hydroxy-3-(5-methylpyridin-2-yl)indolin-2-one (74 mg, 45% yield) as a yellow solid.

1H-NMR (400 MHz, CDCl3) delta 8.45 (1H, d, J=1.8 Hz), 8.04 (1H, brs), 7.43 (1H, dd, J=8.7, 2.3 Hz), 7.29 (1H, ddd, J=7.8, 7.8, 1.4 Hz), 7.14 (1H, d, J=7.3 Hz), 7.04 (1H, ddd, J=7.5, 7.5, 0.9 Hz), 6.94 (1H, d, J=7.8 Hz), 6.87 (1H, d, J=7.8 Hz), 6.31 (1H, brs), 2.34 (3H, s).

Intermediate-4

3-(5-fluoro-6-methylpyridin-2-yl)-3-hydroxyindolin-2-one

[Chem. 18]

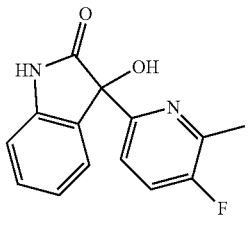

To a cooled solution (−78° C.) of 6-bromo-3-fluoro-2-methylpyridine (0.258 g, 1.36 mmol) in toluene (3 mL) is added n-BuLi solution 2.6 M in hexane (0.523 mL, 1.36 mmol) dropwise. The mixture is stirred at −78° C. for 30 minutes. A solution of indoline-2,3-dione (0.10 g, 0.68 mmol) in THF (2 mL) is added and the resulting mixture is slowly warmed to 0° C. during a period of 2 hours. The mixture is diluted with saturated aqueous ammonium chloride solution (20 mL) and the residue is extracted with EtOAc (20 mL×2). The combined organic layers are washed with brine (10 mL), dried over Na2SO4, filtered and concentrated in vacuo. The crude material is purified by silica gel column chromatography (n-hexane/EtOAc) to give 3-(5-fluoro-6-methylpyridin-2-yl)-3-hydroxyindolin-2-one (83 mg, 47% yield) as a solid.

1H-NMR (400 MHz, CDCl3) delta 8.06 (1H, brs), 7.31 (1H, ddd, J=7.8, 7.8, 1.4 Hz), 7.26 (1H, dd, J=8.7, 8.7 Hz), 7.14 (1H, brd, J=6.9 Hz), 7.05 (1H, ddd, J=7.3, 7.3, 0.9 Hz), 6.95 (1H, brd, J=7.8 Hz), 6.76 (1H, dd, J=7.8, 3.2 Hz), 6.31 (1H, brs), 2.60 (3H, d, J=3.2 Hz).

Intermediate-5

3-hydroxy-3-(6-methylpyridin-2-yl)indolin-2-one

[Chem. 19]

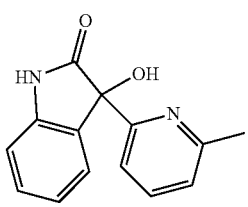

The title compound is prepared in 53% yield (87 mg, a pale yellow solid) in a similar manner to Intermediate-4 using 2-bromo-6-methylpyridine (234 mg, 1.36 mmol) in place of 6-bromo-3-fluoro-2-methylpyridine.

¹H-NMR (400 MHz, CDCl₃) delta 7.97 (1H, brs), 7.50 (1H, dd, J=7.8, 7.8 Hz), 7.30 (1H, ddd, J=7.8, 7.8, 1.4 Hz), 7.14-7.12 (2H, m), 7.04 (1H, dd, J=7.8, 7.8 Hz), 6.95 (1H, d, J=7.8 Hz), 6.83 (1H, s), 6.70 (1H, d, J=7.8 Hz), 2.64 (3H, s).

Intermediate-6

3-hydroxy-3-(6-methoxypyridin-2-yl)indolin-2-one

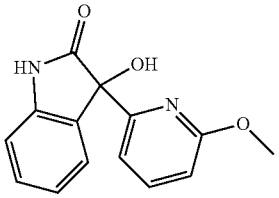

[Chem.20]

The title compound is prepared in 67% yield (116 mg, a pale yellow solid) in a similar manner to Intermediate-4 using 2-bromo-6-methoxypyridine (256 mg, 1.36 mmol) in place of 6-bromo-3-fluoro-2-methylpyridine.

¹H-NMR (400 MHz, CDCl₃) delta 7.96 (1H, brs), 7.50 (1H, dd, J=8.2, 7.3 Hz), 7.30 (1H, ddd, J=7.8, 7.8, 1.4 Hz), 7.18 (1H, d, J=7.3 Hz), 7.05 (1H, dd, J=7.8, 7.3 Hz), 6.94 (1H, d, J=7.8 Hz), 6.72 (1H, d, J=8.2 Hz), 6.54 (1H, d, J=7.3 Hz), 5.96 (1H, brs), 4.05 (3H, s).

Intermediate-7

3-(3-fluoropyridin-4-yl)-3-hydroxyindolin-2-one

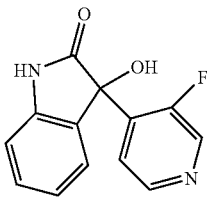

[Chem.21]

<Step-1>: 3-(2-bromo-5-fluoropyridin-4-yl)-3-hydroxyindolin-2-one

To a cooled solution (−78° C.) of 2-bromo-5-fluoropyridine (0.239 g, 1.36 mmol) in THF (3 mL) is added n-BuLi solution 2.6 M in hexane (0.52 mL, 1.36 mmol) dropwise. The mixture is stirred at −78° C. for 30 min. A solution of indoline-2,3-dione (0.10 g, 0.68 mmol) in THF (2 mL) is added and the resulting mixture is slowly warmed to 0° C. during a period of 2 hours. The mixture is diluted with saturated aqueous ammonium chloride solution (20 mL) and the residue is extracted with EtOAc (20 mL×2). The combined organic layers are washed with brine (10 mL), dried over Na₂SO₄, filtered and concentrated in vacuo. The crude material is purified by silica gel column chromatography (n-hexane/EtOAc) to give 3-(2-bromo-5-fluoropyridin-4-yl)-3-hydroxyindolin-2-one (109 mg, 50% yield) as a solid.

¹H-NMR (400 MHz, DMSO-d₆) delta 10.75 (1H, s), 8.31 (1H, d, J=1.8 Hz), 8.02 (1H, d, J=5.9 Hz), 7.30-7.26 (2H, m), 7.06 (1H, d, J=6.9 Hz), 6.94 (1H, ddd, J=7.8, 7.3, 0.9 Hz), 6.92 (1H, d, J=7.8 Hz).

<Step-2>:3-(3-fluoropyridin-4-yl)-3-hydroxyindolin-2-one

A mixture of 3-(2-bromo-5-fluoropyridin-4-yl)-3-hydroxyindolin-2-one (30 mg, 0.093 mmol, Step-1 of Intermediate-7) and 10% Pd/C (10 mg) in MeOH (5 mL) is stirred under H₂ balloon for 2 hours. The reaction mixture is filtered through a celite pad and the filtrate is concentrated to dryness to give 3-(3-fluoropyridin-4-yl)-3-hydroxyindolin-2-one (23 mg, quantitative yield).

¹H-NMR (400 MHz, CDCl₃) delta 8.54 (1H, d, J=5.0 Hz), 8.35 (1H, d, J=2.3 Hz), 7.85 (1H, dd, J=6.4, 5.0 Hz), 7.48 (1H, brs), 7.34 (1H, ddd, J=7.8, 7.8, 1.4 Hz), 7.13 (1H, d, J=7.8 Hz), 7.05 (1H, ddd, J=7.8, 7.3, 0.9 Hz), 6.97 (1H, d, J=8.2 Hz), 3.21 (1H, brs).

Intermediate-8

3-hydroxy-3-(5-methoxypyridin-2-yl)indolin-2-one

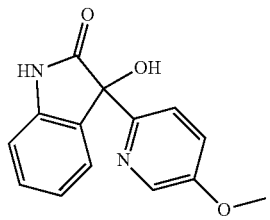

[Chem.22]

The title compound is prepared in 67% yield (116 mg, a pale yellow solid) in a similar manner to Intermediate-4 using 2-bromo-5-methoxypyridine (256 mg, 1.36 mmol) in place of 6-bromo-3-fluoro-2-methylpyridine.

¹H-NMR (400 MHz, CDCl₃) delta 8.54 (1H, brs), 8.29 (1H, d, J=3.2 Hz), 7.30-7.26 (1H, m), 7.16-7.13 (2H, m), 7.03 (1H, dd, J=7.8, 7.3 Hz), 6.95-6.92 (2H, m), 6.11 (1H, brs), 3.85 (3H, s).

Intermediate-9

3-hydroxy-3-(5-(trifluoromethyl)pyridin-2-yl)indolin-2-one

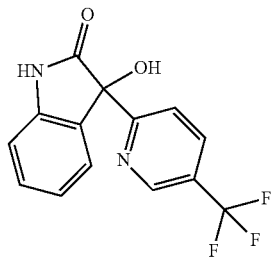

[Chem.23]

The title compound is prepared in 58% yield (116 mg, a pale yellow solid) in a similar manner to Intermediate-4 using 2-bromo-5-(trifluoromethyl)pyridine (307 mg, 1.36 mmol) in place of 6-bromo-3-fluoro-2-methylpyridine.

¹H-NMR (400 MHz, CDCl₃) delta 8.89 (1H, s), 7.90 (1H, dd, J=8.2, 2.3 Hz), 7.83 (1H, brs), 7.34 (1H, ddd, J=7.8, 7.8, 1.4 Hz), 7.29-7.26 (1H, m), 7.16 (1H, d, J=7.3 Hz), 7.07 (1H, dd, J=8.2, 7.3 Hz), 6.98 (1H, d, J=7.8 Hz), 5.71 (1H, brs).

Intermediate-10

3-(5-chloropyridin-2-yl)-3-hydroxyindolin-2-one

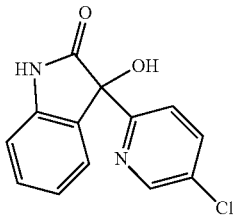

[Chem.24]

The title compound is prepared in 67% yield (119 mg, a pale yellow solid) in a similar manner to Intermediate-4 using 2-bromo-5-chloropyridine (262 mg, 1.36 mmol) in place of 6-bromo-3-fluoro-2-methylpyridine.

¹H-NMR (400 MHz, CDCl₃) delta 8.58 (1H, d, J=2.3 Hz), 7.92 (1H, brs), 7.63 (1H, dd, J=8.2, 2.3 Hz), 7.32 (1H, ddd, J=7.8, 7.8, 1.4 Hz), 7.16 (1H, brd, J=7.8 Hz), 7.08-7.02 (2H, m), 6.96 (1H, d, J=7.8 Hz), 5.72 (1H, s).

Intermediate-11

3-hydroxy-3-(thiazol-2-yl)indolin-2-one

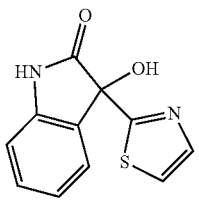

[Chem.25]

To a cooled solution (−78° C.) of thiazole (116 mg, 1.36 mmol) in THF (3 mL) is added n-BuLi solution 2.6 M in hexane (0.52 mL, 1.36 mmol) dropwise. The mixture is stirred at −78° C. for 30 min. A solution of indoline-2,3-dione (100 mg, 0.68 mmol) in THF (2 mL) is added and the resulting mixture is slowly warmed to 0° C. during a period of 2 hours. The mixture is diluted with saturated aqueous ammonium chloride solution (20 mL) and the mixture is extracted with EtOAc (20 mL×2). The combined organic layers are washed with brine, dried over Na₂SO₄, filtered and concentrated in vacuo. The crude material is purified by silica gel column chromatography (n-hexane/EtOAc) to give the title compound (87 mg, 55% yield) as a solid.

¹H-NMR (400 MHz, DMSO-d₆) delta 7.65-7.64 (2H, m), 7.36 (1H, d, J=5.0 Hz), 7.25 (1H, dd, J=7.8, 7.8 Hz), 7.11 (1H, d, J=7.3 Hz), 7.25 (1H, dd, J=7.8, 7.3 Hz), 6.88 (1H, d, J=7.8 Hz), OH proton is not observed.

Intermediate-12

3-hydroxy-3-(4-(trifluoromethyl)pyridin-2-yl)indolin-2-one

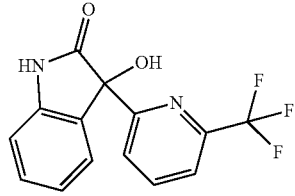

[Chem.26]

The title compound is prepared in 64% yield (127 mg, a pale yellow solid) in a similar manner to Intermediate-4 using 2-bromo-4-(trifluoromethyl)pyridine (307 mg, 1.36 mmol) in place of 6-bromo-3-fluoro-2-methylpyridine.

¹H-NMR (400 MHz, CDCl₃) delta 8.80 (1H, d, J=5.0 Hz), 7.88 (1H, brs), 7.52 (1H, dd, J=5.0, 0.9 Hz), 7.37-7.33 (2H, m), 7.17 (1H, d, J=6.9 Hz), 7.08 (1H, ddd, J=7.3, 7.3, 0.9 Hz), 6.99 (1H, d, J=8.2 Hz), 5.59 (1H, brs).

Intermediate-13

3-(5-fluoropyridin-2-yl)-3-hydroxyindolin-2-one

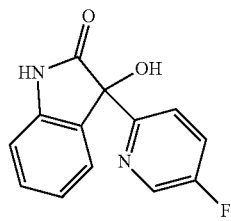

[Chem.27]

The title compound is prepared in 72% yield (119 mg, a pale yellow solid) in a similar manner to Intermediate-4 using 2-bromo-5-fluoropyridine (239 mg, 1.36 mmol) in place of 6-bromo-3-fluoro-2-methylpyridine.

¹H-NMR (400 MHz, CDCl₃) delta 8.47 (1H, d, J=2.7 Hz), 8.39 (1H, brs), 7.37 (1H, ddd, J=8.2, 7.8, 2.7 Hz), 7.31 (1H, ddd, J=7.8, 7.8, 0.9 Hz), 7.15 (1H, d, J=7.3 Hz), 7.11-7.04 (2H, m), 6.96 (1H, d, J=8.2 Hz), 5.80 (1H, s).

Intermediate-14

3-(3-fluoropyridin-2-yl)-3-hydroxyindolin-2-one

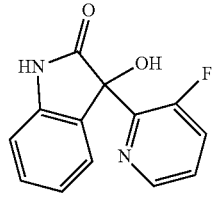

[Chem.28]

The title compound is prepared in 77% yield (127 mg, a pale yellow solid) in a similar manner to Intermediate-4 using 2-bromo-3-fluoropyridine (263 mg, 1.49 mmol) in place of 6-bromo-3-fluoro-2-methylpyridine.

$^1$H-NMR (400 MHz, CDCl$_3$) delta 8.48 (1H, ddd, J=4.6, 4.6, 1.4 Hz), 7.54 (1H, brs), 7.42-7.35 (2H, m), 7.30 (1H, ddd, J=7.3, 7.3, 1.4 Hz), 7.05 (1H, d, J=5.9 Hz), 7.01 (1H, ddd, J=7.3, 7.3, 0.9 Hz), 6.93 (1H, d, J=7.8 Hz), 6.62 (1H, s).

Intermediate-15

3-(5-fluoropyridin-3-yl)-3-hydroxyindolin-2-one

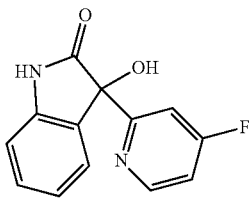

[Chem.29]

The title compound is prepared in 48% yield (79 mg, a pale yellow solid) in a similar manner to Intermediate-4 using 3-bromo-5-fluoropyridine (239 mg, 1.36 mmol) in place of 6-bromo-3-fluoro-2-methylpyridine.

$^1$H-NMR (400 MHz, CDCl$_3$) delta 8.42 (1H, d, J=2.7 Hz), 8.35 (1H, s), 7.61 (1H, ddd, J=9.1, 2.7, 1.8 Hz), 7.45 (1H, brs), 7.36 (1H, ddd, J=7.8, 7.8, 1.4 Hz), 7.29-7.26 (1H, m), 7.13 (1H, ddd, J=7.8, 6.9, 0.9 Hz), 6.98 (1H, d, J=7.8 Hz), 3.27 (1H, brs).

Intermediate-16

3-(3-chloropyridin-4-yl)-3-hydroxyindolin-2-one

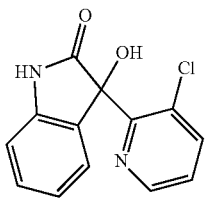

[Chem.30]

To a cooled solution (−78° C.) of 3-chloropyridine (162 mg, 1.43 mmol) in THF (3 mL) is added LDA solution 1.0 M in THF/hexanes (1.43 mL, 1.43 mmol) dropwise. The mixture is stirred at −78° C. for 30 min. A solution of indoline-2,3-dione (100 mg, 0.684 mmol) in THF (2 mL) is added and the mixture is slowly warmed to 0° C. during a period of 2 hours. The mixture is diluted with saturated aqueous ammonium chloride solution (20 mL) and the mixture is extracted with EtOAc (20 mL×2). The combined organic layers are washed with brine, dried over Na$_2$SO$_4$, filtered and concentrated in vacuo. The crude material is purified by silica gel column chromatography (n-hexane/EtOAc) to give 3-(3-chloropyridin-4-yl)-3-hydroxyindolin-2-one (91 mg, 51% yield) as a solid.

$^1$H-NMR (400 MHz, CDCl$_3$) delta 8.63 (1H, d, J=5.5 Hz), 8.47 (1H, s), 8.55 (1H, d, J=5.5 Hz), 7.77 (1H, brs), 7.34 (1H, ddd, J=7.8, 7.8, 1.4 Hz), 7.03 (1H, ddd, J=7.8, 7.8, 1.4 Hz), 6.99-6.95 (2H, m), OH proton is not observed.

Intermediate-17

3-(3-chloropyridin-2-yl)-3-hydroxyindolin-2-one

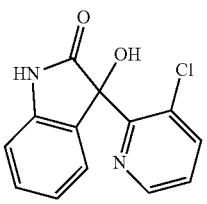

[Chem.31]

The title compound is prepared in 72% yield (127 mg, a pale yellow solid) in a similar manner to Intermediate-4 using 2-bromo-3-chloropyridine (288 mg, 1.49 mmol) in place of 6-bromo-3-fluoro-2-methylpyridine.

$^1$H-NMR (400 MHz, CDCl$_3$) delta 8.59 (1H, dd, J=4.6, 1.4 Hz), 7.70 (1H, dd, J=8.2, 1.4 Hz), 7.69 (1H, brs), 7.38 (1H, dd, J=8.2, 4.6 Hz), 7.29 (1H, ddd, J=7.8, 7.8, 1.4 Hz), 7.11 (1H, s), 7.00 (1H, ddd, J=7.8, 7.8, 0.9 Hz), 6.94 (1H, d, J=8.2 Hz), 6.91 (1H, d, J=7.8 Hz).

Intermediate-18

3-(3,5-difluoropyridin-2-yl)-3-hydroxyindolin-2-one

[Chem. 32]

3,5-Difluoropyridine (164 mg, 1.43 mmol) in THF (5 mL) is cooled to −78° C. LDA solution 1.0 M in THF/hexanes (1.43 mL, 1.43 mmol) is added dropwise at the same temperature. The reaction mixture is stirred for 30 minutes. Trimethylchlorosilane (0.182 mL, 1.43 mmol) is added dropwise. The reaction mixture is stirred for 30 min. LDA solution 1.0 M in THF/hexanes (1.43 mL, 1.43 mmol) is added dropwise, and the reaction mixture is allowed to stir for 2 hours. A THF (2 mL) solution of indoline-2,3-dione (100 mg, 0.680 mmol) is added to the reaction mixture and the resulting mixture is warmed to −30° C. for 2 hours. The reaction is quenched by adding saturated aqueous ammonium chloride solution (20 mL). The residue is extracted by ethyl acetate (20 mL×2). The combined organic layer are washed with brine (20 mL), dried with sodium sulfate and concentrated. The THF (1 mL) solution of crude product is added to tetrabutyl ammonium fluoride 1.0 M solution in THF (1 mL) at 0° C. The resulting mixture is stirred for 1 hour at room temperature, and concentrated. The residue is purified by silica gel chromatography (n-hexane/EtOAc) to give 3-(3,5-difluoropyridin-2-yl)-3-hydroxyindolin-2-one (73 mg, 41% yield).

$^1$H-NMR (400 MHz, CDCl$_3$) delta 8.40 (1H, d, J=2.3 Hz), 7.43 (1H, brs), 7.31 (1H, ddd, J=7.8, 6.9, 1.8 Hz), 7.20 (1H, ddd, J=9.6, 7.8, 2.3 Hz), 7.06-7.00 (2H, m), 6.93 (1H, d, J=8.2 Hz), 6.21 (1H, s).

Intermediate-19

3-(5-chloropyridin-3-yl)-3-hydroxyindolin-2-one

[Chem. 33]

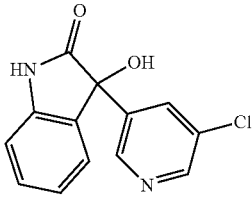

The title compound is prepared in 73% yield (129 mg, a pale yellow solid) in a similar manner to Intermediate-4 using 3-bromo-5-chloropyridine (268 mg, 1.39 mmol) in place of 6-bromo-3-fluoro-2-methylpyridine.

$^1$H-NMR (400 MHz, CDCl$_3$) delta 8.52 (1H, s), 8.43 (1H, d, J=2.3 Hz), 7.84 (1H, dd, J=2.3, 2.3 Hz), 7.47 (1H, brs), 7.37 (1H, ddd, J=7.8, 7.8, 0.9 Hz), 7.28 (1H, d, J=8.2 Hz), 7.13 (1H, ddd, J=7.8, 7.3, 0.9 Hz), 6.98 (1H, d, J=7.8 Hz), 3.29 (1H, brs).

Intermediate-20

3-(5-fluoro-2-methoxypyridin-4-yl)-3-hydroxyindolin-2-one

[Chem. 34]

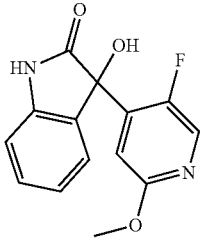

The title compound is prepared in 67% yield (124 mg, a pale yellow solid) in a similar manner to Step-1 of Intermediate-7 using 5-fluoro-2-methoxypyridine (181 mg, 1.43 mmol) in place of 2-bromo-5-fluoropyridine.

$^1$H-NMR (400 MHz, CDCl$_3$) delta 7.86 (1H, d, J=2.3 Hz), 7.44 (1H, brs), 7.32 (1H, ddd, J=7.8, 7.8, 1.4 Hz), 7.25 (1H, d, J=5.0 Hz), 7.15 (1H, dd, J=6.9, 1.4 Hz), 7.05 (1H, ddd, J=7.8, 7.8, 0.9 Hz), 6.95 (1H, d, J=7.8 Hz), 3.93 (3H, s), 3.13 (1H, s).

Intermediate-21

3-(5-chloro-3-fluoropyridin-2-yl)-3-hydroxyindolin-2-one

[Chem. 35]

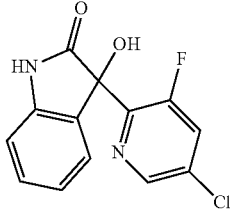

<Step-1> 3-(5-chloro-3-fluoro-4-(trimethylsilyl)pyridin-2-yl)-3-hydroxyindolin-2-one A solution of 3-chloro-5-fluoropyridine (188 mg, 1.43 mmol) in THF (2 mL) is cooled to −78° C. LDA solution 1.0 M in THF/hexanes (1.43 mL, 1.43 mmol) is added dropwise at the same temperature. The reaction mixture is stirred for 30 min. Trimethylchlorosilane (155 mg, 1.43 mmol) is added in a relatively fast fashion. LDA solution 1.0 M in THF/hexanes (1.43 mL, 1.43 mmol) is added dropwise at the same temperature, and the reaction mixture is allowed to stir for 2 hours. Indoline-2,3-dione (100 mg, 0.680 mmol) is added. The reaction mixture is warmed to −30° C. for 1 hour. The reaction is quenched by adding saturated aqueous ammonium chloride solution (20 mL). The residue is extracted by ethyl acetate (20 mL×2). The combined organic layers are washed with brine (20 mL), dried over sodium sulfate and concentrated. Purification by silica gel chromatography (n-hexane/EtOAc), gave 3-(5-chloro-3-fluoro-4-(trimethylsilyl)pyridin-2-yl)-3-hydroxyindolin-2-one (134 mg, 56% yield).

$^1$H-NMR (400 MHz, CDCl$_3$) delta 8.39 (1H, d, J=0.9 Hz), 7.49 (1H, br), 7.30 (1H, ddd, J=7.8, 6.9, 1.8 Hz), 7.05-6.99 (2H, m), 6.92 (1H, d, J=7.8 Hz), 6.29 (1H, s), 0.37 (9H, d, J=1.8 Hz).

<Step-2>: 3-(5-chloro-3-fluoropyridin-2-yl)-3-hydroxyindolin-2-one

To a THF (1 mL) solution of 3-(5-chloro-3-fluoro-4-(trimethylsilyl)pyridin-2-yl)-3-hydroxyindolin-2-one (134 mg, 0.382 mmol, Step-1 of Intermediate-21) is added tetrabutyl ammonium fluoride 1.0 M solution in THF (1 mL) at 0° C. The resulting mixture is stirred for 1 hour at room temperature, and concentrated in vacuo. The residue is purified by silica gel column chromatography (n-hexane/EtOAc) to give 3-(5-chloro-3-fluoropyridin-2-yl)-3-hydroxyindolin-2-one (90 mg, 85% yield) as a solid.

$^1$H-NMR (400 MHz, CDCl$_3$) delta 8.47 (1H, dd, J=1.8, 0.9 Hz), 7.42 (1H, dd, J=9.1, 1.8 Hz), 7.42 (1H, br), 7.31 (1H, ddd, J=7.8, 7.3, 1.8 Hz), 7.06 (1H, dd, J=7.3, 1.8 Hz), 7.02 (1H, ddd, J=7.3, 7.3, 0.9 Hz), 6.93 (1H, d, J=7.8 Hz), 6.17 (1H, s).

Intermediate-22

6-fluoro-3-hydroxy-3-phenylindolin-2-one

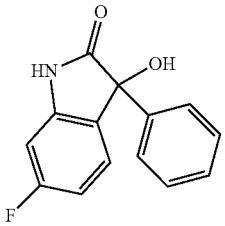

[Chem. 36]

To a solution of 6-fluoroindoline-2,3-dione (80 mg, 0.48 mmol) in THF (1 mL) is added phenylmagnesium bromide solution 1.02 M in THF (0.95 mL, 0.97 mmol) at 0° C. The mixture is stirred at rt for 2 hours. The reaction mixture is diluted with saturated aqueous ammonium chloride solution. The mixture is extracted with EtOAc. The organic layer is concentrated. The resultant residue is purified by column chromatography on silica-gel eluting with 0-75% EtOAc in n-hexane to give 71 mg (60% yield) of the title compound as a pale yellow solid.

$^1$H-NMR (400 MHz, DMSO-$d_6$) delta 10.55 (1H, s), 7.35-7.24 (5H, m), 7.11 (1H, dd, J=8.2, 5.5 Hz), 6.80-6.70 (2H, m), 6.67 (1H, s).

MS (ESI) m/z: 244.2 (M+H)$^+$.

Intermediate-23

3-hydroxy-3-(thiazol-4-yl)indolin-2-one

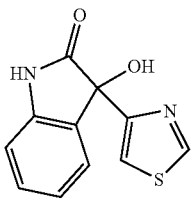

[Chem. 37]

To a cooled solution (−78° C.) of 4-bromo-2-(trimethylsilyl)thiazole (321 mg, 1.36 mmol) in toluene (3 mL) is added n-BuLi solution 2.6 M in hexane (0.52 mL, 1.36 mmol) dropwise. The mixture is stirred at −78° C. for 30 min. A solution of indoline-2,3-dione (100 mg, 0.68 mmol) in THF (2 mL) is added and the mixture is slowly warmed to 0° C. during a period of 2 hours. The mixture is diluted with saturated aqueous ammonium chloride solution (20 mL) and the mixture is extracted with EtOAc (20 mL×2). The combined organic layers are washed with brine (20 mL), dried over Na$_2$SO$_4$, filtered and concentrated in vacuo. To the THF (1 mL) solution of crude product is added tetrabutyl ammonium fluoride 1 M solution in THF (1 mL) at 0° C. The resulting mixture is stirred for 1 hour at room temperature, and concentrated. The crude product is purified by silica gel chromatography (n-hexane/EtOAc) to give 3-hydroxy-3-(thiazol-4-yl)indolin-2-one (65 mg, 35% yield).

$^1$H-NMR (400 MHz, CDCl$_3$) delta 8.82 (1H, d, J=2.3 Hz), 7.41-7.30 (4H, m), 7.10 (1H, ddd, J=7.8, 7.8, 0.9 Hz), 6.94 (1H, d, J=7.8 Hz), 3.88 (1H, s).

Intermediate-24

3-hydroxy-3-(2-methoxythiazol-5-yl)indolin-2-one

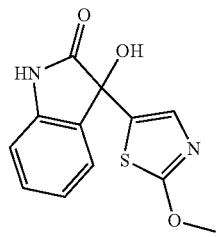

[Chem. 38]

The title compound is prepared in 68% yield (122 mg, a pale yellow amorphous) in a similar manner to Intermediate-3 using 2-methoxythiazole (157 mg, 1.36 mmol) in place of 2-bromo-5-methylpyridine.

$^1$H-NMR (400 MHz, DMSO-$d_6$) delta 10.50 (1H, s), 7.38 (1H, d, J=6.9 Hz), 7.30 (1H, ddd, J=7.8, 7.8, 1.4 Hz), 7.06 (1H, ddd, J=7.8, 7.3, 0.9 Hz), 6.90-6.88 (2H, m), 6.64 (1H, s), 3.97 (3H, s).

Intermediate-25

3-cyclopentyl-3-hydroxyindolin-2-one

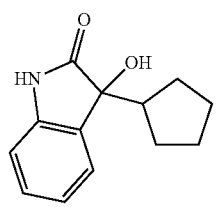

[Chem. 39]

To a solution of indoline-2,3-dione (50 mg, 0.180 mmol) in THF (0.90 mL) is added cyclopentylmagnesium bromide 1 M in THF (0.27 mL, 0.27 mmol) at 0° C., and stirred at room temperature for 1 hour. The mixture is diluted with 28% aqueous ammonia solution, followed by extraction with EtOAc. The organic layer is dried over sodium sulfate, filtered and concentrated. The residue is purified by column chromatography on silica-gel eluting with 0-20% EtOAc in n-hexane to give 43 mg (quantitative yield) of the title compound as an orange solid.

MS (ESI) m/z: 218.0 (M+H)$^+$.

$^1$H-NMR (400 MHz, DMSO-$d_6$) delta 10.16 (1H, s), 7.26 (1H, d, J=6.8 Hz), 7.18 (1H, ddd, J=6.8, 6.8, 1.6 Hz), 6.93 (1H, ddd, J=7.2, 7.2, 0.8 Hz), 6.77 (1H, d, J=7.2 Hz), 2.10-1.95 (1H, m), 1.95-1.30 (8H, m), OH proton is not observed.

Intermediate-26

3-hydroxy-3-phenethylindolin-2-one

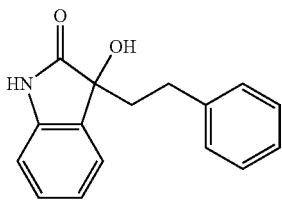

[Chem. 40]

A mixture of 3-hydroxy-3-(phenylethynyl)indolin-2-one (20 mg, 0.080 mmol) and 10% palladium on carbon (2 mg) in EtOAc (1 mL) is stirred at room temperature for 1 day under hydrogen atmosphere. The mixture is filtered through a pad of celite, washed with EtOAc, and the filtrate is concentrated to give 20 mg (quantitative yield) of the title compound as an off-white solid.

MS (ESI) m/z: 254.0 (M+H)$^+$.

Intermediate-27

5-chloro-2-(difluoromethyl)-N-((1r,4r)-4-((2,3-dioxoindolin-1-yl)methyl)cyclohexyl) nicotinamide

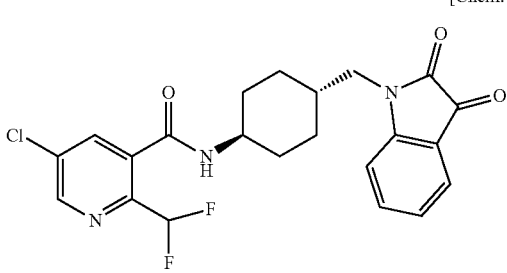

[Chem. 41]

<Step-1>: spiro[indoline-3,2'-[1,3]dioxolan]-2-one

A suspension of indoline-2,3-dione (3.00 g, 20.4 mmol), ethylene glycol (5.69 mL, 102 mmol), and p-toluenesulfonic acid (3.88 g, 20.4 mmol) in toluene (100 mL) is stirred for 7 hours. After removal of solvent, the residue is purified by column chromatography on silica-gel eluting with 0-100% EtOAc in n-hexane to give 750 mg (19% yield) of the title compound as an orange solid.

MS (ESI) m/z: 192.0 (M+H)$^+$.

$^1$H-NMR (400 MHz, CDCl$_3$) delta 7.52 (1H, brs), 7.35 (1H, d, J=7.8 Hz), 7.30 (1H, ddd, J=7.8, 7.8, 1.1 Hz), 7.06 (1H, ddd, J=7.8, 7.8, 1.1 Hz), 6.80 (1H, d, J=7.8 Hz), 4.65-4.47 (2H, m), 4.40-4.24 (2H, m).

<Step-2>: 5-chloro-2-(difluoromethyl)-N-((1r,4r)-4-((2-oxospiro[indoline-3,2'-[1,3]dioxolan]-1-yl)methyl)cyclohexyl)nicotinamide A mixture of ((1r,4r)-4-(5-chloro-2-(difluoromethyl)nicotinamido)cyclohexyl)methyl methanesulfonate (1.00 g, 2.52 mmol, Intermediate-B), spiro[indoline-3,2'-[1,3]dioxolan]-2-one (0.482 g, 2.52 mmol, Step-1 of Intermediate-27), and cesium carbonate (2.46 g, 7.56 mmol) in NMP (17 mL) is stirred at 80° C. for 11 hours. The mixture is diluted with water, followed by extraction with EtOAc. The organic layer is dried over sodium sulfate, filtered and concentrated. The residue is purified by column chromatography on silica-gel eluting with 0-100% EtOAc in n-hexane to give 0.99 g (80% yield) of the title compound as an orange solid.

MS (ESI) m/z: 491.8 (M+H)$^+$.

$^1$H-NMR (400 MHz, CDCl$_3$) delta 8.64 (1H, d, J=2.4 Hz), 7.92 (1H, d, J=2.4 Hz), 7.39-7.31 (2H, m), 7.09 (1H, ddd, J=7.6, 7.6, 0.8 Hz), 6.85 (1H, t, J=54.4 Hz), 6.79 (1H, d, J=7.6 Hz), 5.85 (1H, brd, J=8.4 Hz), 4.61-4.55 (2H, m), 4.34-4.31 (2H, m), 3.95-3.92 (1H, m), 3.48 (2H, d, J=7.2 Hz), 2.16-2.11 (2H, m), 1.87-1.82 (2H, m), 1.80-1.75 (1H, m), 1.30-1.13 (4H, m).

<Step-3>: 5-chloro-2-(difluoromethyl)-N-((1r,4r)-4-((2,3-dioxoindolin-1-yl)methyl)cyclohexyl)nicotinamide A solution of 5-chloro-2-(difluoromethyl)-N-((1r,4r)-4-((2,3-dioxoindolin-1-yl)methyl)cyclohexyl)nicotinamide (990 mg, 2.01 mmol, Step-2 of Intermediate-27) in MeOH (10 mL)/concentrated hydrochloric acid (3 mL) is stirred at 70° C. for 3 hours. The mixture is diluted with water to afford an orange precipitate. The precipitate is collected by filtration and washed with water and diisopropyl ether. The cake is dried in vacuo to give 700 mg (78% yield) of the title compound as an orange solid.

MS (ESI) m/z: 447.8 (M+H)$^+$.

$^1$H-NMR (400 MHz, CDCl$_3$) delta 8.64 (1H, d, J=1.6 Hz), 7.93 (1H, d, J=1.6 Hz), 7.63-7.57 (2H, m), 7.13 (1H, dd, J=7.6, 7.6 Hz), 6.89 (1H, d, J=8.0 Hz), 6.84 (1H, t, J=54.8 Hz), 5.87 (1H, brd, J=8.0 Hz), 4.00-3.90 (1H, m), 3.59 (2H, d, J=6.8 Hz), 2.19-2.14 (2H, m), 1.90-1.85 (3H, m), 1.33-1.17 (4H, m).

Intermediate-28

3-(2,3-difluorophenyl)-3-hydroxyindolin-2-one

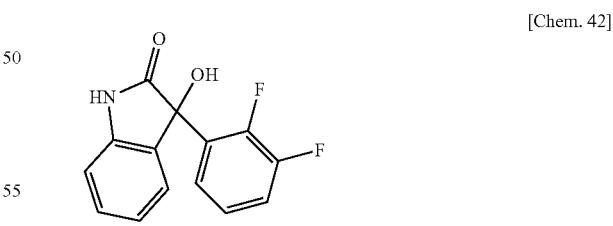

[Chem. 42]

The title compound is prepared in 74% yield (132 mg, a pale yellow amorphous) in a similar manner to Intermediate-3 using 1,2-difluorobenzene (163 mg, 1.43 mmol) in place of 2-bromo-5-methylpyridine.

$^1$H-NMR (400 MHz, CDCl$_3$) delta 7.64 (1H, dddd, J=7.8, 6.4, 1.8, 1.8 Hz), 7.42 (1H, brs), 7.31 (1H, ddd, J=7.8, 7.8, 1.4 Hz), 7.20-7.17 (2H, m), 7.15 (1H, d, J=6.9 Hz), 7.04 (1H, ddd, J=7.8, 7.3, 0.9 Hz), 6.95 (1H, d, J=8.2 Hz), 3.12 (1H, s).

Intermediate-29

3-(2-fluoro-6-methoxyphenyl)-3-hydroxyindolin-2-one

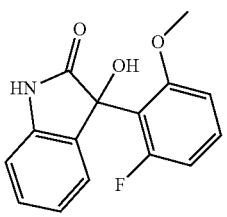

[Chem. 43]

The title compound is prepared in 52% yield (96 mg, a pale yellow amorphous) in a similar manner to Intermediate-3 using 1-fluoro-3-methoxybenzene (180 mg, 1.43 mmol) in place of 2-bromo-5-methylpyridine.

$^1$H-NMR (400 MHz, CDCl$_3$) delta 7.65 (1H, brs), 7.30 (1H, d, J=7.3 Hz), 7.27-7.21 (2H, m), 6.98 (1H, ddd, J=7.8, 7.3, 0.9 Hz), 6.89 (1H, d, J=7.8 Hz), 6.78 (1H, d, J=8.2 Hz), 6.72 (1H, ddd, J=11.0, 8.2, 0.9 Hz), 5.33 (1H, brs), 3.91 (3H, s).

Intermediate-30

3-(2,4-difluorophenyl)-3-hydroxyindolin-2-one

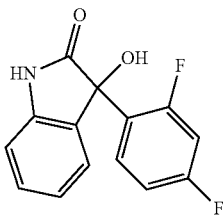

[Chem. 44]

The title compound is prepared in 44% yield (78 mg, a pale yellow amorphous) in a similar manner to Intermediate-4 using 1-bromo-2,4-difluorobenzene (275 mg, 1.43 mmol) in place of 6-bromo-3-fluoro-2-methylpyridine.

$^1$H-NMR (400 MHz, DMSO-d$_6$) delta 10.52 (1H, s), 7.93 (1H, ddd, J=9.1, 8.7, 6.9 Hz), 7.25-7.16 (2H, m), 7.09 (1H, ddd, J=11.4, 9.1, 2.7 Hz), 6.93-6.86 (4H, m).

Intermediate-31

3-(2-fluoro-4-methoxyphenyl)-3-hydroxyindolin-2-one

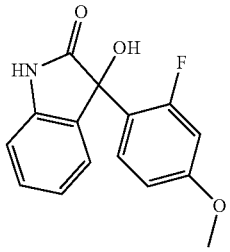

[Chem. 45]

The title compound is prepared in 79% yield (147 mg, a pale yellow amorphous) in a similar manner to Intermediate-4 using 1-bromo-2-fluoro-4-methoxybenzene (293 mg, 1.43 mmol) in place of 6-bromo-3-fluoro-2-methylpyridine.

$^1$H-NMR (400 MHz, CDCl$_3$) delta 7.72 (1H, brs), 7.72 (1H, dd, J=9.1, 8.7 Hz), 7.27 (1H, ddd, J=7.8, 7.8, 1.4 Hz), 7.16 (1H, d, J=6.9 Hz), 7.02 (1H, ddd, J=7.8, 7.3, 0.9 Hz), 6.92 (1H, d, J=7.8 Hz), 6.76 (1H, dd, J=8.7, 1.8 Hz), 6.54 (1H, dd, J=12.8, 2.7 Hz), 3.78 (3H, s), 3.26 (1H, s).

Intermediate-32

3-(5-chloro-6-methoxypyridin-2-yl)-3-hydroxyindolin-2-one

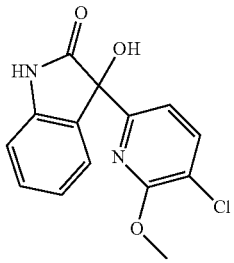

[Chem. 46]

The title compound is prepared in 85% yield (167 mg, a pale yellow amorphous) in a similar manner to Intermediate-4 using 6-bromo-3-chloro-2-methoxypyridine (302 mg, 1.36 mmol) in place of 6-bromo-3-fluoro-2-methylpyridine.

$^1$H-NMR (400 MHz, CDCl$_3$) delta 7.91 (1H, brs), 7.57 (1H, d, J=7.8 Hz), 7.32 (1H, ddd, J=7.8, 7.8, 1.4 Hz), 7.19 (1H, d, J=6.9 Hz), 7.07 (1H, ddd, J=7.8, 7.3, 0.9 Hz), 6.94 (1H, d, J=7.8 Hz), 6.60 (1H, d, J=7.8 Hz), 5.40 (1H, s), 4.11 (3H, s).

Intermediate-33

3-hydroxy-3-(4-methylthiazol-2-yl)indolin-2-one

[Chem. 47]

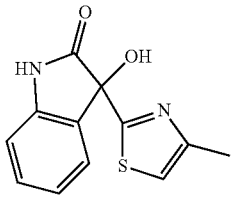

The title compound is prepared in 85% yield (142 mg, a pale yellow amorphous) in a similar manner to Intermediate-3 using 4-methylthiazole (135 mg, 1.36 mmol) in place of 2-bromo-5-methylpyridine.

$^1$H-NMR (400 MHz, CDCl$_3$) delta 7.37-7.32 (2H, m), 7.30 (1H, brs), 7.10 (1H, ddd, J=7.8, 7.3, 0.9 Hz), 6.94 (1H, d, J=7.8 Hz), 6.88 (1H, d, J=0.9 Hz), 4.33 (1H, s), 2.43 (3H, d, J=0.9 Hz).

Intermediate-34

3-(2,5-difluorophenyl)-3-hydroxyindolin-2-one

[Chem. 48]

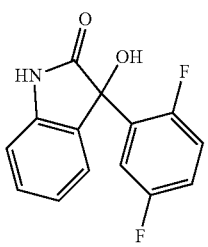

The title compound is prepared in 86% yield (153 mg, a pale yellow amorphous) in a similar manner to Intermediate-4 using 2-bromo-1,4-difluorobenzene (275 mg, 1.43 mmol) in place of 6-bromo-3-fluoro-2-methylpyridine.

$^1$H-NMR (400 MHz, CDCl$_3$) delta 7.62 (1H, ddd, J=9.1, 5.9, 3.2 Hz), 7.43 (1H, brs), 7.31 (1H, ddd, J=7.8, 7.8, 1.4 Hz), 7.15 (1H, d, J=6.9 Hz), 7.04 (1H, ddd, J=7.8, 7.3, 0.9 Hz), 7.01-6.89 (3H, m), 3.09 (1H, d, J=0.9 Hz).

Intermediate-35

4-fluoro-3-(3-hydroxy-2-oxoindolin-3-yl)benzonitrile

[Chem. 49]

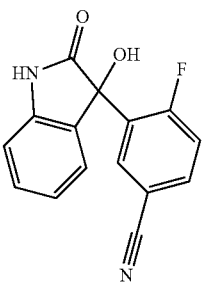

The title compound is prepared in 73% yield (133 mg, a pale yellow amorphous) in a similar manner to Intermediate-4 using 3-bromo-4-fluorobenzonitrile (285 mg, 1.43 mmol) in place of 6-bromo-3-fluoro-2-methylpyridine.

$^1$H-NMR (400 MHz, CDCl$_3$) delta 8.29 (1H, dd, J=6.9, 2.3 Hz), 7.66 (1H, ddd, J=8.2, 4.6, 1.8 Hz), 7.51 (1H, brs), 7.33 (1H, ddd, J=7.8, 7.8, 1.4 Hz), 7.11 (1H, d, J=6.9 Hz), 7.09 (1H, dd, J=10.1, 8.2 Hz), 7.05 (1H, ddd, J=7.8, 7.3, 0.9 Hz), 6.97 (1H, d, J=7.8 Hz), 3.18 (1H, s).

Intermediate-36

3-(2,6-difluorophenyl)-3-hydroxyindolin-2-one

[Chem. 50]

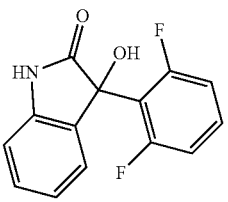

The title compound is prepared in 81% yield (143 mg, a pale yellow amorphous) in a similar manner to Intermediate-4 using 2-bromo-1,3-difluorobenzene (275 mg, 1.43 mmol) in place of 6-bromo-3-fluoro-2-methylpyridine.

$^1$H-NMR (400 MHz, DMSO-d$_6$) delta 10.48 (1H, s), 7.41-7.33 (1H, m), 7.23 (1H, ddd, J=7.8, 7.8, 1.4 Hz), 7.17 (1H, d, J=7.3 Hz), 7.04 (2H, dd, J=10.1, 8.2 Hz), 6.91 (1H, ddd, J=7.8, 7.8, 0.9 Hz), 6.86 (1H, d J=7.8 Hz), 6.75 (1H, s).

Intermediate-37

3-(3-fluoro-2-methoxy-6-methylpyridin-4-yl)-3-hydroxyindolin-2-one

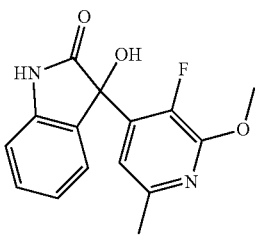

[Chem. 51]

The title compound is prepared in 89% yield (174 mg, a pale yellow amorphous) in a similar manner to Intermediate-3 using 3-fluoro-2-methoxy-6-methylpyridine (201 mg, 1.43 mmol) in place of 2-bromo-5-methylpyridine.

$^1$H-NMR (400 MHz, CDCl$_3$) delta 7.56 (1H, brs), 7.30 (1H, ddd J=7.8, 7.8, 1.4 Hz), 7.18-7.15 (2H, m), 7.02 (1H, ddd, J=7.8, 7.3, 0.9 Hz), 6.93 (1H, d, J=8.2 Hz), 3.93 (3H, s), 3.18 (1H, s), 2.47 (3H, d, J=0.9 Hz).

Intermediate-38

3-(2-fluoro-3-methylphenyl)-3-hydroxyindolin-2-one

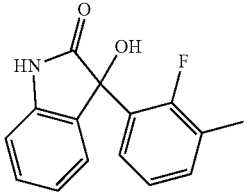

[Chem. 52]

To a cooled solution (−78° C.) of 1-bromo-2-fluoro-3-methylbenzene (270 mg, 1.43 mmol) in diethyl ether (3 mL) is added n-BuLi solution 2.3 M in THF (0.62 mL, 1.43 mmol) dropwise. The mixture is stirred at −78° C. for 30 min. A solution of indoline-2,3-dione (100 mg, 0.68 mmol) in THF (2 mL) is added and the mixture is slowly warmed to 0° C. during a period of 2 hours. The mixture is diluted with saturated aqueous ammonium chloride solution (20 mL) and the mixture is extracted with EtOAc (20 mL×2). The combined organic layers are washed with brine (20 mL), dried over Na$_2$SO$_4$, filtered and concentrated in vacuo. The crude material is purified by silica gel column chromatography (n-hexane/EtOAc) to give 3-(2-fluoro-3-methylphenyl)-3-hydroxyindolin-2-one (98 mg, 56% yield) as a pale yellow amorphous.

$^1$H-NMR (400 MHz, CDCl$_3$) delta 7.69 (1H, ddd, J=7.3, 7.3, 2.7 Hz), 7.46 (1H, brs), 7.29 (1H, ddd, J=7.8, 7.8, 1.4 Hz), 7.18-7.11 (3H, m), 7.02 (1H, ddd, J=7.5, 7.5, 0.9 Hz), 6.94 (1H, d, J=7.8 Hz), 3.10 (1H, d, J=1.4 Hz), 2.17 (3H, d, J=2.3 Hz).

Intermediate-39

3-(3-fluoro-2-methoxypyridin-4-yl)-3-hydroxyindolin-2-one

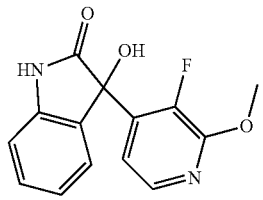

[Chem. 53]

The title compound is prepared in 97% yield (181 mg, a pale yellow amorphous) in a similar manner to Intermediate-3 using 3-fluoro-2-methoxypyridine (181 mg, 1.43 mmol) in place of 2-bromo-5-methylpyridine.

$^1$H-NMR (400 MHz, CDCl$_3$) delta 8.01 (1H, d, J=5.5 Hz), 7.56 (1H, brs), 7.38 (1H, dd, J=5.5, 4.6 Hz), 7.31 (1H, ddd, J=7.8, 7.8, 1.4 Hz), 7.15 (1H, d, J=6.9 Hz), 7.03 (1H, ddd, J=7.8, 7.8, 0.9 Hz), 6.94 (1H, d, J=7.8 Hz), 3.96 (3H, s), 3.23 (1H, d, J=0.9 Hz).

Intermediate-40

3-(2-fluoro-3-methoxyphenyl)-3-hydroxyindolin-2-one

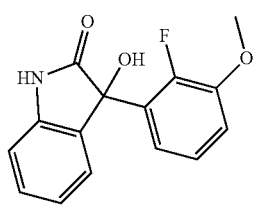

[Chem. 54]

The title compound is prepared in 20% yield (37 mg, a pale yellow amorphous) in a similar manner to Intermediate-4 using 1-bromo-2-fluoro-3-methoxybenzene (293 mg, 1.43 mmol) in place of 6-bromo-3-fluoro-2-methylpyridine.

$^1$H-NMR (400 MHz, CDCl$_3$) delta 7.47 (1H, brs), 7.43 (1H, ddd, J=8.2, 6.4, 1.8 Hz), 7.27 (1H, ddd, J=7.8, 7.8, 1.4 Hz), 7.19-7.13 (2H, m), 7.02-6.91 (3H, m), 3.82 (3H, s), 3.12 (1H, s).

Intermediate-41

3-(3-chloro-2-fluorophenyl)-3-hydroxyindolin-2-one

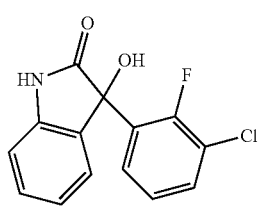

[Chem. 55]

The title compound is prepared in 47% yield (89 mg, a pale yellow amorphous) in a similar manner to Intermediate-3 using 1-bromo-3-chloro-2-fluorobenzene (299 mg, 1.43 mmol) in place of 2-bromo-5-methylpyridine.

$^1$H-NMR (400 MHz, CDCl$_3$) delta 7.82 (1H, ddd, J=8.2, 6.9, 1.4 Hz), 7.41-7.36 (2H, m), 7.31 (1H, ddd, J=7.8, 7.8, 1.4 Hz), 7.21 (1H, ddd, J=8.2, 7.8, 1.4 Hz), 7.12 (1H, dd, J=6.9, 0.9 Hz), 7.03 (1H, ddd, J=7.8, 0.9 Hz), 6.95 (1H, d, J=7.8 Hz), 3.06 (1H, s).

Intermediate-42

3-(3,4-difluorophenyl)-3-hydroxyindolin-2-one

[Chem. 56]

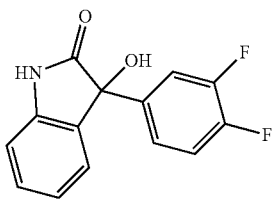

<Step-1>: tert-butyl 3-(3,4-difluorophenyl)-1H-indole-1-carboxylate

A mixture of tert-butyl 3-bromo-1H-indole-1-carboxylate (500 mg, 1.69 mmol), (3,4-difluorophenyl)boronic acid (400 mg, 2.53 mmol), and bis(di-tert-butyl(4-dimethylaminophenyl)phosphine)dichloropalladium (II) (69 mg, 0.085 mmol) in 1,4-dioxane (2.5 mL)/saturated aqueous sodium bicarbonate (2.5 mL) is stirred at 80° C. for 1 hour. The mixture is extracted with EtOAc. The organic layer is concentrated. The residue is purified by column chromatography on silica-gel eluting with 0-20% EtOAc in n-hexane to give 621 mg (quantitative yield) of the title compound as a colorless syrup.

MS (ESI) m/z: 329.9 (M+H)$^+$.

$^1$H-NMR (400 MHz, CDCl$_3$) delta 8.21 (1H, d, J=8.2 Hz), 7.73 (1H, d, J=7.3 Hz), 7.66 (1H, s), 7.42 (1H, ddd, J=11.3, 7.7, 2.2 Hz), 7.39-7.35 (1H, m), 7.35-7.27 (1H, m), 7.28-7.19 (2H, m), 1.69 (9H, s).

<Step-2>: tert-butyl 3-(3,4-difluorophenyl)-3-hydroxy-2-oxoindoline-1-carboxylate A solution of tert-butyl 3-(3,4-difluorophenyl)-1H-indole-1-carboxylate (50 mg, 0.15 mmol, Step-1 of Intermediate-42) and [bis(trifluoroacetoxy)iodo]benzene (163 mg, 0.380 mmol) in 2,2,2-trifluoroethanol (2 mL)/water (0.7 mL) is stirred at room temperature for 1 hour. The mixture is diluted with EtOAc and saturated aqueous sodium bicarbonate. The separated organic layer is washed with saturated aqueous sodium thiosulfate and brine, dried over sodium sulfate, filtered and concentrated. The residue is purified by column chromatography on silica-gel eluting with EtOAc in n-hexane to give 27 mg (49% yield) of the title compound as a colorless gum.

MS (ESI) m/z: 361.9 (M+H)$^+$.

$^1$H-NMR (400 MHz, CDCl$_3$) delta 7.95 (1H, d, J=8.4 Hz), 7.44 (1H, ddd, J=8.4, 7.2, 1.6 Hz), 7.31-7.22 (3H, m), 7.15-7.08 (1H, m), 7.05-7.01 (1H, m), 1.63 (9H, s), OH proton is not observed.

<Step-3>: 3-(3,4-difluorophenyl)-3-hydroxyindolin-2-one

A mixture of tert-butyl 3-(3,4-difluorophenyl)-3-hydroxy-2-oxoindoline-1-carboxylate (25 mg, 0.07 mmol, Step-2 of Intermediate-42) and hydrogen chloride solution 4 M in 1,4-dioxane (1 mL) is stirred at room temperature for 2 hours. The mixture is diluted with saturated aqueous sodium bicarbonate, followed by extraction with EtOAc. The organic layer is dried over sodium sulfate, filtered and concentrated to give 22 mg (quantitative yield) of the title compound as a beige solid.

MS (ESI) m/z: 261.8 (M+H)$^+$.

$^1$H-NMR (400 MHz, DMSO-d$_6$) delta 10.49 (1H, s), 7.39-7.32 (2H, m), 7.28 (1H, td, J=7.6, 1.2 Hz), 7.13 (1H, d, J=6.8 Hz), 6.99 (1H, td, J=7.6, 1.2 Hz), 6.94-6.90 (2H, m), 6.84 (1H, brs).

Intermediate-43

3-(3-(difluoromethyl)phenyl)-3-hydroxyindolin-2-one

[Chem. 57]

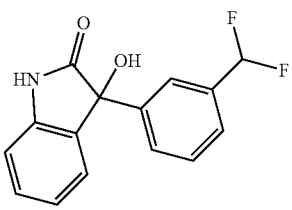

The title compound is prepared in 84% yield (157 mg, a pale yellow amorphous) in a similar manner to Intermediate-3 using 1-bromo-3-(difluoromethyl)benzene (295 mg, 1.43 mmol) in place of 2-bromo-5-methylpyridine.

$^1$H-NMR (400 MHz, DMSO-d$_6$) delta 10.47 (1H, s), 7.54 (1H, s), 7.49-7.44 (2H, m), 7.36 (1H, brd, J=6.9 Hz), 7.28 (1H, ddd, J=7.8, 7.8, 1.4 Hz), 7.11 (1H, d, J=7.3 Hz), 7.04 (1H, t, J=56.0 Hz), 6.99 (1H, dd, J=7.8, 7.3 Hz), 6.92 (1H, d, J=7.3 Hz), 6.79 (1H, s).

Intermediate-44

3-(2-fluoro-3-(trifluoromethyl)phenyl)-3-hydroxyindolin-2-one

[Chem. 58]

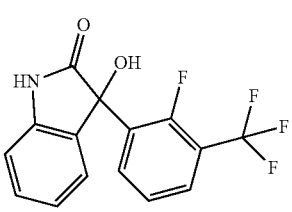

The title compound is prepared in 75% yield (159 mg, a yellow solid) in a similar manner to Intermediate-4 using 1-bromo-2-fluoro-3-(trifluoromethyl)benzene (347 mg, 1.43 mmol) in place of 6-bromo-3-fluoro-2-methylpyridine.

¹H-NMR (400 MHz, CDCl₃) delta 8.17 (1H, ddd, J=7.5, 7.5, 1.8 Hz), 7.60 (1H, ddd, J=7.3, 7.3, 1.4 Hz), 7.42 (1H, brs), 7.37 (1H, dd, J=7.8, 7.8 Hz), 7.32 (1H, ddd, J=7.8, 7.8, 1.4 Hz), 7.12 (1H, dd, J=8.2, 0.9 Hz), 7.04 (1H, ddd, J=7.3, 7.3, 0.9 Hz), 6.96 (1H, d, J=8.2 Hz), 3.09 (1H, s).

Intermediate-45

2-fluoro-3-(3-hydroxy-2-oxoindolin-3-yl)benzonitrile

[Chem. 59]

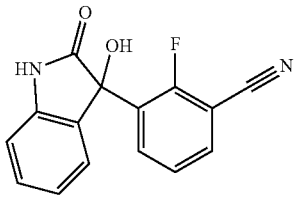

The title compound is prepared in 45% yield (82 mg, a yellow solid) in a similar manner to Intermediate-3 using 3-bromo-2-fluorobenzonitrile (285 mg, 1.43 mmol) in place of 2-bromo-5-methylpyridine.

¹H-NMR (400 MHz, CDCl₃) delta 8.22 (1H, ddd, J=7.8, 7.8, 1.8 Hz), 7.62 (1H, ddd, J=7.8, 5.9, 1.8 Hz), 7.44 (1H, s), 7.39 (1H, dd, J=7.8, 7.8 Hz), 7.34 (1H, ddd, J=7.8, 7.8, 1.4 Hz), 7.10 (1H, d, J=5.9 Hz), 7.05 (1H, ddd, J=7.8, 7.8, 0.9 Hz), 6.98 (1H, d, J=7.8 Hz), 3.06 (1H, s).

Intermediate-46

3-(3-(1,1-difluoroethyl)phenyl)-3-hydroxyindolin-2-one

[Chem. 60]

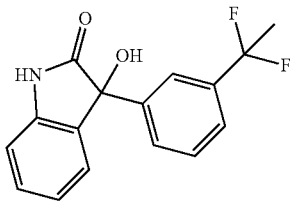

The title compound is prepared in 85% yield (167 mg, a pale yellow amorphous) in a similar manner to Intermediate-3 using 1-bromo-3-(1,1-difluoroethyl)benzene (315 mg, 1.43 mmol) in place of 2-bromo-5-methylpyridine.

¹H-NMR (400 MHz, CDCl₃) delta 7.64 (1H, s), 7.59 (1H, s), 7.47-7.39 (3H, m), 7.32 (1H, ddd, J=7.8, 7.8, 1.4 Hz), 7.25 (1H, s), 7.09 (1H, ddd, J=7.8, 7.8, 0.9 Hz), 6.96 (1H, d, J=7.8 Hz), 3.20 (1H, s), 1.90 (3H, t, J=18.3 Hz).

Intermediate-47

3-hydroxy-3-(3-(methylthio)phenyl)indolin-2-one

[Chem. 61]

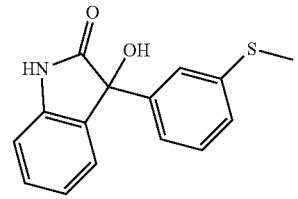

The title compound is prepared in 81% yield (149 mg, a pale yellow amorphous) in a similar manner to Intermediate-3 using (3-bromophenyl)(methyl)sulfane (290 mg, 1.43 mmol) in place of 2-bromo-5-methylpyridine.

¹H-NMR (400 MHz, DMSO-d₆) delta 10.41 (1H, s), 7.28-7.22 (3H, m), 7.18-7.15 (1H, m), 7.10 (1H, brd, J=6.9 Hz), 6.97 (1H, ddd, J=7.3, 7.3, 0.9 Hz), 6.91-6.89 (2H, m), 6.67 (1H, s), 2.44 (3H, s).

Intermediate-48

3-(2-fluoro-5-methoxyphenyl)-3-hydroxyindolin-2-one

[Chem. 62]

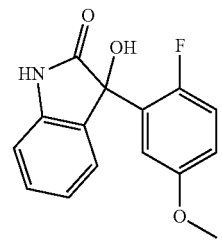

The title compound is prepared in 82% yield (153 mg, a pale yellow amorphous) in a similar manner to Intermediate-3 using 2-bromo-1-fluoro-4-methoxybenzene (293 mg, 1.43 mmol) in place of 2-bromo-5-methylpyridine.

¹H-NMR (400 MHz, CDCl₃) delta 7.54 (1H, brs), 7.42 (1H, dd, J=5.9, 3.2 Hz), 7.29 (1H, ddd, J=7.8, 7.8, 1.4 Hz), 7.16 (1H, dd, J=7.3, 1.4 Hz), 7.02 (1H, ddd, J=7.8, 7.3, 0.9 Hz), 6.93 (1H, d, J=7.8 Hz), 6.88 (1H, dd, J=10.1, 9.1 Hz), 6.80 (1H, ddd, J=9.1, 4.1, 3.2 Hz), 3.84 (3H, s), 3.18 (1H, d, J=1.4 Hz).

Intermediate-49

3-(3-fluoro-4-methoxypyridin-2-yl)-3-hydroxyindolin-2-one

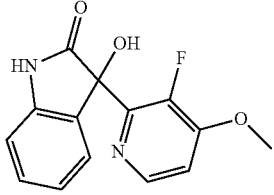

[Chem. 63]

The title compound is prepared in 59% yield (109 mg, a pale yellow amorphous) in a similar manner to Intermediate-3 using 3-fluoro-4-methoxypyridine (181 mg, 1.43 mmol) in place of 2-bromo-5-methylpyridine.

$^1$H-NMR (400 MHz, CDCl$_3$) delta 8.32 (1H, d, J=5.5 Hz), 7.54 (1H, brs), 7.54 (1H, ddd, J=7.8, 7.8, 1.4 Hz), 7.06 (1H, dd, J=7.3, 1.4 Hz), 7.00 (1H, ddd, J=7.8, 7.8, 0.9 Hz), 6.96 (1H, dd, J=5.5, 5.5 Hz), 6.91 (1H, d, J=7.8 Hz), 6.69 (1H, s), 3.90 (3H, s).

Intermediate-50

3-hydroxy-3-(quinolin-2-yl)indolin-2-one

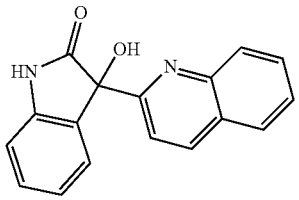

[Chem. 64]

To a solution of 2-bromoquinoline (212 mg, 1.02 mmol) in THF (1 mL) is added n-BuLi solution 1.6 M in hexane (0.70 mL, 1.12 mmol) at 0° C., and stirred for 3 hours. To the mixture is added indoline-2,3-dione (75 mg, 0.51 mmol) at 0° C., and stirred for 3 hours. The mixture is diluted with saturated aqueous ammonium chloride, followed by extraction with EtOAc. The organic layer is dried over sodium sulfate, filtered and concentrated. The residue is purified by column chromatography on silica-gel eluting with 0-100% EtOAc in n-hexane to give 141 mg (quantitative yield) of the title compound as a yellow solid.

$^1$H-NMR (400 MHz, DMSO-d$_6$) delta 8.32 (1H, br), 8.21 (1H, dd, J=8.0, 0.8 Hz), 8.08 (1H, d, J=8.0 Hz), 7.83-7.77 (2H, m), 7.59 (1H, ddd, J=7.6, 6.8, 1.6 Hz), 7.31 (1H, td, J=7.6, 1.6 Hz), 7.14-7.10 (2H, m), 7.04 (1H, dd, J=7.6, 0.8 Hz), 6.98 (1H, d, J=8.0 Hz), 6.76 (1H, d, J=8.8 Hz).

MS (ESI) m/z: 276.9 (M+H)$^+$.

Intermediate-51

3-hydroxy-3-(isoquinolin-1-yl)indolin-2-one

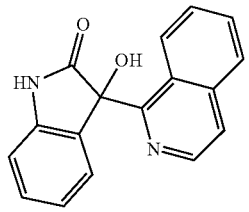

[Chem. 65]

The title compound is prepared in quantitative yield (141 mg, a yellow solid) in a similar manner to Intermediate-50 using 1-bromoisoquinoline (212 mg, 1.02 mmol) in place of 2-bromoquinoline.

$^1$H-NMR (400 MHz, DMSO-d$_6$) delta 8.91 (1H, brs), 8.57 (1H, d, J=6.0 Hz), 7.86 (1H, d, J=8.4 Hz), 7.76 (1H, d, J=5.6 Hz), 7.62 (1H, t, J=7.2 Hz), 7.45 (1H, d, J=8.8 Hz), 7.37 (1H, t, J=7.2 Hz), 7.31-7.27 (1H, m), 7.03 (1H, d, J=7.6 Hz), 7.00-6.90 (2H, m), OH proton is not observed.

MS (ESI) m/z: 276.9 (M+H)$^+$.

Intermediate-52

7-fluoro-3-(5-fluoropyridin-2-yl)-3-hydroxyindolin-2-one

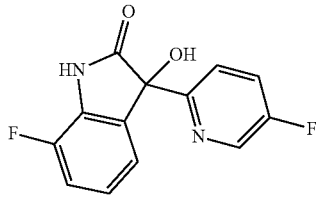

[Chem. 66]

The title compound is prepared in 53% yield (72 mg, an orange solid) in a similar manner to Intermediate-4 using 2-bromo-5-fluoropyridine (199 mg, 1.13 mmol) and 7-fluoroindoline-2,3-dione (85 mg, 0.515 mmol) in place of 6-bromo-3-fluoro-2-methylpyridine and indoline-2,3-dione.

MS (ESI) m/z: 262.9 (M+H)$^+$.

$^1$H-NMR (400 MHz, CDCl$_3$) delta 10.94 (1H, s), 8.38 (1H, d, J=3.2 Hz), 7.91 (1H, dd, J=8.8, 4.8 Hz), 7.81 (1H, td, J=8.8, 3.2 Hz), 7.13 (1H, ddd, J=10.4, 8.4, 1.2 Hz), 7.07 (1H, s), 6.91 (1H, td, J=7.6, 4.8 Hz), 6.84 (1H, dd, J=7.6, 1.2 Hz).

Intermediate-53

6-fluoro-3-(5-fluoropyridin-2-yl)-3-hydroxyindolin-2-one

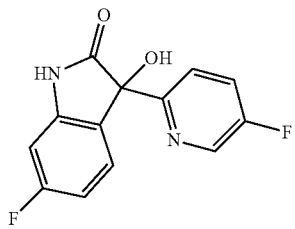

[Chem. 67]

The title compound is prepared in 53% yield (72 mg, an orange solid) in a similar manner to Intermediate-4 using 2-bromo-5-fluoropyridine (199 mg, 1.13 mmol) and 6-fluoroindoline-2,3-dione (85 mg, 0.515 mmol) in place of 6-bromo-3-fluoro-2-methylpyridine and indoline-2,3-dione.

MS (ESI) m/z: 262.9 (M+H)$^+$.

$^1$H-NMR (400 MHz, DMSO-d$_6$) delta 10.23 (1H, s), 8.34 (1H, d, J=2.8 Hz), 7.87 (1H, dd, J=8.8, 4.0 Hz), 7.76 (1H, ddd, J=8.8, 8.8, 2.8 Hz), 6.96 (1H, dd, J=8.8, 5.6 Hz), 6.92 (1H, s), 6.67-6.62 (2H, m).

Intermediate-54

5-fluoro-3-(5-fluoropyridin-2-yl)-3-hydroxyindolin-2-one

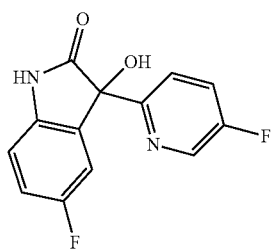

[Chem. 68]

The title compound is prepared in 32% yield (44 mg, a yellow solid) in a similar manner to Intermediate-4 using 2-bromo-5-fluoropyridine (199 mg, 1.13 mmol) and 5-fluoroindoline-2,3-dione (85 mg, 0.515 mmol) in place of 6-bromo-3-fluoro-2-methylpyridine and indoline-2,3-dione.

MS (ESI) m/z: 262.9 (M+H)$^+$.

$^1$H-NMR (400 MHz, DMSO-d$_6$) delta 10.43 (1H, s), 8.37 (1H, d, J=2.8 Hz), 7.91 (1H, dd, J=8.8, 4.8 Hz), 7.80 (1H, ddd, J=8.8, 8.8, 2.8 Hz), 7.06-7.01 (2H, m), 6.88-6.82 (2H, m).

Intermediate-55

4-fluoro-3-(5-fluoropyridin-2-yl)-3-hydroxyindolin-2-one

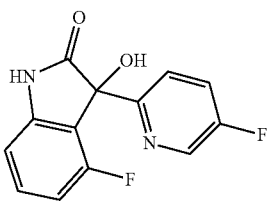

[Chem. 69]

The title compound is prepared in 41% yield (55 mg, a yellow solid) in a similar manner to Intermediate-4 using 2-bromo-5-fluoropyridine (199 mg, 1.13 mmol) and 4-fluoroindoline-2,3-dione (85 mg, 0.515 mmol) in place of 6-bromo-3-fluoro-2-methylpyridine and indoline-2,3-dione.

MS (ESI) m/z: 262.9 (M+H)$^+$.

$^1$H-NMR (400 MHz, DMSO-d$_6$) delta 10.56 (1H, s), 8.37 (1H, d, J=2.8 Hz), 7.90 (1H, dd, J=8.8, 4.4 Hz), 7.79 (1H, ddd, J=8.8, 8.8, 2.8 Hz), 6.99 (1H, d, J=8.8, 5.6 Hz), 6.95 (1H, s), 6.70-6.64 (2H, m).

Intermediate-56

7-fluoro-3-(2-fluorophenyl)-3-hydroxyindolin-2-one

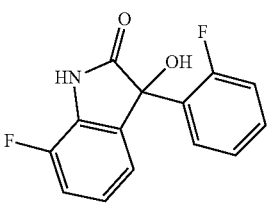

[Chem. 70]

The title compound is prepared in 68% yield (107 mg, a yellow solid) in a similar manner to Intermediate-3 using 1-fluoro-2-iodobenzene (336 mg, 1.51 mmol) and 7-fluoroindoline-2,3-dione (100 mg, 0.606 mmol) in place of 2-bromo-5-methylpyridine and indoline-2,3-dione.

MS (ESI) m/z: 262.0 (M+H)$^+$.

$^1$H-NMR (400 MHz, DMSO-d$_6$) delta 11.02 (1H, s), 7.89 (1H, ddd, J=7.6, 7.6, 1.6 Hz), 7.38-7.26 (2H, m), 7.13 (1H, ddd, J=10.8, 8.8, 1.2 Hz), 7.03 (1H, ddd, J=9.6, 8.0, 1.2 Hz), 6.96 (1H, s), 6.88 (1H, ddd, J=8.8, 8.8, 4.8 Hz), 6.74 (1H, dd, J=7.2, 1.2 Hz).

Intermediate-57

6-fluoro-3-(2-fluorophenyl)-3-hydroxyindolin-2-one

[Chem. 71]

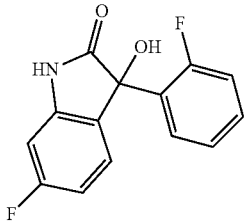

The title compound is prepared in 74% yield (117 mg, a yellow solid) in a similar manner to Intermediate-3 using 1-fluoro-2-iodobenzene (336 mg, 1.51 mmol) and 6-fluoroindoline-2,3-dione (100 mg, 0.606 mmol) in place of 2-bromo-5-methylpyridine and indoline-2,3-dione.

MS (ESI) m/z: 262.0 (M+H)$^+$.

$^1$H-NMR (400 MHz, DMSO-$d_6$) delta 10.64 (1H, brs), 7.88 (1H, ddd, J=8.0, 8.0, 2.0 Hz), 7.36-7.30 (1H, m), 7.28 (1H, ddd, J=7.2, 7.2, 1.2 Hz), 7.02 (1H, ddd, J=11.2, 8.0, 1.2 Hz), 6.89 (1H, dd, J=8.4, 6.0 Hz), 6.83 (1H, s), 6.68-6.62 (2H, m).

Intermediate-58

7-fluoro-3-(3-fluoropyridin-4-yl)-3-hydroxyindolin-2-one

[Chem. 72]

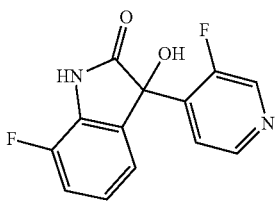

The title compound is prepared in 63% yield (101 mg, a yellow solid) in a similar manner to Intermediate-7 using 7-fluoroindoline-2,3-dione (100 mg, 0.606 mmol) in place of indoline-2,3-dione.

MS (ESI) m/z: 263.0 (M+H)$^+$.

$^1$H-NMR (400 MHz, DMSO-$d_6$) delta 11.22 (1H, s), 8.55 (1H, d, J=4.8 Hz), 8.43 (1H, d, J=2.0 Hz), 7.92 (1H, dd, J=7.2, 5.2 Hz), 7.19 (1H, dd, J=8.4, 8.4 Hz), 6.95-6.89 (1H, m), 6.81 (1H, d, J=7.2 Hz), OH proton is not observed.

Intermediate-59

6-fluoro-3-(3-fluoropyridin-4-yl)-3-hydroxyindolin-2-one

[Chem. 73]

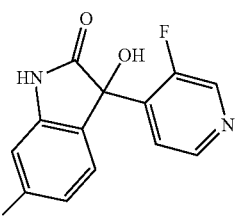

The title compound is prepared in 61% yield (96 mg, a yellow solid) in a similar manner to Intermediate-7 using 6-fluoroindoline-2,3-dione (100 mg, 0.606 mmol) in place of indoline-2,3-dione.

MS (ESI) m/z: 262.9 (M+H)$^+$.

$^1$H-NMR (400 MHz, DMSO-$d_6$) delta 10.84 (1H, s), 8.55 (1H, dd, J=4.8, 1.2 Hz), 8.42 (1H, d, J=2.4 Hz), 7.91 (1H, dd, J=6.8, 4.8 Hz), 6.98 (1H, dd, J=8.4, 5.6 Hz), 6.75-6.65 (2H, m), OH proton is not observed.

Intermediate-60

5-fluoro-3-(3-fluoropyridin-4-yl)-3-hydroxyindolin-2-one

[Chem. 74]

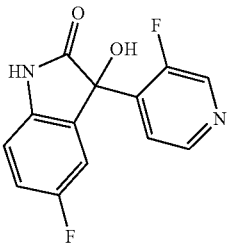

The title compound is prepared in 22% yield (35 mg, a yellow solid) in a similar manner to Intermediate-7 using 5-fluoroindoline-2,3-dione (100 mg, 0.606 mmol) in place of indoline-2,3-dione.

MS (ESI) m/z: 262.9 (M+H)$^+$.

$^1$H-NMR (400 MHz, DMSO-$d_6$) delta 10.72 (1H, s), 8.57 (1H, d, J=4.8 Hz), 8.45 (1H, d, J=2.4 Hz), 7.92 (1H, dd, J=6.4, 4.8 Hz), 7.09 (1H, ddd, J=8.8, 8.8, 2.4 Hz), 6.91-6.84 (2H, m), OH proton is not observed.

Intermediate-61

4-fluoro-3-(3-fluoropyridin-4-yl)-3-hydroxyindolin-2-one

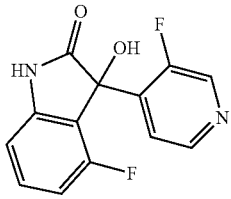
[Chem. 75]

The title compound is prepared in 24% yield (39 mg, a yellow solid) in a similar manner to Intermediate-7 using 4-fluoroindoline-2,3-dione (100 mg, 0.606 mmol) in place of indoline-2,3-dione.

MS (ESI) m/z: 262.9 (M+H)$^+$.

$^1$H-NMR (400 MHz, DMSO-d$_6$) delta 10.84 (1H, s), 8.54 (1H, d, J=4.8 Hz), 8.42 (1H, d, J=2.4 Hz), 7.91 (1H, dd, J=6.4, 4.8 Hz), 6.97 (1H, dd, J=7.6, 5.2 Hz), 6.73-6.66 (2H, m), OH proton is not observed.

Intermediate-62

3-(5-fluoropyridin-2-yl)-3-hydroxy-6-(trifluoromethyl)indolin-2-one

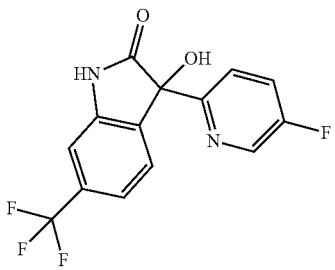
[Chem. 76]

The title compound is prepared in 46% yield (66 mg, a yellow solid) in a similar manner to Intermediate-4 using 2-bromo-5-fluoropyridine (180 mg, 1.02 mmol) and 6-(trifluoromethyl)indoline-2,3-dione (100 mg, 0.465 mmol) in place of 6-bromo-3-fluoro-2-methylpyridine and indoline-2,3-dione.

MS (ESI) m/z: 312.9 (M+H)$^+$.

$^1$H-NMR (400 MHz, DMSO-d$_6$) delta 10.72 (1H, s), 8.38 (1H, d, J=3.2 Hz), 7.94 (1H, dd, J=8.8, 4.4, Hz), 7.82 (1H, ddd, J=8.8, 8.8, 3.2 Hz), 7.26 (1H, d, J=8.0 Hz), 7.20 (1H, d, J=7.6 Hz), 7.15 (1H, s), 7.09 (1H, s).

Intermediate-63

3-(5-fluoropyridin-2-yl)-3-hydroxy-6-(trifluoromethoxy)indolin-2-one

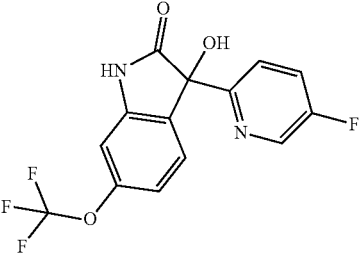
[Chem. 77]

The title compound is prepared in 38% yield (58 mg, a yellow solid) in a similar manner to Intermediate-4 using 2-bromo-5-fluoropyridine (180 mg, 1.02 mmol) and 6-(trifluoromethoxy)indoline-2,3-dione (107 mg, 0.465 mmol) in place of 6-bromo-3-fluoro-2-methylpyridine and indoline-2,3-dione.

MS (ESI) m/z: 328.9 (M+H)$^+$.

$^1$H-NMR (400 MHz, DMSO-d$_6$) delta 10.63 (1H, s), 8.38 (1H, d, J=2.8 Hz), 7.92 (1H, dd, J=8.8, 4.4 Hz), 7.81 (1H, ddd, J=8.8, 8.8, 2.8 Hz), 7.09 (1H, d, J=7.6 Hz), 7.05 (1H, s), 6.87-6.84 (1H, m), 6.80 (1H, s).

Intermediate-64

3-(2-fluorophenyl)-3-hydroxy-6-(trifluoromethyl)indolin-2-one

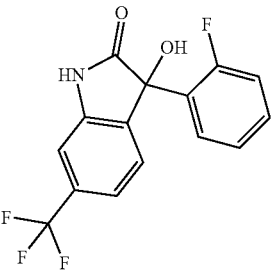
[Chem. 78]

The title compound is prepared in 53% yield (77 mg, an off-white solid) in a similar manner to Intermediate-3 using 1-fluoro-2-iodobenzene (258 mg, 1.16 mmol) and 6-(trifluoromethyl)indoline-2,3-dione (100 mg, 0.465 mmol) in place of 2-bromo-5-methylpyridine and indoline-2,3-dione.

MS (ESI) m/z: 310.1 (M−H)$^-$.

$^1$H-NMR (400 MHz, DMSO-d$_6$) delta 10.83 (1H, s), 7.94 (1H, ddd, J=7.8, 7.8, 2.3 Hz), 7.43-7.33 (1H, m), 7.30 (1H, ddd, J=7.4, 7.4, 1.2 Hz), 7.24 (1H, brd, J=7.8 Hz), 7.13 (1H, d, J=7.8 Hz), 7.11 (1H, s), 7.06-7.01 (1H, m), 7.05 (1H, s).

Intermediate-65

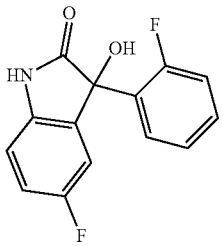

[Chem. 79]

The title compound is prepared in 73% yield (115 mg, a yellow solid) in a similar manner to Intermediate-3 using 1-fluoro-2-iodobenzene (336 mg, 1.51 mmol) and 5-fluoroindoline-2,3-dione (100 mg, 0.606 mmol) in place of 2-bromo-5-methylpyridine and indoline-2,3-dione.

MS (ESI) m/z: 262.0 (M+H)$^+$.

$^1$H-NMR (400 MHz, DMSO-d$_6$) delta 11.04 (1H, s), 7.92 (1H, ddd, J=7.6, 7.6, 1.6 Hz), 7.41-7.34 (1H, m), 7.29 (1H, ddd, J=7.6, 7.6, 1.6 Hz), 7.13 (1H, ddd, J=10.4, 8.4, 1.2 Hz), 7.05 (1H, ddd, J=12.0, 8.4, 1.2 Hz), 6.98 (1H, s), 6.91 (1H, ddd, J=7.2, 7.2, 4.4 Hz), 6.77 (1H, dd, J=7.2, 1.2 Hz).

Intermediate-66

3-(2-fluorophenyl)-3-hydroxy-1,3-dihydro-2H-pyrrolo[2,3-b]pyridin-2-one

[Chem. 80]

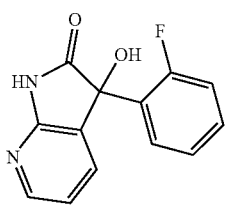

The title compound is prepared in 27% yield (22 mg, an off-white solid) in a similar manner to Intermediate-3 using 1-fluoro-2-iodobenzene (187 mg, 0.844 mmol) and 1H-pyrrolo[2,3-b]pyridine-2,3-dione (50 mg, 0.338 mmol) in place of 2-bromo-5-methylpyridine and indoline-2,3-dione.

MS (ESI) m/z: 244.9 (M+H)$^+$.

$^1$H-NMR (400 MHz, DMSO-d$_6$) delta 11.14 (1H, s), 8.08 (1H, dd, J=5.6, 2.0 Hz), 7.88 (1H, ddd, J=7.6, 7.6, 2.0 Hz), 7.39-7.32 (1H, m), 7.32-7.25 (2H, m), 7.04 (1H, ddd, J=11.6, 8.4, 1.6 Hz), 7.02 (1H, s), 6.88 (1H, dd, J=7.2, 5.6 Hz).

Intermediate-67

3-(3-fluorothiophen-2-yl)-3-hydroxyindolin-2-one

[Chem. 81]

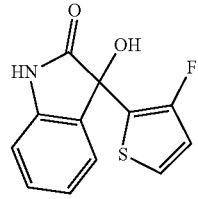

The title compound is prepared in 94% yield (225 mg, a pale yellow amorphous) in a similar manner to Intermediate-3 using 3-fluorothiophene (200 mg, 1.96 mmol) in place of 2-bromo-5-methylpyridine.

$^1$H-NMR (400 MHz, CDCl$_3$) delta 7.43 (2H, m), 7.32 (1H, ddd, J=7.8, 7.8, 1.4 Hz), 7.14 (1H, dd, J=5.5, 3.7 Hz), 7.10 (1H, ddd, J=7.8, 7.3, 0.9 Hz), 6.92 (1H, brd, J=7.8 Hz), 6.75 (1H, d, J=5.5 Hz), 3.48 (1H, d, J=0.9 Hz).

Intermediate-68

3-hydroxy-3-(4-methoxythiophen-2-yl)indolin-2-one

[Chem. 82]

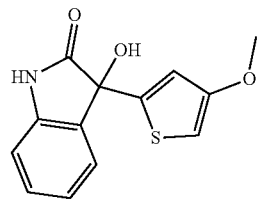

The title compound is prepared in 97% yield (173 mg, a pale yellow amorphous) in a similar manner to Intermediate-18 using 3-methoxythiophene (163 mg, 1.43 mmol) in place of 3,5-difluoropyridine.

$^1$H-NMR (400 MHz, DMSO-d$_6$) delta 10.41 (1H, s), 7.30-7.25 (2H, m), 7.01 (1H, ddd, J=7.5, 7.3, 0.9 Hz), 6.87 (1H, d, J=7.3 Hz), 6.84 (1H, s), 6.50 (1H, d, J=1.8 Hz), 6.40 (1H, d, J=1.8 Hz), 3.67 (3H, s).

Intermediate-69

3-(benzo[d]thiazol-2-yl)-3-hydroxyindolin-2-one

[Chem. 83]

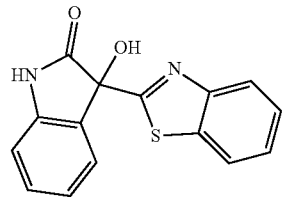

The title compound is prepared in 60% yield (115 mg, a yellow solid) in a similar manner to Intermediate-3 using benzo[d]thiazole (184 mg, 1.36 mmol) in place of 2-bromo-5-methylpyridine.

MS (ESI) m/z: 282.9 (M+H)+.

$^1$H-NMR (400 MHz, DMSO-$d_6$) delta 10.66 (1H, s), 8.13 (1H, dd, J=7.2, 1.2 Hz), 7.86 (1H, dd, J=7.2, 1.6 Hz), 7.62 (1H, s), 7.46-7.38 (2H, m), 7.28 (1H, ddd, J=7.8, 7.8, 1.4 Hz), 7.18 (1H, d, J=7.2 Hz), 7.01-6.88 (2H, m).

Intermediate-70

3-(4-fluorothiophen-2-yl)-3-hydroxyindolin-2-one

[Chem. 84]

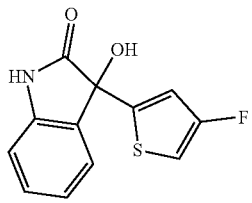

The title compound is prepared in quantitative yield (135 mg, a pale yellow amorphous) in a similar manner to Intermediate-18 using 3-fluorothiophene (100 mg, 0.98 mmol) in place of 3,5-difluoropyridine.

$^1$H-NMR (400 MHz, DMSO-$d_6$) delta 10.49 (1H, s), 7.32-7.28 (2H, m), 7.12 (1H, dd, J=1.8, 1.4 Hz), 7.03 (1H, dd, J=7.3, 7.3 Hz), 7.00 (1H, s), 6.89 (1H, d, J=8.7 Hz), 6.61 (1H, d, J=0.9 Hz).

Intermediate-71

3-hydroxy-3-(5-methoxythiophen-2-yl)indolin-2-one

[Chem. 85]

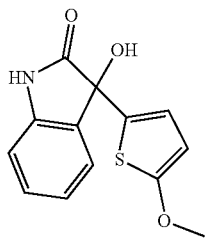

The title compound is prepared in 60% yield (106 mg, a white solid) in a similar manner to Intermediate-3 using 2-methoxythiophene (163 mg, 143 mmol) in place of 2-bromo-5-methylpyridine.

$^1$H-NMR (400 MHz, CDCl$_3$) delta 7.51 (1H, d, J=6.9 Hz), 7.36 (1H, br), 7.32 (1H, ddd, J=7.8, 7.8, 1.4 Hz), 7.14 (1H, ddd, J=7.8, 7.3, 0.9 Hz), 6.90 (1H, d, J=7.8 Hz), 6.60 (1H, d, J=4.1 Hz), 6.02 (1H, d, J=4.1 Hz), 3.86 (3H, s), 3.18 (1H, s).

Intermediate-72

3-(3-fluoropyridin-4-yl)-3-hydroxy-1,3-dihydro-2H-pyrrolo[2,3-b]pyridin-2-one

[Chem. 86]

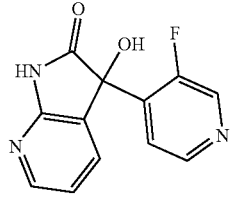

The title compound is prepared in 67% yield (57 mg, a yellow solid) in a similar manner to Intermediate-7 using 1H-pyrrolo[2,3-b]pyridine-2,3-dione (50 mg, 0.338 mmol) in place of indoline-2,3-dione.

MS (ESI) m/z: 245.9 (M+H)+.

$^1$H-NMR (400 MHz, DMSO-$d_6$) delta 11.36 (1H, s), 8.58-8.56 (2H, m), 8.44 (1H, s), 8.15 (1H, dd, J=5.0, 1.6 Hz), 7.91 (1H, dd, J=6.4, 5.0 Hz), 7.38 (1H, dd, J=7.3, 1.6 Hz), 6.95 (1H, dd, J=7.3, 5.5 Hz).

Intermediate-73

3-(2-fluorophenyl)-3-hydroxy-1,3-dihydro-2H-pyrrolo[3,2-c]pyridin-2-one

[Chem. 87]

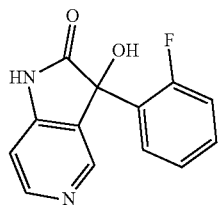

The title compound is prepared in 23% yield (19 mg, a brown gum) in a similar manner to Intermediate-3 using 1-bromo-2-fluorobenzene (124 mg, 0.709 mmol) and 1H-pyrrolo[3,2-c]pyridine-2,3-dione (50 mg, 0.338 mmol) in place of 2-bromo-5-methylpyridine and indoline-2,3-dione.

MS (ESI) m/z: 245.0 (M+H)+.

$^1$H-NMR (400 MHz, DMSO-$d_6$) delta 10.44 (1H, s), 7.89 (1H, ddd, J=7.8, 7.8, 1.6 Hz), 7.50-7.31 (1H, m), 7.26 (1H, ddd, J=7.8, 7.8, 1.6 Hz), 7.02 (1H, ddd, J=11.4, 8.0, 1.6 Hz), 6.80 (1H, d, J=8.7 Hz), 6.66 (1H, s), 6.43-6.37 (2H, m).

Intermediate-74

3-(2-fluorophenyl)-3-hydroxy-6-methoxyindolin-2-one

[Chem. 88]

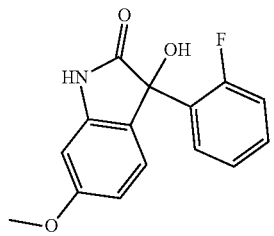

The title compound is prepared in 73% yield (112 mg, a pale yellow solid) in a similar manner to Intermediate-3 using 1-fluoro-2-iodobenzene (263 mg, 1.19 mmol) and 6-methoxyindoline-2,3-dione (100 mg, 0.564 mmol) in place of 2-bromo-5-methylpyridine and indoline-2,3-dione.

MS (ESI) m/z: 274.0 (M+H)$^+$.

$^1$H-NMR (400 MHz, DMSO-d$_6$) delta 10.49 (1H, s), 7.89 (1H, ddd, J=7.8, 7.8, 1.8 Hz), 7.39-7.30 (1H, m), 7.28 (1H, ddd, J=7.4, 7.4, 1.3 Hz), 7.02 (1H, ddd, J=11.5, 7.8, 1.3 Hz), 6.86-6.77 (1H, m), 6.65 (1H, s), 6.46-6.38 (2H, m), 3.73 (3H, s).

Intermediate-75

3-(3-fluoropyridin-4-yl)-3-hydroxy-6-methoxyindolin-2-one

[Chem. 89]

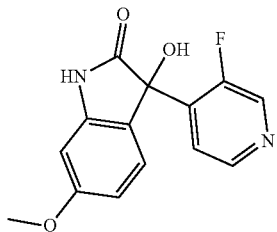

The title compound is prepared in 50% yield (78 mg, a brown solid) in a similar manner to Intermediate-7 using 6-methoxyindoline-2,3-dione (100 mg, 0.564 mmol) in place of indoline-2,3-dione.

MS (ESI) m/z: 274.9 (M+H)$^+$.

$^1$H-NMR (400 MHz, DMSO-d$_6$) delta 10.62 (1H, s), 8.54 (1H, d, J=5.2 Hz), 8.42 (1H, d, J=2.8 Hz), 7.91 (1H, dd, J=6.8, 5.2 Hz), 6.84 (1H, d, J=8.8 Hz), 6.44-6.41 (2H, m), 3.72 (3H, s), OH proton is not observed.

Intermediate-76

3-(2-fluorophenyl)-3-hydroxy-5-methoxyindolin-2-one

[Chem. 90]

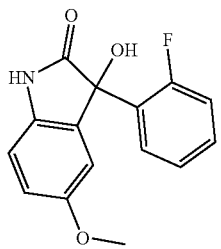

The title compound is prepared in 54% yield (83 mg, a pale yellow solid) in a similar manner to Intermediate-3 using 1-fluoro-2-iodobenzene (263 mg, 1.19 mmol) and 5-methoxyindoline-2,3-dione (100 mg, 0.564 mmol) in place of 2-bromo-5-fluoropyridine and indoline-2,3-dione.

MS (ESI) m/z: 274.1 (M+H)$^+$.

$^1$H-NMR (400 MHz, DMSO-d$_6$) delta 10.32 (1H, s), 7.90 (1H, ddd, J=7.8, 7.8, 1.8 Hz), 7.39-7.32 (1H, m), 7.28 (1H, ddd, J=7.4, 7.4, 1.2 Hz), 7.03 (1H, ddd, J=11.4, 8.0, 1.1 Hz), 6.80 (1H, s), 6.79-6.76 (2H, m), 6.48 (1H, dd, J=1.4, 1.4 Hz), 3.59 (3H, s).

Intermediate-77

3-(2-fluorophenyl)-3-hydroxy-7-methoxyindolin-2-one

[Chem. 91]

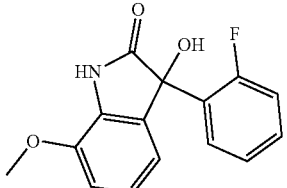

The title compound is prepared in 49% yield (76 mg, a pale yellow solid) in a similar manner to Intermediate-3 using 1-fluoro-2-iodobenzene (313 mg, 1.41 mmol) and 7-methoxyindoline-2,3-dione (100 mg, 0.564 mmol) in place of 2-bromo-5-methylpyridine and indoline-2,3-dione.

MS (ESI) m/z: 274.0 (M+H)$^+$.

$^1$H-NMR (400 MHz, DMSO-d$_6$) delta 10.52 (1H, s), 7.90 (1H, ddd, J=8.2, 8.2, 2.1 Hz), 7.39-7.31 (1H, m), 7.29 (1H, ddd, J=7.3, 7.3, 1.4 Hz), 7.02 (1H, ddd, J=11.4, 8.2, 1.4 Hz), 6.97-6.90 (2H, m), 6.88-6.81 (1H, m), 6.52 (1H, d, J=7.3 Hz), 3.84-3.82 (3H, m).

Intermediate-78

3-(3-fluoropyridin-4-yl)-3-hydroxy-7-methoxyindolin-2-one

[Chem. 92]

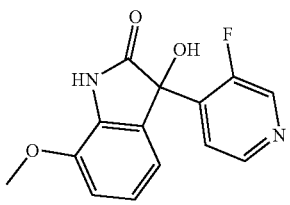

The title compound is prepared in 36% yield (66 mg, a pale yellow solid) in a similar manner to Intermediate-7 using 7-methoxyindoline-2,3-dione (100 mg, 0.564 mmol) in place of indoline-2,3-dione.

MS (ESI) m/z: 274.9 (M+H)$^+$.

Intermediate-79

6-fluoro-3-(5-fluoro-2-methoxypyridin-4-yl)-3-hydroxyindolin-2-one

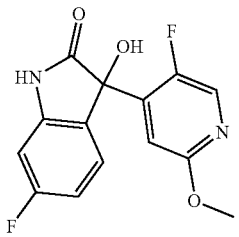

[Chem. 93]

The title compound is prepared in 79% yield (70 mg, a yellow solid) in a similar manner to Intermediate-3 using 5-fluoro-2-methoxypyridine (169 mg, 1.33 mmol) and 6-fluoroindoline-2,3-dione (100 mg, 0.606 mmol) in place of 2-bromo-5-methylpyridine and indoline-2,3-dione.

MS (ESI) m/z: 292.9 (M+H)$^+$.

$^1$H-NMR (400 MHz, DMSO-d$_6$) delta 10.82 (1H, s), 7.98 (1H, d, J=2.3 Hz), 7.23 (1H, d, J=5.0 Hz), 7.13 (1H, s), 7.03 (1H, dd, J=8.2, 5.5 Hz), 6.77-6.67 (2H, m), 3.86 (3H, s).

Intermediate-80

3-(2,3-difluorophenyl)-6-fluoro-3-hydroxyindolin-2-one

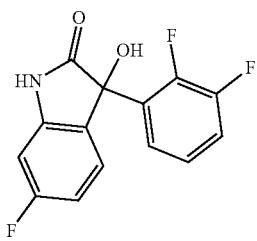

[Chem. 94]

The title compound is prepared in 98% yield (166 mg, an off-white solid) in a similar manner to Intermediate-3 using 1,2-difluorobenzene (1.52 mg, 1.33 mmol) and 6-fluoroindoline-2,3-dione (100 mg, 0.606 mmol) in place of 2-bromo-5-methylpyridine and indoline-2,3-dione.

MS (ESI) m/z: 280.0 (M+H)$^+$.

$^1$H-NMR (400 MHz, DMSO-d$_6$) delta 10.77 (1H, s), 7.74-7.65 (1H, m), 7.46-7.36 (1H, m), 7.35-7.27 (1H, m), 7.03 (1H, s), 6.97 (1H, dd, J=8.2, 5.5 Hz), 6.79-6.65 (2H, m).

Intermediate-81

3-(3-chloro-2-fluorophenyl)-6-fluoro-3-hydroxyindolin-2-one

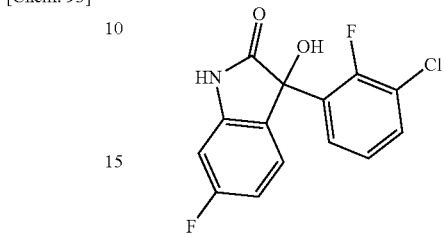

[Chem. 95]

The title compound is prepared in 73% yield (131 mg, an off-white solid) in a similar manner to Intermediate-3 using 1-bromo-3-chloro-2-fluorobenzene (279 mg, 1.33 mmol) and 6-fluoroindoline-2,3-dione (100 mg, 0.606 mmol) in place of 2-bromo-5-methylpyridine and indoline-2,3-dione.

MS (ESI) m/z: 312.9 (M+NH$_4$)$^+$.

$^1$H-NMR (400 MHz, DMSO-d$_6$) delta 10.77 (1H, s), 7.87 (1H, ddd, J=7.5, 7.5, 1.5 Hz), 7.55 (1H, ddd, J=7.5, 7.5, 1.5 Hz), 7.35 (1H, ddd, J=8.2, 8.2, 0.9 Hz), 7.05 (1H, s), 6.96 (1H, dd, J=8.2, 5.5 Hz), 6.74-6.66 (2H, m).

Intermediate-82

3-(2,5-difluorophenyl)-6-fluoro-3-hydroxyindolin-2-one

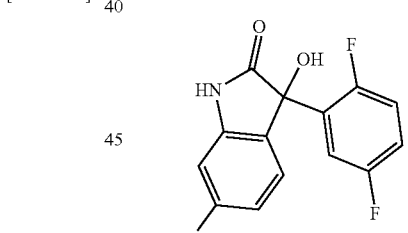

[Chem. 96]

The title compound is prepared in 52% yield (88 mg, a yellow solid) in a similar manner to Intermediate-4 using 2-bromo-1,4-difluorobenzene (257 mg, 1.33 mmol) and 6-fluoroindoline-2,3-dione (100 mg, 0.606 mmol) in place of 6-bromo-3-fluoro-2-methylpyridine and indoline-2,3-dione.

MS (ESI) m/z: 280.0 (M+H)$^+$.

$^1$H-NMR (400 MHz, DMSO-d$_6$) delta 10.72 (1H, brs), 7.67-7.55 (1H, m), 7.26-7.16 (1H, m), 7.16-7.08 (1H, m), 7.03 (1H, s), 6.99 (1H, dd, J=7.8, 5.5 Hz), 6.78-6.64 (2H, m).

Intermediate-83

3-(5-chloropyridin-2-yl)-6-fluoro-3-hydroxyindolin-2-one

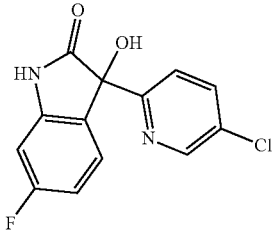

[Chem. 97]

The title compound is prepared in 32% yield (54 mg, a brown gum) in a similar manner to Intermediate-4 using 2-bromo-5-chloropyridine (256 mg, 1.33 mmol) and 6-fluoroindoline-2,3-dione (100 mg, 0.606 mmol) in place of 6-bromo-3-fluoro-2-methylpyridine and indoline-2,3-dione.

MS (ESI) m/z: 279.0 (M+H)$^+$.

$^1$H-NMR (400 MHz, DMSO-d$_6$) delta 10.59 (1H, s), 8.42 (1H, dd, J=2.8, 1.2 Hz), 8.01 (1H, dd, J=8.5, 2.8 Hz), 7.87 (1H, dd, J=8.5, 1.2 Hz), 7.06-6.92 (2H, m), 6.78-6.58 (2H, m).

Intermediate-84

3-(2-fluorophenyl)-3-hydroxy-4-methoxyindolin-2-one

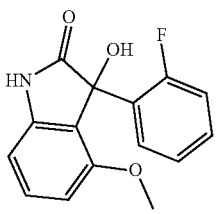

[Chem. 98]

The title compound is prepared in 9% yield (14 mg, an orange solid) in a similar manner to Intermediate-3 using 1-fluoro-2-iodobenzene (263 mg, 1.19 mmol) and 4-methoxyindoline-2,3-dione (100 mg, 0.564 mmol) in place of 2-bromo-5-methylpyridine and indoline-2,3-dione.

MS (ESI) m/z: 274.1 (M+H)$^+$.

$^1$H-NMR (400 MHz, DMSO-d$_6$) delta 10.41 (1H, s), 7.91 (1H, ddd, J=8.0, 8.0, 1.8 Hz), 7.33-7.24 (1H, m), 7.23 (1H, ddd, J=7.8, 7.8, 1.4 Hz), 7.18 (1H, dd, J=8.0, 8.0 Hz), 6.97 (1H, ddd, J=11.4, 7.8, 1.4 Hz), 6.60-6.40 (3H, m), 3.51 (3H, s).

Intermediate-85

3-(2,3-difluorophenyl)-3-hydroxy-1,3-dihydro-2H-pyrrolo[2,3-b]pyridin-2-one

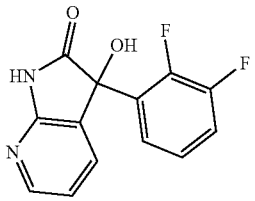

[Chem. 99]

The title compound is prepared in 59% yield (52 mg, an off-white solid) in a similar manner to Intermediate-3 using 1,2-difluorobenzene (96 mg, 0.844 mmol) and 1H-pyrrolo[2,3-b]pyridine-2,3-dione (50 mg, 0.338 mmol) in place of 2-bromo-5-methylpyridine and indoline-2,3-dione.

MS (ESI) m/z: 263.2 (M+H)$^+$.

$^1$H-NMR (400 MHz, DMSO-d$_6$) delta 11.27 (1H, s), 8.14 (1H, dd, J=5.3, 1.6 Hz), 7.76-7.65 (1H, m), 7.49-7.38 (1H, m), 7.38-7.28 (2H, m), 7.21 (1H, s), 6.94 (1H, dd, J=7.3, 5.5 Hz).

Intermediate-86

3-(2,5-difluorophenyl)-3-hydroxy-1,3-dihydro-2H-pyrrolo[2,3-b]pyridin-2-one

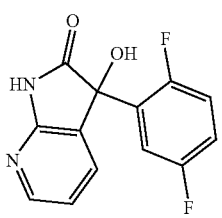

[Chem. 100]

The title compound is prepared in 64% yield (57 mg, an off-white solid) in a similar manner to Intermediate-3 using 2-bromo-1,4-difluorobenzene (163 mg, 0.844 mmol) and 1H-pyrrolo[2,3-b]pyridine-2,3-dione (50 mg, 0.388 mmol) in place of 2-bromo-5-methylpyridine and indoline-2,3-dione.

MS (ESI) m/z: 263.2 (M+H)$^+$.

$^1$H-NMR (400 MHz, DMSO-d$_6$) delta 11.24 (1H, s), 8.12 (1H, dd, J=5.5, 1.8 Hz), 7.66-7.60 (1H, m), 7.37 (1H, dd, J=7.3, 1.8 Hz), 7.29-7.22 (1H, m), 7.21 (1H, s), 7.16 (1H, dd, J=10.3, 4.3 Hz), 6.93 (1H, dd, J=7.3, 5.5 Hz).

Intermediate-87

3-(2,3-difluorophenyl)-5-fluoro-3-hydroxyindolin-2-one

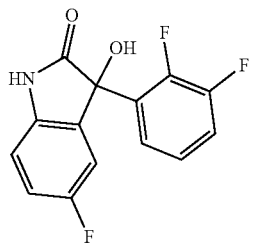

[Chem. 101]

The title compound is prepared in 63% yield (106 mg, an off-white solid) in a similar manner to Intermediate-3 using 1,2-difluorobenzene (69 mg, 1.33 mmol) and 5-fluoroindoline-2,3-dione (100 mg, 0.606 mmol) in place of 2-bromo-5-methylpyridine and indoline-2,3-dione.

MS (ESI) m/z: 280.2 (M+H)$^+$.

Intermediate-88

5-fluoro-3-(5-fluoro-2-methoxypyridin-4-yl)-3-hydroxyindolin-2-one

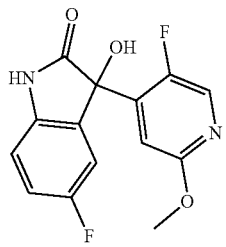

[Chem. 102]

The title compound is prepared in 58% yield (102 mg, a yellow solid) in a similar manner to Intermediate-3 using 5-fluoro-2-methoxypyridine (169 mg, 1.33 mmol) and 5-fluoroindoline-2,3-dione (100 mg, 0.606 mmol) in place of 2-bromo-5-methylpyridine and indoline-2,3-dione.

MS (ESI) m/z: 292.9 (M+H)$^+$.

Intermediate-89

3-(5-chloropyridin-2-yl)-5-fluoro-3-hydroxyindolin-2-one

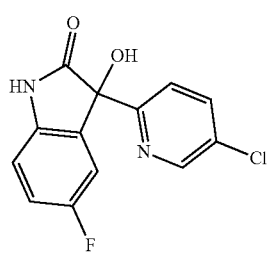

[Chem. 103]

The title compound is prepared in 50% yield (85 mg, a brown gum) in a similar manner to Intermediate-4 using 2-bromo-5-chloropyridine (256 mg, 1.33 mmol) and 5-fluoroindoline-2,3-dione (100 mg, 0.606 mmol) in place of 6-bromo-3-fluoro-2-methylpyridine and indoline-2,3-dione.

MS (ESI) m/z: 279.0 (M+H)$^+$.

Intermediate-90

3-(2,5-difluorophenyl)-5-fluoro-3-hydroxyindolin-2-one

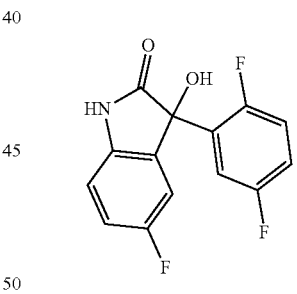

[Chem. 104]

The title compound is prepared in 46% yield (77 mg, a yellow solid) in a similar manner to Intermediate-4 using 2-bromo-1,4-difluorobenzene (257 mg, 1.33 mmol) and 5-fluoroindoline-2,3-dione (100 mg, 0.606 mmol) in place of 6-bromo-3-fluoro-2-methylpyridine and indoline-2,3-dione.

MS (ESI) m/z: 280.2 (M+H)$^+$.

$^1$H-NMR (400 MHz, DMSO-d$_6$) delta 10.60 (1H, s), 7.64 (1H, ddd, J=8.8, 5.6, 3.2 Hz), 7.24-7.17 (1H, m), 7.17-7.11 (1H, m), 7.12 (1H, s), 7.11-6.99 (1H, m), 6.90-6.78 (2H, m).

Intermediate-91

3-(2-fluoro-5-(trifluoromethyl)phenyl)-3-hydroxyindolin-2-one

[Chem. 105]

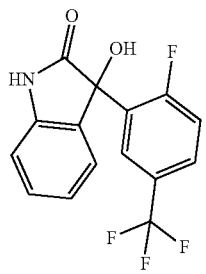

The title compound is prepared in 60% yield (127 mg, a pale yellow solid) in a similar manner to Intermediate-3 using 1-fluoro-4-(trifluoromethyl)benzene (229 mg, 1.39 mmol) in place of 2-bromo-5-methylpyridine.

$^1$H-NMR (400 MHz, CDCl$_3$) delta 8.26 (1H, dd, J=6.9, 2.3 Hz), 7.63-7.59 (2H, m), 7.32 (1H, ddd, J=7.8, 7.8, 1.4 Hz), 7.13-7.02 (3H, m), 6.96 (1H, d, J=7.8 Hz), 3.34 (1H, s).

Intermediate-92

3-hydroxy-3-(2,3,5-trifluorophenyl)indolin-2-one

[Chem. 106]

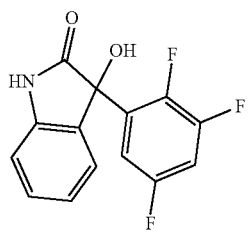

The title compound is prepared in 86% yield (164 mg, a pale yellow amorphous) in a similar manner to Intermediate-4 using 1-bromo-2,3,5-trifluorobenzene (294 mg, 1.39 mmol) in place of 6-bromo-3-fluoro-2-methylpyridine.

$^1$H-NMR (400 MHz, CDCl$_3$) delta 7.51 (1H, brs), 7.48-7.43 (1H, m), 7.33 (1H, ddd, J=7.8, 7.8, 1.4 Hz), 7.14 (1H, brd, J=7.3 Hz), 7.05 (1H, ddd, J=7.8, 7.3, 0.9 Hz), 6.96 (1H, d, J=8.2 Hz), 6.93-6.88 (1H, m), 3.26 (1H, s).

Intermediate-93

3-(5-chloro-2-fluorophenyl)-3-hydroxyindolin-2-one

[Chem. 107]

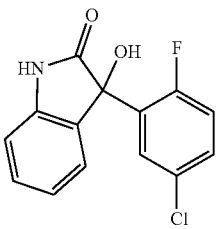

The title compound is prepared in 90% yield (169 mg, a pale yellow solid) in a similar manner to Intermediate-3 using 1-chloro-4-fluorobenzene (182 mg, 1.39 mmol) in place of 2-bromo-5-methylpyridine.

$^1$H-NMR (400 MHz, DMSO-d$_6$) delta 10.58 (1H, s), 7.88 (1H, dd, J=5.9, 1.8 Hz), 7.45-7.41 (1H, m), 7.23 (1H, dd, J=7.8, 7.3 Hz), 7.23 (1H, dd, J=10.5, 9.1 Hz), 7.00 (1H, d, J=1.4 Hz), 6.97 (1H, d, J=7.3 Hz), 6.92-6.87 (2H, m).

Intermediate-94

3-(2,3-difluoro-4-methoxyphenyl)-3-hydroxyindolin-2-one

[Chem. 108]

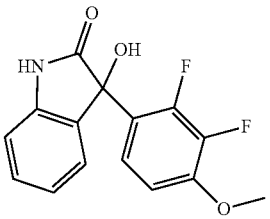

The title compound is prepared in 64% yield (127 mg, a pale yellow amorphous) in a similar manner to Intermediate-4 using 1-bromo-2,3-difluoro-4-methoxybenzene (311 mg, 1.39 mmol) in place of 6-bromo-3-fluoro-2-methylpyridine.

$^1$H-NMR (400 MHz, DMSO-d$_6$) delta 10.54 (1H, s), 7.60 (1H, ddd, J=8.7, 8.7, 2.3 Hz), 7.23 (1H, ddd, J=7.8, 7.3, 1.8 Hz), 7.11 (1H, ddd, J=8.5, 8.5, 1.8 Hz), 7.09-6.86 (4H, m), 3.88 (3H, s).

Intermediate-95

3-(5-chloropyridin-2-yl)-4-fluoro-3-hydroxyindolin-2-one

[Chem. 109]

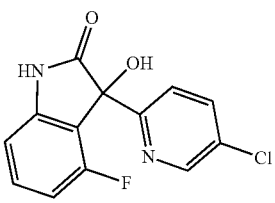

The title compound is prepared in 21% yield (36 mg, a brown solid) in a similar manner to Intermediate-4 using 2-bromo-5-chloropyridine (256 mg, 1.33 mmol) and 4-fluoroindoline-2,3-dione (100 mg, 0.606 mmol) in place of 6-bromo-3-fluoro-2-methylpyridine and indoline-2,3-dione.
MS (ESI) m/z: 279.0 (M+H)$^+$.

Intermediate-96

7-chloro-3-(2-fluorophenyl)-3-hydroxyindolin-2-one

[Chem. 110]

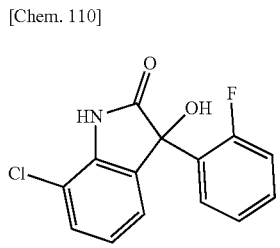

The title compound is prepared in 35% yield (54 mg, a black solid) in a similar manner to Intermediate-4 using 1-fluoro-2-iodobenzene (269 mg, 1.21 mmol) and 7-chloroindoline-2,3-dione (100 mg, 0.551 mmol) in place of 6-bromo-3-fluoro-2-methylpyridine and indoline-2,3-dione.
MS (ESI) m/z: 276.3 (M−H)$^−$.

Intermediate-97

3-(2-fluorophenyl)-3-hydroxy-5-methylindolin-2-one

[Chem. 111]

The title compound is prepared in 63% yield (100 mg, a red solid) in a similar manner to Intermediate-3 using 1-fluoro-2-iodobenzene (303 mg, 1.37 mmol) and 5-methylindoline-2,3-dione (100 mg, 0.621 mmol) in place of 2-bromo-5-methylpyridine and indoline-2,3-dione.
MS (ESI) m/z: 258.0 (M+H)$^+$.

Intermediate-98

3-(5-fluoropyridin-2-yl)-3-hydroxy-6-methylindolin-2-one

[Chem. 112]

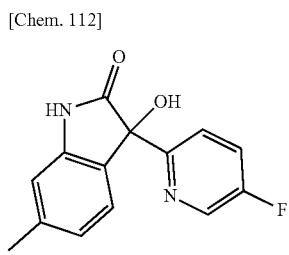

The title compound is prepared in 19% yield (30 mg, an off-white solid) in a similar manner to Intermediate-4 using 2-bromo-5-fluoropyridine (240 mg, 1.37 mmol) and 6-methylindoline-2,3-dione (100 mg, 0.621 mmol) in place of 6-bromo-3-fluoro-2-methylpyridine and indoline-2,3-dione.
MS (ESI) m/z: 259.1 (M+H)$^+$.
$^1$H-NMR (400 MHz, DMSO-d$_6$) delta 10.34 (1H, s), 8.35 (1H, d, J=2.7 Hz), 7.88 (1H, dd, J=8.7, 4.6 Hz), 7.77 (1H, ddd, J=8.7, 8.7, 2.7 Hz), 6.84 (1H, d, J=7.6 Hz), 6.82 (1H, s), 6.68 (1H, d, J=7.6 Hz), 6.66 (1H, s), 2.26 (3H, s).

Intermediate-99

3-(2-fluorophenyl)-3-hydroxy-6-methylindolin-2-one

[Chem. 113]

The title compound is prepared in 28% yield (45 mg, an orange solid) in a similar manner to Intermediate-3 using 1-fluoro-2-iodobenzene (303 mg, 1.37 mmol) and 6-methylindoline-2,3-dione (100 mg, 0.621 mmol) in place of 2-bromo-5-methylpyridine and indoline-2,3-dione.
MS (ESI) m/z: 258.1 (M+H)$^+$.

Intermediate-100

3-(3-fluoropyridin-4-yl)-3-hydroxy-6-methylindolin-2-one

[Chem. 114]

The title compound is prepared in 21% yield (34 mg, a brown solid) in a similar manner to Intermediate-7 using 6-methylindoline-2,3-dione (100 mg, 0.621 mmol) in place of indoline-2,3-dione.

MS (ESI) m/z: 259.1 (M+H)+.

$^1$H-NMR (400 MHz, DMSO-$d_6$) delta 10.63 (1H, s), 8.55 (1H, d, J=5.0 Hz), 8.41 (1H, d, J=2.3 Hz), 7.92 (1H, dd, J=6.4, 5.0 Hz), 6.83 (1H, d, J=7.8 Hz), 6.74-6.67 (2H, m), 2.27 (3H, s), OH proton is not observed.

Intermediate-101

1-(((1r,4r)-4-aminocyclohexyl)methyl)-3-(2,5-difluorophenyl)-3-hydroxyindolin-2-one

[Chem. 115]

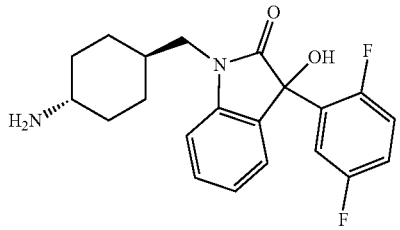

<Step-1>: tert-butyl ((1r,4r)-4-((3-(2,5-difluorophenyl)-3-hydroxy-2-oxoindolin-1-yl)methyl)cyclohexyl)carbamate To a mixture of ((1r,4r)-4-((tert-butoxycarbonyl)amino)cyclohexyl)methyl methanesulfonate (118 mg, 0.383 mmol), 3-(2,5-difluorophenyl)-3-hydroxyindolin-2-one (100 mg, 0.383 mmol), and cesium carbonate (374 mg, 1.15 mmol) in DMSO (2 mL) is stirred at 70° C. for 3 hours. The reaction mixture is diluted with EtOAc (50 mL) and washed with water (100 mL×2). The organic layer is dried over Na$_2$SO$_4$ and concentrated. The residue is purified by silica-gel column chromatography (hexane/EtOAc=1/1-1/3) to give tert-butyl ((1r,4r)-4-((3-(2,5-difluorophenyl)-3-hydroxy-2-oxoindolin-1-yl)methyl)cyclohexyl)carbamate (146 mg, 81% yield).

$^1$H-NMR (400 MHz, CDCl$_3$) delta 7.64 (1H, ddd, J=9.1, 5.9, 3.2 Hz), 7.34 (1H, ddd, J=7.8, 7.8, 1.4 Hz), 7.13 (1H, brd, J=7.3 Hz), 7.03 (1H, dd, J=7.3, 7.3 Hz), 7.01-6.95 (1H, m), 6.91-6.86 (2H, m), 4.36 (1H, br), 3.66 (1H, dd, J=14.2, 6.4 Hz), 3.52 (1H, dd, J=14.2, 7.3 Hz), 3.41 (1H, br), 3.32-3.31 (1H, m), 2.07-2.00 (2H, m), 1.88-1.80 (3H, m), 1.28 (9H, s), 1.26-1.04 (4H, m).

<Step-2>: 1-(((1r,4r)-4-aminocyclohexyl)methyl)-3-(2,5-difluorophenyl)-3-hydroxyindolin-2-one hydrochloride To a solution of tert-butyl ((1r,4r)-4-((3-(2,5-difluorophenyl)-3-hydroxy-2-oxoindolin-1-yl)methyl)cyclohexyl)carbamate (146 mg, 0.309 mmol, Step-1 of Intermediate-101) in methanol (2 mL) is added 4 M HCl in 1,4-dioxane (1 mL). The resulting mixture is stirred at room temperature for 2 hours. The reaction mixture is concentrated under reduced pressure to give 1-(((1r,4r)-4-aminocyclohexyl)methyl)-3-(2,5-difluorophenyl)-3-hydroxyindolin-2-one hydrochloride (128 mg, quantitative yield) as a pale yellow solid.

MS (ESI) m/z: 373.2 (M+H)+.

$^1$H-NMR (400 MHz, CDCl$_3$) delta 7.96 (2H, br), 7.68 (1H, ddd, J=9.1, 5.9, 3.2 Hz), 7.33 (1H, ddd, J=7.8, 7.8, 1.4 Hz), 7.25-7.19 (1H, m), 7.14-6.96 (5H, m), 3.65-3.55 (2H, m), 2.99-2.90 (1H, m), 1.99-1.92 (2H, m), 1.85-1.65 (3H, m), 1.35-1.10 (4H, m).

Intermediate-102

2-bromo-5-chloro-N-((1r,4r)-4-((3-(2,5-difluorophenyl)-3-hydroxy-2-oxoindolin-1-yl)methyl)cyclohexyl)nicotinamide

[Chem. 116]

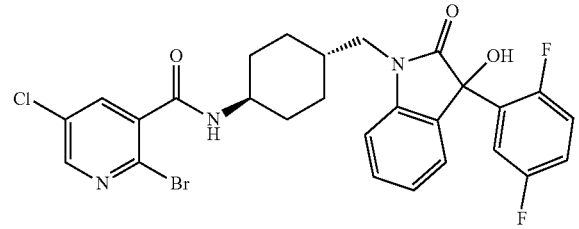

To a mixture of 2-bromo-5-chloronicotinic acid (26.0 mg, 0.110 mmol), 1-(((1r,4r)-4-aminocyclohexyl)methyl)-3-(2,5-difluorophenyl)-3-hydroxyindolin-2-one hydrochloride (30 mg, 0.073 mmol, Intermediate-101), and DIEA (37.9 mg, 0.293 mmol) in DMF (1 mL) is added HATU (55.8 mg, 0.147 mmol), and the resulting mixture is stirred at room temperature for 2 hours. The reaction mixture is diluted with EtOAc (30 mL) and washed with water (30 mL×2). The organic fraction is dried over Na$_2$SO$_4$. After removal of the solvent, the residue is purified by column (amino functional silica gel: eluted with n-hexane/EtOAc) to give 2-bromo-5-chloro-N-((1r,4r)-4-((3-(2,5-difluorophenyl)-3-hydroxy-2-oxoindolin-1-yl) methyl)cyclohexyl)nicotinamide (36 mg, 83% yield).

MS (ESI) m/z: 590.0 (M+H)+.

$^1$H-NMR (400 MHz, CDCl$_3$) delta 8.37 (1H, d, J=2.3 Hz), 7.86 (1H, d, J=2.7 Hz), 7.65 (1H, ddd, J=9.1, 5.9, 3.2 Hz), 7.35 (1H, ddd, J=7.8, 7.8, 0.9 Hz), 7.13 (1H, dd, J=7.3, 1.4 Hz), 7.04 (1H, ddd, J=7.8, 7.8, 0.9 Hz), 7.01-6.94 (1H, m), 6.92-6.86 (2H, m), 6.07 (1H, d, J=7.8 Hz), 4.01-3.93 (1H, m), 3.69 (1H, dd, J=13.7, 5.9 Hz), 3.59-3.54 (2H, m), 2.21-2.12 (2H, m), 1.92 (3H, brd, J=10.1 Hz), 1.32-1.24 (4H, m).

Intermediate-103

6-fluoro-3-(3-fluoro-2-methoxypyridin-4-yl)-3-hydroxyindolin-2-one

[Chem. 117]

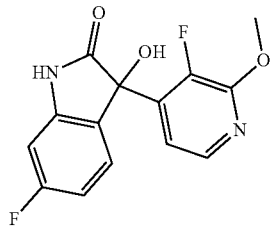

The title compound is prepared in 58% yield (102 mg, a yellow solid) by the similar manner to Intermediate-3 using 3-fluoro-2-methoxypyridine (169 mg, 1.33 mmol) and 6-fluoroindoline-2,3-dione (100 mg, 0.606 mmol) in place of 2-bromo-5-methylpyridine and indoline-2,3-dione.

MS (ESI) m/z: 293.1 (M+H)+.

$^1$H-NMR (400 MHz, DMSO-$d_6$) delta 10.81 (1H, s), 8.06 (1H, d, J=5.0 Hz), 7.47 (1H, dd, J=5.0, 5.0 Hz), 7.11 (1H, s), 7.00 (1H, dd, J=7.8, 5.5 Hz), 6.80-6.66 (2H, m), 3.88 (3H, s).

Intermediate-104

6-fluoro-3-(2-fluoro-5-methoxyphenyl)-3-hydroxy-indolin-2-one

[Chem. 118]

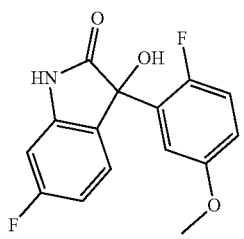

The title compound is prepared in 51% yield (89 mg, a yellow solid) in a similar manner to Intermediate-3 using 2-bromo-1-fluoro-4-methoxybenzene (273 mg, 1.33 mmol) and 6-fluoroindoline-2,3-dione (100 mg, 0.606 mmol) in place of 2-bromo-5-methylpyridine and indoline-2,3-dione.

MS (ESI) m/z: 292.1 (M+H)+.

Intermediate-105

3-(5-chloropyridin-2-yl)-3-hydroxy-4-methoxyindolin-2-one

[Chem. 119]

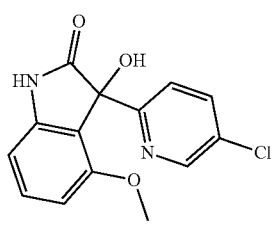

The title compound is prepared in quantitative yield (85 mg, a yellow solid) in a similar manner to Intermediate-4 using 2-bromo-5-chloropyridine (119 mg, 0.621 mmol) and 4-methoxyindoline-2,3-dione (50 mg, 0.282 mmol) in place of 6-bromo-3-fluoro-2-methylpyridine and indoline-2,3-dione.

MS (ESI) m/z: 291.0 (M+H)+.

Intermediate-106

3-(2,3-difluorophenyl)-3-hydroxy-4-methoxyindolin-2-one

[Chem. 120]

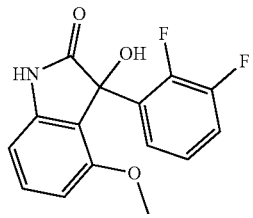

The title compound is prepared in 18% yield (15 mg, a pale yellow solid) in a similar manner to Intermediate-3 using 1,2-difluorobenzene (71 mg, 0.621 mmol) and 4-methoxyindoline-2,3-dione (50 mg, 0.282 mmol) in place of 2-bromo-5-methylpyridine and indoline-2,3-dione.

MS (ESI) m/z: 290.1 (M+H)+.

$^1$H-NMR (400 MHz, DMSO-$d_6$) delta 10.51 (1H, s), 7.70 (1H, dd, J=7.3, 7.3 Hz), 7.39-7.15 (3H, m), 6.69 (1H, s), 6.56 (1H, d, J=8.2 Hz), 6.51 (1H, d, J=7.3 Hz), 3.56 (3H, s).

Intermediate-107

1-(((1r,4r)-4-aminocyclohexyl)methyl)-3-(2,3-difluorophenyl)-3-hydroxyindolin-2-one

[Chem. 121]

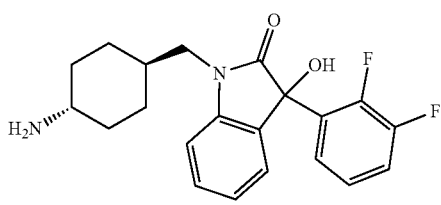

<Step-1>: tert-butyl ((1r,4r)-4-((3-(2,3-difluorophenyl)-3-hydroxy-2-oxoindolin-1-yl)methyl)cyclohexyl)carbamate The title compound is prepared in 64% yield (148 mg, a pale yellow amorphous) in a similar manner to Step-1 of Intermediate-101 using 3-(2,3-difluorophenyl)-3-hydroxy-indolin-2-one (150 mg, 0.488 mmol) in place of 3-(2,5-difluorophenyl)-3-hydroxyindolin-2-one.

$^1$H-NMR (400 MHz, CDCl$_3$) delta 7.67 (1H, ddd, J=7.8, 6.4, 1.8 Hz), 7.34 (1H, ddd, J=7.8, 7.8, 1.4 Hz), 7.21-7.10 (3H, m), 7.03 (1H, ddd, J=8.2, 7.8, 0.9 Hz), 6.91 (1H, d, J=7.8 Hz), 4.37 (1H, br), 3.66 (1H, dd, J=14.2, 6.4 Hz), 3.53 (1H, dd, J=14.2, 7.8 Hz), 3.41 (2H, m), 2.08-2.00 (2H, m), 1.90-1.79 (3H, m), 1.44 (9H, s), 1.22-1.06 (4H, m).

<Step-2>: 1-(((1r,4r)-4-aminocyclohexyl)methyl)-3-(2,3-difluorophenyl)-3-hydroxyindolin-2-one hydrochloride The title compound is prepared in quantitative yield (129 mg, a pale yellow solid) in a similar manner to Step-2 of Intermediate-101 using tert-butyl ((1r,4r)-4-((3-(2,3-difluorophenyl)-3-hydroxy-2-oxoindolin-1-yl)methyl)cyclohexyl)carbamate (148 mg, 0.313 mmol, Step-1 of Intermediate-107) in place of tert-butyl ((1r,4r)-4-((3-(2,5-difluorophenyl)-3-hydroxy-2-oxoindolin-1-yl)methyl)cyclohexyl)carbamate.

$^1$H-NMR (400 MHz, DMSO-d$_6$) delta 7.84 (2H, br), 7.74 (1H, brt, J=7.8 Hz), 7.44-7.31 (3H, m), 7.15 (1H, d, J=7.8 Hz), 7.06 (1H, s), 7.02-6.97 (2H, m), 3.58-3.56 (2H, m), 2.99-2.90 (1H, m), 1.99-1.91 (2H, m), 1.82 (2H, brd, J=11.4 Hz), 1.76-1.68 (1H, m), 1.30-1.10 (4H, m).

Intermediate-108

[Chem. 122]

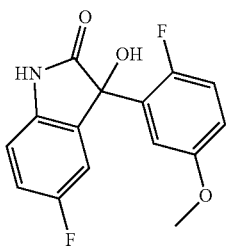

The title compound is prepared in quantitative yield (188 mg, a yellow solid) in a similar manner to Intermediate-3 using 2-bromo-1-fluoro-4-methoxybenzene (273 mg, 1.33 mmol) and 5-fluoroindoline-2,3-dione (100 mg, 0.606 mmol) in place of 2-bromo-5-methylpyridine and indoline-2,3-dione.

MS (ESI) m/z: 290.1 (M+H)$^+$.

$^1$H-NMR (400 MHz, DMSO-d$_6$) delta 10.52 (1H, s), 7.42 (1H, dd, J=6.4, 3.2 Hz), 7.05 (1H, ddd, J=10.5, 7.8, 1.8 Hz), 7.01-6.94 (2H, m), 6.91-6.83 (2H, m), 6.81 (1H, dd, J=7.8, 2.7 Hz), 3.80 (3H, s).

Intermediate-109

[Chem. 123]

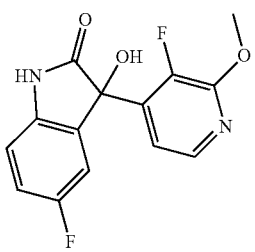

The title compound is prepared in 28% yield (50 mg, an orange solid) in a similar manner to Intermediate-3 using 3-fluoro-2-methoxypyridine (169 mg, 1.33 mmol) and 5-fluoroindoline-2,3-dione (100 mg, 0.606 mmol) in place of 2-bromo-5-methylpyridine and indoline-2,3-dione.

MS (ESI) m/z: 293.0 (M+H)$^+$.

$^1$H-NMR (400 MHz, DMSO-d$_6$) delta 10.68 (1H, s), 8.07 (1H, d, J=5.5 Hz), 7.45 (1H, dd, J=5.3, 5.3 Hz), 7.19 (1H, s), 7.10 (1H, ddd, J=10.5, 7.8, 1.8 Hz), 6.94-6.82 (2H, m), 3.88 (3H, s).

Intermediate-110

6-chloro-3-(2-fluorophenyl)-3-hydroxyindolin-2-one

[Chem. 124]

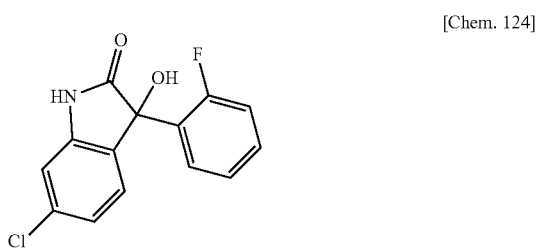 [SMILES: O=C1Nc2cc(Cl)ccc2C1(O)c1ccccc1F]

The title compound is prepared in 35% yield (54 mg, a yellow solid) in a similar manner to Intermediate-4 using 1-fluoro-2-iodobenzene (213 mg, 1.21 mmol) and 6-chloroindoline-2,3-dione (100 mg, 0.551 mmol) in place of 6-bromo-3-fluoro-2-methylpyridine and indoline-2,3-dione.

MS (ESI) m/z: 278.5 (M+H)$^+$.

$^1$H-NMR (400 MHz, DMSO-d$_6$) delta 10.67 (1H, s), 7.90 (1H, ddd, J=7.9, 7.9, 2.1 Hz), 7.42-7.33 (1H, m), 7.30 (1H, ddd, J=7.9, 7.9, 1.2 Hz), 7.05 (1H, ddd, J=11.4, 7.9, 1.2 Hz), 6.97-6.87 (4H, m).

Intermediate-111

2-bromo-5-chloro-N-((1r,4r)-4-((3-(2,3-difluorophenyl)-3-hydroxy-2-oxoindolin-1-yl)methyl)cyclohexyl)nicotinamide

[Chem. 125]

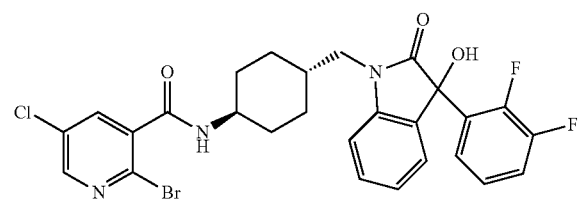

The title compound is prepared in 53% yield (54 mg, a pale yellow amorphous) in a similar manner to Intermediate-102 using 1-(((1r,4r)-4-aminocyclohexyl)methyl)-3-(2,3-difluorophenyl)-3-hydroxyindolin-2-one hydrochloride (70 mg, 0.171 mmol, Intermediate-107) in place of 1-(((1r,4r)-4-aminocyclohexyl)methyl)-3-(2,5-difluorophenyl)-3-hydroxyindolin-2-one hydrochloride.

MS (ESI) m/z: 590.1 (M+H)$^+$.

$^1$H-NMR (400 MHz, CDCl$_3$) delta 8.37 (1H, d, J=2.3 Hz), 7.87 (1H, d, J=2.7 Hz), 7.68 (1H, dddd, J=7.8, 6.4, 1.8, 1.8 Hz), 7.35 (1H, ddd, J=7.8, 7.8, 1.4 Hz), 7.22-7.11 (3H, m), 7.04 (1H, dd, J=7.8, 6.9 Hz), 6.93 (1H, d, J=7.8 Hz), 6.04 (1H, d, J=7.8 Hz), 4.01-3.93 (1H, m), 3.71 (1H, dd, J=14.2, 5.9 Hz), 3.57 (1H, dd, J=14.2, 7.8 Hz), 3.45 (1H, s), 2.19 (2H, br), 1.93 (3H, brd, J=10.5 Hz), 1.32-1.24 (4H, m).

Intermediate-112

3,4-difluoro-5-(3-hydroxy-2-oxoindolin-3-yl)benzonitrile

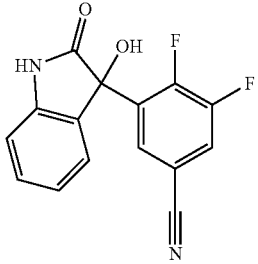

[Chem. 126]

The title compound is prepared in 10% yield (19 mg, a pale yellow amorphous) in a similar manner to Intermediate-4 using 3-bromo-4,5-difluorobenzonitrile (304 mg, 1.39 mmol) in place of 6-bromo-3-fluoro-2-methylpyridine.

$^1$H-NMR (400 MHz, CDCl$_3$) delta 8.09 (1H, ddd, J=5.9, 1.8, 1.8 Hz), 7.76 (1H, br), 7.48 (1H, ddd, J=8.7, 6.9, 1.8 Hz), 7.34 (1H, ddd, J=7.8, 7.8, 1.8 Hz), 7.10 (1H, dd, J=7.8, 1.4 Hz), 7.06 (1H, ddd, J=7.3, 7.3, 0.9 Hz), 6.97 (1H, d, J=7.8 Hz), 3.64 (1H, s).

Intermediate-113

3-(5-fluoropyridin-2-yl-3-hydroxy-7-methylindolin-2-one

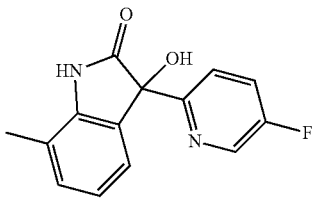

[Chem. 127]

The title compound is prepared in 28% yield (28 mg, an orange solid) in a similar manner to Intermediate-4 using 2-bromo-5-fluoropyridine (240 mg, 1.37 mmol) and 7-methylindoline-2,3-dione (100 mg, 0.621 mmol) in place of 6-bromo-3-fluoro-2-methylpyridine and indoline-2,3-dione.

MS (ESI) m/z: 259.1 (M+H)$^+$.

$^1$H-NMR (400 MHz, DMSO-d$_6$) delta 10.44 (1H, s), 8.36 (1H, d, J=3.2 Hz), 7.89 (1H, dd, J=8.8, 4.6 Hz), 7.78 (1H, ddd, J=8.8, 8.8, 3.2 Hz), 7.06-6.96 (1H, m), 6.86 (1H, s), 6.81-6.76 (2H, m), 2.20 (3H, s).

Intermediate-114

3-(2-fluorophenyl)-3-hydroxy-7-methylindolin-2-one

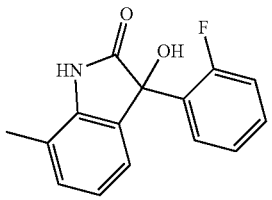

[Chem. 128]

The title compound is prepared in 24% yield (38 mg, an orange solid) in a similar manner to Intermediate-3 using 1-fluoro-2-iodobenzene (303 mg, 1.37 mmol) and 7-methylindoline-2,3-dione (100 mg, 0.621 mmol) in place of 2-bromo-5-methylpyridine and indoline-2,3-dione.

MS (ESI) m/z: 258.1 (M+H)$^+$.

$^1$H-NMR (400 MHz, DMSO-d$_6$) delta 10.53 (1H, s), 7.91 (1H, ddd, J=7.8, 7.8, 1.8 Hz), 7.39-7.24 (2H, m), 7.11-6.94 (2H, m), 6.79 (1H, dd, J=7.3, 7.3 Hz), 6.74 (1H, s), 6.71 (1H, d, J=7.3 Hz), 2.24 (3H, s).

Intermediate-115

3-(3-fluoropyridin-4-yl)-3-hydroxy-7-methylindolin-2-one

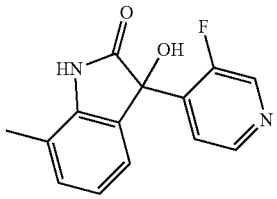

[Chem. 129]

The title compound is prepared in 30% yield (48 mg, a yellow solid) in a similar manner to Intermediate-7 using 7-methylindoline-2,3-dione (100 mg, 0.621 mmol) in place of indoline-2,3-dione.

MS (ESI) m/z: 259.1 (M+H)$^+$.

Intermediate-116

4,6-difluoro-3-(2-fluorophenyl)-3-hydroxyindolin-2-one

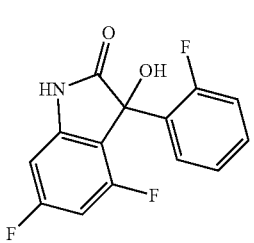

[Chem. 130]

The title compound is prepared in 62% yield (94 mg, a yellow solid) in a similar manner to Intermediate-3 using 1-fluoro-2-iodobenzene (364 mg, 1.64 mmol) and 4,6-difluoroindoline-2,3-dione (100 mg, 0.546 mmol) in place of 2-bromo-5-methylpyridine and indoline-2,3-dione.

MS (ESI) m/z: 278.1 (M−H)⁻.

¹H-NMR (400 MHz, DMSO-d₆) delta 10.90 (1H, s), 7.92 (1H, ddd, J=7.8, 7.8, 1.8 Hz), 7.43-7.33 (1H, m), 7.30 (1H, ddd, J=7.8, 7.8, 1.8 Hz), 7.08 (1H, s), 7.07 (1H, ddd, J=11.2, 7.8, 0.8 Hz), 6.66 (1H, ddd, J=9.9, 9.9, 2.0 Hz), 6.63-6.54 (1H, m).

Intermediate-117

3-(5-fluoropyridin-2-yl)-3-hydroxy-4-methylindolin-2-one

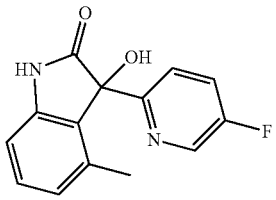

[Chem. 131]

The title compound is prepared in 28% yield (44 mg, an orange solid) in a similar manner to Intermediate-4 using 2-bromo-5-fluoropyridine (240 mg, 1.37 mmol) and 4-methylindoline-2,3-dione (100 mg, 0.621 mmol) in place of 6-bromo-3-fluoro-2-methylpyridine and indoline-2,3-dione.

MS (ESI) m/z: 259.1 (M+H)⁺.

¹H-NMR (400 MHz, DMSO-d₆) delta 10.33 (1H, s), 8.36 (1H, d, J=2.9 Hz), 7.91 (1H, dd, J=8.8, 4.6 Hz), 7.78 (1H, ddd, J=8.8, 8.8, 2.9 Hz), 7.10 (1H, dd, J=7.8, 7.8 Hz), 6.79 (1H, s), 6.68 (1H, d, J=7.8 Hz), 6.65 (1H, d, J=7.8 Hz), 1.87 (3H, s).

Intermediate-118

3-(2-fluorophenyl)-3-hydroxy-4-methylindolin-2-one

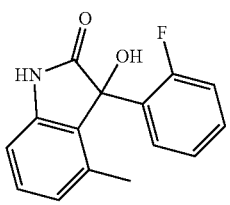

[Chem. 132]

The title compound is prepared in 24% yield (38 mg, an orange solid) in a similar manner to Intermediate-3 using 1-fluoro-2-iodobenzene (303 mg, 1.37 mmol) and 4-methylindoline-2,3-dione (100 mg, 0.621 mmol) in place of 2-bromo-5-methylpyridine and indoline-2,3-dione.

MS (ESI) m/z: 258.1 (M+H)⁺.

¹H-NMR (400 MHz, DMSO-d₆) delta 10.44 (1H, s), 7.96 (1H, ddd, J=8.1, 8.1, 2.0 Hz), 7.39-7.31 (1H, m), 7.29 (1H, ddd, J=7.8, 7.8, 1.3 Hz), 7.11 (1H, dd, J=7.8, 7.8 Hz), 7.02 (1H, ddd, J=11.5, 8.1, 1.3 Hz), 7.00 (1H, s), 6.69 (1H, d, J=7.8 Hz), 6.64 (1H, d, J=7.8 Hz), 1.84 (3H, s).

Intermediate-119

3-(3-fluoropyridin-4-yl)-3-hydroxy-4-methylindolin-2-one

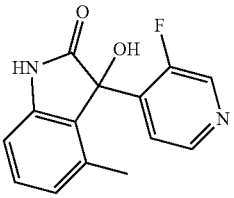

[Chem. 133]

The title compound is prepared in 30% yield (48 mg, an off-white solid) in a similar manner to Intermediate-7 using 4-methylindoline-2,3-dione (100 mg, 0.621 mmol) in place of indoline-2,3-dione.

MS (ESI) m/z: 259.1 (M+H)⁺.

¹H-NMR (400 MHz, DMSO-d₆) delta 10.64 (1H, s), 8.55 (1H, d, J=5.0 Hz), 8.41 (1H, d, J=2.7 Hz), 7.97 (1H, dd, J=6.9, 5.0 Hz), 7.16 (1H, dd, J=7.8, 7.8 Hz), 6.73 (1H, d, J=7.8 Hz), 6.69 (1H, d, J=7.8 Hz), 1.87 (3H, s), OH proton is not observed.

Intermediate-120

4-fluoro-3-(2-fluoro-5-methoxyphenyl)-3-hydroxy-indolin-2-one

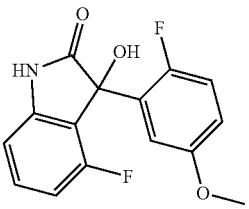

[Chem. 134]

The title compound is prepared in 45% yield (79 mg, a pale yellow solid) in a similar manner to Intermediate-3 using 2-bromo-1-fluoro-4-methoxybenzene (372 mg, 1.82 mmol) and 4-fluoroindoline-2,3-dione (100 mg, 0.606 mmol) in place of 2-bromo-5-methylpyridine and indoline-2,3-dione.

MS (ESI) m/z: 290.0 (M−H)⁻.

¹H-NMR (400 MHz, DMSO-d₆) delta 10.72 (1H, brs), 7.43 (1H, dd, J=6.4, 3.2 Hz), 7.27 (1H, td, J=8.1, 5.6 Hz), 7.04 (1H, s), 6.98 (1H, dd, J=10.5, 8.7 Hz), 6.88 (1H, dd, J=8.7, 3.7 Hz), 6.72 (1H, d, J=7.3 Hz) 6.66 (1H, t, J=8.9 Hz), 3.78 (3H, s).

109

Intermediate-121

3-(3-chloro-2-fluorophenyl)-4-fluoro-3-hydroxyindolin-2-one

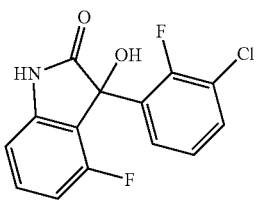

[Chem. 135]

The title compound is prepared in 85% yield (153 mg, a yellow solid) in a similar manner to Intermediate-3 using 1-bromo-3-chloro-2-fluorobenzene (317 mg, 1.51 mmol) and 4-fluoroindoline-2,3-dione (100 mg, 0.606 mmol) in place of 2-bromo-5-methylpyridine and indoline-2,3-dione.

MS (ESI) m/z: 294.0 (M−H)⁻.

$^1$H-NMR (400 MHz, DMSO-d$_6$) delta 10.76 (1H, s), 7.87 (1H, td, J=7.4, 1.4 Hz), 7.60-7.51 (1H, m), 7.35 (1H, dd, J=8.2, 7.3 Hz), 7.05 (1H, s), 6.96 (1H, dd, J=8.2, 5.5 Hz), 6.75-6.65 (2H, m).

Intermediate-122

4-fluoro-3-(2-fluorophenyl)-3-hydroxyindolin-2-one

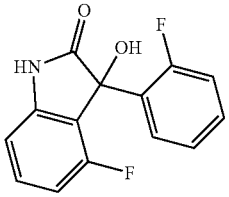

[Chem. 136]

The title compound is prepared in 97% yield (153 mg, a yellow solid) in a similar manner to Intermediate-3 using 1-bromo-2-fluorobenzene (265 mg, 1.51 mmol) and 4-fluoroindoline-2,3-dione (100 mg, 0.606 mmol) in place of 2-bromo-5-methylpyridine and indoline-2,3-dione.

MS (ESI) m/z: 260.1 (M−H)⁻.

Intermediate-123

3-(2,3-difluorophenyl)-4-fluoro-3-hydroxyindolin-2-one

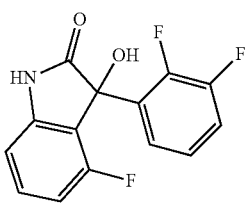

[Chem. 137]

110

The title compound is prepared in 97% yield (153 mg, a yellow solid) in a similar manner to Intermediate-3 using 1,2-difluorobenzene (173 mg, 1.51 mmol) and 4-fluoroindoline-2,3-dione (100 mg, 0.606 mmol) in place of 2-bromo-5-methylpyridine and indoline-2,3-dione.

MS (ESI) m/z: 278.1 (M−H)⁻.

$^1$H-NMR (400 MHz, DMSO-d$_6$) delta 10.76 (1H, s), 7.78-7.66 (1H, m), 7.47-7.35 (1H, m), 7.35-7.26 (1H, m), 7.03 (1H, s), 6.97 (1H, dd, J=8.0, 5.7 Hz), 6.80-6.65 (2H, m).

EXAMPLE SYNTHESIS PART

Unless otherwise noted, a compound with a chiral center is synthesized as a racemate in the Example synthesis part.

Representative Procedure for Method A1

The following preparation of Example 1 represents the Method A1.

Example 1

5-chloro-N-((1r,4r)-4-((3-hydroxy-2-oxo-3-phenylindolin-1-yl)methyl)cyclohexyl)-2-methylnicotinamide

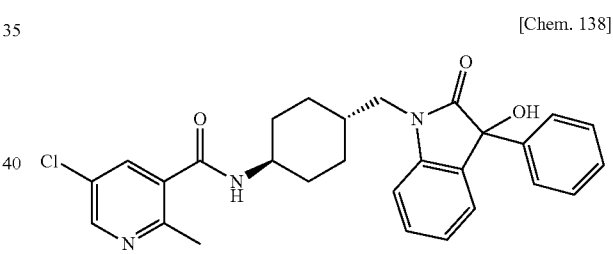

[Chem. 138]

A mixture of ((1r,4r)-4-(5-chloro-2-methylnicotinamido)cyclohexyl)methyl methanesulfonate (20 mg, 0.055 mmol, Intermediate-A), 3-hydroxy-3-phenylindolin-2-one (12 mg, 0.055 mmol), and cesium carbonate (45.1 mg, 0.139 mmol) in NMP (0.5 mL) is stirred at 80° C. for 6 hours. The mixture is diluted with saturated aqueous sodium bicarbonate, followed by extraction with EtOAc. The organic layer is dried over sodium sulfate, filtered and concentrated. The residue is purified by a strong anion exchange cartridge (ISOLUTE (registered trademark) SCX-2, 1 g/6 mL, Biotage) and then purified by preparative LC-MS to give 5.1 mg (20% yield) of the title compound.

Representative Procedure for Method A2

The following preparation of Example 19 represents the Method A2.

Example 19

5-chloro-2-(difluoromethyl)-N-((1r,4r)-4-((3-(3-fluoropyridin-2-yl)-3-hydroxy-2-oxoindolin-1-yl)methyl)cyclohexyl)nicotinamide

[Chem. 139]

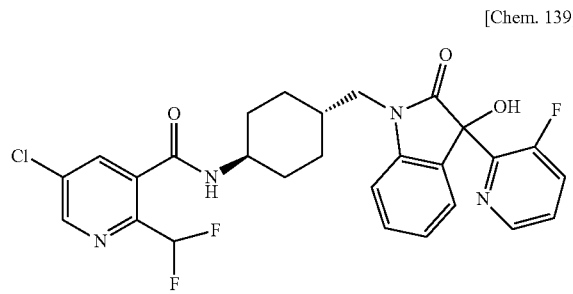 [SMILES: O=C(N[C@H]1CC[C@H](CN2C(=O)C(O)(c3ncccc3F)c3ccccc32)CC1)c1cc(Cl)cnc1C(F)F]

A mixture of ((1r,4r)-4-(5-chloro-2-(difluoromethyl)nicotinamido)cyclohexyl)methyl methanesulfonate (15 mg, 0.038 mmol, Intermediate-B), 3-(3-fluoropyridin-2-yl)-3-hydroxyindolin-2-one (10.2 mg, 0.042 mmol, Intermediate-14), and cesium carbonate (36.9 mg, 0.113 mmol) in DMSO (0.2 mL) is stirred at 80° C. overnight. The reaction mixture is diluted with saturated aqueous ammonium chloride solution (2 mL), followed by extraction with EtOAc (3 mL). The organic layer is dried over sodium sulfate and concentrated. The residue is purified by preparative LC-MS to give 6.9 mg (34% yield) of the title compound.

Example 23

5-chloro-2-(difluoromethyl)-N-((1r,4r)-4-((3-hydroxy-2-oxo-3-(2-oxo-2-phenylethyl) indolin-1-yl)methyl)cyclohexyl)nicotinamide

[Chem. 140]

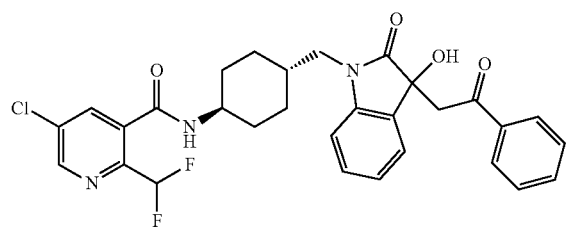

A mixture of acetophenone (6.44 mg, 0.054 mmol) and diethylamine (4.57 mg, 0.063 mmol) in EtOH (0.3 mL) is stirred at room temperature for 20 minutes. To the mixture is added 5-chloro-2-(difluoromethyl)-N-((1r,4r)-4-((2,3-dioxoindolin-1-yl)methyl)cyclohexyl)nicotinamide (20 mg, 0.045 mmol, Intermediate-27), and stirred at room temperature overnight. After removal of solvent, the residue is diluted with water, followed by extraction with EtOAc, and the extract is filtered through short column of silica-gel and concentrated. The crude compound is purified by preparative LC-MS to give 7.9 mg (30% yield) of the title compound.

Representative Procedure for Method A3

The following preparation of Example 24 represents the Method A3.

Example 24

5-chloro-N-((1r,4r)-4-((3-(3-chloropyridin-2-yl)-3-hydroxy-2-oxoindolin-1-yl)methyl)cyclohexyl)-2-(difluoromethyl)nicotinamide

[Chem. 141]

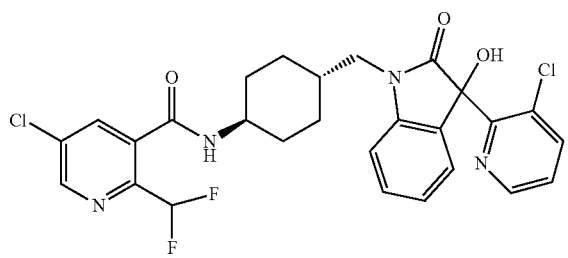

A mixture of ((1r,4r)-4-(5-chloro-2-(difluoromethyl)nicotinamido)cyclohexyl)methyl methanesulfonate (15 mg, 0.038 mmol, Intermediate-B), 3-(3-chloropyridin-2-yl)-3-hydroxyindolin-2-one (10.8 mg, 0.042 mmol, Intermediate-17), and cesium carbonate (24.6 mg, 0.076 mmol) in DMSO (0.2 mL) is stirred at 60° C. for 4 hours. The reaction mixture is diluted with saturated aqueous ammonium chloride solution (2 mL), followed by extraction with EtOAc (3 mL). The organic layer is dried over sodium sulfate and concentrated. The residue is purified by preparative LC-MS to give 6.0 mg (28% yield) of the title compound.

Example 34

5-chloro-2-(difluoromethyl)-N-((1r,4r)-4-((3-hydroxy-3-(2-hydroxy-2-phenylethyl)-2-oxoindolin-1-yl)methyl)cyclohexyl)nicotinamide

[Chem. 142]

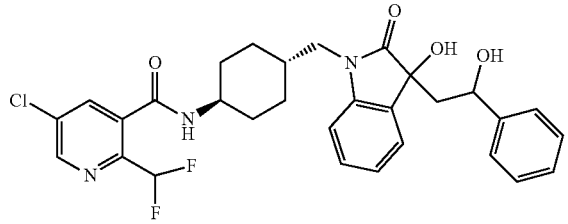

A mixture of 5-chloro-2-(difluoromethyl)-N-((1r,4r)-4-((3-hydroxy-2-oxo-3-(2-oxo-2-phenylethyl)indolin-1-yl)methyl)cyclohexyl)nicotinamide (29 mg, 0.051 mmol, Example 23), and sodium borohydride (2.7 mg, 0.071 mmol) in MeOH (0.5 mL) is stirred at room temperature for 4 days. The mixture is diluted with 28% aqueous ammonia solution, followed by extraction with EtOAc. The organic layer is dried over sodium sulfate, filtered and concentrated. The residue is purified by preparative LC-MS to give 4.2 mg (14% yield) of the title compound.

Representative Procedure for Method B1

The following preparation of Example 39 represents the Method B1

Example 39

5-chloro-2-(difluoromethyl)-N-((1r,4r)-4-((3-hydroxy-3-(1-methyl-1H-indazol-5-yl)-2-oxoindolin-1-yl)methyl)cyclohexyl)nicotinamide

[Chem. 143]

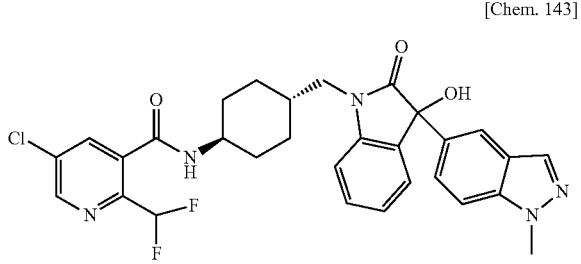 [SMILES: Cn1ncc2cc(C3(O)C(=O)N(C[C@H]4CC[C@H](NC(=O)c5cc(Cl)cnc5C(F)F)CC4)c4ccccc43)ccc21]

A mixture of 5-chloro-2-(difluoromethyl)-N-((1r,4r)-4-((2,3-dioxoindolin-1-yl)methyl)cyclohexyl)nicotinamide (20 mg, 0.045 mmol, Intermediate-27), (1-methyl-1H-indazol-5-yl)boronic acid (16 mg, 0.089 mmol), rhodium(II) acetate dimer (2.0 mg, 0.0045 mmol), tritert-butylphosphonium tetrafluoroborate (2.6 mg, 0.0089 mmol), and potassium carbonate (2.5 mg, 0.018 mmol) in DME (0.5 mL)/water (0.2 mL) is stirred at 90° C. for 1 hour. The mixture is concentrated and passed through an amino-functional silica gel pad. The filtrate is concentrated. The residue is purified by preparative LC-MS to give 5.9 mg (23% yield) of the title compound.

Example 52

N-((1r,4r)-4-((3-(5-amino-3-methyl-1-(pyridin-2-yl)-1H-pyrazol-4-yl)-3-hydroxy-2-oxoindolin-1-yl)methyl)cyclohexyl)-5-chloro-2-(difluoromethyl)nicotinamide

[Chem. 144]

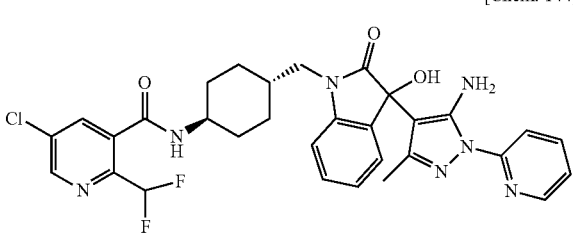

A mixture of 5-chloro-2-(difluoromethyl)-N-((1r,4r)-4-((2,3-dioxoindolin-1-yl)methyl)cyclohexyl)nicotinamide (20 mg, 0.045 mmol, Intermediate-27) and 3-methyl-1-(pyridin-2-yl)-1H-pyrazol-5-amine (7.8 mg, 0.045 mmol) in DMF (0.5 mL)/water (0.5 mL) is stirred at 90° C. for 1 day. The mixture is concentrated. The residue is purified by a strong anion exchange cartridge (ISOLUTE (registered trademark) SCX-2, 1 g/6 mL, Biotage). The residue is purified by preparative LC-MS to give 11 mg (40% yield) of the title compound.

Example 60

5-chloro-2-(difluoromethyl)-N-((1r,4r)-4-((3-hydroxy-3-(1-hydroxy-2-phenylethyl)-2-oxoindolin-1-yl)methyl)cyclohexyl)nicotinamide

[Chem. 145]

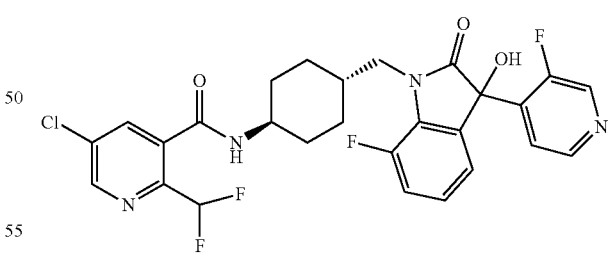

To a mixture of 5-chloro-2-(difluoromethyl)-N-((1r,4r)-4-((2,3-dioxoindolin-1-yl)methyl)cyclohexyl)nicotinamide (30 mg, 0.067 mmol, Intermediate-27), 2-phenylacetaldehyde (16 mg, 0.134 mmol), and zinc (8.76 mg, 0.134 mmol) in THF (0.7 mL) is added titanium(IV) chloride (0.007 mL, 0.067 mmol) dropwise at 0° C. and stirred at room temperature for 1 hour. The mixture is diluted with 1 M hydrochloric acid, followed by extraction with EtOAc. The organic layer is washed with water and brine, dried over sodium sulfate, filtered and concentrated. The residue is purified by column chromatography on silica-gel eluting with 40-100% EtOAc in n-hexane and then purified by preparative LC-MS to give 4.5 mg (12% yield) of the title compound.

Representative Procedure for Method A4

The following preparation of Example 84 represents the Method A4

Example 84

5-chloro-2-(difluoromethyl)-N-((1r,4r)-4-((7-fluoro-3-(3-fluoropyridin-4-yl)-3-hydroxy-2-oxoindolin-1-yl)methyl)cyclohexyl)nicotinamide

[Chem. 146]

A mixture of ((1r,4r)-4-(5-chloro-2-(difluoromethyl)nicotinamido)cyclohexyl)methyl methanesulfonate (15 mg, 0.038 mmol, Intermediate-B), 7-fluoro-3-(3-fluoropyridin-4-yl)-3-hydroxyindolin-2-one (9.9 mg, 0.038 mmol, Intermediate-58), and cesium carbonate (37 mg, 0.113 mmol) in NMP (0.4 mL) is stirred at 65° C. for 6 hours. The mixture is diluted with water, followed by extraction with EtOAc. The organic layer is dried over sodium sulfate, filtered and concentrated. The residue is purified by preparative LC-MS to give 4.9 mg (23% yield) of the title compound.

Representative Procedure for Method A5

The following preparation of Example 118 represents the Method A5.

Example 118

5-chloro-2-(difluoromethyl)-N-((1r,4r)-4-((3-(2,5-difluorophenyl)-6-fluoro-3-hydroxy-2-oxoindolin-1-yl)methyl)cyclohexyl)nicotinamide

[Chem. 147]

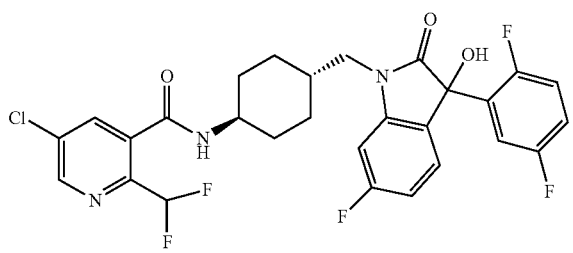

A mixture of ((1r,4r)-4-(5-chloro-2-(difluoromethyl)nicotinamido)cyclohexyl)methyl methanesulfonate (20 mg, 0.050 mmol, Intermediate-B), 3-(2,5-difluorophenyl)-6-fluoro-3-hydroxyindolin-2-one (14 mg, 0.050 mmol, Intermediate-82), and cesium carbonate (49 mg, 0.151 mmol) in DMF (0.4 mL) is stirred at 70° C. for 6 hours. The mixture is diluted with water, followed by extraction with EtOAc. The organic layer is dried over sodium sulfate, filtered and concentrated. The residue is purified by preparative LC-MS to give 11 mg (38% yield) of the title compound.

Representative Procedure for Method C1

The following preparation of Example 151 represents the Method C1.

Example 151

N-((1r,4r)-4-((3-(2,5-difluorophenyl)-3-hydroxy-2-oxoindolin-1-yl)methyl)cyclohexyl)-2-methyl-2H-indazole-3-carboxamide

[Chem. 148]

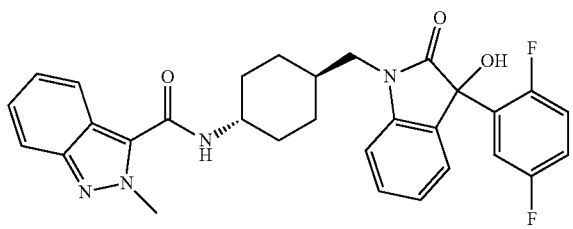

A mixture of 2-methyl-2H-indazole-3-carboxylic acid (7.8 mg, 0.044 mmol), 1-(((1r,4r)-4-aminocyclohexyl)methyl)-3-(2,5-difluorophenyl)-3-hydroxyindolin-2-one hydrochloride (12 mg, 0.029 mmol, Intermediate-101), HATU (22.3 mg, 0.059 mmol), and diisopropylethylamine (18.9 mg, 0.147 mmol) in DMF (0.2 mL) is stirred at 50° C. for 1 hour. The reaction mixture is diluted with EtOAc (3 mL) and washed with water (3 mL×2). The organic fraction is dried over Na$_2$SO$_4$. After removal of the solvent, the crude product is purified by preparative LC-MS to give 7.1 mg (46% yield) of the title compound.

Representative Procedure for Method D1

The following preparation of Example 154 represents the Method D1.

Example 154

5-chloro-2-(cyclobutylamino)-N-((1r,4r)-4-((3-(2,5-difluorophenyl)-3-hydroxy-2-oxoindolin-1-yl)methyl)cyclohexyl)nicotinamide

[Chem. 149]

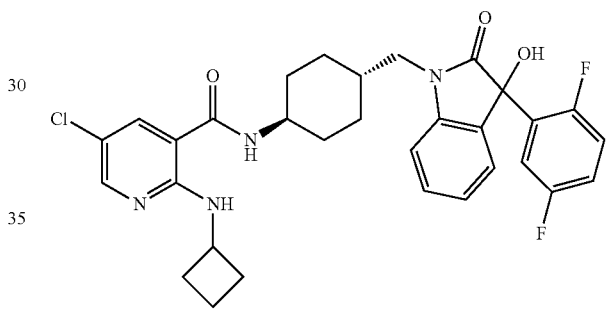

A mixture of the 2-bromo-5-chloro-N-((1r,4r)-4-((3-(2,5-difluorophenyl)-3-hydroxy-2-oxoindolin-1-yl) methyl)cyclohexyl)nicotinamide (18 mg, 0.030 mmol, Intermediate-102), and cyclobutanamine (0.3 mL, 3.82 mmol) in sealed tube is heated at 80° C. overnight. The reaction mixture is concentrated in vacuo. The crude product is purified by preparative LC-MS to give 7.9 mg (45% yield) of the title compound.

Other examples are prepared according to the procedure described in the Methods A to D using reactants shown in Table 1. The reactants are commercially available materials or obtained by conventional methods known to those skilled in the art, unless otherwise noted in the synthesis part. All Examples are racemic in Table 1.

The observed MS (positive or negative mode) and retention time by LC-MS of all examples are described in Table 2.

The $^1$H-NMR data of selected examples are described in Table 3.

TABLE 1

| | | (Examples) | | |
|---|---|---|---|---|
| Ex. | Structure | Name | Reactants | Method |

Table 1-1

| Ex. | Structure | Name | Reactants | Method |
|---|---|---|---|---|
| 1 | 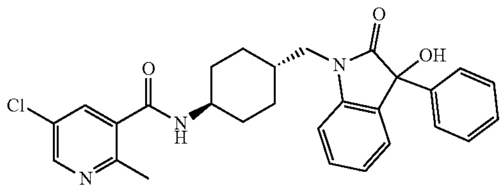 [SMILES: Cc1ncc(Cl)cc1C(=O)N[C@H]1CC[C@H](CN2C(=O)C(O)(c3ccccc3)c3ccccc32)CC1] | 5-chloro-N-((1r,4r)-4-((3-hydroxy-2-oxo-3-phenylindolin-1-yl)methyl)cyclohexyl)-2-methylnicotinamide | Intermediate-A, | A1 |
| 2 | 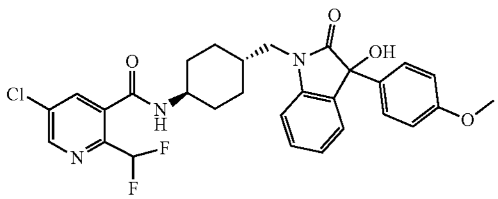 [SMILES: COc1ccc(C2(O)C(=O)N(C[C@H]3CC[C@H](NC(=O)c4cc(Cl)cnc4C(F)F)CC3)c3ccccc32)cc1] | 5-chloro-2-(difluoromethyl)-N-((1r,4r)-4-((3-hydroxy-3-(4-methoxyphenyl)-2-oxoindolin-1-yl)methyl)cyclohexyl)nicotinamide | Intermediate-B, | A1 |
| 3 | 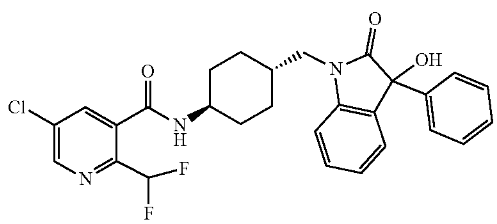 [SMILES: O=C(N[C@H]1CC[C@H](CN2C(=O)C(O)(c3ccccc3)c3ccccc32)CC1)c1cc(Cl)cnc1C(F)F] | 5-chloro-2-(difluoromethyl)-N-((1r,4r)-4-((3-hydroxy-2-oxo-3-phenylindolin-1-yl)methyl)cyclohexyl)nicotinamide | Intermediate-B, | A1 |
| 4 | 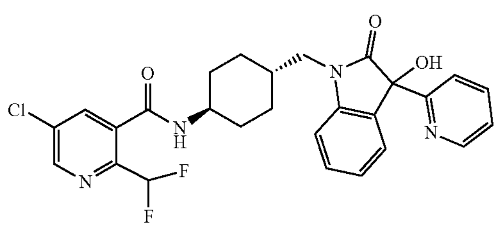 [SMILES: O=C(N[C@H]1CC[C@H](CN2C(=O)C(O)(c3ccccn3)c3ccccc32)CC1)c1cc(Cl)cnc1C(F)F] | 5-chloro-2-(difluoromethyl)-N-((1r,4r)-4-((3-hydroxy-2-oxo-3-(pyridin-2-yl)indolin-1-yl)methyl)cyclohexyl)nicotinamide | Intermediate-B, Intermediate-1 | A1 |
| 5 | 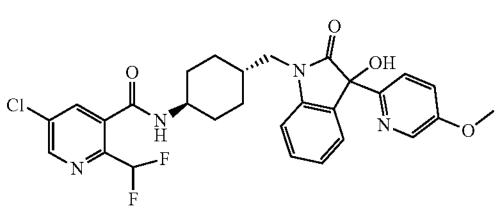 | 5-chloro-2-(difluoromethyl)-N-((1r,4r)-4-((3-hydroxy-3-(6-methoxypyridin-3-yl)-2-oxoindolin-1-yl)methyl)cyclohexyl)nicotinamide | Intermediate-B, Intermediate-2 | A1 |
| 6 | 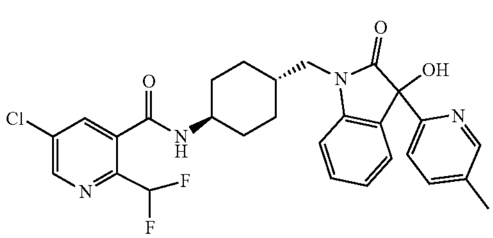 [SMILES: Cc1ccc(C2(O)C(=O)N(C[C@H]3CC[C@H](NC(=O)c4cc(Cl)cnc4C(F)F)CC3)c3ccccc32)nc1] | 5-chloro-2-(difluoromethyl)-N-((1r,4r)-4-((3-hydroxy-3-(5-methylpyridin-2-yl)-2-oxoindolin-1-yl)methyl)cyclohexyl)nicotinamide | Intermediate-B, Intermediate-3 | A1 |

TABLE 1-continued (Examples)

| Ex. | Structure | Name | Reactants | Method |
|---|---|---|---|---|
| 7 | 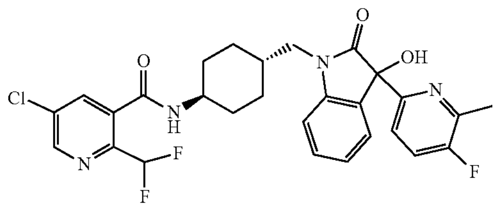 [SMILES: Cc1nc(C2(O)C(=O)N(C[C@H]3CC[C@H](NC(=O)c4cc(Cl)cnc4C(F)F)CC3)c3ccccc32)ccc1F] | 5-chloro-2-(difluoromethyl)-N-((1r,4r)-4-((3-(5-fluoro-6-methylpyridin-2-yl)-3-hydroxy-2-oxoindolin-1-yl)methyl)cyclohexyl)nicotinamide | Intermediate-B, Intermediate-4 | A1 |

Table 1-2

| 8 | | 5-chloro-2-(difluoromethyl)-N-((1r,4r)-4-((3-hydroxy-3-(6-methylpyridin-2-yl)-2-oxoindolin-1-yl)methyl)cyclohexyl)nicotinamide | Intermediate-B, Intermediate-5 | A1 |
| 9 | | 5-chloro-2-(difluoromethyl)-N-((1r,4r)-4-((3-hydroxy-3-(6-methoxypyridin-2-yl)-2-oxoindolin-1-yl)methyl)cyclohexyl)nicotinamide | Intermediate-B, Intermediate-6 | A1 |
| 10 | | 5-chloro-2-(difluoromethyl)-N-((1r,4r)-4-((3-(3-fluoropyridin-4-yl)-3-hydroxy-2-oxoindolin-1-yl)methyl)cyclohexyl)nicotinamide | Intermediate-B, Intermediate-7 | A1 |
| 11 | | 5-chloro-2-(difluoromethyl)-N-((1r,4r)-4-((3-hydroxy-3-(5-methoxypyridin-2-yl)-2-oxoindolin-1-yl)methyl)cyclohexyl)nicotinamide | Intermediate-B, Intermediate-8 | A1 |
| 12 | | 5-chloro-2-(difluoromethyl)-N-((1r,4r)-4-((3-hydroxy-2-oxo-3-(5-(trifluoromethyl)pyridin-2-yl)indolin-1-yl)methyl)cyclohexyl)nicotinamide | Intermediate-B, Intermediate-9 | A1 |
| 13 | | 5-chloro-N-((1r,4r)-4-((3-(5-chloropyridin-2-yl)-3-hydroxy-2-oxoindolin-1-yl)methyl)cyclohexyl)-2-(difluoromethyl)nicotinamide | Intermediate-B, Intermediate-10 | A1 |

TABLE 1-continued (Examples)

| Ex. | Structure | Name | Reactants | Method |
|---|---|---|---|---|
| 14 | 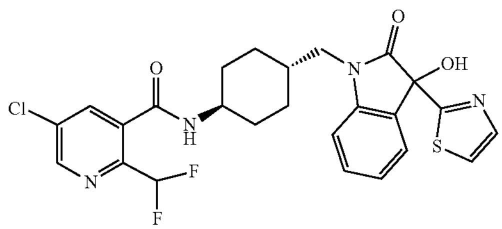 [SMILES: O=C(N[C@H]1CC[C@H](CN2C(=O)C(O)(c3nccs3)c3ccccc32)CC1)c1cc(Cl)cnc1C(F)F] | 5-chloro-2-(difluoromethyl)-N-((1r,4r)-4-((3-hydroxy-2-oxo-3-(thiazol-2-yl)indolin-1-yl)methyl)cyclohexyl)nicotinamide | Intermediate-B, Intermediate-11 | A1 |
| 15 | 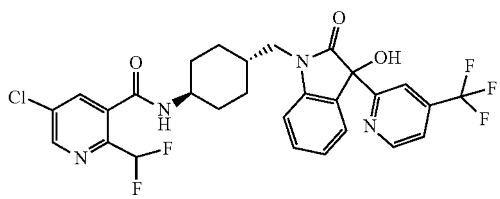 [SMILES: O=C(N[C@H]1CC[C@H](CN2C(=O)C(O)(c3cc(C(F)(F)F)ccn3)c3ccccc32)CC1)c1cc(Cl)cnc1C(F)F] | 5-chloro-2-(difluoromethyl)-N-((1r,4r)-4-((3-hydroxy-2-oxo-3-(4-(trifluoromethyl)pyridin-2-yl)indolin-1-yl)methyl)cyclohexyl)nicotinamide | Intermediate-B, Intermediate-12 | A1 |

Table 1-3

| Ex. | Structure | Name | Reactants | Method |
|---|---|---|---|---|
| 16 | 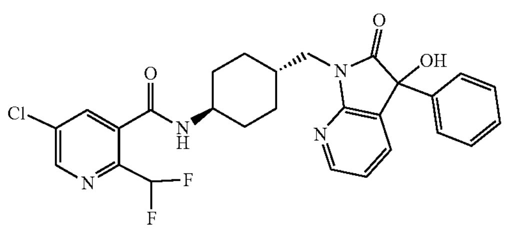 [SMILES: O=C(N[C@H]1CC[C@H](CN2C(=O)C(O)(c3ccccc3)c3cccnc32)CC1)c1cc(Cl)cnc1C(F)F] | 5-chloro-2-(difluoromethyl)-N-((1r,4r)-4-((3-hydroxy-2-oxo-3-phenyl-2,3-dihydro-1H-pyrrolo[2,3-b]pyridin-1-yl)methyl)cyclohexyl)nicotinamide | Intermediate-B, | A1 |
| 17 | 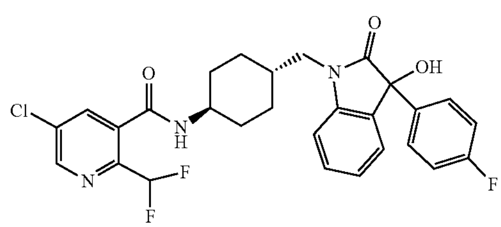 [SMILES: O=C(N[C@H]1CC[C@H](CN2C(=O)C(O)(c3ccc(F)cc3)c3ccccc32)CC1)c1cc(Cl)cnc1C(F)F] | 5-chloro-2-(difluoromethyl)-N-((1r,4r)-4-((3-(4-fluorophenyl)-3-hydroxy-2-oxoindolin-1-yl)methyl)cyclohexyl)nicotinamide | Intermediate-B, | A1 |
| 18 | 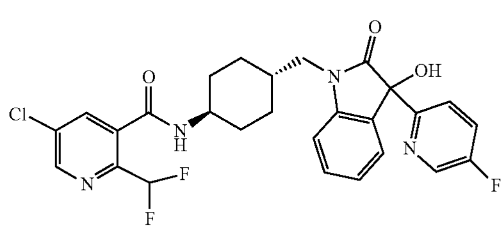 [SMILES: O=C(N[C@H]1CC[C@H](CN2C(=O)C(O)(c3ccc(F)cn3)c3ccccc32)CC1)c1cc(Cl)cnc1C(F)F] | 5-chloro-2-(difluoromethyl)-N-((1r,4r)-4-((3-(5-fluoropyridin-2-yl)-3-hydroxy-2-oxoindolin-1-yl)methyl)cyclohexyl)nicotinamide | Intermediate-B, Intermediate-13 | A1 |
| 19 | 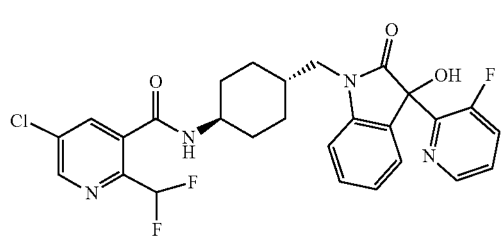 [SMILES: O=C(N[C@H]1CC[C@H](CN2C(=O)C(O)(c3ncccc3F)c3ccccc32)CC1)c1cc(Cl)cnc1C(F)F] | 5-chloro-2-(difluoromethyl)-N-((1r,4r)-4-((3-(3-fluoropyridin-2-yl)-3-hydroxy-2-oxoindolin-1-yl)methyl)cyclohexyl)nicotinamide | Intermediate-B, Intermediate-14 | A2 |

TABLE 1-continued (Examples)

| Ex. | Structure | Name | Reactants | Method |
|---|---|---|---|---|
| 20 | 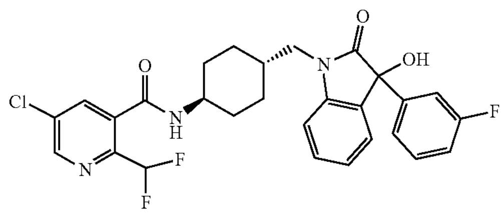 [SMILES: O=C(N[C@H]1CC[C@H](CN2C(=O)C(O)(c3cccc(F)c3)c3ccccc32)CC1)c1cc(Cl)cnc1C(F)F] | 5-chloro-2-(difluoromethyl)-N-((1r,4r)-4-((3-(3-fluorophenyl)-3-hydroxy-2-oxoindolin-1-yl)methyl)cyclohexyl)nicotinamide | Intermediate-B, | A2 |
| 21 | 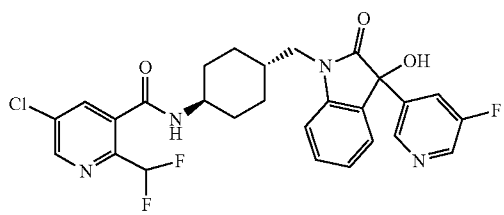 [SMILES: O=C(N[C@H]1CC[C@H](CN2C(=O)C(O)(c3cncc(F)c3)c3ccccc32)CC1)c1cc(Cl)cnc1C(F)F] | 5-chloro-2-(difluoromethyl)-N-((1r,4r)-4-((3-(5-fluoropyridin-3-yl)-3-hydroxy-2-oxoindolin-1-yl)methyl)cyclohexyl)nicotinamide | Intermediate-B, Intermediate-15 | A2 |
| 22 | 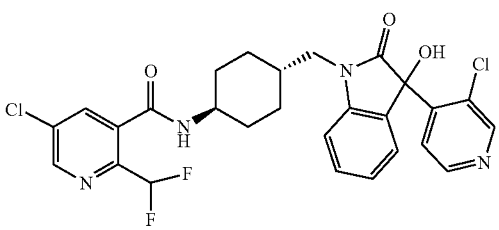 [SMILES: O=C(N[C@H]1CC[C@H](CN2C(=O)C(O)(c3ccncc3Cl)c3ccccc32)CC1)c1cc(Cl)cnc1C(F)F] | 5-chloro-N-((1r,4r)-4-((3-(3-chloropyridin-4-yl)-3-hydroxy-2-oxoindolin-1-yl)methyl)cyclohexyl)-2-(difluoromethyl)nicotinamide | Intermediate-B, Intermediate-16 | A2 |
| 23 | 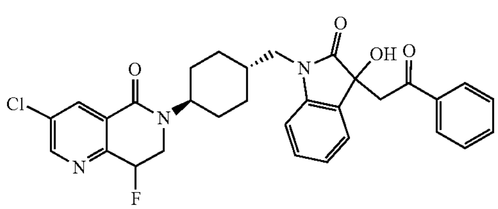 [SMILES: O=C(CC1(O)C(=O)N(C[C@H]2CC[C@H](N3CC(F)c4ncc(Cl)cc4C3=O)CC2)c2ccccc21)c1ccccc1] | 5-chloro-2-(difluoromethyl)-N-((1r,4r)-4-((3-hydroxy-2-oxo-3-(2-oxo-2-phenylethyl)indolin-1-yl)methyl)cyclohexyl)nicotinamide | See Example synthesis part | |

Table 1-4

| 24 | | 5-chloro-N-((1r,4r)-4-((3-(3-chloropyridin-2-yl)-3-hydroxy-2-oxoindolin-1-yl)methyl)cyclohexyl)-2-(difluoromethyl)nicotinamide | Intermediate-B, Intermediate-17 | A3 |
| 25 | | 5-chloro-2-(difluoromethyl)-N-((1r,4r)-4-((3-(3,5-difluoropyridin-2-yl)-3-hydroxy-2-oxoindolin-1-yl)methyl)cyclohexyl)nicotinamide | Intermediate-B, Intermediate-18 | A3 |

TABLE 1-continued (Examples)

| Ex. | Structure | Name | Reactants | Method |
|---|---|---|---|---|
| 26 | 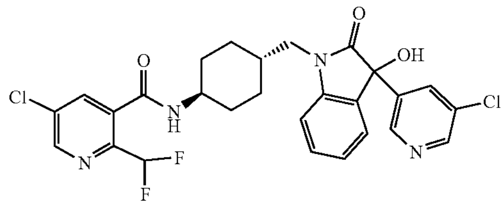 [SMILES: O=C(N[C@H]1CC[C@H](CN2C(=O)C(O)(c3cncc(Cl)c3)c3ccccc32)CC1)c1cc(Cl)cnc1C(F)F] | 5-chloro-N-((1r,4r)-4-((3-(5-chloropyridin-3-yl)-3-hydroxy-2-oxoindolin-1-yl)methyl)cyclohexyl)-2-(difluoromethyl)nicotinamide | Intermediate-B, Intermediate-19 | A2 |
| 27 | 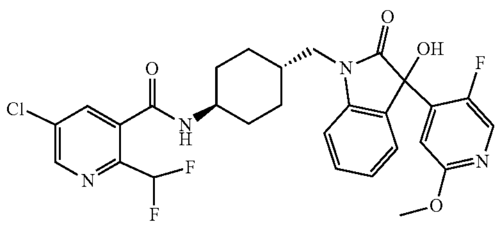 [SMILES: COc1cc(C2(O)C(=O)N(C[C@H]3CC[C@H](NC(=O)c4cc(Cl)cnc4C(F)F)CC3)c3ccccc32)c(F)cn1] | 5-chloro-2-(difluoromethyl)-N-((1r,4r)-4-((3-(5-fluoro-2-methoxypyridin-4-yl)-3-hydroxy-2-oxoindolin-1-yl)methyl)cyclohexyl)nicotinamide | Intermediate-B, Intermediate-20 | A2 |
| 28 | 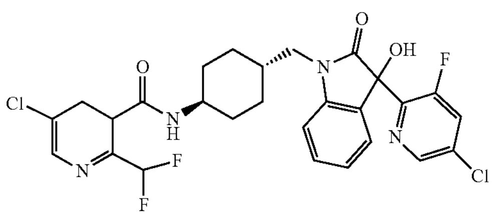 [SMILES: O=C(N[C@H]1CC[C@H](CN2C(=O)C(O)(c3ncc(Cl)cc3F)c3ccccc32)CC1)C1CC(Cl)=CN=C1C(F)F] | 5-chloro-N-((1r,4r)-4-((3-(5-chloro-3-fluoropyridin-2-yl)-3-hydroxy-2-oxoindolin-1-yl)methyl)cyclohexyl)-2-(difluoromethyl)nicotinamide | Intermediate-B, Intermediate-21 | A2 |
| 29 | 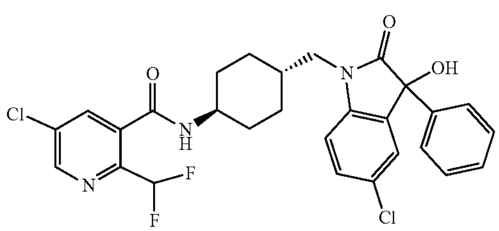 [SMILES: O=C(N[C@H]1CC[C@H](CN2C(=O)C(O)(c3ccccc3)c3cc(Cl)ccc32)CC1)c1cc(Cl)cnc1C(F)F] | 5-chloro-N-((1r,4r)-4-((5-chloro-3-hydroxy-2-oxo-3-phenylindolin-1-yl)methyl)cyclohexyl)-2-(difluoromethyl)nicotinamide | Intermediate-B, | A1 |
| 30 | 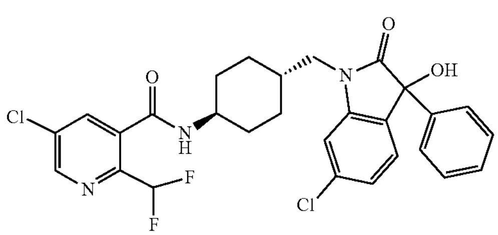 [SMILES: O=C(N[C@H]1CC[C@H](CN2C(=O)C(O)(c3ccccc3)c3ccc(Cl)cc32)CC1)c1cc(Cl)cnc1C(F)F] | 5-chloro-N-((1r,4r)-4-((6-chloro-3-hydroxy-2-oxo-3-phenylindolin-1-yl)methyl)cyclohexyl)-2-(difluoromethyl)nicotinamide | Intermediate-B, | A1 |
| 31 | 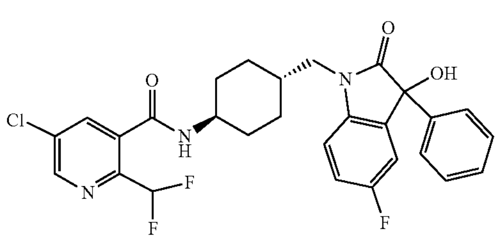 [SMILES: O=C(N[C@H]1CC[C@H](CN2C(=O)C(O)(c3ccccc3)c3cc(F)ccc32)CC1)c1cc(Cl)cnc1C(F)F] | 5-chloro-2-(difluoromethyl)-N-((1r,4r)-4-((5-fluoro-3-hydroxy-2-oxo-3-phenylindolin-1-yl)methyl)cyclohexyl)nicotinamide | Intermediate-B, | A1 |

TABLE 1-continued (Examples)

| Ex. | Structure | Name | Reactants | Method |
|---|---|---|---|---|
| | | Table 1-5 | | |
| 32 | 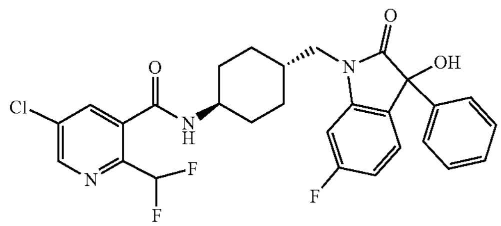 [SMILES: O=C(N[C@H]1CC[C@H](CN2C(=O)C(O)(c3ccccc3)c3ccc(F)cc32)CC1)c1cc(Cl)cnc1C(F)F] | 5-chloro-2-(difluoromethyl)-N-((1r,4r)-4-((6-fluoro-3-hydroxy-2-oxo-3-phenylindolin-1-yl)methyl)cyclohexyl)nicotinamide | Intermediate-B, Intermediate-22 | A2 |
| 33 | 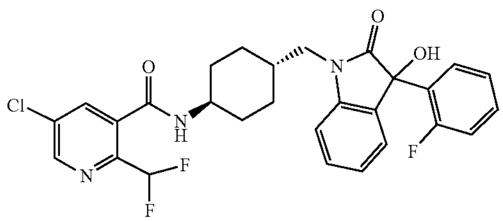 [SMILES: O=C(N[C@H]1CC[C@H](CN2C(=O)C(O)(c3ccccc3F)c3ccccc32)CC1)c1cc(Cl)cnc1C(F)F] | 5-chloro-2-(difluoromethyl)-N-((1r,4r)-4-((3-(2-fluorophenyl)-3-hydroxy-2-oxoindolin-1-yl)methyl)cyclohexyl)nicotinamide | Intermediate-B, | A2 |
| 34 | 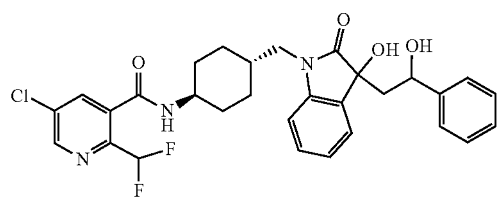 [SMILES: O=C(N[C@H]1CC[C@H](CN2C(=O)C(O)(CC(O)c3ccccc3)c3ccccc32)CC1)c1cc(Cl)cnc1C(F)F] | 5-chloro-2-(difluoromethyl)-N-((1r,4r)-4-((3-hydroxy-3-(2-hydroxy-2-phenylethyl)-2-oxoindolin-1-yl)methyl)cyclohexyl)nicotinamide | See Example synthesis part | |
| 35 | 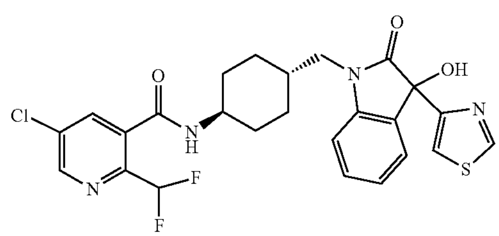 [SMILES: O=C(N[C@H]1CC[C@H](CN2C(=O)C(O)(c3cscn3)c3ccccc32)CC1)c1cc(Cl)cnc1C(F)F] | 5-chloro-2-(difluoromethyl)-N-((1r,4r)-4-((3-hydroxy-2-oxo-3-(thiazol-4-yl)indolin-1-yl)methyl)cyclohexyl)nicotinamide | Intermediate-B, Intermediate-23 | A2 |
| 36 | 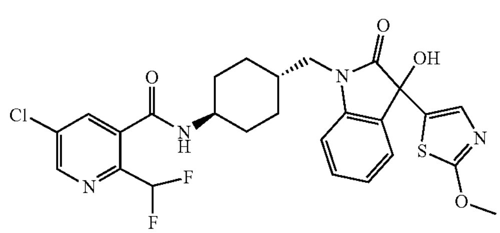 [SMILES: COc1ncc(C2(O)C(=O)N(C[C@H]3CC[C@H](NC(=O)c4cc(Cl)cnc4C(F)F)CC3)c3ccccc32)s1] | 5-chloro-2-(difluoromethyl)-N-((1r,4r)-4-((3-hydroxy-3-(2-methoxythiazol-5-yl)-2-oxoindolin-1-yl)methyl)cyclohexyl)nicotinamide | Intermediate-B, Intermediate-24 | A2 |
| 37 | 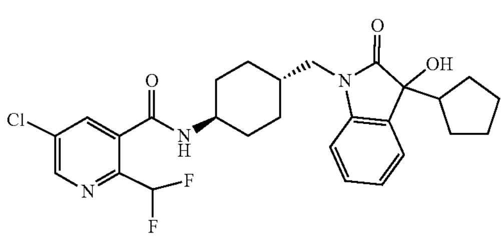 [SMILES: O=C(N[C@H]1CC[C@H](CN2C(=O)C(O)(C3CCCC3)c3ccccc32)CC1)c1cc(Cl)cnc1C(F)F] | 5-chloro-N-((1r,4r)-4-((3-cyclopentyl-3-hydroxy-2-oxoindolin-1-yl)methyl)cyclohexyl)-2-(difluoromethyl)nicotinamide | Intermediate-B, Intermediate-25 | A1 |

TABLE 1-continued (Examples)

| Ex. | Structure | Name | Reactants | Method |
|---|---|---|---|---|
| 38 | 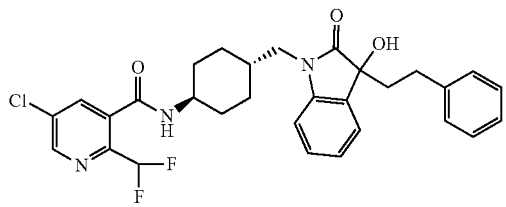 [SMILES: O=C(N[C@H]1CC[C@H](CN2C(=O)C(O)(CCc3ccccc3)c3ccccc32)CC1)c1cc(Cl)cnc1C(F)F] | 5-chloro-2-(difluoromethyl)-N-((1r,4r)-4-((3-hydroxy-2-oxo-3-phenethylindolin-1-yl)methyl)cyclohexyl)nicotinamide | Intermediate-B, Intermediate-26 | A1 |
| 39 | 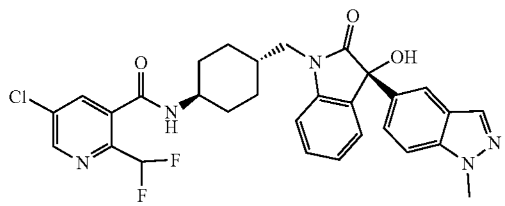 [SMILES: Cn1ncc2cc([C@]3(O)C(=O)N(C[C@H]4CC[C@H](NC(=O)c5cc(Cl)cnc5C(F)F)CC4)c4ccccc43)ccc21] | 5-chloro-2-(difluoromethyl)-N-((1r,4r)-4-((3-hydroxy-3-(1-methyl-1H-indazol-5-yl)-2-oxoindolin-1-yl)methyl)cyclohexyl)nicotinamide | Intermediate-27, (HO)$_2$B-indazole | B1 |

Table 1-6

| Ex. | Structure | Name | Reactants | Method |
|---|---|---|---|---|
| 40 | 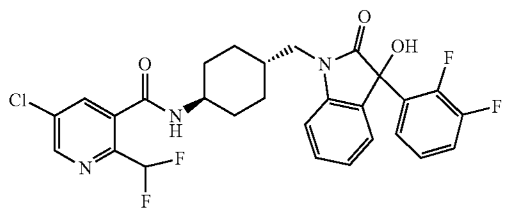 [SMILES: O=C(N[C@H]1CC[C@H](CN2C(=O)C(O)(c3cccc(F)c3F)c3ccccc32)CC1)c1cc(Cl)cnc1C(F)F] | 5-chloro-2-(difluoromethyl)-N-((1r,4r)-4-((3-(2,3-difluorophenyl)-3-hydroxy-2-oxoindolin-1-yl)methyl)cyclohexyl)nicotinamide | Intermediate-B, Intermediate-28 | A3 |
| 41 | 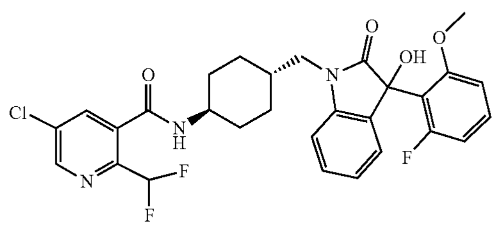 [SMILES: COc1cccc(F)c1C1(O)C(=O)N(C[C@H]2CC[C@H](NC(=O)c3cc(Cl)cnc3C(F)F)CC2)c2ccccc21] | 5-chloro-2-(difluoromethyl)-N-((1r,4r)-4-((3-(2-fluoro-6-methoxyphenyl)-3-hydroxy-2-oxoindolin-1-yl)methyl)cyclohexyl)nicotinamide | Intermediate-B, Intermediate-29 | A3 |
| 42 | 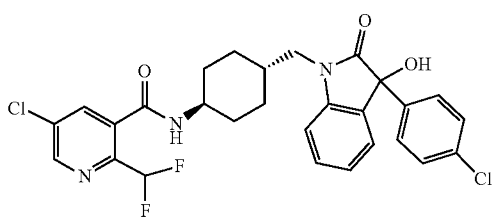 [SMILES: O=C(N[C@H]1CC[C@H](CN2C(=O)C(O)(c3ccc(Cl)cc3)c3ccccc32)CC1)c1cc(Cl)cnc1C(F)F] | 5-chloro-N-((1r,4r)-4-((3-(4-chlorophenyl)-3-hydroxy-2-oxoindolin-1-yl)methyl)cyclohexyl)-2-(difluoromethyl)nicotinamide | Intermediate-27, (HO)$_2$B-(4-Cl-C$_6$H$_4$) | B1 |
| 43 | 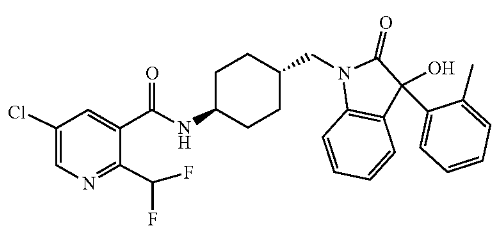 [SMILES: Cc1ccccc1C1(O)C(=O)N(C[C@H]2CC[C@H](NC(=O)c3cc(Cl)cnc3C(F)F)CC2)c2ccccc21] | 5-chloro-2-(difluoromethyl)-N-((1r,4r)-4-((3-hydroxy-2-oxo-3-(o-tolyl)indolin-1-yl)methyl)cyclohexyl)nicotinamide | Intermediate-27, (HO)$_2$B-(2-Me-C$_6$H$_4$) | B1 |
| 44 | 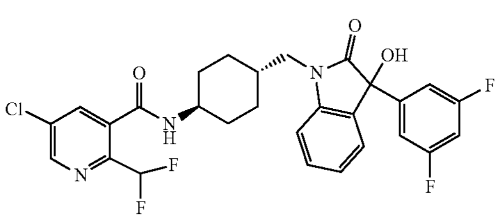 [SMILES: O=C(N[C@H]1CC[C@H](CN2C(=O)C(O)(c3cc(F)cc(F)c3)c3ccccc32)CC1)c1cc(Cl)cnc1C(F)F] | 5-chloro-2-(difluoromethyl)-N-((1r,4r)-4-((3-(3,5-difluorophenyl)-3-hydroxy-2-oxoindolin-1-yl)methyl)cyclohexyl)nicotinamide | Intermediate-27, (HO)$_2$B-(3,5-F$_2$-C$_6$H$_3$) | B1 |

TABLE 1-continued (Examples)

| Ex. | Structure | Name | Reactants | Method |
|---|---|---|---|---|
| 45 | 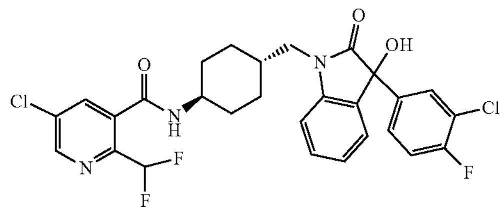 [SMILES: O=C(N[C@H]1CC[C@H](CN2C(=O)C(O)(c3ccc(F)c(Cl)c3)c3ccccc32)CC1)c1cc(Cl)cnc1C(F)F] | 5-chloro-N-((1r,4r)-4-((3-(3-chloro-4-fluorophenyl)-3-hydroxy-2-oxoindolin-1-yl)methyl)cyclohexyl)-2-(difluoromethyl)nicotinamide | Intermediate-27, (HO)$_2$B-(3-Cl-4-F-C$_6$H$_3$) | B1 |
| 46 | 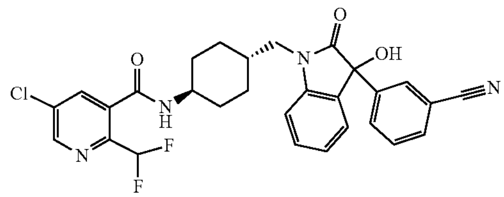 [SMILES: N#Cc1cccc(C2(O)C(=O)N(C[C@H]3CC[C@H](NC(=O)c4cc(Cl)cnc4C(F)F)CC3)c3ccccc32)c1] | 5-chloro-N-((1r,4r)-4-((3-(3-cyanophenyl)-3-hydroxy-2-oxoindolin-1-yl)methyl)cyclohexyl)-2-(difluoromethyl)nicotinamide | Intermediate-27, (HO)$_2$B-(3-CN-C$_6$H$_4$) | B1 |
| 47 | 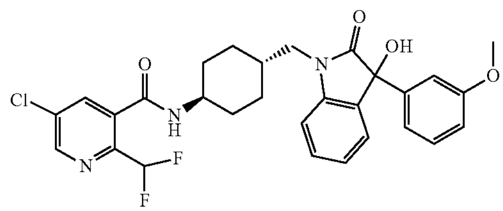 [SMILES: COc1cccc(C2(O)C(=O)N(C[C@H]3CC[C@H](NC(=O)c4cc(Cl)cnc4C(F)F)CC3)c3ccccc32)c1] | 5-chloro-2-(difluoromethyl)-N-((1r,4r)-4-((3-hydroxy-3-(3-methoxyphenyl)-2-oxoindolin-1-yl)methyl)cyclohexyl)nicotinamide | Intermediate-27, (HO)$_2$B-(3-OMe-C$_6$H$_4$) | B1 |

Table 1-7

| Ex. | Structure | Name | Reactants | Method |
|---|---|---|---|---|
| 48 | 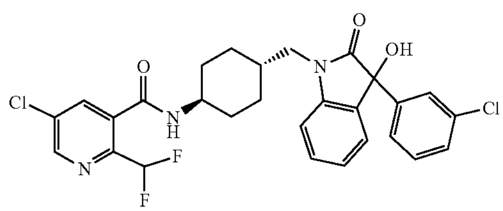 [SMILES: O=C(N[C@H]1CC[C@H](CN2C(=O)C(O)(c3cccc(Cl)c3)c3ccccc32)CC1)c1cc(Cl)cnc1C(F)F] | 5-chloro-N-((1r,4r)-4-((3-(3-chlorophenyl)-3-hydroxy-2-oxoindolin-1-yl)methyl) cyclohexyl)-2-(difluoromethyl)nicotinamide | Intermediate-27, (HO)$_2$B-(3-Cl-C$_6$H$_4$) | B1 |
| 49 | 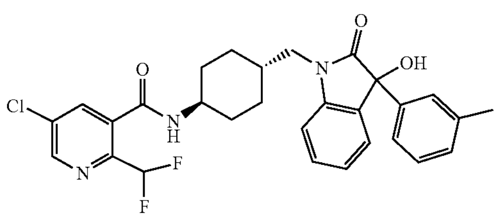 [SMILES: Cc1cccc(C2(O)C(=O)N(C[C@H]3CC[C@H](NC(=O)c4cc(Cl)cnc4C(F)F)CC3)c3ccccc32)c1] | 5-chloro-2-(difluoromethyl)-N-((1r,4r)-4-((3-hydroxy-2-oxo-3-(m-tolyl)indolin-1-yl)methyl)cyclohexyl) nicotinamide | Intermediate-27, (HO)$_2$B-(3-Me-C$_6$H$_4$) | B1 |
| 50 | 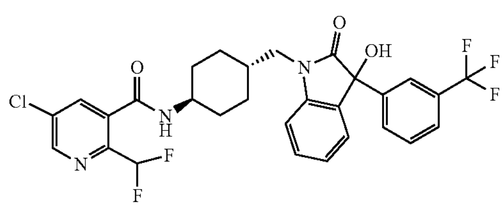 [SMILES: O=C(N[C@H]1CC[C@H](CN2C(=O)C(O)(c3cccc(C(F)(F)F)c3)c3ccccc32)CC1)c1cc(Cl)cnc1C(F)F] | 5-chloro-2-(difluoromethyl)-N-((1r,4r)-4-((3-hydroxy-2-oxo-3-(3-(trifluoromethyl)phenyl)indolin-1-yl)methyl)cyclohexyl) nicotinamide | Intermediate-27, (HO)$_2$B-(3-CF$_3$-C$_6$H$_4$) | B1 |
| 51 | 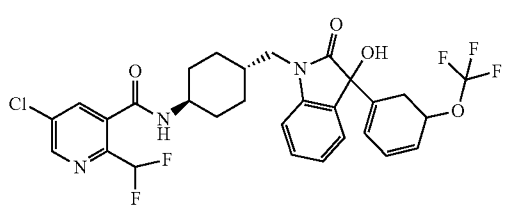 [SMILES: O=C(N[C@H]1CC[C@H](CN2C(=O)C(O)(C3=CC=CC(OC(F)(F)F)C3)c3ccccc32)CC1)c1cc(Cl)cnc1C(F)F] | 5-chloro-2-(difluoromethyl)-N-((1r,4r)-4-((3-hydroxy-2-oxo-3-(3-(trifluoromethoxy)phenyl)indolin-1-yl)methyl)cyclohexyl) nicotinamide | Intermediate-27, (HO)$_2$B-(3-OCF$_3$-C$_6$H$_4$) | B1 |

TABLE 1-continued (Examples)

| Ex. | Structure | Name | Reactants | Method |
|---|---|---|---|---|
| 52 | 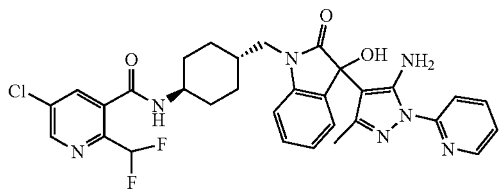 [SMILES: Cc1nn(-c2ccccn2)c(N)c1C1(O)C(=O)N(C[C@H]2CC[C@H](NC(=O)c3cc(Cl)cnc3C(F)F)CC2)c2ccccc21] | N-((1r,4r)-4-((3-(5-amino-3-methyl-1-(pyridin-2-yl)-1H-pyrazol-4-yl)-3-hydroxy-2-oxoindolin-1-yl)methyl)cyclohexyl)-5-chloro-2-(difluoromethyl)nicotinamide | See Example synthesis part | |
| 53 | 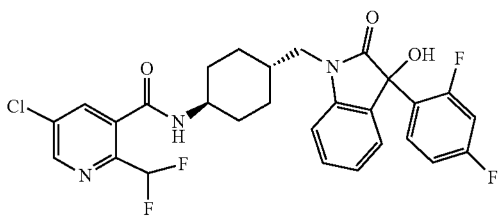 [SMILES: O=C(N[C@H]1CC[C@H](CN2C(=O)C(O)(c3ccc(F)cc3F)c3ccccc32)CC1)c1cc(Cl)cnc1C(F)F] | 5-chloro-2-(difluoromethyl)-N-((1r,4r)-4-((3-(2,4-difluorophenyl)-3-hydroxy-2-oxoindolin-1-yl)methyl)cyclohexyl)nicotinamide | Intermediate-B, Intermediate-30 | A2 |
| 54 | 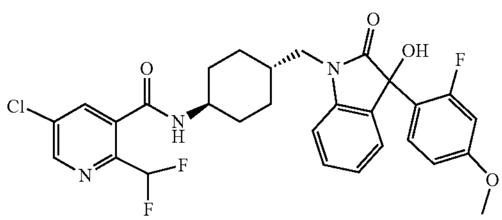 [SMILES: COc1ccc(C2(O)C(=O)N(C[C@H]3CC[C@H](NC(=O)c4cc(Cl)cnc4C(F)F)CC3)c3ccccc32)c(F)c1] | 5-chloro-2-(difluoromethyl)-N-((1r,4r)-4-((3-(2-fluoro-4-methoxyphenyl)-3-hydroxy-2-oxoindolin-1-yl)methyl)cyclohexyl)nicotinamide | Intermediate-B, Intermediate-31 | A2 |
| 55 | 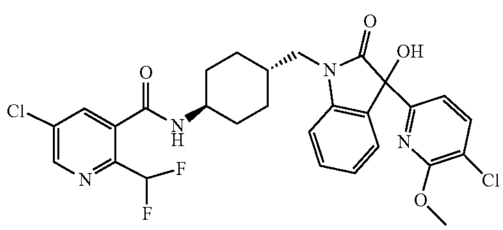 [SMILES: COc1nc(C2(O)C(=O)N(C[C@H]3CC[C@H](NC(=O)c4cc(Cl)cnc4C(F)F)CC3)c3ccccc32)ccc1Cl] | 5-chloro-N-((1r,4r)-4-((3-(5-chloro-6-methoxypyridin-2-yl)-3-hydroxy-2-oxoindolin-1-yl)methyl)cyclohexyl)-2-(difluoromethyl)nicotinamide | Intermediate-B, Intermediate-32 | A2 |

Table 1-8

| Ex. | Structure | Name | Reactants | Method |
|---|---|---|---|---|
| 56 | 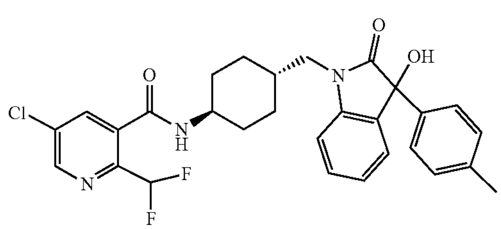 [SMILES: Cc1ccc(C2(O)C(=O)N(C[C@H]3CC[C@H](NC(=O)c4cc(Cl)cnc4C(F)F)CC3)c3ccccc32)cc1] | 5-chloro-2-(difluoromethyl)-N-((1r,4r)-4-((3-hydroxy-2-oxo-3-(p-tolyl)indolin-1-yl)methyl)cyclohexyl)nicotinamide | Intermediate-27, (HO)$_2$B-C$_6$H$_4$-CH$_3$ | B1 |
| 57 | 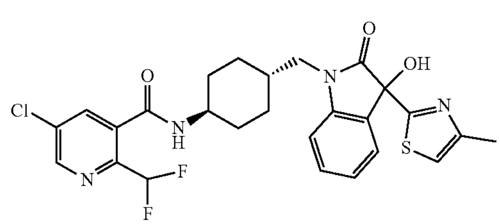 [SMILES: Cc1csc(C2(O)C(=O)N(C[C@H]3CC[C@H](NC(=O)c4cc(Cl)cnc4C(F)F)CC3)c3ccccc32)n1] | 5-chloro-2-(difluoromethyl)-N-((1r,4r)-4-((3-hydroxy-3-(4-methylthiazol-2-yl)-2-oxoindolin-1-yl)methyl)cyclohexyl)nicotinamide | Intermediate-B, Intermediate-33 | A2 |

//

TABLE 1-continued (Examples)

| Ex. | Structure | Name | Reactants | Method |
|---|---|---|---|---|
| 58 | 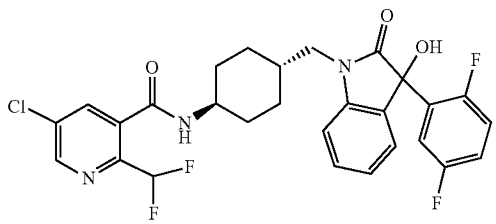 [SMILES: O=C(N[C@H]1CC[C@H](CN2C(=O)C(O)(c3cc(F)ccc3F)c3ccccc32)CC1)c1cc(Cl)cnc1C(F)F] | 5-chloro-2-(difluoromethyl)-N-((1r,4r)-4-((3-(2,5-difluorophenyl)-3-hydroxy-2-oxoindolin-1-yl)methyl)cyclohexyl)nicotinamide | Intermediate-B, Intermediate-34 | A2 |
| 59 | 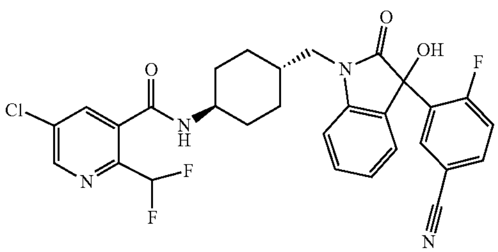 [SMILES: N#Cc1ccc(F)c(C2(O)C(=O)N(C[C@H]3CC[C@H](NC(=O)c4cc(Cl)cnc4C(F)F)CC3)c3ccccc32)c1] | 5-chloro-N-((1r,4r)-4-((3-(5-cyano-2-fluorophenyl)-3-hydroxy-2-oxoindolin-1-yl)methyl)cyclohexyl)-2-(difluoromethyl)nicotinamide | Intermediate-B, Intermediate-35 | A2 |
| 60 | 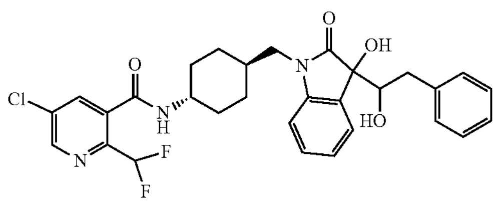 [SMILES: O=C(N[C@H]1CC[C@H](CN2C(=O)C(O)(C(O)Cc3ccccc3)c3ccccc32)CC1)c1cc(Cl)cnc1C(F)F] | 5-chloro-2-(difluoromethyl)-N-((1r,4r)-4-((3-hydroxy-3-(1-hydroxy-2-phenylethyl)-2-oxoindolin-1-yl)methyl)cyclohexyl)nicotinamide | See Example synthesis part | |
| 61 | 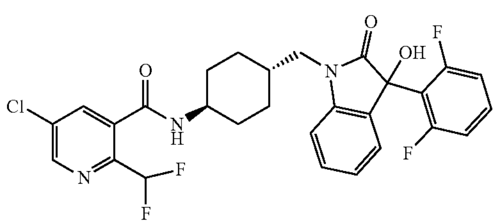 [SMILES: O=C(N[C@H]1CC[C@H](CN2C(=O)C(O)(c3c(F)cccc3F)c3ccccc32)CC1)c1cc(Cl)cnc1C(F)F] | 5-chloro-2-(difluoromethyl)-N-((1r,4r)-4-((3-(2,6-difluorophenyl)-3-hydroxy-2-oxoindolin-1-yl)methyl)cyclohexyl)nicotinamide | Intermediate-B, Intermediate-36 | A2 |
| 62 | 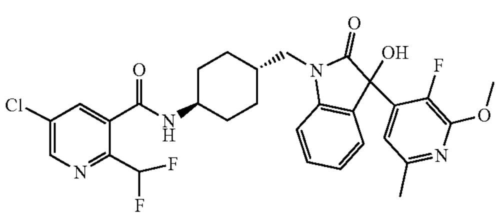 [SMILES: COc1nc(C)cc(C2(O)C(=O)N(C[C@H]3CC[C@H](NC(=O)c4cc(Cl)cnc4C(F)F)CC3)c3ccccc32)c1F] | 5-chloro-2-(difluoromethyl)-N-((1r,4r)-4-((3-(3-fluoro-2-methoxy-6-methylpyridin-4-yl)-3-hydroxy-2-oxoindolin-1-yl)methyl)cyclohexyl)nicotinamide | Intermediate-B, Intermediate-37 | A2 |
| 63 | 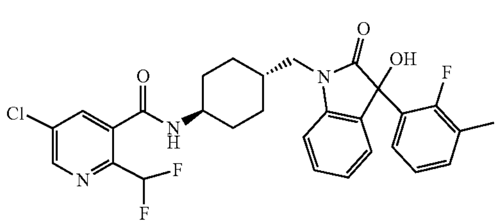 [SMILES: Cc1cccc(C2(O)C(=O)N(C[C@H]3CC[C@H](NC(=O)c4cc(Cl)cnc4C(F)F)CC3)c3ccccc32)c1F] | 5-chloro-2-(difluoromethyl)-N-((1r,4r)-4-((3-(2-fluoro-3-methylphenyl)-3-hydroxy-2-oxoindolin-1-yl)methyl)cyclohexyl)nicotinamide | Intermediate-B, Intermediate-38 | A2 |

TABLE 1-continued (Examples)

| Ex. | Structure | Name | Reactants | Method |
|---|---|---|---|---|
| | | Table 1-9 | | |
| 64 | 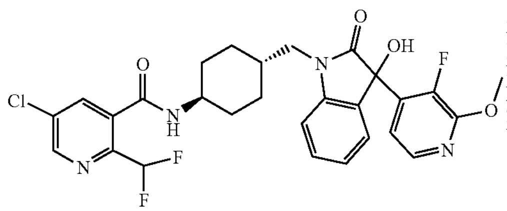 | 5-chloro-2-(difluoromethyl)-N-((1r,4r)-4-((3-(3-fluoro-2-methoxypyridin-4-yl)-3-hydroxy-2-oxoindolin-1-yl)methyl)cyclohexyl)nicotinamide | Intermediate-B, Intermediate-39 | A2 |
| 65 | 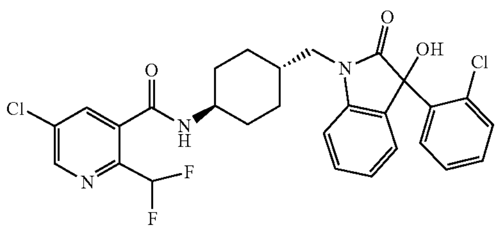 [SMILES: O=C(N[C@H]1CC[C@H](CN2C(=O)C(O)(c3ccccc3Cl)c3ccccc32)CC1)c1cc(Cl)cnc1C(F)F] | 5-chloro-N-((1r,4r)-4-((3-(2-chlorophenyl)-3-hydroxy-2-oxoindolin-1-yl)methyl)cyclohexyl)-2-(difluoromethyl)nicotinamide | Intermediate-B, | A2 |
| 66 | 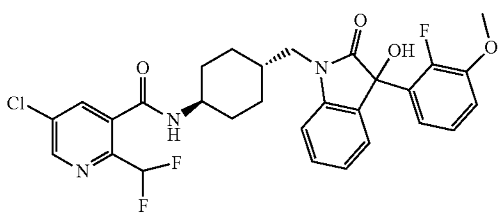 [SMILES: COc1cccc(C2(O)C(=O)N(C[C@H]3CC[C@H](NC(=O)c4cc(Cl)cnc4C(F)F)CC3)c3ccccc32)c1F] | 5-chloro-2-(difluoromethyl)-N-((1r,4r)-4-((3-(2-fluoro-3-methoxyphenyl)-3-hydroxy-2-oxoindolin-1-yl)methyl)cyclohexyl)nicotinamide | Intermediate-B, Intermediate-40 | A2 |
| 67 | 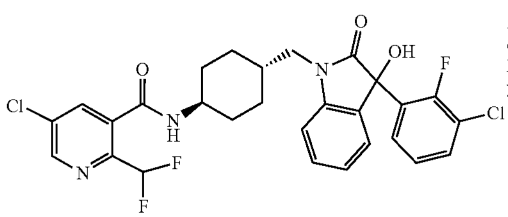 | 5-chloro-N-((1r,4r)-4-((3-(3-chloro-2-fluorophenyl)-3-hydroxy-2-oxoindolin-1-yl)methyl)cyclohexyl)-2-(difluoromethyl)nicotinamide | Intermediate-B, Intermediate-41 | A2 |
| 68 | 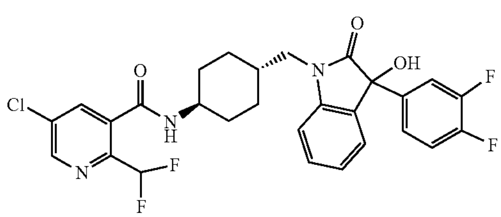 [SMILES: O=C(N[C@H]1CC[C@H](CN2C(=O)C(O)(c3ccc(F)c(F)c3)c3ccccc32)CC1)c1cc(Cl)cnc1C(F)F] | 5-chloro-2-(difluoromethyl)-N-((1r,4r)-4-((3-(3,4-difluorophenyl)-3-hydroxy-2-oxoindolin-1-yl)methyl)cyclohexyl)nicotinamide | Intermediate-B, Intermediate-42 | A1 |
| 69 | 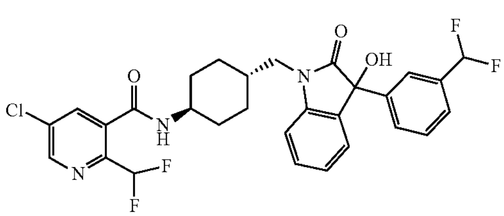 [SMILES: O=C(N[C@H]1CC[C@H](CN2C(=O)C(O)(c3cccc(C(F)F)c3)c3ccccc32)CC1)c1cc(Cl)cnc1C(F)F] | 5-chloro-2-(difluoromethyl)-N-((1r,4r)-4-((3-(3-(difluoromethyl)phenyl)-3-hydroxy-2-oxoindolin-1-yl)methyl)cyclohexyl)nicotinamide | Intermediate-B, Intermediate-43 | A2 |
| 70 | 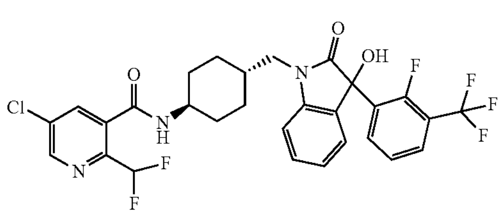 [SMILES: O=C(N[C@H]1CC[C@H](CN2C(=O)C(O)(c3cccc(C(F)(F)F)c3F)c3ccccc32)CC1)c1cc(Cl)cnc1C(F)F] | 5-chloro-2-(difluoromethyl)-N-((1r,4r)-4-((3-(2-fluoro-3-(trifluoromethyl)phenyl)-3-hydroxy-2-oxoindolin-1-yl)methyl)cyclohexyl)nicotinamide | Intermediate-B, Intermediate-44 | A2 |

TABLE 1-continued (Examples)

| Ex. | Structure | Name | Reactants | Method |
|---|---|---|---|---|
| 71 | | 5-chloro-N-((1r,4r)-4-((3-(3-cyano-2-fluorophenyl)-3-hydroxy-2-oxoindolin-1-yl)methyl)cyclohexyl)-2-(difluoromethyl)nicotinamide | Intermediate-B, Intermediate-45 | A2 |

Table 1-10

| Ex. | Structure | Name | Reactants | Method |
|---|---|---|---|---|
| 72 | 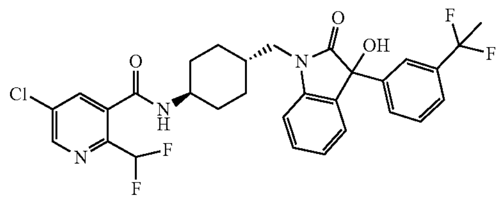 [SMILES: CC(F)(F)c1cccc(C2(O)C(=O)N(C[C@H]3CC[C@H](NC(=O)c4cc(Cl)cnc4C(F)F)CC3)c3ccccc32)c1] | 5-chloro-N-((1r,4r)-4-((3-(3-(1,1-difluoroethyl)phenyl)-3-hydroxy-2-oxoindolin-1-yl)methyl)cyclohexyl)-2-(difluoromethyl)nicotinamide | Intermediate-B, Intermediate-46 | A2 |
| 73 | 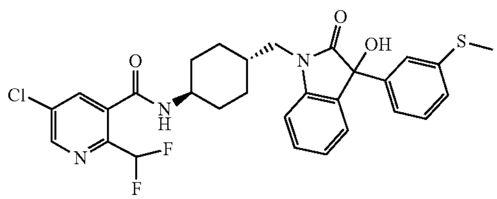 [SMILES: CSc1cccc(C2(O)C(=O)N(C[C@H]3CC[C@H](NC(=O)c4cc(Cl)cnc4C(F)F)CC3)c3ccccc32)c1] | 5-chloro-2-(difluoromethyl)-N-((1r,4r)-4-((3-hydroxy-3-(3-(methylthio)phenyl)-2-oxoindolin-1-yl)methyl)cyclohexyl)nicotinamide | Intermediate-B, Intermediate-47 | A2 |
| 74 | 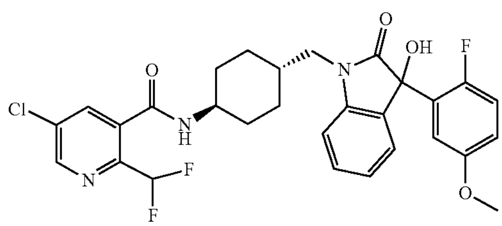 [SMILES: COc1ccc(F)c(C2(O)C(=O)N(C[C@H]3CC[C@H](NC(=O)c4cc(Cl)cnc4C(F)F)CC3)c3ccccc32)c1] | 5-chloro-2-(difluoromethyl)-N-((1r,4r)-4-((3-(2-fluoro-5-methoxyphenyl)-3-hydroxy-2-oxoindolin-1-yl)methyl)cyclohexyl)nicotinamide | Intermediate-B, Intermediate-48 | A2 |
| 75 | 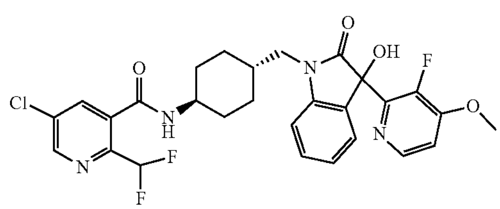 [SMILES: COc1ccnc(C2(O)C(=O)N(C[C@H]3CC[C@H](NC(=O)c4cc(Cl)cnc4C(F)F)CC3)c3ccccc32)c1F] | 5-chloro-2-(difluoromethyl)-N-((1r,4r)-4-((3-(3-fluoro-4-methoxypyridin-2-yl)-3-hydroxy-2-oxoindolin-1-yl)methyl)cyclohexyl)nicotinamide | Intermediate-B, Intermediate-49 | A2 |
| 76 | 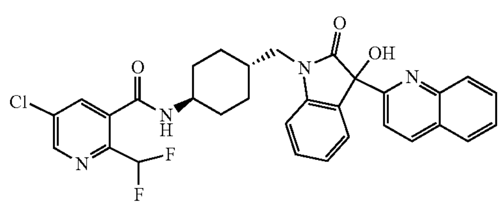 [SMILES: O=C(N[C@H]1CC[C@H](CN2C(=O)C(O)(c3ccc4ccccc4n3)c3ccccc32)CC1)c1cc(Cl)cnc1C(F)F] | 5-chloro-2-(difluoromethyl)-N-((1r,4r)-4-((3-hydroxy-2-oxo-3-(quinolin-2-yl)indolin-1-yl)methyl)cyclohexyl)nicotinamide | Intermediate-B, Intermediate-50 | A1 |
| 77 | 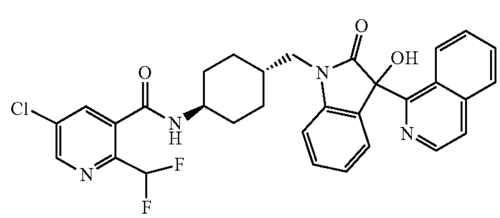 [SMILES: O=C(N[C@H]1CC[C@H](CN2C(=O)C(O)(c3nccc4ccccc34)c3ccccc32)CC1)c1cc(Cl)cnc1C(F)F] | 5-chloro-2-(difluoromethyl)-N-((1r,4r)-4-((3-hydroxy-3-(isoquinolin-1-yl)-2-oxoindolin-1-yl)methyl)cyclohexyl)nicotinamide | Intermediate-B, Intermediate-51 | A1 |

TABLE 1-continued (Examples)

| Ex. | Structure | Name | Reactants | Method |
|---|---|---|---|---|
| 78 | 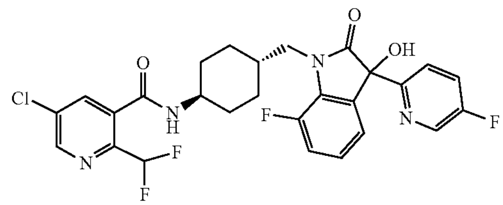 [SMILES: O=C(N[C@H]1CC[C@H](CN2C(=O)C(O)(c3ccc(F)cn3)c3cccc(F)c32)CC1)c1cc(Cl)cnc1C(F)F] | 5-chloro-2-(difluoromethyl)-N-((1r,4r)-4-((7-fluoro-3-(5-fluoropyridin-2-yl)-3-hydroxy-2-oxoindolin-1-yl)methyl)cyclohexyl)nicotinamide | Intermediate-B, Intermediate-52 | A1 |
| 79 | 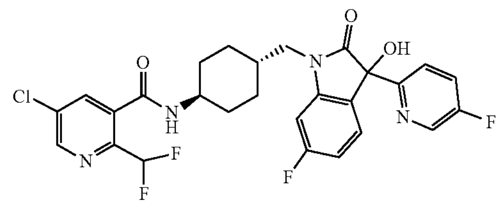 [SMILES: O=C(N[C@H]1CC[C@H](CN2C(=O)C(O)(c3ccc(F)cn3)c3ccc(F)cc32)CC1)c1cc(Cl)cnc1C(F)F] | 5-chloro-2-(difluoromethyl)-N-((1r,4r)-4-((6-fluoro-3-(5-fluoropyridin-2-yl)-3-hydroxy-2-oxoindolin-1-yl)methyl)cyclohexyl)nicotinamide | Intermediate-B, Intermediate-53 | A1 |

Table 1-11

| Ex. | Structure | Name | Reactants | Method |
|---|---|---|---|---|
| 80 | 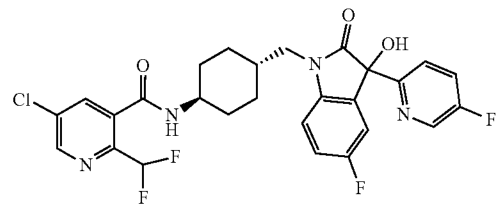 [SMILES: O=C(N[C@H]1CC[C@H](CN2C(=O)C(O)(c3ccc(F)cn3)c3cc(F)ccc32)CC1)c1cc(Cl)cnc1C(F)F] | 5-chloro-2-(difluoromethyl)-N-((1r,4r)-4-((5-fluoro-3-(5-fluoropyridin-2-yl)-3-hydroxy-2-oxoindolin-1-yl)methyl)cyclohexyl)nicotinamide | Intermediate-B, Intermediate-54 | A1 |
| 81 | 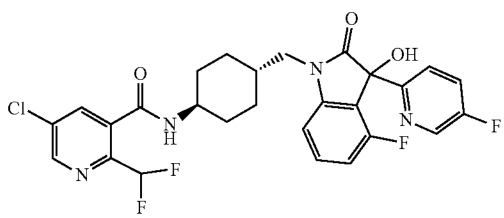 [SMILES: O=C(N[C@H]1CC[C@H](CN2C(=O)C(O)(c3ccc(F)cn3)c3c(F)cccc32)CC1)c1cc(Cl)cnc1C(F)F] | 5-chloro-2-(difluoromethyl)-N-((1r,4r)-4-((4-fluoro-3-(5-fluoropyridin-2-yl)-3-hydroxy-2-oxoindolin-1-yl)methyl)cyclohexyl)nicotinamide | Intermediate-B, Intermediate-55 | A1 |
| 82 | 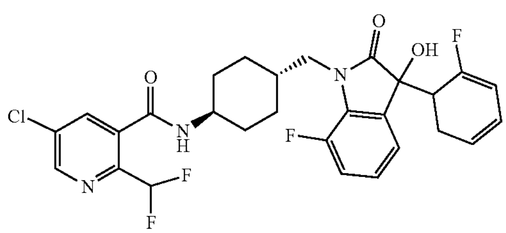 [SMILES: O=C(N[C@H]1CC[C@H](CN2C(=O)C(O)(C3CC=CC=C3F)c3cccc(F)c32)CC1)c1cc(Cl)cnc1C(F)F] | 5-chloro-2-(difluoromethyl)-N-((1r,4r)-4-((7-fluoro-3-(2-fluorophenyl)-3-hydroxy-2-oxoindolin-1-yl)methyl)cyclohexyl)nicotinamide | Intermediate-B, Intermediate-56 | A1 |
| 83 | 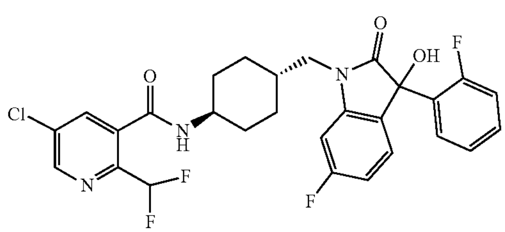 [SMILES: O=C(N[C@H]1CC[C@H](CN2C(=O)C(O)(c3ccccc3F)c3ccc(F)cc32)CC1)c1cc(Cl)cnc1C(F)F] | 5-chloro-2-(difluoromethyl)-N-((1r,4r)-4-((6-fluoro-3-(2-fluorophenyl)-3-hydroxy-2-oxoindolin-1-yl)methyl)cyclohexyl)nicotinamide | Intermediate-B, Intermediate-57 | A1 |
| 84 | 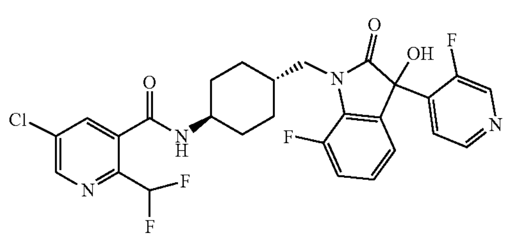 [SMILES: O=C(N[C@H]1CC[C@H](CN2C(=O)C(O)(c3ccncc3F)c3cccc(F)c32)CC1)c1cc(Cl)cnc1C(F)F] | 5-chloro-2-(difluoromethyl)-N-((1r,4r)-4-((7-fluoro-3-(3-fluoropyridin-4-yl)-3-hydroxy-2-oxoindolin-1-yl)methyl)cyclohexyl)nicotinamide | Intermediate-B, Intermediate-58 | A4 |

TABLE 1-continued (Examples)

| Ex. | Structure | Name | Reactants | Method |
|---|---|---|---|---|
| 85 | 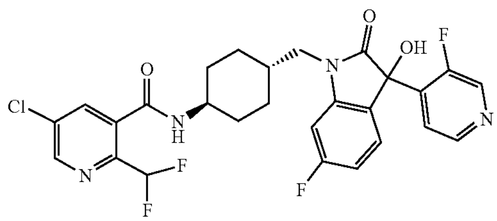 [SMILES: O=C(N[C@H]1CC[C@H](CN2C(=O)C(O)(c3ccncc3F)c3ccc(F)cc32)CC1)c1cc(Cl)cnc1C(F)F] | 5-chloro-2-(difluoromethyl)-N-((1r,4r)-4-((6-fluoro-3-(3-fluoropyridin-4-yl)-3-hydroxy-2-oxoindolin-1-yl)methyl)cyclohexyl)nicotinamide | Intermediate-B, Intermediate-59 | A4 |
| 86 | 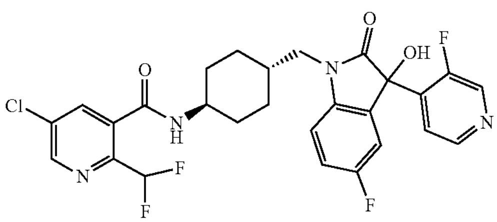 [SMILES: O=C(N[C@H]1CC[C@H](CN2C(=O)C(O)(c3ccncc3F)c3cc(F)ccc32)CC1)c1cc(Cl)cnc1C(F)F] | 5-chloro-2-(difluoromethyl)-N-((1r,4r)-4-((5-fluoro-3-(3-fluoropyridin-4-yl)-3-hydroxy-2-oxoindolin-1-yl)methyl)cyclohexyl)nicotinamide | Intermediate-B, Intermediate-60 | A4 |
| 87 | 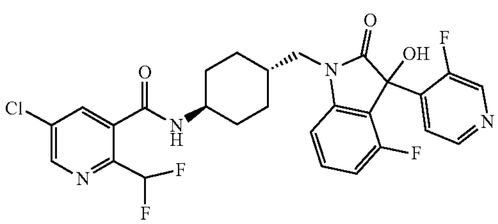 [SMILES: O=C(N[C@H]1CC[C@H](CN2C(=O)C(O)(c3ccncc3F)c3c(F)cccc32)CC1)c1cc(Cl)cnc1C(F)F] | 5-chloro-2-(difluoromethyl)-N-((1r,4r)-4-((4-fluoro-3-(3-fluoropyridin-4-yl)-3-hydroxy-2-oxoindolin-1-yl)methyl)cyclohexyl)nicotinamide | Intermediate-B, Intermediate-61 | A4 |

Table 1-12

| Ex. | Structure | Name | Reactants | Method |
|---|---|---|---|---|
| 88 | 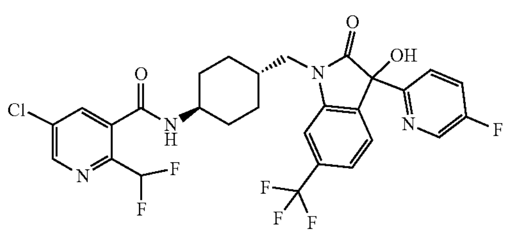 [SMILES: O=C(N[C@H]1CC[C@H](CN2C(=O)C(O)(c3ccc(F)cn3)c3ccc(C(F)(F)F)cc32)CC1)c1cc(Cl)cnc1C(F)F] | 5-chloro-2-(difluoromethyl)-N-((1r,4r)-4-((3-(5-fluoropyridin-2-yl)-3-hydroxy-2-oxo-6-(trifluoromethyl)indolin-1-yl)methyl)cyclohexyl)nicotinamide | Intermediate-B, Intermediate-62 | A1 |
| 89 | 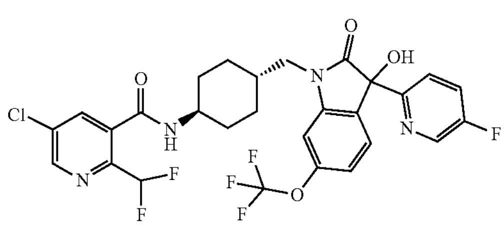 [SMILES: O=C(N[C@H]1CC[C@H](CN2C(=O)C(O)(c3ccc(F)cn3)c3ccc(OC(F)(F)F)cc32)CC1)c1cc(Cl)cnc1C(F)F] | 5-chloro-2-(difluoromethyl)-N-((1r,4r)-4-((3-(5-fluoropyridin-2-yl)-3-hydroxy-2-oxo-6-(trifluoromethoxy)indolin-1-yl)methyl)cyclohexyl)nicotinamide | Intermediate-B, Intermediate-63 | A1 |
| 90 | 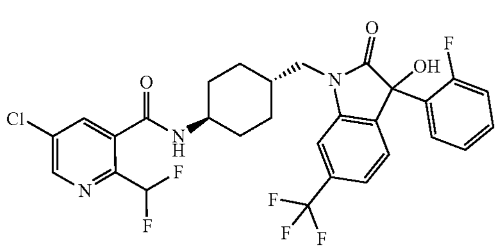 [SMILES: O=C(N[C@H]1CC[C@H](CN2C(=O)C(O)(c3ccccc3F)c3ccc(C(F)(F)F)cc32)CC1)c1cc(Cl)cnc1C(F)F] | 5-chloro-2-(difluoromethyl)-N-((1r,4r)-4-((3-(2-fluorophenyl)-3-hydroxy-2-oxo-6-(trifluoromethyl)indolin-1-yl)methyl)cyclohexyl)nicotinamide | Intermediate-B, Intermediate-64 | A1 |

TABLE 1-continued (Examples)

| Ex. | Structure | Name | Reactants | Method |
|---|---|---|---|---|
| 91 | 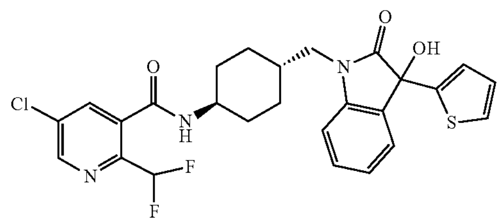 [SMILES: O=C(N[C@H]1CC[C@H](CN2C(=O)C(O)(c3cccs3)c3ccccc32)CC1)c1cc(Cl)cnc1C(F)F] | 5-chloro-2-(difluoromethyl)-N-((1r,4r)-4-((3-hydroxy-2-oxo-3-(thiophen-2-yl)indolin-1-yl)methyl)cyclohexyl)nicotinamide | Intermediate-B, | A2 |
| 92 | 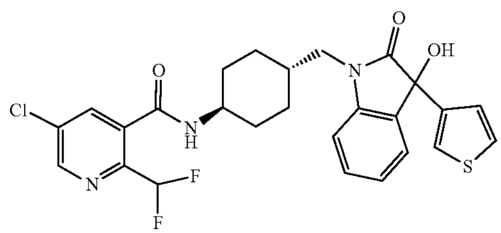 [SMILES: O=C(N[C@H]1CC[C@H](CN2C(=O)C(O)(c3ccsc3)c3ccccc32)CC1)c1cc(Cl)cnc1C(F)F] | 5-chloro-2-(difluoromethyl)-N-((1r,4r)-4-((3-hydroxy-2-oxo-3-(thiophen-3-yl)indolin-1-yl)methyl)cyclohexyl)nicotinamide | Intermediate-27, (HO)$_2$B | B1 |
| 93 | 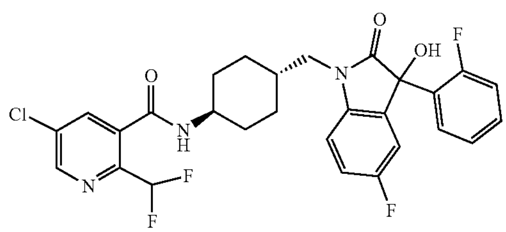 [SMILES: O=C(N[C@H]1CC[C@H](CN2C(=O)C(O)(c3ccccc3F)c3cc(F)ccc32)CC1)c1cc(Cl)cnc1C(F)F] | 5-chloro-2-(difluoromethyl)-N-((1r,4r)-4-((5-fluoro-3-(2-fluorophenyl)-3-hydroxy-2-oxoindolin-1-yl)methyl)cyclohexyl)nicotinamide | Intermediate-B, Intermediate-65 | A1 |
| 94 | 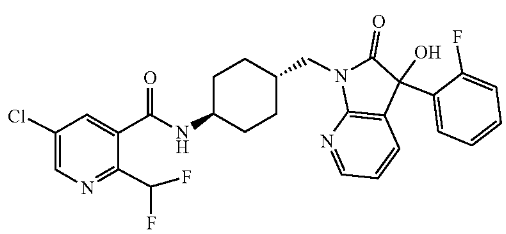 [SMILES: O=C(N[C@H]1CC[C@H](CN2C(=O)C(O)(c3ccccc3F)c3cccnc32)CC1)c1cc(Cl)cnc1C(F)F] | 5-chloro-2-(difluoromethyl)-N-((1r,4r)-4-((3-(2-fluorophenyl)-3-hydroxy-2-oxo-2,3-dihydro-1H-pyrrolo[2,3-b]pyridin-1-yl)methyl)cyclohexyl)nicotinamide | Intermediate-B, Intermediate-66 | A1 |

Table 1-13

| 95 | | 5-chloro-2-(difluoromethyl)-N-((1r,4r)-4-((3-(3-fluorothiophen-2-yl)-3-hydroxy-2-oxoindolin-1-yl)methyl)cyclohexyl)nicotinamide | Intermediate-B, Intermediate-67 | A2 |
| 96 | | 5-chloro-2-(difluoromethyl)-N-((1r,4r)-4-((3-hydroxy-3-(4-methoxythiophen-2-yl)-2-oxoindolin-1-yl)methyl)cyclohexyl)nicotinamide | Intermediate-B, Intermediate-68 | A2 |

TABLE 1-continued (Examples)

| Ex. | Structure | Name | Reactants | Method |
|---|---|---|---|---|
| 97 | 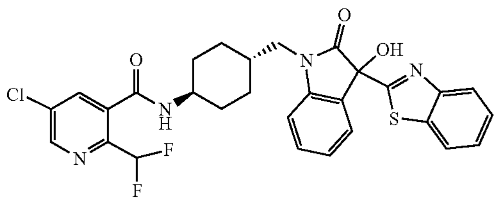 [SMILES: O=C(N[C@H]1CC[C@H](CN2C(=O)C(O)(c3nc4ccccc4s3)c3ccccc32)CC1)c1cc(Cl)cnc1C(F)F] | N-((1r,4r)-4-((3-(benzo[d]thiazol-2-yl)-3-hydroxy-2-oxoindolin-1-yl)methyl)cyclohexyl)-5-chloro-2-(difluoromethyl)nicotinamide | Intermediate-B, Intermediate-69 | A1 |
| 98 | 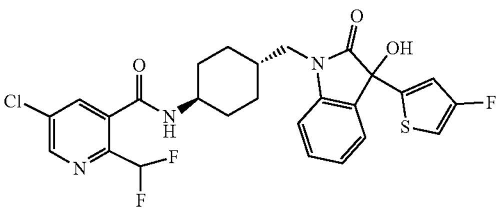 [SMILES: O=C(N[C@H]1CC[C@H](CN2C(=O)C(O)(c3cc(F)cs3)c3ccccc32)CC1)c1cc(Cl)cnc1C(F)F] | 5-chloro-2-(difluoromethyl)-N-((1r,4r)-4-((3-(4-fluorothiophen-2-yl)-3-hydroxy-2-oxoindolin-1-yl)methyl)cyclohexyl)nicotinamide | Intermediate-B, Intermediate-70 | A2 |
| 99 | 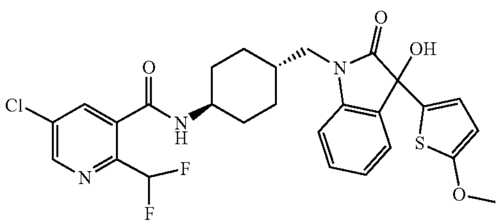 [SMILES: COc1ccc(C2(O)C(=O)N(C[C@H]3CC[C@H](NC(=O)c4cc(Cl)cnc4C(F)F)CC3)c3ccccc32)s1] | 5-chloro-2-(difluoromethyl)-N-((1r,4r)-4-((3-hydroxy-3-(5-methoxythiophen-2-yl)-2-oxoindolin-1-yl)methyl)cyclohexyl)nicotinamide | Intermediate-B, Intermediate-71 | A2 |
| 100 | 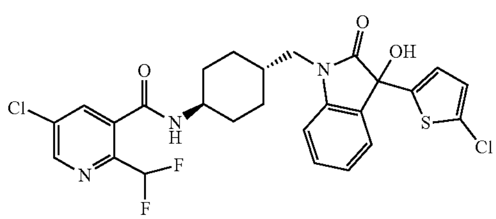 [SMILES: O=C(N[C@H]1CC[C@H](CN2C(=O)C(O)(c3ccc(Cl)s3)c3ccccc32)CC1)c1cc(Cl)cnc1C(F)F] | 5-chloro-N-((1r,4r)-4-((3-(5-chlorothiophen-2-yl)-3-hydroxy-2-oxoindolin-1-yl)methyl)cyclohexyl)-2-(difluoromethyl)nicotinamide | Intermediate-B, | A2 |
| 101 | 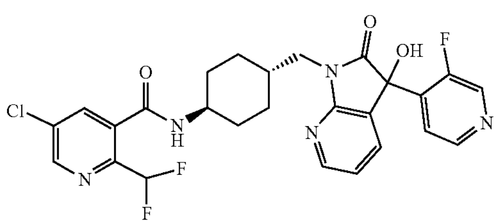 [SMILES: O=C(N[C@H]1CC[C@H](CN2C(=O)C(O)(c3ccncc3F)c3cccnc32)CC1)c1cc(Cl)cnc1C(F)F] | 5-chloro-2-(difluoromethyl)-N-((1r,4r)-4-((3-(3-fluoropyridin-4-yl)-3-hydroxy-2-oxo-2,3-dihydro-1H-pyrrolo[2,3-b]pyridin-1-yl)methyl)cyclohexyl)nicotinamide | Intermediate-B, Intermediate-72 | A1 |
| 102 | 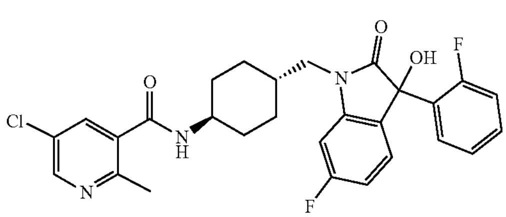 [SMILES: Cc1ncc(Cl)cc1C(=O)N[C@H]1CC[C@H](CN2C(=O)C(O)(c3ccccc3F)c3ccc(F)cc32)CC1] | 5-chloro-N-((1r,4r)-4-((6-fluoro-3-(2-fluorophenyl)-3-hydroxy-2-oxoindolin-1-yl)methyl)cyclohexyl)-2-methylnicotinamide | Intermediate-A, Intermediate-57 | A1 |

TABLE 1-continued (Examples)

| Ex. | Structure | Name | Reactants | Method |
|---|---|---|---|---|
| | | Table 1-14 | | |
| 103 | 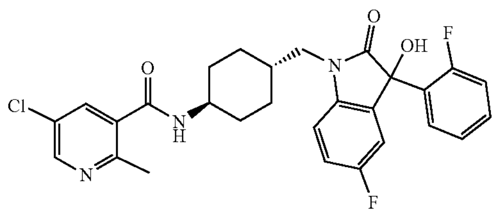 [SMILES: Cc1ncc(Cl)cc1C(=O)N[C@H]1CC[C@H](CN2C(=O)C(O)(c3ccccc3F)c3cc(F)ccc32)CC1] | 5-chloro-N-((1r,4r)-4-((5-fluoro-3-(2-fluorophenyl)-3-hydroxy-2-oxoindolin-1-yl)methyl)cyclohexyl)-2-methylnicotinamide | Intermediate-A, Intermediate-65 | A1 |
| 104 | 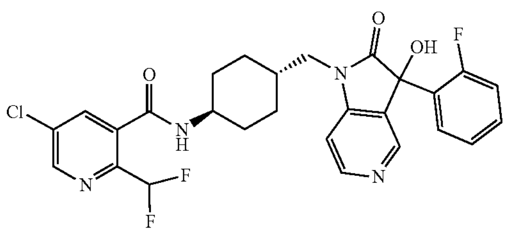 [SMILES: O=C(N[C@H]1CC[C@H](CN2C(=O)C(O)(c3ccccc3F)c3cnccc32)CC1)c1cc(Cl)cnc1C(F)F] | 5-chloro-2-(difluoromethyl)-N-((1r,4r)-4-((3-(2-fluorophenyl)-3-hydroxy-2-oxo-2,3-dihydro-1H-pyrrolo[3,2-c]pyridin-1-yl)methyl)cyclohexyl)nicotinamide | Intermediate-B, Intermediate-73 | A1 |
| 105 | 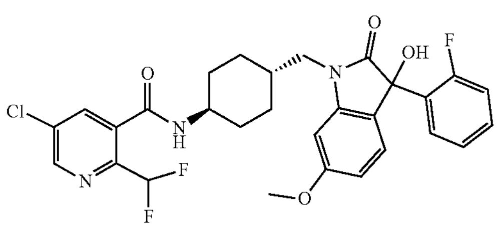 [SMILES: COc1ccc2c(c1)N(C[C@H]1CC[C@H](NC(=O)c3cc(Cl)cnc3C(F)F)CC1)C(=O)C2(O)c1ccccc1F] | 5-chloro-2-(difluoromethyl)-N-((1r,4r)-4-((3-(2-fluorophenyl)-3-hydroxy-6-methoxy-2-oxoindolin-1-yl)methyl)cyclohexyl)nicotinamide | Intermediate-B, Intermediate-74 | A1 |
| 106 | 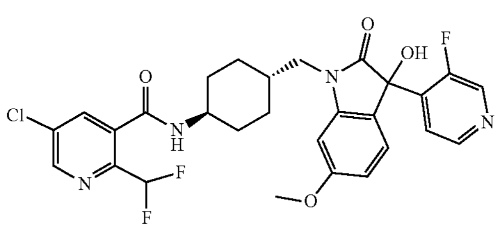 [SMILES: COc1ccc2c(c1)N(C[C@H]1CC[C@H](NC(=O)c3cc(Cl)cnc3C(F)F)CC1)C(=O)C2(O)c1ccncc1F] | 5-chloro-2-(difluoromethyl)-N-((1r,4r)-4-((3-(3-fluoropyridin-4-yl)-3-hydroxy-6-methoxy-2-oxoindolin-1-yl)methyl)cyclohexyl)nicotinamide | Intermediate-B, Intermediate-75 | A1 |
| 107 | 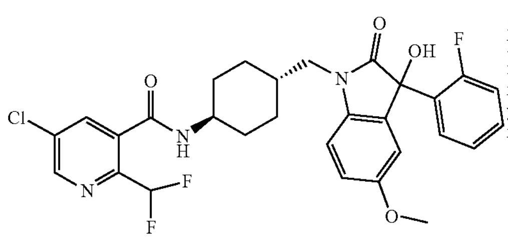 | 5-chloro-2-(difluoromethyl)-N-((1r,4r)-4-((3-(2-fluorophenyl)-3-hydroxy-5-methoxy-2-oxoindolin-1-yl)methyl)cyclohexyl)nicotinamide | Intermediate-B, Intermediate-76 | A1 |
| 108 | 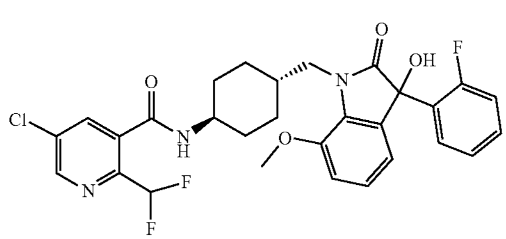 [SMILES: COc1cccc2c1N(C[C@H]1CC[C@H](NC(=O)c3cc(Cl)cnc3C(F)F)CC1)C(=O)C2(O)c1ccccc1F] | 5-chloro-2-(difluoromethyl)-N-((1r,4r)-4-((3-(2-fluorophenyl)-3-hydroxy-7-methoxy-2-oxoindolin-1-yl)methyl)cyclohexyl)nicotinamide | Intermediate-B, Intermediate-77 | A1 |

TABLE 1-continued (Examples)

| Ex. | Structure | Name | Reactants | Method |
|---|---|---|---|---|
| 109 | | 5-chloro-2-(difluoromethyl)-N-((1r,4r)-4-((3-(3-fluoropyridin-4-yl)-3-hydroxy-7-methoxy-2-oxoindolin-1-yl)methyl)cyclohexyl)nicotinamide | Intermediate-B, Intermediate-78 | A1 |
| 110 | | 5-chloro-2-(difluoromethyl)-N-((1r,4r)-4-((3-(furan-3-yl)-3-hydroxy-2-oxoindolin-1-yl)methyl)cyclohexyl)nicotinamide | Intermediate-27, (HO)$_2$B-furan | B1 |

Table 1-15

| Ex. | Structure | Name | Reactants | Method |
|---|---|---|---|---|
| 111 | 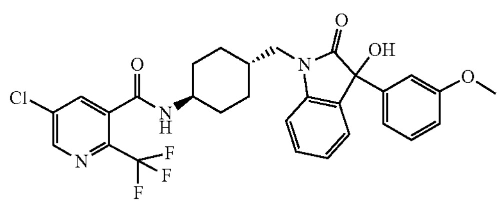 [SMILES: COc1cccc(C2(O)C(=O)N(C[C@H]3CC[C@H](NC(=O)c4cc(Cl)cnc4C(F)(F)F)CC3)c3ccccc32)c1] | 5-chloro-N-((1r,4r)-4-((3-hydroxy-3-(3-methoxyphenyl)-2-oxoindolin-1-yl)methyl)cyclohexyl)-2-(trifluoromethyl)nicotinamide | Intermediate-C, | A2 |
| 112 | 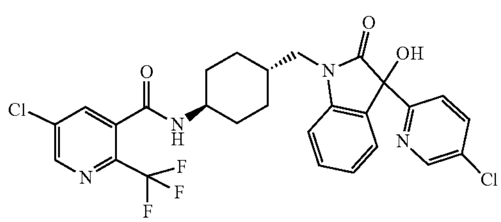 [SMILES: O=C(N[C@H]1CC[C@H](CN2C(=O)C(O)(c3ccc(Cl)cn3)c3ccccc32)CC1)c1cc(Cl)cnc1C(F)(F)F] | 5-chloro-N-((1r,4r)-4-((3-(5-chloropyridin-2-yl)-3-hydroxy-2-oxoindolin-1-yl)methyl)cyclohexyl)-2-(trifluoromethyl)nicotinamide | Intermediate-C, Intermediate-10 | A2 |
| 113 | 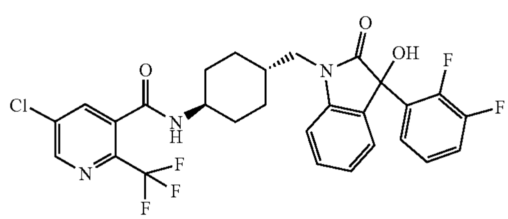 [SMILES: O=C(N[C@H]1CC[C@H](CN2C(=O)C(O)(c3cccc(F)c3F)c3ccccc32)CC1)c1cc(Cl)cnc1C(F)(F)F] | 5-chloro-N-((1r,4r)-4-((3-(2,3-difluorophenyl)-3-hydroxy-2-oxoindolin-1-yl)methyl) cyclohexyl)-2-(trifluoromethyl)nicotinamide | Intermediate-C, | A2 |
| 114 | 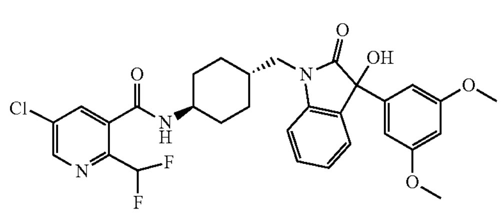 [SMILES: COc1cc(OC)cc(C2(O)C(=O)N(C[C@H]3CC[C@H](NC(=O)c4cc(Cl)cnc4C(F)F)CC3)c3ccccc32)c1] | 5-chloro-2-(difluoromethyl)-N-((1r,4r)-4-((3-(3,5-dimethoxyphenyl)-3-hydroxy-2-oxoindolin-1-yl)methyl)cyclohexyl)nicotinamide | Intermediate-27, (HO)$_2$B-(3,5-dimethoxyphenyl) | B1 |

TABLE 1-continued (Examples)

| Ex. | Structure | Name | Reactants | Method |
|---|---|---|---|---|
| 115 | 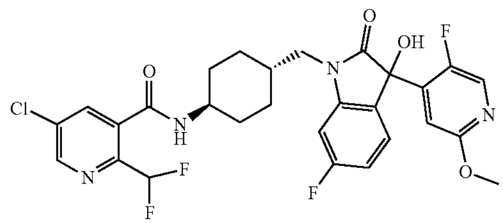 [SMILES: COc1cc(C2(O)C(=O)N(C[C@H]3CC[C@H](NC(=O)c4cc(Cl)cnc4C(F)F)CC3)c3cc(F)ccc32)c(F)cn1] | 5-chloro-2-(difluoromethyl)-N-((1r,4r)-4-((6-fluoro-3-(5-fluoro-2-methoxypyridin-4-yl)-3-hydroxy-2-oxoindolin-1-yl)methyl)cyclohexyl)nicotinamide | Intermediate-B, Intermediate-79 | A1 |
| 116 | 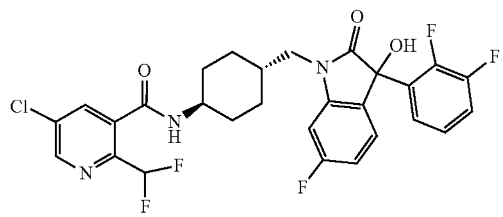 [SMILES: O=C(N[C@H]1CC[C@H](CN2C(=O)C(O)(c3cccc(F)c3F)c3ccc(F)cc32)CC1)c1cc(Cl)cnc1C(F)F] | 5-chloro-2-(difluoromethyl)-N-((1r,4r)-4-((3-(2,3-difluorophenyl)-6-fluoro-3-hydroxy-2-oxoindolin-1-yl)methyl) cyclohexyl) nicotinamide | Intermediate-B, Intermediate-80 | A1 |
| 117 | 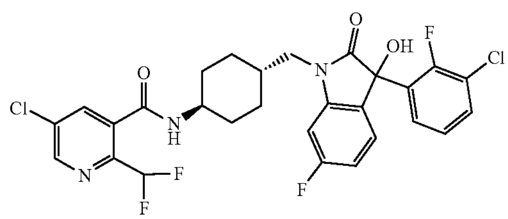 [SMILES: O=C(N[C@H]1CC[C@H](CN2C(=O)C(O)(c3cccc(Cl)c3F)c3ccc(F)cc32)CC1)c1cc(Cl)cnc1C(F)F] | 5-chloro-N-((1r,4r)-4-((3-(3-chloro-2-fluorophenyl)-6-fluoro-3-hydroxy-2-oxoindolin-1-yl)methyl)cyclohexyl)-2-(difluoromethyl)nicotinamide | Intermediate-B, Intermediate-81 | A1 |
| 118 | 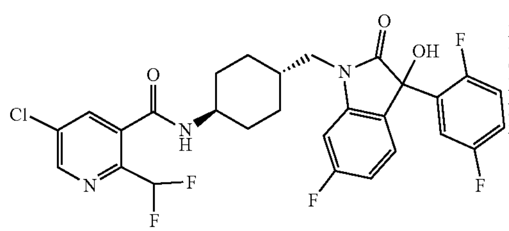 | 5-chloro-2-(difluoromethyl)-N-((1r,4r)-4-((3-(2,5-difluorophenyl)-6-fluoro-3-hydroxy-2-oxoindolin-1-yl)methyl) cyclohexyl) nicotinamide | Intermediate-B, Intermediate-82 | A5 |

Table 1-16

| Ex. | Structure | Name | Reactants | Method |
|---|---|---|---|---|
| 119 | 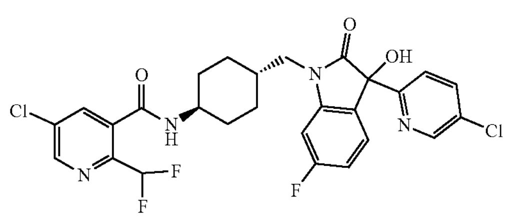 [SMILES: O=C(N[C@H]1CC[C@H](CN2C(=O)C(O)(c3ccc(Cl)cn3)c3ccc(F)cc32)CC1)c1cc(Cl)cnc1C(F)F] | 5-chloro-N-((1r,4r)-4-((3-(5-chloropyridin-2-yl)-6-fluoro-3-hydroxy-2-oxoindolin-1-yl)methyl)cyclohexyl)-2-(difluoromethyl)nicotinamide | Intermediate-B, Intermediate-83 | A5 |
| 120 | 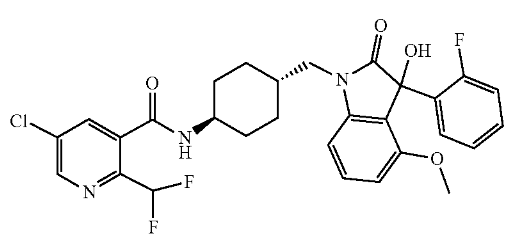 [SMILES: COc1cccc2c1C(O)(c1ccccc1F)C(=O)N2C[C@H]1CC[C@H](NC(=O)c2cc(Cl)cnc2C(F)F)CC1] | 5-chloro-2-(difluoromethyl)-N-((1r,4r)-4-((3-(2-fluorophenyl)-3-hydroxy-4-methoxy-2-oxoindolin-1-yl)methyl)cyclohexyl)nicotinamide | Intermediate-B, Intermediate-84 | A5 |

TABLE 1-continued (Examples)

| Ex. | Structure | Name | Reactants | Method |
|---|---|---|---|---|
| 121 | 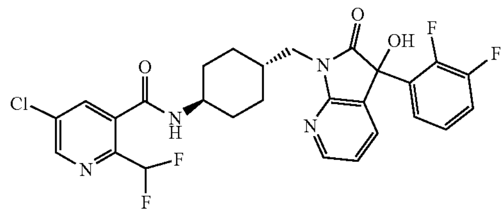 [SMILES: O=C(N[C@H]1CC[C@H](CN2C(=O)C(O)(c3cccc(F)c3F)c3cccnc32)CC1)c1cc(Cl)cnc1C(F)F] | 5-chloro-2-(difluoromethyl)-N-((1r,4r)-4-((3-(2,3-difluorophenyl)-3-hydroxy-2-oxo-2,3-dihydro-1H-pyrrolo[2,3-b]pyridin-1-yl)methyl)cyclohexyl)nicotinamide | Intermediate-B, Intermediate-85 | A5 |
| 122 | 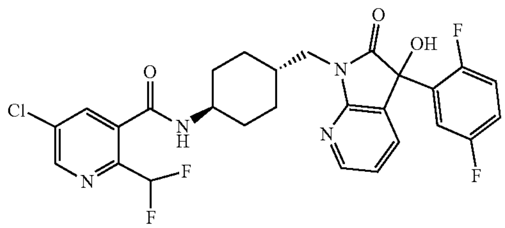 [SMILES: O=C(N[C@H]1CC[C@H](CN2C(=O)C(O)(c3cc(F)ccc3F)c3cccnc32)CC1)c1cc(Cl)cnc1C(F)F] | 5-chloro-2-(difluoromethyl)-N-((1r,4r)-4-((3-(2,5-difluorophenyl)-3-hydroxy-2-oxo-2,3-dihydro-1H-pyrrolo[2,3-b]pyridin-1-yl)methyl)cyclohexyl)nicotinamide | Intermediate-B, Intermediate-86 | A5 |
| 123 | 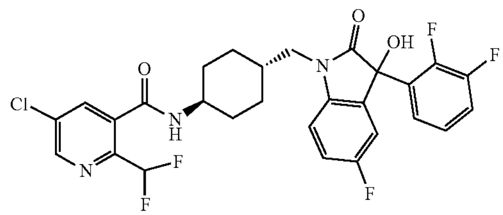 [SMILES: O=C(N[C@H]1CC[C@H](CN2C(=O)C(O)(c3cccc(F)c3F)c3cc(F)ccc32)CC1)c1cc(Cl)cnc1C(F)F] | 5-chloro-2-(difluoromethyl)-N-((1r,4r)-4-((3-(2,3-difluorophenyl)-5-fluoro-3-hydroxy-2-oxoindolin-1-yl)methyl)cyclohexyl)nicotinamide | Intermediate-B, Intermediate-87 | A5 |
| 124 | 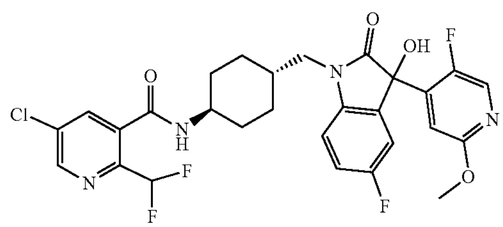 [SMILES: COc1cc(C2(O)C(=O)N(C[C@H]3CC[C@H](NC(=O)c4cc(Cl)cnc4C(F)F)CC3)c3ccc(F)cc32)c(F)cn1] | 5-chloro-2-(difluoromethyl)-N-((1r,4r)-4-((5-fluoro-3-(5-fluoro-2-methoxypyridin-4-yl)-3-hydroxy-2-oxoindolin-1-yl)methyl)cyclohexyl)nicotinamide | Intermediate-B, Intermediate-88 | A5 |
| 125 | 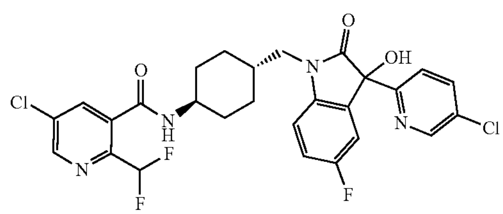 [SMILES: O=C(N[C@H]1CC[C@H](CN2C(=O)C(O)(c3ccc(Cl)cn3)c3cc(F)ccc32)CC1)c1cc(Cl)cnc1C(F)F] | 5-chloro-N-((1r,4r)-4-((3-(5-chloropyridin-2-yl)-5-fluoro-3-hydroxy-2-oxoindolin-1-yl)methyl)cyclohexyl)-2-(difluoromethyl)nicotinamide | Intermediate-B, Intermediate-89 | A5 |
| 126 | 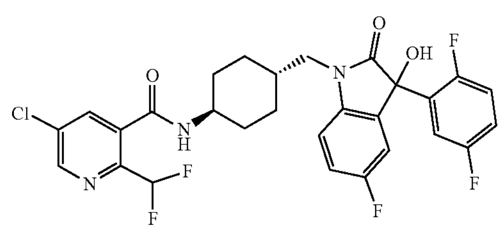 [SMILES: O=C(N[C@H]1CC[C@H](CN2C(=O)C(O)(c3cc(F)ccc3F)c3cc(F)ccc32)CC1)c1cc(Cl)cnc1C(F)F] | 5-chloro-2-(difluoromethyl)-N-((1r,4r)-4-((3-(2,5-difluorophenyl)-5-fluoro-3-hydroxy-2-oxoindolin-1-yl)methyl)cyclohexyl)nicotinamide | Intermediate-B, Intermediate-90 | A5 |

Table 1-17

| 127 | | 5-chloro-N-((1r,4r)-4-((3-(2,5-difluorophenyl)-3-hydroxy-2-oxoindolin-1-yl)methyl)cyclohexyl)-2-methylnicotinamide | Intermediate-A, Intermediate-34 | A2 |

TABLE 1-continued (Examples)

| Ex. | Structure | Name | Reactants | Method |
|---|---|---|---|---|
| 128 | 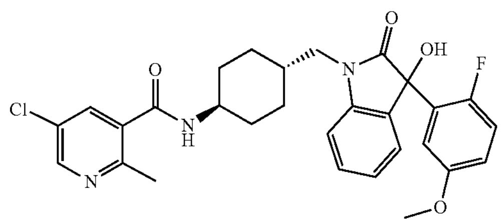 [SMILES: COc1ccc(F)c(C2(O)C(=O)N(C[C@H]3CC[C@H](NC(=O)c4cc(Cl)cnc4C)CC3)c3ccccc32)c1] | 5-chloro-N-((1r,4r)-4-((3-(2-fluoro-5-methoxyphenyl)-3-hydroxy-2-oxoindolin-1-yl)methyl)cyclohexyl)-2-methylnicotinamide | Intermediate-A, Intermediate-48 | A2 |
| 129 | 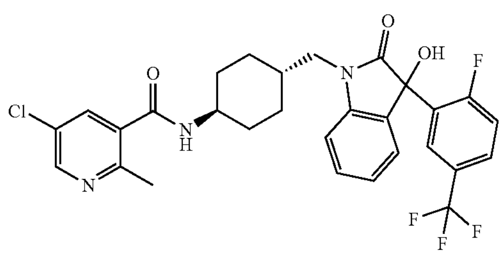 [SMILES: Cc1ncc(Cl)cc1C(=O)N[C@H]1CC[C@H](CN2C(=O)C(O)(c3cc(C(F)(F)F)ccc3F)c3ccccc32)CC1] | 5-chloro-N-((1r,4r)-4-((3-(2-fluoro-5-(trifluoromethyl)phenyl)-3-hydroxy-2-oxoindolin-1-yl)methyl)cyclohexyl)-2-methylnicotinamide | Intermediate-A, Intermediate-91 | A2 |
| 130 | 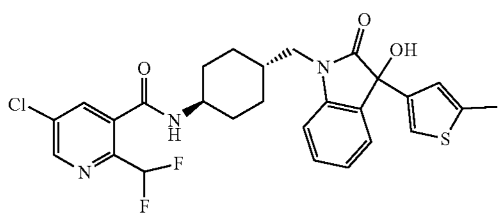 [SMILES: Cc1cc(C2(O)C(=O)N(C[C@H]3CC[C@H](NC(=O)c4cc(Cl)cnc4C(F)F)CC3)c3ccccc32)cs1] | 5-chloro-2-(difluoromethyl)-N-((1r,4r)-4-((3-hydroxy-3-(5-methylthiophen-3-yl)-2-oxoindolin-1-yl)methyl)cyclohexyl)nicotinamide | Intermediate-27, (HO)$_2$B-(5-methylthiophene) | B1 |
| 131 | 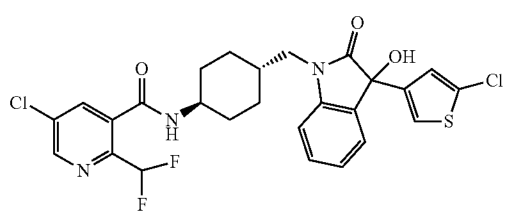 [SMILES: O=C(N[C@H]1CC[C@H](CN2C(=O)C(O)(c3csc(Cl)c3)c3ccccc32)CC1)c1cc(Cl)cnc1C(F)F] | 5-chloro-N-((1r,4r)-4-((3-(5-chlorothiophen-3-yl)-3-hydroxy-2-oxoindolin-1-yl)methyl)cyclohexyl)-2-(difluoromethyl)nicotinamide | Intermediate-27, (HO)$_2$B-(5-chlorothiophene) | B1 |
| 132 | 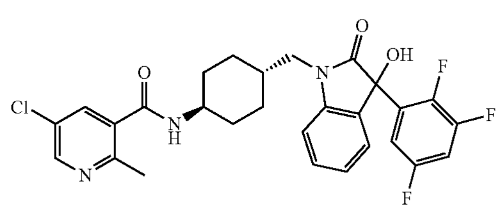 [SMILES: Cc1ncc(Cl)cc1C(=O)N[C@H]1CC[C@H](CN2C(=O)C(O)(c3cc(F)cc(F)c3F)c3ccccc32)CC1] | 5-chloro-N-((1r,4r)-4-((3-hydroxy-2-oxo-3-(2,3,5-trifluorophenyl)indolin-1-yl)methyl)cyclohexyl)-2-methylnicotinamide | Intermediate-A, Intermediate-92 | A2 |
| 133 | 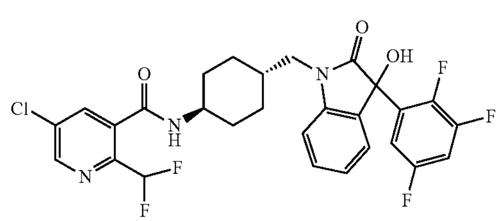 [SMILES: O=C(N[C@H]1CC[C@H](CN2C(=O)C(O)(c3cc(F)cc(F)c3F)c3ccccc32)CC1)c1cc(Cl)cnc1C(F)F] | 5-chloro-2-(difluoromethyl)-N-((1r,4r)-4-((3-hydroxy-2-oxo-3-(2,3,5-trifluorophenyl)indolin-1-yl)methyl)cyclohexyl)nicotinamide | Intermediate-B, Intermediate-92 | A2 |

TABLE 1-continued (Examples)

| Ex. | Structure | Name | Reactants | Method |
|---|---|---|---|---|
| 134 | 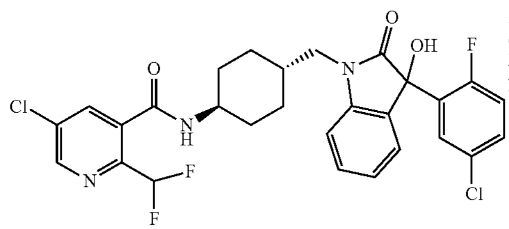 | 5-chloro-N-((1r,4r)-4-((3-(5-chloro-2-fluorophenyl)-3-hydroxy-2-oxoindolin-1-yl)methyl)cyclohexyl)-2-(difluoromethyl)nicotinamide | Intermediate-B, Intermediate-93 | A2 |

Table 1-18

| 135 | | 5-chloro-2-(difluoromethyl)-N-((1r,4r)-4-((3-hydroxy-2-oxo-3-(2,3,4-trifluorophenyl)indolin-1-yl)methyl)cyclohexyl)nicotinamide | Intermediate-B, | A2 |
| 136 | | 5-chloro-2-(difluoromethyl)-N-((1r,4r)-4-((3-(2-fluoro-5-(trifluoromethyl)phenyl)-3-hydroxy-2-oxoindolin-1-yl)methyl)cyclohexyl)nicotinamide | Intermediate-B, Intermediate-91 | A2 |
| 137 | | 5-chloro-N-((1r,4r)-4-((3-(5-chloro-2-fluorophenyl)-3-hydroxy-2-oxoindolin-1-yl)methyl)cyclohexyl)-2-methylnicotinamide | Intermediate-A, Intermediate-93 | A2 |
| 138 | | 5-chloro-N-((1r,4r)-4-((3-hydroxy-2-oxo-3-(2,3,4-trifluorophenyl)indolin-1-yl)methyl)cyclohexyl)-2-methylnicotinamide | Intermediate-A, | A2 |
| 139 | | 5-chloro-N-((1r,4r)-4-((3-(2,3-difluoro-4-methoxyphenyl)-3-hydroxy-2-oxoindolin-1-yl)methyl)cyclohexyl)-2-methylnicotinamide | Intermediate-A, Intermediate-94 | A2 |

TABLE 1-continued (Examples)

| Ex. | Structure | Name | Reactants | Method |
|---|---|---|---|---|
| 140 | 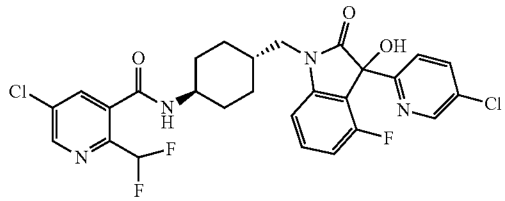 [SMILES: O=C(N[C@H]1CC[C@H](CN2C(=O)C(O)(c3ccc(Cl)cn3)c3c(F)cccc32)CC1)c1cc(Cl)cnc1C(F)F] | 5-chloro-N-((1r,4r)-4-((3-(5-chloropyridin-2-yl)-4-fluoro-3-hydroxy-2-oxoindolin-1-yl)methyl)cyclohexyl)-2-(difluoromethyl)nicotinamide | Intermediate-B, Intermediate-95 | A5 |
| 141 | 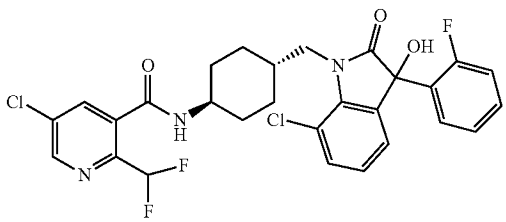 [SMILES: O=C(N[C@H]1CC[C@H](CN2C(=O)C(O)(c3ccccc3F)c3cccc(Cl)c32)CC1)c1cc(Cl)cnc1C(F)F] | 5-chloro-N-((1r,4r)-4-((7-chloro-3-(2-fluorophenyl)-3-hydroxy-2-oxoindolin-1-yl)methyl)cyclohexyl)-2-(difluoromethyl)nicotinamide | Intermediate-B, Intermediate-96 | A5 |
| 142 | 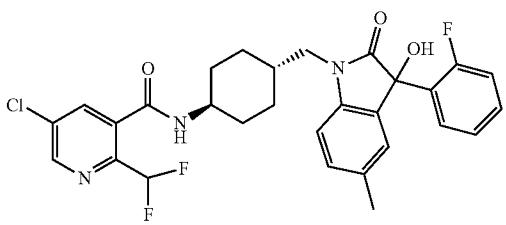 [SMILES: Cc1ccc2c(c1)C(O)(c1ccccc1F)C(=O)N2C[C@H]1CC[C@H](NC(=O)c2cc(Cl)cnc2C(F)F)CC1] | 5-chloro-2-(difluoromethyl)-N-((1r,4r)-4-((3-(2-fluorophenyl)-3-hydroxy-5-methyl-2-oxoindolin-1-yl)methyl)cyclohexyl)nicotinamide | Intermediate-B, Intermediate-97 | A5 |

Table 1-19

| 143 | | 5-chloro-N-((1r,4r)-4-((3-(2,3-difluorophenyl)-6-fluoro-3-hydroxy-2-oxoindolin-1-yl)methyl)cyclohexyl)-2-methylnicotinamide | Intermediate-A, Intermediate-80 | A5 |
| 144 | | 5-chloro-N-((1r,4r)-4-((6-fluoro-3-(5-fluoro-2-methoxypyridin-4-yl)-3-hydroxy-2-oxoindolin-1-yl)methyl)cyclohexyl)-2-methylnicotinamide | Intermediate-A, Intermediate-79 | A5 |
| 145 | | 5-chloro-N-((1r,4r)-4-((3-(5-chloropyridin-2-yl)-6-fluoro-3-hydroxy-2-oxoindolin-1-yl)methyl)cyclohexyl)-2-methylnicotinamide | Intermediate-A, Intermediate-83 | A5 |
| 146 | | 5-chloro-N-((1r,4r)-4-((3-(2-fluorophenyl)-3-hydroxy-6-methoxy-2-oxoindolin-1-yl)methyl)cyclohexyl)-2-methylnicotinamide | Intermediate-A, Intermediate-74 | A5 |

TABLE 1-continued (Examples)

| Ex. | Structure | Name | Reactants | Method |
|---|---|---|---|---|
| 147 | 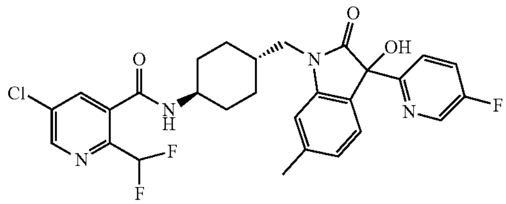 [SMILES: Cc1ccc2c(c1)N(C[C@H]1CC[C@H](NC(=O)c3cc(Cl)cnc3C(F)F)CC1)C(=O)C2(O)c1ccc(F)cn1] | 5-chloro-2-(difluoromethyl)-N-((1r,4r)-4-((3-(5-fluoropyridin-2-yl)-3-hydroxy-6-methyl-2-oxoindolin-1-yl)methyl)cyclohexyl)nicotinamide | Intermediate-B, Intermediate-98 | A5 |
| 148 | 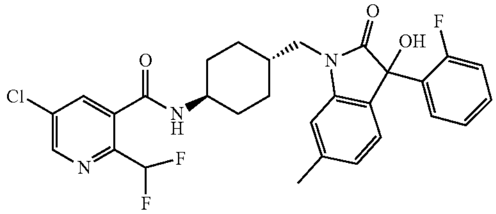 [SMILES: Cc1ccc2c(c1)N(C[C@H]1CC[C@H](NC(=O)c3cc(Cl)cnc3C(F)F)CC1)C(=O)C2(O)c1ccccc1F] | 5-chloro-2-(difluoromethyl)-N-((1r,4r)-4-((3-(2-fluorophenyl)-3-hydroxy-6-methyl-2-oxoindolin-1-yl)methyl)cyclohexyl)nicotinamide | Intermediate-B, Intermediate-99 | A5 |
| 149 | 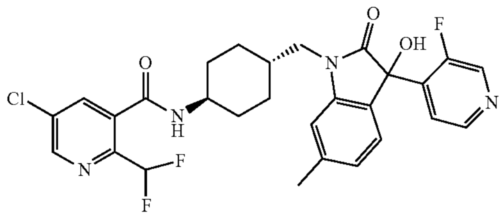 [SMILES: Cc1ccc2c(c1)N(C[C@H]1CC[C@H](NC(=O)c3cc(Cl)cnc3C(F)F)CC1)C(=O)C2(O)c1ccncc1F] | 5-chloro-2-(difluoromethyl)-N-((1r,4r)-4-((3-(3-fluoropyridin-4-yl)-3-hydroxy-6-methyl-2-oxoindolin-1-yl)methyl)cyclohexyl)nicotinamide | Intermediate-B, Intermediate-100 | A5 |
| 150 | 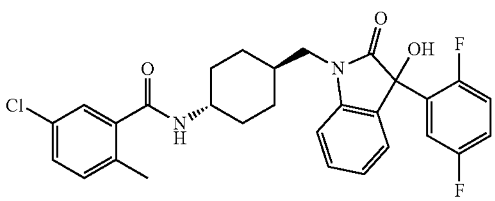 [SMILES: Cc1ccc(Cl)cc1C(=O)N[C@H]1CC[C@H](CN2C(=O)C(O)(c3cc(F)ccc3F)c3ccccc32)CC1] | 5-chloro-N-((1r,4r)-4-((3-(2,5-difluorophenyl)-3-hydroxy-2-oxoindolin-1-yl)methyl) cyclohexyl)-2-methylbenzamide | Intermediate-101, | C1 |

Table 1-20

| 151 | | N-((1r,4r)-4-((3-(2,5-difluorophenyl)-3-hydroxy-2-oxoindolin-1-yl)methyl)cyclohexyl)-2-methyl-2H-indazole-3-carboxamide | Intermediate-101, | C1 |
|---|---|---|---|---|
| 152 | | 5-chloro-N-((1r,4r)-4-((3-(2,5-difluorophenyl)-3-hydroxy-2-oxoindolin-1-yl)methyl)cyclohexyl)-2-(trifluoromethoxy)benzamide | Intermediate-101, | C1 |
| 153 | | 5-chloro-N-((1r,4r)-4-((3-(2,3-difluoro-4-methoxyphenyl)-3-hydroxy-2-oxoindolin-1-yl)methyl)cyclohexyl)-2-(difluoromethyl)nicotinamide | Intermediate-B, Intermediate-94 | A2 |

TABLE 1-continued (Examples)

| Ex. | Structure | Name | Reactants | Method |
|---|---|---|---|---|
| 154 | 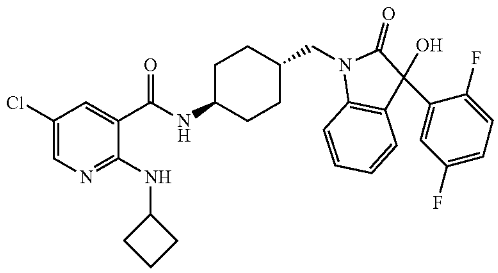 [SMILES: O=C(N[C@H]1CC[C@H](CN2C(=O)C(O)(c3cc(F)ccc3F)c3ccccc32)CC1)c1cc(Cl)cnc1NC1CCC1] | 5-chloro-2-(cyclobutylamino)-N-((1r,4r)-4-((3-(2,5-difluorophenyl)-3-hydroxy-2-oxoindolin-1-yl)methyl)cyclohexyl)nicotinamide | Intermediate-102, cyclobutylamine | D1 |
| 155 | 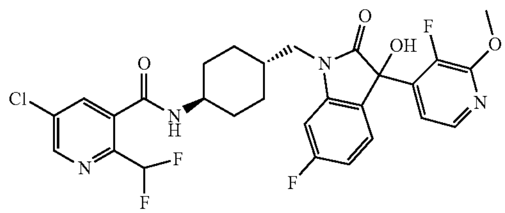 [SMILES: COc1nccc(C2(O)C(=O)N(C[C@H]3CC[C@H](NC(=O)c4cc(Cl)cnc4C(F)F)CC3)c3cc(F)ccc32)c1F] | 5-chloro-2-(difluoromethyl)-N-((1r,4r)-4-((6-fluoro-3-(3-fluoro-2-methoxypyridin-4-yl)-3-hydroxy-2-oxoindolin-1-yl)methyl)cyclohexyl)nicotinamide | Intermediate-B, Intermediate-103 | A5 |
| 156 | 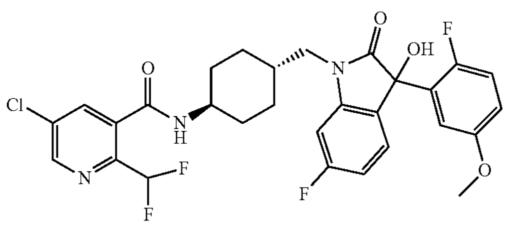 [SMILES: COc1ccc(F)c(C2(O)C(=O)N(C[C@H]3CC[C@H](NC(=O)c4cc(Cl)cnc4C(F)F)CC3)c3cc(F)ccc32)c1] | 5-chloro-2-(difluoromethyl)-N-((1r,4r)-4-((6-fluoro-3-(2-fluoro-5-methoxyphenyl)-3-hydroxy-2-oxoindolin-1-yl)methyl)cyclohexyl)nicotinamide | Intermediate-B, Intermediate-104 | A5 |
| 157 | 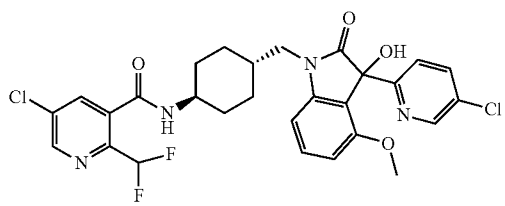 [SMILES: COc1cccc2c1C(O)(c1ccc(Cl)cn1)C(=O)N2C[C@H]1CC[C@H](NC(=O)c2cc(Cl)cnc2C(F)F)CC1] | 5-chloro-N-((1r,4r)-4-((3-(5-chloropyridin-2-yl)-3-hydroxy-4-methoxy-2-oxoindolin-1-yl)methyl)cyclohexyl)-2-(difluoromethyl)nicotinamide | Intermediate-B, Intermediate-105 | A5 |
| 158 | 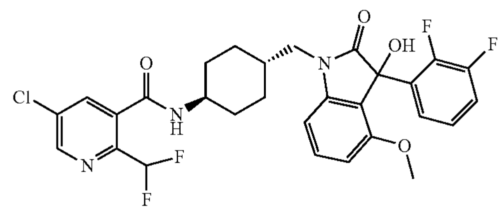 [SMILES: COc1cccc2c1C(O)(c1cccc(F)c1F)C(=O)N2C[C@H]1CC[C@H](NC(=O)c2cc(Cl)cnc2C(F)F)CC1] | 5-chloro-2-(difluoromethyl)-N-((1r,4r)-4-((3-(2,3-difluorophenyl)-3-hydroxy-4-methoxy-2-oxoindolin-1-yl)methyl)cyclohexyl)nicotinamide | Intermediate-B, Intermediate-106 | A5 |

Table 1-21

| 159 | | 5-chloro-N-((1r,4r)-4-((3-(2,3-difluorophenyl)-3-hydroxy-2-oxo-2,3-dihydro-1H-pyrrolo[2,3-b]pyridin-1-yl)methyl)cyclohexyl)-2-methylnicotinamide | Intermediate-A, Intermediate-85 | A5 |
| 160 | | 5-chloro-N-((1r,4r)-4-((3-(5-chloropyridin-2-yl)-5-fluoro-3-hydroxy-2-oxoindolin-1-yl)methyl)cyclohexyl)-2-methylnicotinamide | Intermediate-A, Intermediate-89 | A5 |

TABLE 1-continued (Examples)

| Ex. | Structure | Name | Reactants | Method |
|---|---|---|---|---|
| 161 | 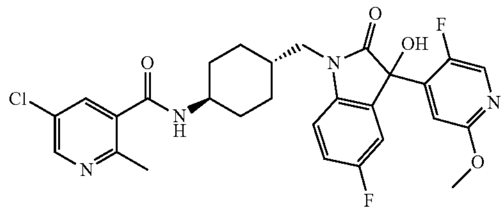 [SMILES: COc1cc(C2(O)C(=O)N(C[C@H]3CC[C@H](NC(=O)c4cc(Cl)cnc4C)CC3)c3ccc(F)cc32)c(F)cn1] | 5-chloro-N-((1r,4r)-4-((5-fluoro-3-(5-fluoro-2-methoxypyridin-4-yl)-3-hydroxy-2-oxoindolin-1-yl)methyl)cyclohexyl)-2-methylnicotinamide | Intermediate-A, Intermediate-88 | A5 |
| 162 | 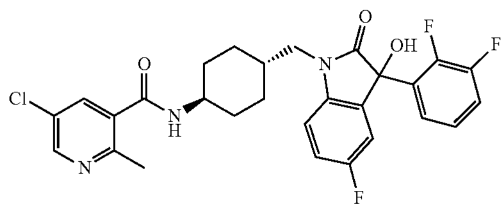 [SMILES: Cc1ncc(Cl)cc1C(=O)N[C@H]1CC[C@H](CN2C(=O)C(O)(c3cccc(F)c3F)c3cc(F)ccc32)CC1] | 5-chloro-N-((1r,4r)-4-((3-(2,3-difluorophenyl)-5-fluoro-3-hydroxy-2-oxoindolin-1-yl)methyl)cyclohexyl)-2-methylnicotinamide | Intermediate-A, Intermediate-87 | A5 |
| 163 | 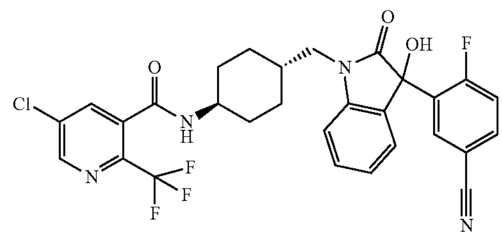 [SMILES: N#Cc1ccc(F)c(C2(O)C(=O)N(C[C@H]3CC[C@H](NC(=O)c4cc(Cl)cnc4C(F)(F)F)CC3)c3ccccc32)c1] | 5-chloro-N-((1r,4r)-4-((3-(5-cyano-2-fluorophenyl)-3-hydroxy-2-oxoindolin-1-yl)methyl)cyclohexyl)-2-(trifluoromethyl)nicotinamide | Intermediate-C, Intermediate-35 | A2 |
| 164 | 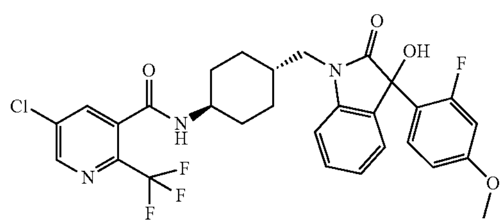 [SMILES: COc1ccc(C2(O)C(=O)N(C[C@H]3CC[C@H](NC(=O)c4cc(Cl)cnc4C(F)(F)F)CC3)c3ccccc32)c(F)c1] | 5-chloro-N-((1r,4r)-4-((3-(2-fluoro-4-methoxyphenyl)-3-hydroxy-2-oxoindolin-1-yl)methyl)cyclohexyl)-2-(trifluoromethyl)nicotinamide | Intermediate-C, Intermediate-31 | A2 |
| 165 | 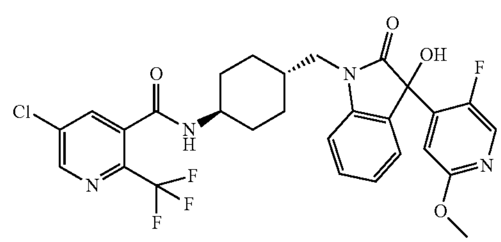 [SMILES: COc1cc(C2(O)C(=O)N(C[C@H]3CC[C@H](NC(=O)c4cc(Cl)cnc4C(F)(F)F)CC3)c3ccccc32)c(F)cn1] | 5-chloro-N-((1r,4r)-4-((3-(5-fluoro-2-methoxypyridin-4-yl)-3-hydroxy-2-oxoindolin-1-yl)methyl)cyclohexyl)-2-(trifluoromethyl)nicotinamide | Intermediate-C, Intermediate-20 | A2 |
| 166 | 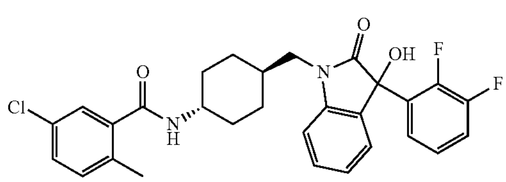 [SMILES: Cc1ccc(Cl)cc1C(=O)N[C@H]1CC[C@H](CN2C(=O)C(O)(c3cccc(F)c3F)c3ccccc32)CC1] | 5-chloro-N-((1r,4r)-4-((3-(2,3-difluorophenyl)-3-hydroxy-2-oxoindolin-1-yl)methyl)cyclohexyl)-2-methylbenzamide | Intermediate-107, | C1 |

Table 1-22

| 167 | | 2,5-dichloro-N-((1r,4r)-4-((3-(2,3-difluorophenyl)-3-hydroxy-2-oxoindolin-1-yl)methyl)cyclohexyl)nicotinamide | Intermediate-107, | C1 |

TABLE 1-continued (Examples)

| Ex. | Structure | Name | Reactants | Method |
|---|---|---|---|---|
| 168 | 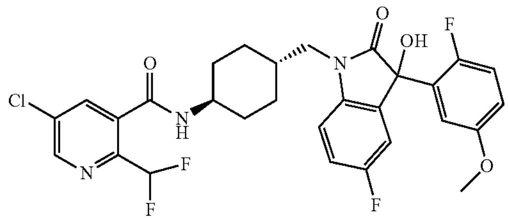 [SMILES: COc1ccc(F)c(C2(O)C(=O)N(C[C@H]3CC[C@H](NC(=O)c4cc(Cl)cnc4C(F)F)CC3)c3ccc(F)cc32)c1] | 5-chloro-2-(difluoromethyl)-N-((1r,4r)-4-((5-fluoro-3-(2-fluoro-5-methoxyphenyl)-3-hydroxy-2-oxoindolin-1-yl)methyl)cyclohexyl)nicotinamide | Intermediate-B, Intermediate-108 | A5 |
| 169 | 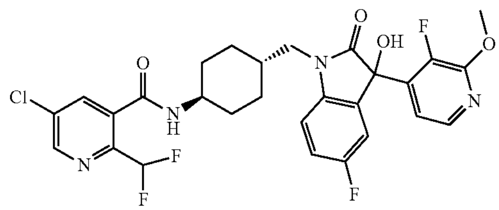 [SMILES: COc1nccc(C2(O)C(=O)N(C[C@H]3CC[C@H](NC(=O)c4cc(Cl)cnc4C(F)F)CC3)c3ccc(F)cc32)c1F] | 5-chloro-2-(difluoromethyl)-N-((1r,4r)-4-((5-fluoro-3-(3-fluoro-2-methoxypyridin-4-yl)-3-hydroxy-2-oxoindolin-1-yl)methyl)cyclohexyl)nicotinamide | Intermediate-B, Intermediate-109 | A5 |
| 170 | 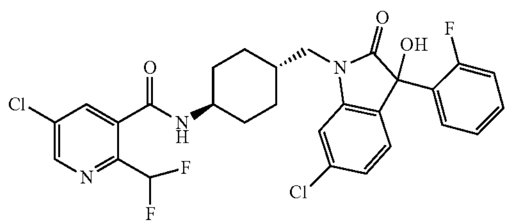 [SMILES: O=C(N[C@H]1CC[C@H](CN2C(=O)C(O)(c3ccccc3F)c3ccc(Cl)cc32)CC1)c1cc(Cl)cnc1C(F)F] | 5-chloro-N-((1r,4r)-4-((6-chloro-3-(2-fluorophenyl)-3-hydroxy-2-oxoindolin-1-yl)methyl)cyclohexyl)-2-(difluoromethyl)nicotinamide | Intermediate-B, Intermediate-110 | A5 |
| 171 | 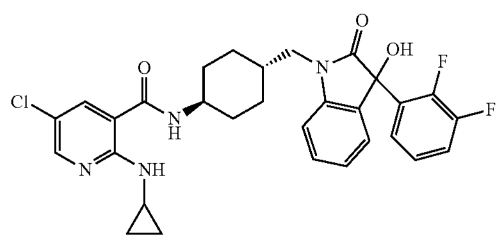 [SMILES: O=C(N[C@H]1CC[C@H](CN2C(=O)C(O)(c3cccc(F)c3F)c3ccccc32)CC1)c1cc(Cl)cnc1NC1CC1] | 5-chloro-2-(cyclopropylamino)-N-((1r,4r)-4-((3-(2,3-difluorophenyl)-3-hydroxy-2-oxoindolin-1-yl)methyl)cyclohexyl)nicotinamide | Intermediate-111, $NH_2$-cyclopropyl | D1 |
| 172 | 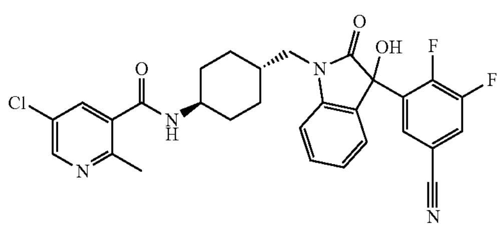 [SMILES: Cc1ncc(Cl)cc1C(=O)N[C@H]1CC[C@H](CN2C(=O)C(O)(c3cc(C#N)cc(F)c3F)c3ccccc32)CC1] | 5-chloro-N-((1r,4r)-4-((3-(5-cyano-2,3-difluorophenyl)-3-hydroxy-2-oxoindolin-1-yl)methyl)cyclohexyl)-2-methylnicotinamide | Intermediate-A, Intermediate-112 | A1 |
| 173 | 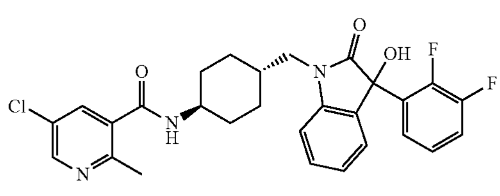 [SMILES: Cc1ncc(Cl)cc1C(=O)N[C@H]1CC[C@H](CN2C(=O)C(O)(c3cccc(F)c3F)c3ccccc32)CC1] | 5-chloro-N-((1r,4r)-4-((3-(2,3-difluorophenyl)-3-hydroxy-2-oxoindolin-1-yl)methyl)cyclohexyl)-2-methylnicotinamide | Intermediate-A, Intermediate-28 | A2 |
| 174 | 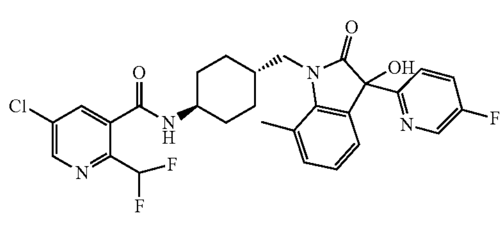 [SMILES: Cc1cccc2c1N(C[C@H]1CC[C@H](NC(=O)c3cc(Cl)cnc3C(F)F)CC1)C(=O)C2(O)c1ccc(F)cn1] | 5-chloro-2-(difluoromethyl)-N-((1r,4r)-4-((3-(5-fluoropyridin-2-yl)-3-hydroxy-7-methyl-2-oxoindolin-1-yl)methyl)cyclohexyl)nicotinamide | Intermediate-B, Intermediate-113 | A5 |

TABLE 1-continued (Examples)

| Ex. | Structure | Name | Reactants | Method |
|---|---|---|---|---|
| | | Table 1-23 | | |
| 175 | 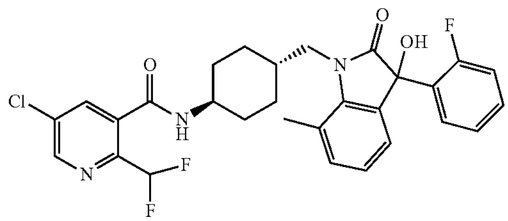 [SMILES: Cc1cccc2c1N(C[C@H]1CC[C@H](NC(=O)c3cc(Cl)cnc3C(F)F)CC1)C(=O)C2(O)c1ccccc1F] | 5-chloro-2-(difluoromethyl)-N-((1r,4r)-4-((3-(2-fluorophenyl)-3-hydroxy-7-methyl-2-oxoindolin-1-yl)methyl)cyclohexyl)nicotinamide | Intermediate-B, Intermediate-114 | A5 |
| 176 | 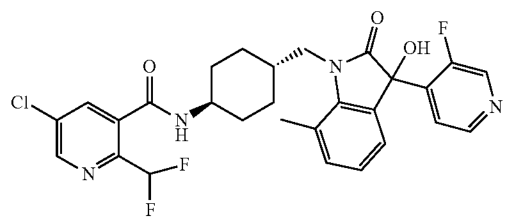 [SMILES: Cc1cccc2c1N(C[C@H]1CC[C@H](NC(=O)c3cc(Cl)cnc3C(F)F)CC1)C(=O)C2(O)c1ccncc1F] | 5-chloro-2-(difluoromethyl)-N-((1r,4r)-4-((3-(3-fluoropyridin-4-yl)-3-hydroxy-7-methyl-2-oxoindolin-1-yl)methyl)cyclohexyl)nicotinamide | Intermediate-B, Intermediate-115 | A5 |
| 177 | 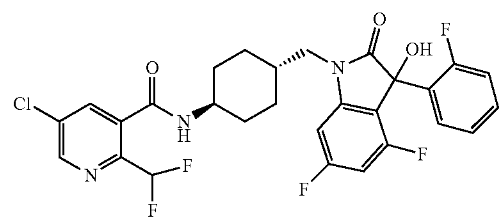 [SMILES: O=C(N[C@H]1CC[C@H](CN2C(=O)C(O)(c3ccccc3F)c3c(F)cc(F)cc32)CC1)c1cc(Cl)cnc1C(F)F] | 5-chloro-N-((1r,4r)-4-((4,6-difluoro-3-(2-fluorophenyl)-3-hydroxy-2-oxoindolin-1-yl)methyl)cyclohexyl)-2-(difluoromethyl)nicotinamide | Intermediate-B, Intermediate-116 | A5 |
| 178 | 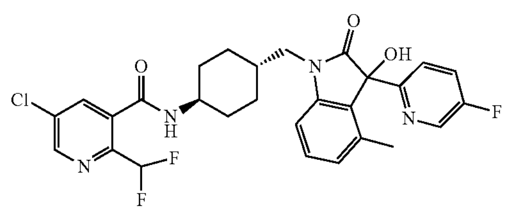 [SMILES: Cc1cccc2c1C(O)(c1ccc(F)cn1)C(=O)N2C[C@H]1CC[C@H](NC(=O)c2cc(Cl)cnc2C(F)F)CC1] | N-((1r,4r)-4-((3-(5-fluoropyridin-2-yl)-3-hydroxy-4-methyl-2-oxoindolin-1-yl)methyl)cyclohexyl)nicotinamide | Intermediate-B, Intermediate-117 | A5 |
| 179 | 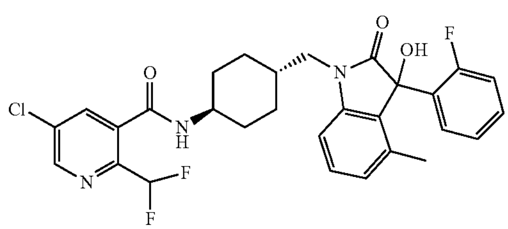 [SMILES: Cc1cccc2c1C(O)(c1ccccc1F)C(=O)N2C[C@H]1CC[C@H](NC(=O)c2cc(Cl)cnc2C(F)F)CC1] | 5-chloro-2-(difluoromethyl)-N-((1r,4r)-4-((3-(2-fluorophenyl)-3-hydroxy-4-methyl-2-oxoindolin-1-yl)methyl)cyclohexyl)nicotinamide | Intermediate-B, Intermediate-118 | A5 |
| 180 | 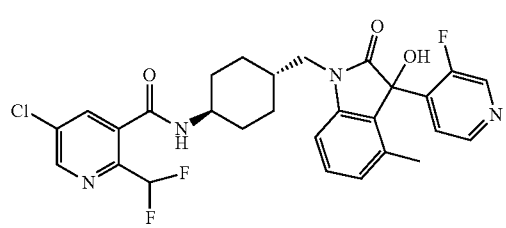 [SMILES: Cc1cccc2c1C(O)(c1ccncc1F)C(=O)N2C[C@H]1CC[C@H](NC(=O)c2cc(Cl)cnc2C(F)F)CC1] | 5-chloro-2-(difluoromethyl)-N-((1r,4r)-4-((3-(3-fluoropyridin-4-yl)-3-hydroxy-4-methyl-2-oxoindolin-1-yl)methyl)cyclohexyl)nicotinamide | Intermediate-B, Intermediate-119 | A5 |
| 181 | 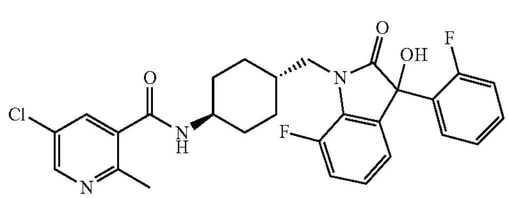 [SMILES: Cc1ncc(Cl)cc1C(=O)N[C@H]1CC[C@H](CN2C(=O)C(O)(c3ccccc3F)c3cccc(F)c32)CC1] | 5-chloro-N-((1r,4r)-4-((7-fluoro-3-(2-fluorophenyl)-3-hydroxy-2-oxoindolin-1-yl)methyl)cyclohexyl)-2-methylnicotinamide | Intermediate-A, Intermediate-56 | A5 |

TABLE 1-continued (Examples)

| Ex. | Structure | Name | Reactants | Method |
|---|---|---|---|---|
| 182 | 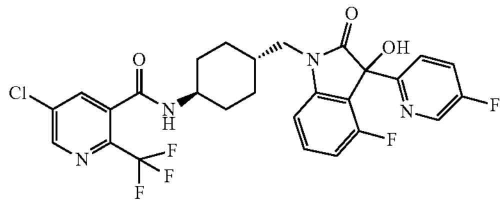 [SMILES: O=C(N[C@H]1CC[C@H](CN2C(=O)C(O)(c3ccc(F)cn3)c3c(F)cccc32)CC1)c1cc(Cl)cnc1C(F)(F)F] | 5-chloro-N-((1r,4r)-4-((4-fluoro-3-(5-fluoropyridin-2-yl)-3-hydroxy-2-oxoindolin-1-yl)methyl)cyclohexyl)-2-(trifluoromethyl)nicotinamide | Intermediate-C, Intermediate-55 | A5 |

Table 1-24

| 183 | | 5-chloro-N-((1r,4r)-4-((3-(5-chloropyridin-2-yl)-4-fluoro-3-hydroxy-2-oxoindolin-1-yl)methyl)cyclohexyl)-2-(trifluoromethyl)nicotinamide | Intermediate-C, Intermediate-95 | A5 |
| 184 | | 5-chloro-N-((1r,4r)-4-((3-(5-fluoropyridin-2-yl)-3-hydroxy-2-oxoindolin-1-yl)methyl)cyclohexyl)-2-(trifluoromethyl)nicotinamide | Intermediate-C, Intermediate-13 | A2 |
| 185 | | 5-chloro-N-((1r,4r)-4-((3-(2-fluoro-5-methoxyphenyl)-3-hydroxy-2-oxoindolin-1-yl)methyl)cyclohexyl)-2-(trifluoromethyl)nicotinamide | Intermediate-C, Intermediate-48 | A2 |
| 186 | | 5-chloro-N-((1r,4r)-4-((3-(3-chloro-2-fluorophenyl)-3-hydroxy-2-oxoindolin-1-yl)methyl)cyclohexyl)-2-(trifluoromethyl)nicotinamide | Intermediate-C, Intermediate-41 | A2 |
| 187 | | 5-chloro-N-((1r,4r)-4-((3-hydroxy-2-oxo-3-phenylindolin-1-yl)methyl)cyclohexyl)-2-(trifluoromethyl)nicotinamide | Intermediate-C, | A5 |

TABLE 1-continued (Examples)

| Ex. | Structure | Name | Reactants | Method |
|---|---|---|---|---|
| 188 | 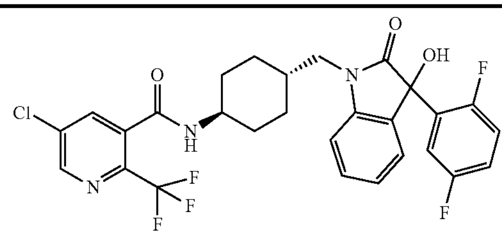 | 5-chloro-N-((1r,4r)-4-((3-(2,5-difluorophenyl)-3-hydroxy-2-oxoindolin-1-yl)methyl)cyclohexyl)-2-(trifluoromethyl)nicotinamide | Intermediate-C, Intermediate-34 | A5 |
| 189 | 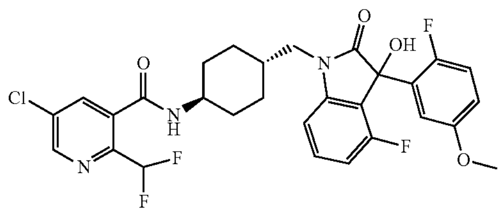 [SMILES: COc1ccc(F)c(C2(O)C(=O)N(C[C@H]3CC[C@H](NC(=O)c4cc(Cl)cnc4C(F)F)CC3)c3cccc(F)c32)c1] | 5-chloro-2-(difluoromethyl)-N-((1r,4r)-4-((4-fluoro-3-(2-fluoro-5-methoxyphenyl)-3-hydroxy-2-oxoindolin-1-yl)methyl)cyclohexyl)nicotinamide | Intermediate-B, Intermediate-120 | A5 |
| 190 | 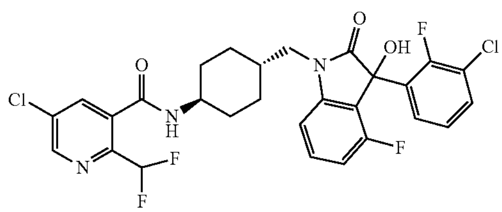 [SMILES: O=C(N[C@H]1CC[C@H](CN2C(=O)C(O)(c3cccc(Cl)c3F)c3c(F)cccc32)CC1)c1cc(Cl)cnc1C(F)F] | 5-chloro-N-((1r,4r)-4-((3-(3-chloro-2-fluorophenyl)-4-fluoro-3-hydroxy-2-oxoindolin-1-yl)methyl)cyclohexyl)-2-(difluoromethyl)nicotinamide | Intermediate-B, Intermediate-121 | A5 |

Table 1-25

| Ex. | Structure | Name | Reactants | Method |
|---|---|---|---|---|
| 191 | 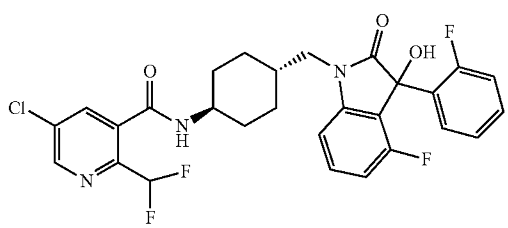 [SMILES: O=C(N[C@H]1CC[C@H](CN2C(=O)C(O)(c3ccccc3F)c3c(F)cccc32)CC1)c1cc(Cl)cnc1C(F)F] | 5-chloro-2-(difluoromethyl)-N-((1r,4r)-4-((4-fluoro-3-(2-fluorophenyl)-3-hydroxy-2-oxoindolin-1-yl)methyl)cyclohexyl)nicotinamide | Intermediate-B, Intermediate-122 | A5 |
| 192 | 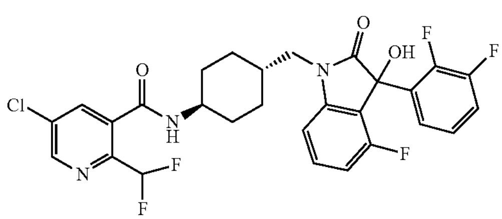 [SMILES: O=C(N[C@H]1CC[C@H](CN2C(=O)C(O)(c3cccc(F)c3F)c3c(F)cccc32)CC1)c1cc(Cl)cnc1C(F)F] | 5-chloro-2-(difluoromethyl)-N-((1r,4r)-4-((3-(2,3-difluorophenyl)-4-fluoro-3-hydroxy-2-oxoindolin-1-yl)methyl)cyclohexyl)nicotinamide | Intermediate-B, Intermediate-123 | A5 |

TABLE 2

| Ex | m/z | RT (min) | Ex | m/z | RT (min) |
|---|---|---|---|---|---|
| 1 | 490.3 | 1.67 | 15 | 595.3 | 1.81 |
| 2 | 554.5 | 1.74 | 16 | 527.2 | 1.67 |
| 3 | 524.5 | 1.75 | 17 | 542.5 | 1.79 |
| 4 | 527.3 | 1.62 | 18 | 545.2 | 1.68 |
| 5 | 557.4 | 1.67 | 19 | 545.2 | 1.71 |
| 6 | 541.3 | 1.70 | 20 | 542.4 | 1.79 |
| 7 | 559.3 | 1.77 | 21 | 545.2 | 1.61 |
| 8 | 541.3 | 1.74 | 22 | 561.1 | 1.63 |
| 9 | 557.4 | 1.76 | 23 | 568.2 | 1.72 |
| 10 | 545.3 | 1.57 | 24 | 561.1 | 1.80 |
| 11 | 557.4 | 1.66 | 25 | 563.1 | 1.74 |
| 12 | 595.4 | 1.81 | 26 | 561.1 | 1.70 |
| 13 | 561.2 | 1.76 | 27 | 575.1 | 1.75 |
| 14 | 533.2 | 1.58 | 28 | 579.1 | 1.83 |

TABLE 2-continued

| Ex | m/z | RT (min) |
|---|---|---|
| 29 | 558.2 | 1.88 |
| 30 | 558.2 | 1.88 |
| 31 | 542.3 | 1.79 |
| 32 | 542.3 | 1.80 |
| 33 | 542.3 | 1.77 |
| 34 | 568.4 | 1.70 |
| 35 | 533.1 | 1.55 |
| 36 | 563.1 | 1.65 |
| 37 | 516.4 | 1.83 |
| 38 | 552.4 | 1.87 |
| 39 | 580.2 | 1.64 |
| 40 | 562.1 | 1.81 |
| 41 | 572.2 | 1.77 |
| 42 | 558.2 | 1.87 |
| 43 | 538.2 | 1.86 |
| 44 | 560.3 | 1.84 |
| 45 | 576.1 | 1.89 |
| 46 | 551.1 | 1.72 |
| 47 | 554.3 | 1.75 |
| 48 | 558.2 | 1.86 |
| 49 | 538.2 | 1.82 |
| 50 | 592.2 | 1.89 |
| 51 | 608.2 | 1.92 |
| 52 | 622.1 | 1.74 |
| 53 | 560.2 | 1.81 |
| 54 | 572.2 | 1.79 |
| 55 | 591.1 | 1.86 |
| 56 | 538.3 | 1.83 |
| 57 | 547.1 | 1.66 |
| 58 | 560.3 | 1.80 |
| 59 | 569.1 | 1.74 |
| 60 | 570.1 | 1.70 |
| 61 | 562.1 | 1.76 |
| 62 | 589.1 | 1.84 |
| 63 | 556.3 | 1.84 |
| 64 | 575.1 | 1.73 |
| 65 | 560.1 | 1.83 |
| 66 | 572.3 | 1.75 |
| 67 | 576.3 | 1.87 |
| 68 | 560.3 | 1.82 |
| 69 | 574.3 | 1.77 |
| 70 | 612.1 | 1.87 |
| 71 | 567.4 | 1.73 |
| 72 | 588.4 | 1.82 |
| 73 | 570.4 | 1.83 |
| 74 | 574.0 | 1.77 |
| 75 | 575.0 | 1.72 |
| 76 | 577.1 | 1.85 |
| 77 | 577.1 | 1.88 |
| 78 | 563.1 | 1.73 |
| 79 | 563.1 | 1.71 |
| 80 | 563.1 | 1.70 |
| 81 | 563.1 | 1.71 |
| 82 | 562.1 | 1.83 |
| 83 | 560.4 | 1.81 |
| 84 | 563.1 | 1.64 |
| 85 | 563.1 | 1.61 |
| 86 | 563.1 | 1.60 |
| 87 | 563.1 | 1.61 |
| 88 | 613.2 | 1.83 |
| 89 | 629.2 | 1.86 |
| 90 | 612.2 | 1.91 |
| 91 | 530.4 | 1.71 |
| 92 | 530.3 | 1.71 |
| 93 | 562.1 | 1.79 |
| 94 | 545.1 | 1.68 |
| 95 | 548.4 | 1.72 |
| 96 | 560.4 | 1.72 |
| 97 | 583.2 | 1.80 |
| 98 | 548.1 | 1.75 |
| 99 | 560.2 | 1.74 |
| 100 | 564.1 | 1.86 |
| 101 | 546.1 | 1.48 |
| 102 | 526.1 | 1.74 |
| 103 | 526.1 | 1.72 |
| 104 | 545.1 | 1.53 |
| 105 | 572.2 | 1.77 |
| 106 | 575.1 | 1.58 |
| 107 | 572.2 | 1.74 |
| 108 | 572.2 | 1.80 |
| 109 | 575.1 | 1.62 |
| 110 | 514.2 | 1.64 |
| 111 | 572.2 | 1.79 |
| 112 | 579.1 | 1.80 |
| 113 | 578.2 | 1.84 |
| 114 | 584.3 | 1.75 |
| 115 | 593.2 | 1.78 |
| 116 | 580.2 | 1.84 |
| 117 | 596.1 | 1.90 |
| 118 | 580.2 | 1.83 |
| 119 | 579.1 | 1.80 |
| 120 | 572.3 | 1.73 |
| 121 | 563.1 | 1.72 |
| 122 | 563.1 | 1.72 |
| 123 | 580.2 | 1.82 |
| 124 | 593.2 | 1.77 |
| 125 | 579.1 | 1.78 |
| 126 | 580.1 | 1.82 |
| 127 | 526.1 | 1.72 |
| 128 | 538.2 | 1.70 |
| 129 | 576.1 | 1.85 |
| 130 | 544.2 | 1.79 |
| 131 | 564.2 | 1.85 |
| 132 | 544.1 | 1.78 |
| 133 | 580.1 | 1.84 |
| 134 | 578.1 | 1.87 |
| 135 | 580.1 | 1.85 |
| 136 | 612.1 | 1.90 |
| 137 | 542.1 | 1.81 |
| 138 | 544.1 | 1.79 |
| 139 | 556.1 | 1.73 |
| 140 | 579.1 | 1.80 |
| 141 | 578.1 | 1.91 |
| 142 | 556.3 | 1.83 |
| 143 | 544.2 | 1.77 |
| 144 | 557.2 | 1.71 |
| 145 | 543.1 | 1.72 |
| 146 | 538.2 | 1.69 |
| 147 | 559.2 | 1.74 |
| 149 | 556.4 | 1.83 |
| 150 | 559.2 | 1.64 |
| 151 | 525.2 | 1.90 |
| 152 | 531.2 | 1.78 |
| 153 | 595.2 | 1.97 |
| 154 | 592.2 | 1.80 |
| 155 | 581.2 | 2.18 |
| 156 | 593.2 | 1.77 |
| 157 | 592.1 | 1.82 |
| 158 | 591.1 | 1.73 |
| 159 | 592.2 | 1.77 |
| 160 | 527.1 | 1.64 |
| 161 | 543.1 | 1.71 |
| 162 | 557.1 | 1.69 |
| 163 | 544.2 | 1.76 |
| 164 | 587.1 | 1.79 |
| 165 | 590.3 | 1.83 |
| 166 | 593.2 | 1.79 |
| 167 | 546.1 | 1.80 |
| 168 | 592.2 | 1.81 |
| 169 | 593.2 | 1.76 |
| 170 | 576.2 | 1.89 |
| 171 | 567.2 | 2.03 |
| 172 | 551.2 | 1.71 |
| 173 | 526.2 | 1.73 |
| 174 | 559.2 | 1.73 |
| 175 | 558.2 | 1.82 |
| 176 | 559.2 | 1.62 |
| 177 | 580.2 | 1.83 |
| 178 | 559.2 | 1.76 |
| 179 | 558.2 | 1.85 |
| 180 | 559.2 | 1.64 |
| 181 | 526.2 | 1.76 |
| 182 | 581.2 | 1.76 |
| 183 | 597.1 | 1.85 |
| 184 | 563.2 | 1.72 |
| 185 | 592.2 | 1.82 |

TABLE 2-continued

| Ex | m/z | RT (min) |
|---|---|---|
| 186 | 596.1 | 1.90 |
| 187 | 542.3 | 1.79 |
| 188 | 580.2 | 1.83 |
| 189 | 592.2 | 1.77 |

TABLE 2-continued

| Ex | m/z | RT (min) |
|---|---|---|
| 190 | 596.1 | 1.90 |
| 191 | 560.3 | 1.80 |
| 192 | 580.2 | 1.83 |

TABLE 3

| | |
|---|---|
| Ex 13 | $^1$H-NMR (400 MHz, CDCl$_3$) delta 8.64 (1H, d, J = 2.3 Hz), 8.55 (1H, d, J = 2.3 Hz), 7.92 (1H, d, J = 2.3 Hz), 7.62 (1H, dd, J = 8.5, 2.5 Hz), 7.37 (1H, td, J = 7.8, 1.4 Hz), 7.17 (1H, d, J = 7.3 Hz), 7.07 (1H, t, J = 7.5 Hz), 7.00 (1H, d, J = 9.1 Hz), 6.93 (1H, d, J = 7.8 Hz), 6.78 (1H, t, J = 54.4 Hz), 5.88 (1H, brd, J = 7.8 Hz), 5.47 (1H, s), 4.06-3.82 (1H, m), 3.64 (1H, dd, J = 14.0, 6.6 Hz), 3.57 (1H, dd, J = 14.2, 6.9 Hz), 2.28-2.09 (2H, m), 1.99-1.79 (3H, m), 1.47-1.09 (4H, m). |
| Ex 78 | $^1$H-NMR (400 MHz, CDCl$_3$) delta 8.63 (1H, d, J = 2.3 Hz), 8.46 (1H, d, J = 2.7 Hz), 7.91 (1H, d, J = 2.3 Hz), 7.39 (1H, ddd, J = 8.2, 8.2, 2.7 Hz), 7.16-7.07 (2H, m), 7.01 (1H, dd d, J = 7.3, 7.3, 4.7 Hz), 6.95 (1H, dd, J = 7.3, 1.4 Hz), 6.80 (1H, t, J = 54.4 Hz), 6.04 (1H, brd, J = 7.8 Hz), 4.00-3.85 (1H, m), 3.76 (2H, d, J = 6.4 Hz), 2.25-2.08 (2H, m), 1.96-1.78 (3H, m), 1.44-1.05 (4H, m), OH proton is not observed. |
| Ex 79 | $^1$H-NMR (400 MHz, CDCl$_3$) delta 8.64 (1H, d, J = 2.3 Hz), 8.43 (1H, d, J = 2.7 Hz), 7.92 (1H, d, J = 2.3 Hz), 7.39 (1H, ddd, J = 8.3, 8.3, 2.7 Hz), 7.20-7.05 (2H, m), 6.94 (1H, t, J = 54.4 Hz), 6.81-6.69 (1H, m), 6.65 (1H, dd, J = 8.7, 2.3 Hz), 6.10 (1H, brs), 4.06-3.80 (1H, m), 3.71-3.44 (2H, m), 2.25-2.07 (2H, m), 1.95-1.75 (3H, m), 1.43-1.01 (4H, m), OH proton is not observed. |
| Ex 80 | $^1$H-NMR (400 MHz, CDCl$_3$) delta 8.72 (1H, d, J = 2.3 Hz), 8.46 (1H, d, J = 2.7 Hz), 7.90 (1H, d, J = 2.3 Hz), 7.39 (1H, ddd, J = 8.3, 8.3, 2.9 Hz), 7.15 (1H, dd, J = 8.7, 4.1 Hz), 7.05 (1H, ddd, J = 8.8, 8.8, 2.6 Hz), 6.90 (1H, dd, J = 7.3, 2.7 Hz), 6.88 (1H, t, J = 54.4 Hz), 6.84 (1H, dd, J = 8.5, 3.9 Hz), 6.33 (1H, brd, J = 7.3 Hz), 5.71 (1H, s), 4.02-3.82 (1H, m), 3.62 (1H, dd, J = 14.2, 6.4 Hz), 3.54 (1H, dd, J = 14.2, 6.9 Hz), 2.29-2.08 (2H, m), 1.95-1.81 (3H, m), 1.54-1.04 (4H, m). |
| Ex 81 | $^1$H-NMR (400 MHz, CDCl$_3$) delta 8.63 (1H, d, J = 1.8 Hz), 8.43 (1H, d, J = 2.7 Hz), 7.91 (1H, d, J = 1.8 Hz), 7.38 (1H, ddd, J = 8.2, 8.2, 2.7 Hz), 7.22-7.06 (2H, m), 6.94 (1H, t, J = 54.4 Hz), 6.84-6.69 (1H, m), 6.65 (1H, dd, J = 8.9, 2.1 Hz), 6.18 (1H, brs), 3.93 (1H, brs), 3.70-3.49 (2H, m), 2.28-2.09 (2H, m), 1.95-1.65 (3H, m), 1.49-1.01 (4H, m), OH proton is not observed. |
| Ex 82 | $^1$H-NMR (400 MHz, CDCl$_3$) delta 8.64 (1H, d, J = 2.3 Hz), 7.92 (1H, d, J = 1.8 Hz), 7.88 (1H, ddd, J = 7.7, 7.7, 2.0 Hz), 7.40-7.20 (2H, m), 7.07 (1H, dd, J = 11.9, 8.2 Hz), 7.03-6.89 (3H, m), 6.80 (1H, t, J = 54.4 Hz), 5.92 (1H, brd, J = 9.1 Hz), 4.05-3.87 (1H, m), 3.88-3.69 (2H, m), 2.25-2.11 (2H, m), 1.97-1.80 (3H, m), 1.43-1.14 (4H, m), OH proton is not observed. |
| Ex 83 | $^1$H-NMR (400 MHz, CDCl$_3$) delta 8.65 (1H, d, J = 2.3 Hz), 7.93 (1H, d, J = 2.3 Hz), 7.88 (1H, ddd, J = 7.8, 7.8, 1.8 Hz), 7.36-7.20 (2H, m), 7.08 (1H, dd, J = 8.2, 5.5 Hz), 6.95 (1H, ddd, J = 11.2, 8.2, 1.1 Hz), 6.79 (1H, t, J = 54.4 Hz), 6.72-6.65 (1H, m), 6.65 (1H, dd, J = 8.9, 2.1 Hz), 5.95 (1H, brd, J = 8.2 Hz), 3.96 (1H, brs), 3.68 (1H, dd, J = 14.0, 6.2 Hz), 3.52 (1H, dd, J = 14.2, 7.3 Hz), 2.28-2.09 (2H, m), 1.97-1.77 (3H, m), 1.43-1.09 (4H, m), OH proton is not observed. |
| Ex 84 | $^1$H-NMR (400 MHz, CDCl$_3$) delta 8.65 (1H, d, J = 2.3 Hz), 8.54 (1H, dd, J = 5.0, 0.9 Hz), 8.33 (1H, d, J = 2.3 Hz), 7.93 (1H, d, J = 2.3 Hz), 7.87 (1H, dd, J = 6.4, 5.0 Hz), 7.12 (1H, ddd, J = 11.7, 8.5, 1.1 Hz), 7.06-6.95 (1H, m), 6.91 (1H, dd, J = 7.3, 1.4 Hz), 6.79 (1H, t, J = 54.9 Hz), 5.94 (1H, brd, J = 7.3 Hz), 3.94 (1H, brs), 3.86-3.72 (2H, m), 2.16-2.07 (2H, m), 1.96-1.72 (3H, m), 1.47-1.03 (4H, m), OH proton is not observed. |
| Ex 85 | $^1$H-NMR (400 MHz, CDCl$_3$) delta 8.65 (1H, d, J = 2.3 Hz), 8.53 (1H, d, J = 5.0 Hz), 8.32 (1H, d, J = 1.8 Hz), 7.93 (1H, d, J = 1.8 Hz), 7.87 (1H, dd, J = 6.4, 5.0 Hz), 7.07 (1H, dd, J = 8.0, 5.3 Hz), 6.93 (1H, t, J = 54.9 Hz), 6.82-6.69 (1H, m), 6.66 (1H, dd, J = 8.9, 2.1 Hz), 5.96 (1H, brd, J = 6.4 Hz), 4.03-3.82 (1H, m), 3.67 (1H, dd, J = 14.0, 6.6 Hz), 3.60 (1H, s), 3.54 (1H, dd, J = 14.6, 7.8 Hz), 2.28-2.10 (2H, m), 1.97-1.73 (3H, m), 1.45-1.09 (4H, m). |
| Ex 87 | $^1$H-NMR (400 MHz, CDCl$_3$) delta 8.65 (1H, d, J = 2.3 Hz), 8.53 (1H, d, J = 5.0 Hz), 8.32 (1H, d, J = 2.3 Hz), 7.93 (1H, d, J = 1.4 Hz), 7.88 (1H, td, J = 5.7, 1.8 Hz), 7.07 (1H, dd, J = 8.2, 5.5 Hz), 6.93 (1H, t, J = 54.9 Hz), 6.76-6.69 (1H, m), 6.67 (1H, dt, J = 8.8, 2.4 Hz), 5.99 (1H, brd, J = 8.2 Hz), 4.03-3.83 (1H, m), 3.75-3.63 (2H, m), 3.62-3.46 (1H, m), 2.29-2.08 (2H, m), 1.96-1.80 (3H, m), 1.47-1.06 (4H, m). |
| Ex 88 | $^1$H-NMR (400 MHz, CDCl$_3$) delta 8.64 (1H, d, J = 2.3 Hz), 8.45 (1H, d, J = 2.7 Hz), 7.93 (1H, d, J = 2.3 Hz), 7.41 (1H, td, J = 8.3, 2.7 Hz), 7.18 (1H, d, J = 8.2 Hz), 7.10 (1H, dd, J = 8.7, 4.1 Hz), 6.97-6.89 (1H, m), 6.85 (1H, t, J = 54.4 Hz), 6.80-6.73 (1H, m), 5.92 (1H, d, J = 7.8 Hz), 5.50 (1H, s), 4.03-3.88 (1H, m), 3.63 (1H, dd, J = 14.0, 7.1 Hz), 3.56 (1H, dd, J = 14.4, 7.1 Hz), 2.26-2.11 (2H, m), 1.97-1.79 (3H, m), 1.42-1.15 (4H, m). |

TABLE 3-continued

| | |
|---|---|
| Ex 89 | $^1$H-NMR (400 MHz, CDCl$_3$) delta 8.64 (1H, d, J = 2.7 Hz), 8.45 (1H, d, J = 2.7 Hz), 7.93 (1H, d, J = 2.3 Hz), 7.41 (1H, td, J = 8.3, 2.9 Hz), 7.36 (1H, d, J = 7.8 Hz), 7.28 (1H, d, J = 7.8 Hz), 7.17-7.07 (2H, m), 6.85 (1H, t, J = 54.7 Hz), 5.94 (1H, d, J = 8.7 Hz), 5.51 (1H, s), 4.02-3.84 (1H, m), 3.69 (1H, dd, J = 14.2, 6.9 Hz), 3.60 (1H, dd, J = 14.2, 6.9 Hz), 2.26-2.09 (2H, m), 1.97-1.79 (3H, m), 1.41-1.08 (4H, m). |
| Ex 94 | $^1$H-NMR (400 MHz, CDCl$_3$) delta 8.62 (1H, d, J = 2.3 Hz), 8.20 (1H, dd, J = 5.3, 1.6 Hz), 7.97-7.80 (2H, m), 7.38 (1H, ddd, J = 12.6, 7.3, 1.6 Hz), 7.34-7.27 (1H, m), 7.22 (1H, t, J = 7.5 Hz), 6.99-6.89 (2H, m), 6.81 (1H, t, J = 54.4 Hz), 6.19 (1H, d, J = 7.8 Hz), 4.64 (1H, brs), 4.05-3.84 (1H, m), 3.75 (2H, d, J = 7.3 Hz), 2.24-2.05 (2H, m), 1.95-1.51 (3H, m), 1.42-1.00 (4H, m). |
| Ex 102 | $^1$H-NMR (400 MHz, CDCl$_3$) delta 8.48 (1H, d, J = 2.3 Hz), 7.88 (1H, td, J = 7.8, 1.8 Hz), 7.61 (1H, d, J = 2.3 Hz), 7.38-7.29 (1H, m), 7.29-7.20 (1H, m), 7.08 (1H, dd, J = 8.2, 5.5 Hz), 6.94 (1H, ddd, J = 11.2, 8.0, 1.1 Hz), 6.69 (1H, ddd, J = 9.8, 7.5, 1.6 Hz), 6.63 (1H, dd, J = 8.9, 2.1 Hz), 5.63 (1H, brd, J = 8.2 Hz), 4.03-3.82 (1H, m), 3.68 (1H, dd, J = 14.2, 6.4 Hz), 3.53 (1H, dd, J = 14.2, 7.8 Hz), 3.49 (1H, s), 2.61 (3H, s), 2.25-2.10 (2H, m), 1.99-1.81 (3H, m), 1.42-1.10 (4H, m). |
| Ex 103 | $^1$H-NMR (400 MHz, CDCl$_3$) delta 8.47 (1H, d, J = 2.3 Hz), 7.86 (1H, td, J = 7.9, 1.5 Hz), 7.59 (1H, d, J = 2.3 Hz), 7.37-7.28 (1H, m), 7.28-7.20 (1H, m), 7.02 (1H, td, J = 8.8, 2.6 Hz), 6.94 (1H, ddd, J = 11.3, 8.1, 1.0 Hz), 6.87 (1H, dd, J = 7.3, 2.7 Hz), 6.82 (1H, dd, J = 8.7, 4.1 Hz), 5.62 (1H, brd, J = 7.8 Hz), 4.01-3.84 (1H, m), 3.68 (1H, dd, J = 14.0, 6.2 Hz), 3.53 (1H, dd, J = 14.0, 7.5 Hz), 2.62 (3H, s), 2.29-2.08 (2H, m), 1.97-1.80 (3H, m), 1.43-1.06 (4H, m), OH proton is not observed. |
| Ex 105 | $^1$H-NMR (400 MHz, CDCl$_3$) delta 8.65 (1H, d, J = 2.3 Hz), 7.97 (1H, d, J = 2.3 Hz), 7.87 (1H, ddd, J = 7.9, 7.9, 2.0 Hz), 7.34-7.27 (1H, m), 7.26-7.20 (1H, m), 7.04 (1H, d, J = 7.9 Hz), 6.96 (1H, ddd, J = 10.8, 8.0, 1.2 Hz), 6.89 (1H, t, J = 54.9 Hz), 6.53-6.44 (2H, m), 5.93 (1H, brd, J = 7.8 Hz), 4.02-3.87 (1H, m), 3.82 (3H, s), 3.67 (1H, dd, J = 14.2, 6.2 Hz), 3.52 (1H, dd, J = 14.2, 7.3 Hz), 2.25-2.10 (2H, m), 1.98-1.83 (3H, m), 1.41-1.04 (4H, m), OH proton is not observed. |
| Ex 106 | $^1$H-NMR (400 MHz, CDCl$_3$) delta 8.63 (1H, d, J = 2.3 Hz), 8.48 (1H, d, J = 4.6 Hz), 8.27 (1H, d, J = 2.3 Hz), 7.91 (1H, d, J = 2.3 Hz), 7.86 (1H, dd, J = 6.4, 5.0 Hz), 7.00 (1H, d, J = 8.2 Hz), 6.79 (1H, t, J = 54.9 Hz), 6.61-6.41 (2H, m), 6.17-5.91 (1H, m), 4.01-3.87 (1H, m), 3.82 (3H, s), 3.63 (1H, dd, J = 14.0, 6.2 Hz), 3.52 (1H, dd, J = 13.7, 7.3 Hz), 2.15 (2H, s), 1.95-1.81 (3H, m), 1.44-1.10 (4H, m), OH proton is not observed. |
| Ex 109 | $^1$H-NMR (400 MHz, CDCl$_3$) delta 8.64 (1H, d, J = 2.3 Hz), 8.49 (1H, dd, J = 5.0, 0.9 Hz), 8.29 (1H, d, J = 2.3 Hz), 7.91 (1H, d, J = 2.3 Hz), 7.84 (1H, dd, J = 6.4, 5.0 Hz), 7.03-6.92 (2H, m), 6.85 (1H, t, J = 54.4 Hz), 6.72 (1H, dd, J = 7.3, 1.4 Hz), 5.92 (1H, brd, J = 8.2 Hz), 4.01-3.80 (6H, m), 2.22-2.07 (2H, m), 1.94-1.76 (3H, m), 1.39-1.10 (4H, m), OH proton is not observed. |
| Ex 116 | $^1$H-NMR (400 MHz, CDCl$_3$) delta 8.64 (1H, d, J = 2.3 Hz), 7.93 (1H, d, J = 2.3 Hz), 7.70-7.59 (1H, m), 7.22-7.11 (2H, m), 7.08 (1H, dd, J = 8.0, 5.3 Hz), 6.86 (1H, t, J = 54.4 Hz), 6.70 (1H, dd, J = 8.5, 2.1 Hz), 6.65 (1H, dd, J = 8.7, 2.3 Hz), 5.95 (1H, brd, J = 7.8 Hz), 4.03-3.86 (1H, m), 3.67 (1H, dd, J = 14.2, 6.4 Hz), 3.54 (1H, dd, J = 14.2, 7.3 Hz), 3.40 (1H, s), 2.26-2.10 (2H, m), 1.97-1.80 (3H, m), 1.38-1.11 (4H, m). |
| Ex 118 | $^1$H-NMR (400 MHz, CDCl$_3$) delta 8.64 (1H, d, J = 2.3 Hz), 7.91 (1H, d, J = 1.8 Hz), 7.67-7.57 (1H, m), 7.08 (1H, dd, J = 8.2, 5.5 Hz), 7.03-6.94 (1H, m), 6.90 (1H, dd, J = 9.6, 4.6 Hz), 6.85 (1H, t, J = 54.4 Hz), 6.78-6.66 (1H, m), 6.63 (1H, dd, J = 8.7, 2.3 Hz), 5.96 (1H, d, J = 8.2 Hz), 4.03-3.85 (1H, m), 3.65 (1H, dd, J = 14.4, 6.2 Hz), 3.61 (1H, s), 3.54 (1H, dd, J = 14.2, 7.3 Hz), 2.28-2.08 (2H, m), 2.02-1.78 (3H, m), 1.41-1.13 (4H, m). |
| Ex 157 | $^1$H-NMR (400 MHz, CDCl$_3$) delta 8.64 (1H, d, J = 2.3 Hz), 8.52 (1H, dd, J = 2.3, 0.9 Hz), 7.92 (1H, d, J = 2.3 Hz), 7.63 (1H, d, J = 8.5 Hz), 7.34 (1H, dd, J = 8.2, 8.2 Hz), 7.15 (1H, d, J = 8.2 Hz), 6.86 (1H, t, J = 54.7 Hz), 6.62 (1H, d, J = 8.2 Hz), 6.57 (1H, d, J = 7.8 Hz), 5.90 (1H, d, J = 7.8 Hz), 4.02-3.83 (1H, m), 3.67 (3H, s), 3.60 (1H, d, J = 6.9 Hz), 3.55 (1H, d, J = 7.3 Hz), 2.26-2.03 (2H, m), 1.93-1.75 (3H, m), 1.41-1.06 (4H, m), OH proton is not observed. |
| Ex 160 | $^1$H-NMR (400 MHz, CDCl$_3$) delta 8.55 (1H, d, J = 2.3 Hz), 8.49 (1H, d, J = 2.3 Hz), 7.65 (1H, dd, J = 8.2, 2.3 Hz), 7.63-7.59 (1H, m), 7.15-7.02 (2H, m), 6.92 (1H, dd, J = 7.3, 2.7 Hz), 6.86 (1H, dd, J = 8.7, 4.1 Hz), 5.56 (1H, d, J = 7.3 Hz), 4.02-3.81 (1H, m), 3.63 (1H, dd, J = 14.0, 6.6 Hz), 3.56 (1H, dd, J = 14.4, 6.6 Hz), 2.58 (3H, s), 2.30-2.08 (2H, m), 2.01-1.74 (3H, m), 1.43-1.04 (4H, m), OH proton is not observed. |
| Ex 162 | $^1$H-NMR (400 MHz, CDCl$_3$) delta 8.49 (1H, d, J = 2.3 Hz), 7.70-7.63 (1H, m), 7.61 (1H, d, J = 2.3 Hz), 7.23-7.12 (2H, m), 7.06 (1H, ddd, J = 8.7, 8.7, 2.7 Hz), 6.89 (1H, dd, J = 7.3, 2.7 Hz), 6.85 (1H, dd, J = 8.7, 4.1 Hz), 5.58 (1H, brd, J = 8.2 Hz), 4.03-3.87 (1H, m), 3.70 (1H, dd, J = 13.7, 6.4 Hz), 3.55 (1H, dd, J = 14.2, 7.3 Hz), 2.61 (3H, s), 2.30-2.07 (2H, m), 2.01-1.82 (3H, m), 1.40-1.06 (4H, m), OH proton is not observed. |

TABLE 3-continued

Ex 183  $^1$H-NMR (400 MHz, CDCl$_3$) delta 8.67 (1H, d, J = 1.8 Hz), 8.54 (1H, d, J = 1.8 Hz), 7.88 (1H, d, J = 2.3 Hz), 7.65 (1H, dd, J = 8.2, 2.3 Hz), 7.12 (1H, dd, J = 8.2, 5.5 Hz), 7.04 (1H, d, J = 8.2 Hz), 6.75 (1H, ddd, J = 8.7, 8.7, 2.3 Hz), 6.65 (1H, dd, J = 8.7, 2.3 Hz), 5.75-5.61 (1H, m), 4.01-3.83 (1H, m), 3.65-3.47 (2H, m), 2.27-2.07 (2H, m), 2.02-1.70 (3H, m), 1.36-1.05 (4H, m), OH proton is not observed.

Pharmacological Assays

The in vitro and in vivo inhibitory activities of the compounds of this invention against CRHR2 are determined by the following procedures.

cAMP functional assay for human CRHR2 The ability of the compounds of this invention to inhibit either CRHR2 is assessed by 3',5'-cyclic adenosine monophosphate (cAMP) production in cells using the LANCE Ultra cAMP assay kit (ParkinElmer), which are designed based on the homogeneous time-resolved fluorescence resonance energy transfer (TR-FRET) immunoassay.

CHO-K1 (Chinese hamster ovary) cells stably expressing human CRHR2-alpha (DiscoveRX, Cat. 95-0048C2) are grown in HAM's F12 media supplemented with 10% fetal bovine serum (FBS), 100 units/mL penicillin G, 100 microg/mL hygromycin and 0.5 microg/mL geneticin at 37° C. in 5% CO$_2$ humidified incubator to 80% confluence. After 7 hours starvation treatment in culture media containing 0.1% FBS, the cells are washed with Hanks balanced salt solution (HBSS) and cryopreserved.

For cAMP assay, frozen cells are thawed and washed with HBSS, followed by resuspending cells in assay buffer (HBSS containing 0.1% bovine serum albumin, 0.5 mM isobutylmethylxanthine and 5 mM Hepes, pH 7.4) at the appropriate concentration for the assay. The cell suspensions are plated on 384-well microplates (Greiner Bio-One) at a density of 4,000 cells per well. After preincubating the cells with various concentrations of the compounds for 30 min at 25° C., an assay buffer containing EC$_{90}$ concentration of agonist is added and the cells are incubated for 30 min at 25° C. Human urocortin2 (Peptide Institute) is used as agonists for CRHR2. For the termination of assay, europium-labeled cAMP tracer and ULight (registered trademark) dye labeled cAMP antibodies, both prepared with Lance-Ultra cAMP detection reagent (PerkinElmer) are added in the plate and incubate for 60 min at 25° C. After incubation, TR-FRET signal is detected by EnVision plate reader (PerkinElmer). The IC$_{50}$ values for compounds are calculated from dose-response curves by fitting the percent inhibition using XLfit (ID Business Solutions).

All compounds (Example 1 to Example 183) show less than about 1 microM of IC so against CRHR2 in the above assays. Preferable compounds show less than about 0.2 microM of IC$_{50}$ against CRHR2 in the above assays.

Compounds with IC$_{50}$ against CRHR2<0.2 microM are: Example 2, 3, 10, 13, 17, 18, 20, 27, 30, 33, 40, 47, 48, 49, 53, 54, 56, 58, 59, 63, 66, 67, 74, 79, 82, 83, 85, 92, 93, 94, 95, 98, 99, 105, 113, 115, 116, 117, 118, 119, 123, 124, 125, 128, 130, 132, 133, 135, 139, 140, 143, 148, 149, 153, 155, 156, 158, 162, 164, 167, 168, 170, 173, 177, 178, 179, 185, 189, 190, 191, 192.

The compounds of this invention show preferable activity, which show the above-mentioned practical use.

Echocardiogram Analysis of Mice Loaded with CRHR2 Agonist

Male C57BL/6 mice at 8 weeks old are purchased from Charles River Japan, and housed in groups of 6 per cage under a 12-h light/dark cycle with access to food and water ad libitum. Under conscious condition, transthoracic echocardiography is performed using Vivo1100 imaging system (FUJIFILM VisualSonics). Left ventricular end-systolic diameter (LVDs) and left ventricular end-diastolic diameters (LVDd) are measured to calculate percent fractional shortening (% FS) in M-mode. The % FS is calculated by the following equation: % FS=(LVDd−LVDs)/LVDd× 100. After measuring % FS, the animals are anesthetized with an anesthetic mixture (medetomidine, midazolam and butorphanol), and an Alzet (registered trademark) osmotic pump (DURECT) that releases mouse urocortin 2 (Peptide Institute) at an infusion rate of 0.11 microL/h (100 ng/g/day) is implanted subcutaneously in the back. Two days after the implantation, examining urocortin 2-induced increase of the % FS, the animals are selected for evaluation and randomized to be nearly equal across all groups. The compounds of the invention or their vehicles are administered systemically. The post-value of % FS is measured at an appropriate time point after compound administration. Statistical analysis is performed by parametric methods.

Human Dofetilide Binding Assay

HERG transfected HEK293S cells are prepared and grown in-house. The collected cells are suspended in 50 mM Tris-HCl (pH 7.4 at 4° C.) and homogenized using a hand held Polytron PT 1200 disruptor set at full power for 20 sec on ice. The homogenates are centrifuged at 48,000×g at 4° C. for 20 min. The pellets are then resuspended, homogenized, and centrifuged once more in the same manner. The final pellets are resuspended in an appropriate volume containing 50 mM Tris-HCl, 10 mM KCl and 1 mM MgCl$_2$ (pH 7.4 at 4° C.), homogenized, ali-quoted and stored at −80° C. until use. An aliquot of membrane fractions is used for protein concentration determination using BCA protein assay kit (PIERCE) and ARVOsx plate reader (Wallac). Binding assays are conducted in a total volume of 30 microL in 384-well plates. The activity is measured by PHERAstar (BMG LABTECH) using fluorescence polarization technology. Ten microL of test compounds are incubated with 10 microL of fluorescence ligand (6 nM Cy3B tagged dofetilide derivative) and 10 microL of membrane homogenate (6 microgram protein) for 120 minutes at room temperature. Nonspecific binding is determined by 10 microM E4031 at the final concentration.

All tested compounds of the invention show higher IC$_{50}$ values in human dofetilide binding than IC$_{50}$ values in CRHR2 Assay. The high IC$_{50}$ values in human dofetilide binding activities lead to reducing the risk of cardiovascular adverse events.

Metabolic Stability Assay:

Half-Life in Human Liver Microsomes (HLM)

Test compounds (1 microM) are incubated with 3.3 mM MgCl$_2$ and 0.78 mg/mL HLM (HL101) or 0.74 mg/mL HLM (Gentest UltraPool 150) in 100 mM potassium phosphate buffer (pH 7.4) at 37° C. on the 96-deep well plate. The reaction mixture is split into two groups, a non-P450 and a P450 group. Nicotinamide Adenine Dinucleotide Phosphate Hydrogen (NADPH) is only added to the reaction mixture of the P450 group. (NADPH generation system is also used instead of NADPH.) An aliquot of samples of P450 group is collected at 0, 10, 30, and 60 min time point, where 0 min time point indicates the time when NADPH is added into the reaction mixture of P450 group. An aliquot of samples of non-P450 group is collected at −10 min and 65 min time point. Collected aliquots are extracted with acetonitrile solution containing an internal standard. The precipitated protein is spun down in centrifuge (2000 rpm, 15 min). The compound concentration in supernatant is measured by LC/MS/MS system.

The half-life value is obtained by plotting the natural logarithm of the peak area ratio of compounds/internal standard versus time. The slope of the line of best fit through the points yield the rate of metabolism (k). This is converted to a half-life value using following equations: Half-life=ln 2/k The compounds of this invention show preferable stability, which show the above-mentioned practical use.

Drug-Drug Interaction Assay

This method essentially involves determining the percent inhibition of metabolites formation from probes (Tacrine (Sigma A3773-1G) 2 microM, Dextromethorphan (Sigma D-9684) 5 microM, Diclofenac (Sigma D-6899-10G) 5 microM, and Midazolam (ULTRAFINE UC-429) 2 microM) at 3 microM of each compound.

More specifically, the assay is carried out as follows. The compounds (60 microM, 10 microL) are pre-incubated in 170 microL of mixture including 0.1 mg protein/mL human liver microsomes, 100 mM potassium phosphate buffer (pH 7.4), 1 mM MgCl$_2$ and probes as substrate for 5 min. Reaction is started by adding a 20 microL of 10 mM NADPH (20 microL of NADPH generating system, which consist of 10 mM NADP$^+$, 50 mM DL-Isocitric acid and 10 U/mL Isocitric Dehydrogenase, is also used). The assay plate is incubated at 37° C. Acetonitrile is added to the incubate solution at appropriate time (e.g. 8 min).

The metabolites' concentration in the supernatant is measured by LC/MS/MS system.

The degree of drug-drug interaction is interpreted based on generation % of metabolites in the presence or absence of test compound.

The compounds of this invention show preferable results, which show the above-mentioned practical use.

Plasma Protein Binding Assay

Plasma protein binding of the test compound (1 microM) is measured by the method of equilibrium dialysis using 96-well plate type equipment. HTD96a (registered trademark), i.e. regenerated cellulose membranes (molecular weight cut-off 12,000-14,000, 22 mm×120 mm) are soaked for overnight in distilled water, then for 15 minutes in 30% ethanol, and finally for 20 minutes in dialysis buffer (Dulbecco's phosphate buffered saline, pH 7.4). Frozen plasma of human, Sprague-Dawley rats, and Beagle dogs are used. The dialysis equipment is assembled and added 150 microL of compound-fortified plasma to one side of each well and 150 microL of dialysis buffer to the other side of each well. After 4 hours incubation at 37° C. for 150 r.p.m, aliquots of plasma and buffer are sampled. The compound in plasma and buffer are extracted with 300 microL of acetonitrile containing an internal standard compound for analysis. The concentration of the compound is determined with LC/MS/MS analysis.

The fraction of the compound unbound (fu) is calculated by the following equation (A) or (B):

[Math. 1]

$$fu = 1 - \{([plasma]_{eq} - [buffer]_{eq})/([plasma]_{eq})\} \quad (A)$$

wherein [plasma]$_{eq}$ and [buffer]$_{eq}$ are the concentrations of the compound in plasma and buffer, respectively.

[Math. 2]

$$fu(\%) = \frac{Cb/Cis, b \times 4}{Cp/Cis, p \times 4/3} \times 100 \quad (B)$$

wherein Cp is the peak area of the compound in plasma sample;
Cis,p is the peak area of the internal standard in plasma sample;
Cb is the peak area of the compound in buffer sample;
Cis,b is the peak area of the internal standard in buffer sample;
4 and 4/3 are the reciprocal of the dilution rate in plasma and buffer, respectively.

The compounds of this invention show preferable plasma protein binding, which show the above-mentioned practical use.

Equilibrium Aqueous Solubility Study

The DMSO solution (2 microL, 30 mM) of each compound is dispensed into each well of a 96-well glass bottom plate. Potassium phosphate buffer solution (50 mM, 198 microL, pH 6.5) is added to each well, and the mixture is incubated at 37° C. with rotate shaking for 24 hours. After centrifugation at 2000 g for 5 minutes, the supernatant is filtered through the polycarbonate iso-pore membrane. The concentration of samples is determined by a general gradient HPLC method (J. Pharm. Sci. 2006, 95, 2115-2122).

The compounds of this invention show preferable aqueous solubility, which show the above-mentioned practical use.

All publications, including but not limited to, issued patents, patent applications, and journal articles, cited in this application are each herein incorporated by reference in their entirety. Although the invention has been described above with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

INDUSTRIAL APPLICABILITY

The 3-hydroxyoxindole derivatives of the present invention are useful in the treatment of a wide range of disorders in which CRHR2 is involved.

The invention claimed is:

1. A compound of the following formula (I):

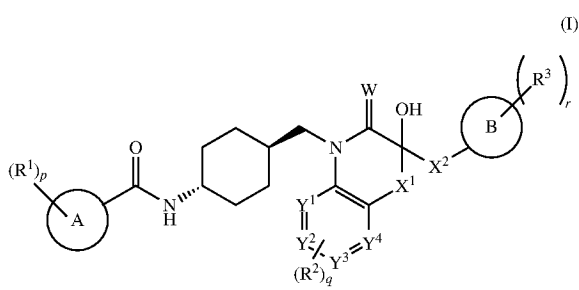

wherein:

A is aryl or heteroaryl;

W is S or O;

$R^1$ is independently selected from the group consisting of: (1) hydrogen, (2) halogen, (3) $C_{1-6}$ alkyl, (4) —O—$C_{1-6}$ alkyl, and (5) —$NR^aR^b$; wherein the $C_{1-6}$ alkyl or the —O—$C_{1-6}$ alkyl is unsubstituted or substituted with one or more substituents independently selected from the group consisting of: halogen and hydroxyl;

$R^a$ and $R^b$ are independently selected from the group consisting of: (1) hydrogen, (2) $C_{1-6}$ alkyl, and (3) $C_{3-7}$ cycloalkyl; or $R^a$ may form a 4 to 7 membered ring with $R^b$ which may contain one or more selected from N, O, S, and carbonyl;

p is 1, 2, or 3;

$Y^1$, $Y^2$, $Y^3$, and $Y^4$ are independently selected from the group consisting of CH, $CR^2$, and N;

wherein the number of nitrogen atom(s) in the $Y^1$, $Y^2$, $Y^3$, and $Y^4$ is 0, 1, or 2;

$R^2$ is independently selected from the group consisting of: (1) hydrogen, (2) halogen, (3) hydroxyl, (4) $C_{1-6}$ alkyl, (5) —O—$C_{1-6}$ alkyl, and (6) —CN; wherein the $C_{1-6}$ alkyl or the —O—$C_{1-6}$ alkyl is unsubstituted or substituted with one or more substituents independently selected from the group consisting of: halogen and hydroxyl;

q is 1, 2, 3, or 4;

$X^1$ is selected from the group consisting of: a chemical bond, $CH_2$, CH($C_{1-6}$ alkyl), and C($C_{1-6}$ alkyl)($C_{1-6}$ alkyl);

$X^2$ is selected from the group consisting of: a chemical bond, $C_{1-6}$ alkylene, and $C_{1-6}$ alkylene-(C=O)—; wherein the $C_{1-6}$ alkylene or the $C_{1-6}$ alkylene-(C=O)— is unsubstituted or substituted with one or more substituents independently selected from the group consisting of: halogen, hydroxyl, and $C_{1-6}$ alkyl;

B is aryl, heteroaryl, or $C_{3-7}$ cycloalkyl;

$R^3$ is independently selected from the group consisting of: (1) hydrogen, (2) halogen, (3) hydroxyl, (4) $C_{1-6}$ alkyl, (5) $C_{2-6}$ alkenyl, (6) $C_{3-7}$ cycloalkyl, (7) —O—$C_{1-6}$ alkyl, (8) —O—$C_{3-7}$ cycloalkyl, (9) heterocyclyl, (10) aryl, (11) heteroaryl, (12) —(C=O)—$R^4$, (13) —(C=O)—$NR^5R^6$, (14) —$NR^5$(C=O)$R^4$, (15) —$NR^5R^6$, (16) —S(O)$_2$—$R^4$, (17) —$NR^5$—S(O)$_2R^4$, (18) —S(O)$_2$—$NR^5R^6$, (19) —CN, and (20) —S—$C_{1-6}$ alkyl; wherein the $C_{1-6}$ alkyl, the $C_{2-6}$ alkenyl, the $C_{3-7}$ cycloalkyl, the —O—$C_{1-6}$ alkyl, the —O—$C_{3-7}$ cycloalkyl, the heterocyclyl, or the —S—$C_{1-6}$ alkyl is unsubstituted or substituted with one or more substituents independently selected from halogen and hydroxyl;

r is 0, 1, 2, 3, or 4;

$R^4$ is selected from the group consisting of: (1) hydroxyl, (2) $C_{1-6}$ alkyl, (3) —O—$C_{1-6}$ alkyl, (4) $C_{3-7}$ cycloalkyl, (5) —O—$C_{3-7}$ cycloalkyl, (6) $C_{2-6}$ alkenyl, (7) aryl, (8) heteroaryl, and (9) heterocyclyl; wherein the $C_{1-6}$ alkyl, the —O—$C_{1-6}$ alkyl, the $C_{3-7}$ cycloalkyl, the —O—$C_{3-7}$ cycloalkyl, the $C_{2-6}$ alkenyl, or the heterocyclyl is unsubstituted or substituted with one or more substituents independently selected from halogen and hydroxyl; wherein the aryl or the heteroaryl is unsubstituted or substituted with one or more substituents independently selected from halogen, hydroxyl, $C_{1-6}$ alkyl, —O—$C_{1-6}$ alkyl, and —CN;

$R^5$ and $R^6$ are independently selected from the group consisting of: (1) hydrogen, (2) $C_{1-6}$ alkyl, (3) $C_{3-7}$ cycloalkyl, (4) heterocyclyl, (5) aryl, and (6) heteroaryl; wherein the $C_{1-6}$ alkyl, the $C_{3-7}$ cycloalkyl, or the heterocyclyl is unsubstituted or substituted with one or more substituents independently selected from the group consisting of: halogen and hydroxyl; wherein the aryl or the heteroaryl is unsubstituted or substituted with one or more substituents independently selected from halogen, hydroxyl, $C_{1-6}$ alkyl, —O—$C_{1-6}$ alkyl, and —CN;

or a pharmaceutically acceptable salt thereof or a prodrug thereof.

2. The compound according to claim 1:

wherein:

A is phenyl, naphthyl, or 5 to 10-membered heteroaryl with 1-4 heteroatoms independently selected from O, N, and S;

W is O;

$Y^1$ and $Y^3$ are independently selected from the group consisting of: CH, $CR^2$, and N;

$Y^2$ and $Y^4$ are independently selected from the group consisting of: CH and $CR^2$;

$R^2$ is independently selected from the group consisting of: (1) hydrogen, (2) halogen, (3) hydroxyl, (4) $C_{1-6}$ alkyl, (5) —O—$C_{1-6}$ alkyl, and (6) —CN; wherein the $C_{1-6}$ alkyl or the —O—$C_{1-6}$ alkyl is unsubstituted or substituted with one or more substituents independently selected from the group consisting of: halogen and hydroxyl;

q is 1, 2, 3, or 4;

$X^1$ is a chemical bond;

$X^2$ is selected from the group consisting of: a chemical bond, —$CH_2$—, —$CH_2CH_2$—, —CH(OH)$CH_2$—, —$CH_2$CH(OH)—, and —$CH_2$—(C=O)—;

B is phenyl, naphthyl, 5 to 10-membered heteroaryl with 1-4 heteroatoms independently selected from O, N, and S, or $C_{3-7}$ cycloalkyl;

or a pharmaceutically acceptable salt thereof or a prodrug thereof.

3. The compound according to claim 1:

wherein:

A is selected from the group consisting of: phenyl, naphthyl, pyridyl, pyridazinyl, pyrazinyl, pyrimidinyl, triazinyl, imidazolyl, pyrazolyl, pyrrolyl, furanyl, thiophenyl, oxazolyl, isoxazolyl, thiazolyl, isothiazolyl, indolyl, indazolyl, benzoimidazolyl, benzofuranyl, benzothiophenyl, quinolinyl, isoquinolinyl, and quinazolinyl;

B is selected from the group consisting of: phenyl, naphthyl, pyridyl, pyridazinyl, pyrazinyl, pyrimidinyl, triazinyl, imidazolyl, pyrazolyl, pyrrolyl, furanyl, thiophenyl, triazolyl, oxazolyl, isoxazolyl, thiazolyl, isothiazolyl, indolyl, indazolyl, benzimidazolyl, benzofuranyl, benzothiophenyl, quinolinyl, isoquinolinyl, and quinazolinyl;

or a pharmaceutically acceptable salt thereof or a prodrug thereof.

4. The compound according to claim 1, wherein the compound of the formula (I) is represented by a compound of the following formula (II):

(II)

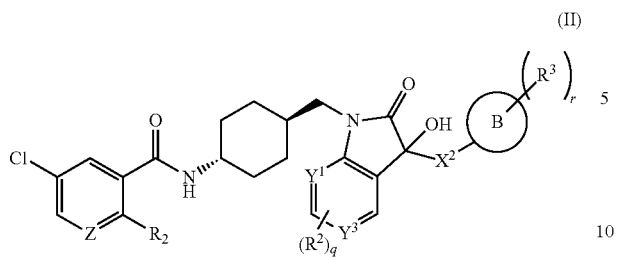

wherein:
Z is CH or N;
R¹ is independently selected from the group consisting of: (1) hydrogen, (2) halogen, (3) $C_{1-6}$ alkyl, (4) —O—$C_{1-6}$ alkyl, and (5) —NR$^a$R$^b$; wherein the $C_{1-6}$ alkyl or the —O—$C_{1-6}$ alkyl is unsubstituted or substituted with one or more substituents independently selected from the group consisting of: halogen and hydroxyl;
R$^a$ and R$^b$ are independently selected from the group consisting of: (1) hydrogen, (2) $C_{1-6}$ alkyl, and (3) $C_{3-7}$ cycloalkyl; or R$^a$ may form a 4 to 7 membered ring with R$^b$ which may contain one or more selected from N, O, S, and carbonyl;
Y¹ and Y³ are independently selected from the group consisting of: CH, CR², and N;
R² is independently selected from the group consisting of: (1) hydrogen, (2) halogen, (3) hydroxyl, (4) $C_{1-6}$ alkyl, (5) —O—$C_{1-6}$ alkyl, and (6) —CN; wherein the $C_{1-6}$ alkyl or the —O—$C_{1-6}$ alkyl is unsubstituted or substituted with one or more substituents independently selected from the group consisting of: halogen and hydroxyl;
q is 1, 2, 3, or 4;
X² is selected from the group consisting of: a chemical bond, $C_{1-6}$ alkylene, and $C_{1-6}$ alkylene-(C=O)—; wherein the $C_{1-6}$ alkylene or the $C_{1-6}$ alkylene-(C=O)— is unsubstituted or substituted with one or more substituents independently selected from the group consisting of: halogen, hydroxyl, and $C_{1-6}$ alkyl;
B is aryl, heteroaryl, or $C_{3-7}$ cycloalkyl;
R³ is independently selected from the group consisting of: (1) hydrogen, (2) halogen, (3) hydroxyl, (4) $C_{1-6}$ alkyl, (5) $C_{2-6}$ alkenyl, (6) $C_{3-7}$ cycloalkyl, (7) —O—$C_{1-6}$ alkyl, (8) —O—$C_{3-7}$ cycloalkyl, (9) heterocyclyl, (10) aryl, (11) heteroaryl, (12) —(C=O)—R⁴, (13) —(C=O)—NR⁵R⁶, (14) —NR⁵(C=O)R⁴, (15) —NR⁵R⁶, (16) —S(O)₂—R⁴, (17) —NR⁵—S(O)₂R⁴, (18) —S(O)₂—NR⁵R⁶, (19) —CN, and (20) —S—$C_{1-6}$ alkyl; wherein the $C_{1-6}$ alkyl, the $C_{2-6}$ alkenyl, the $C_{3-7}$ cycloalkyl, the —O—$C_{1-6}$ alkyl, the —O—$C_{3-7}$ cycloalkyl, the heterocyclyl, or the —S—$C_{1-6}$ alkyl is unsubstituted or substituted with one or more substituents independently selected from halogen and hydroxyl;
r is 0, 1, 2, 3, or 4; when B is aryl or heteroaryl, r is 0, 1, 2, 3, or 4; or when B is $C_{3-7}$ cycloalkyl, r is 0;
R⁴ is selected from the group consisting of: (1) hydroxyl, (2) $C_{1-6}$ alkyl, (3) —O—$C_{1-6}$ alkyl, (4) $C_{3-7}$ cycloalkyl, (5) —O—$C_{3-7}$ cycloalkyl, (6) $C_{2-6}$ alkenyl, (7) aryl, (8) heteroaryl, and (9) heterocyclyl; wherein the $C_{1-6}$ alkyl, the —O—$C_{1-6}$ alkyl, the $C_{3-7}$ cycloalkyl, the —O—$C_{3-7}$ cycloalkyl, the $C_{2-6}$ alkenyl, or the heterocyclyl is unsubstituted or substituted with one or more substituents independently selected from halogen or hydroxyl; wherein the aryl or the heteroaryl is unsubstituted or substituted with one or more substituents independently selected from halogen, hydroxyl, $C_{1-6}$ alkyl, —O—$C_{1-6}$ alkyl, and —CN;
R⁵ and R⁶ are independently selected from the group consisting of: (1) hydrogen, (2) $C_{1-6}$ alkyl, (3) $C_{3-7}$ cycloalkyl, (4) heterocyclyl, (5) aryl, and (6) heteroaryl; wherein the $C_{1-6}$ alkyl, the $C_{3-7}$ cycloalkyl, or the heterocyclyl is unsubstituted or substituted with one or more substituents independently selected from the group consisting of: halogen and hydroxyl; wherein the aryl or the heteroaryl is unsubstituted or substituted with one or more substituents independently selected from halogen, hydroxyl, $C_{1-6}$ alkyl, —O—$C_{1-6}$ alkyl, and —CN;
or a pharmaceutically acceptable salt thereof or a prodrug thereof.

5. The compound according to claim 4:
wherein:
X² is selected from the group consisting of: a chemical bond, —CH₂—, —CH₂CH₂—, —CH(OH)CH₂—, —CH₂CH(OH)—, and —CH₂—(C=O)—;
B is phenyl, 5 to 10-membered heteroaryl with 1-4 heteroatoms independently selected from O, N, and S, or $C_{3-7}$ cycloalkyl;
r is 0, 1, 2, 3, or 4; when B is phenyl or 5 to 10-membered heteroaryl, r is 0, 1, 2, 3, or 4; or when B is $C_{3-7}$ cycloalkyl, r is 0;
or a pharmaceutically acceptable salt thereof or a prodrug thereof.

6. The compound according to claim 5:
wherein:
B is selected from the group consisting of: phenyl, naphthyl, pyridyl, pyridazinyl, pyrazinyl, pyrimidinyl, triazinyl, imidazolyl, pyrazolyl, pyrrolyl, furanyl, thiophenyl, triazolyl, oxazolyl, isoxazolyl, thiazolyl, isothiazolyl, indolyl, indazolyl, benzimidazolyl, benzofuranyl, benzothiophenyl, quinolinyl, isoquinolinyl, and quinazolinyl;
R³ is hydrogen, methyl, methoxyl, fluoro, chloro, trifluoromethyl, and trifluoromethoxyl;
or a pharmaceutically acceptable salt thereof or a prodrug thereof.

7. The compound according to claim 1, which is selected from the group consisting of:
5-chloro-N-((1r,4r)-4-((3-hydroxy-2-oxo-3-phenylindolin-1-yl)methyl)cyclohexyl)-2-methylnicotinamide;
5-chloro-2-(difluoromethyl)-N-((1r,4r)-4-((3-hydroxy-3-(4-methoxyphenyl)-2-oxoindolin-1-yl)methyl)cyclohexyl)nicotinamide;
5-chloro-2-(difluoromethyl)-N-((1r,4r)-4-((3-hydroxy-2-oxo-3-phenylindolin-1-yl)methyl)cyclohexyl)nicotinamide;
5-chloro-2-(difluoromethyl)-N-((1r,4r)-4-((3-hydroxy-2-oxo-3-(pyridin-2-yl)indolin-1-yl)methyl)cyclohexyl)nicotinamide;
5-chloro-2-(difluoromethyl)-N-((1r,4r)-4-((3-hydroxy-3-(6-methoxypyridin-3-yl)-2-oxoindolin-1-yl)methyl)cyclohexyl)nicotinamide;
5-chloro-2-(difluoromethyl)-N-((1r,4r)-4-((3-hydroxy-3-(5-methylpyridin-2-yl)-2-oxoindolin-1-yl)methyl)cyclohexyl)nicotinamide;
5-chloro-2-(difluoromethyl)-N-((1r,4r)-4-((3-(5-fluoro-6-methylpyridin-2-yl)-3-hydroxy-2-oxoindolin-1-yl)methyl)cyclohexyl)nicotinamide;

5-chloro-2-(difluoromethyl)-N-((1r,4r)-4-((3-hydroxy-3-(6-methylpyridin-2-yl)-2-oxoindolin-1-yl)methyl)cyclohexyl)nicotinamide;

5-chloro-2-(difluoromethyl)-N-((1r,4r)-4-((3-hydroxy-3-(6-methoxypyridin-2-yl)-2-oxoindolin-1-yl)methyl)cyclohexyl)nicotinamide;

5-chloro-2-(difluoromethyl)-N-((1r,4r)-4-((3-(3-fluoropyridin-4-yl)-3-hydroxy-2-oxoindolin-1-yl)methyl)cyclohexyl)nicotinamide;

5-chloro-2-(difluoromethyl)-N-((1r,4r)-4-((3-hydroxy-3-(5-methoxypyridin-2-yl)-2-oxoindolin-1-yl)methyl)cyclohexyl)nicotinamide;

5-chloro-2-(difluoromethyl)-N-((1r,4r)-4-((3-hydroxy-2-oxo-3-(5-(trifluoromethyl)pyridin-2-yl)indolin-1-yl)methyl)cyclohexyl)nicotinamide;

5-chloro-N-((1r,4r)-4-((3-(5-chloropyridin-2-yl)-3-hydroxy-2-oxoindolin-1-yl)methyl)cyclohexyl)-2-(difluoromethyl)nicotinamide;

5-chloro-2-(difluoromethyl)-N-((1r,4r)-4-((3-hydroxy-2-oxo-3-(thiazol-2-yl)indolin-1-yl)methyl)cyclohexyl)nicotinamide;

5-chloro-2-(difluoromethyl)-N-((1r,4r)-4-((3-hydroxy-2-oxo-3-(4-(trifluoromethyl)pyridin-2-yl)indolin-1-yl)methyl)cyclohexyl)nicotinamide;

5-chloro-2-(difluoromethyl)-N-((1r,4r)-4-((3-hydroxy-2-oxo-3-phenyl-2,3-dihydro-1H-pyrrolo[2,3-b]pyridin-1-yl)methyl)cyclohexyl)nicotinamide;

5-chloro-2-(difluoromethyl)-N-((1r,4r)-4-((3-(4-fluorophenyl)-3-hydroxy-2-oxoindolin-1-yl)methyl)cyclohexyl)nicotinamide;

5-chloro-2-(difluoromethyl)-N-((1r,4r)-4-((3-(5-fluoropyridin-2-yl)-3-hydroxy-2-oxoindolin-1-yl)methyl)cyclohexyl)nicotinamide;

5-chloro-2-(difluoromethyl)-N-((1r,4r)-4-((3-(3-fluoropyridin-2-yl)-3-hydroxy-2-oxoindolin-1-yl)methyl)cyclohexyl)nicotinamide;

5-chloro-2-(difluoromethyl)-N-((1r,4r)-4-((3-(3-fluorophenyl)-3-hydroxy-2-oxoindolin-1-yl)methyl)cyclohexyl)nicotinamide;

5-chloro-2-(difluoromethyl)-N-((1r,4r)-4-((3-(5-fluoropyridin-3-yl)-3-hydroxy-2-oxoindolin-1-yl)methyl)cyclohexyl)nicotinamide;

5-chloro-N-((1r,4r)-4-((3-(3-chloropyridin-4-yl)-3-hydroxy-2-oxoindolin-1-yl)methyl)cyclohexyl)-2-(difluoromethyl)nicotinamide;

5-chloro-2-(difluoromethyl)-N-((1r,4r)-4-((3-hydroxy-2-oxo-3-(2-oxo-2-phenylethyl)indolin-1-yl)methyl)cyclohexyl)nicotinamide;

5-chloro-N-((1r,4r)-4-((3-(3-chloropyridin-2-yl)-3-hydroxy-2-oxoindolin-1-yl)methyl)cyclohexyl)-2-(difluoromethyl)nicotinamide;

5-chloro-2-(difluoromethyl)-N-((1r,4r)-4-((3-(3,5-difluoropyridin-2-yl)-3-hydroxy-2-oxoindolin-1-yl)methyl)cyclohexyl)nicotinamide;

5-chloro-N-((1r,4r)-4-((3-(5-chloropyridin-3-yl)-3-hydroxy-2-oxoindolin-1-yl)methyl)cyclohexyl)-2-(difluoromethyl)nicotinamide;

5-chloro-2-(difluoromethyl)-N-((1r,4r)-4-((3-(5-fluoro-2-methoxypyridin-4-yl)-3-hydroxy-2-oxoindolin-1-yl)methyl)cyclohexyl)nicotinamide;

5-chloro-N-((1r,4r)-4-((3-(5-chloro-3-fluoropyridin-2-yl)-3-hydroxy-2-oxoindolin-1-yl)methyl)cyclohexyl)-2-(difluoromethyl)nicotinamide;

5-chloro-N-((1r,4r)-4-((5-chloro-3-hydroxy-2-oxo-3-phenylindolin-1-yl)methyl)cyclohexyl)-2-(difluoromethyl)nicotinamide;

5-chloro-N-((1r,4r)-4-((6-chloro-3-hydroxy-2-oxo-3-phenylindolin-1-yl)methyl)cyclohexyl)-2-(difluoromethyl)nicotinamide;

5-chloro-2-(difluoromethyl)-N-((1r,4r)-4-((5-fluoro-3-hydroxy-2-oxo-3-phenylindolin-1-yl)methyl)cyclohexyl)nicotinamide;

5-chloro-2-(difluoromethyl)-N-((1r,4r)-4-((6-fluoro-3-hydroxy-2-oxo-3-phenylindolin-1-yl)methyl)cyclohexyl)nicotinamide;

5-chloro-2-(difluoromethyl)-N-((1r,4r)-4-((3-(2-fluorophenyl)-3-hydroxy-2-oxoindolin-1-yl)methyl)cyclohexyl)nicotinamide;

5-chloro-2-(difluoromethyl)-N-((1r,4r)-4-((3-hydroxy-3-(2-hydroxy-2-phenylethyl)-2-oxoindolin-1-yl)methyl)cyclohexyl)nicotinamide;

5-chloro-2-(difluoromethyl)-N-((1r,4r)-4-((3-hydroxy-2-oxo-3-(thiazol-4-yl)indolin-1-yl)methyl)cyclohexyl)nicotinamide;

5-chloro-2-(difluoromethyl)-N-((1r,4r)-4-((3-hydroxy-3-(2-methoxythiazol-5-yl)-2-oxoindolin-1-yl)methyl)cyclohexyl)nicotinamide;

5-chloro-N-((1r,4r)-4-((3-cyclopentyl-3-hydroxy-2-oxoindolin-1-yl)methyl)cyclohexyl)-2-(difluoromethyl)nicotinamide;

5-chloro-2-(difluoromethyl)-N-((1r,4r)-4-((3-hydroxy-2-oxo-3-phenethylindolin-1-yl)methyl)cyclohexyl)nicotinamide;

5-chloro-2-(difluoromethyl)-N-((1r,4r)-4-((3-hydroxy-3-(1-methyl-1H-indazol-5-yl)-2-oxoindolin-1-yl)methyl)cyclohexyl)nicotinamide;

5-chloro-2-(difluoromethyl)-N-((1r,4r)-4-((3-(2,3-difluorophenyl)-3-hydroxy-2-oxoindolin-1-yl)methyl)cyclohexyl)nicotinamide;

5-chloro-2-(difluoromethyl)-N-((1r,4r)-4-((3-(2-fluoro-6-methoxyphenyl)-3-hydroxy-2-oxoindolin-1-yl)methyl)cyclohexyl)nicotinamide;

5-chloro-N-((1r,4r)-4-((3-(4-chlorophenyl)-3-hydroxy-2-oxoindolin-1-yl)methyl)cyclohexyl)-2-(difluoromethyl)nicotinamide;

5-chloro-2-(difluoromethyl)-N-((1r,4r)-4-((3-hydroxy-2-oxo-3-(o-tolyl)indolin-1-yl)methyl)cyclohexyl)nicotinamide;

5-chloro-2-(difluoromethyl)-N-((1r,4r)-4-((3-(3,5-difluorophenyl)-3-hydroxy-2-oxoindolin-1-yl)methyl)cyclohexyl)nicotinamide;

5-chloro-N-((1r,4r)-4-((3-(3-chloro-4-fluorophenyl)-3-hydroxy-2-oxoindolin-1-yl)methyl)cyclohexyl)-2-(difluoromethyl)nicotinamide;

5-chloro-N-((1r,4r)-4-((3-(3-cyanophenyl)-3-hydroxy-2-oxoindolin-1-yl)methyl)cyclohexyl)-2-(difluoromethyl)nicotinamide;

5-chloro-2-(difluoromethyl)-N-((1r,4r)-4-((3-hydroxy-3-(3-methoxyphenyl)-2-oxoindolin-1-yl)methyl)cyclohexyl)nicotinamide;

5-chloro-N-((1r,4r)-4-((3-(3-chlorophenyl)-3-hydroxy-2-oxoindolin-1-yl)methyl)cyclohexyl)-2-(difluoromethyl)nicotinamide;

5-chloro-2-(difluoromethyl)-N-((1r,4r)-4-((3-hydroxy-2-oxo-3-(m-tolyl)indolin-1-yl)methyl)cyclohexyl)nicotinamide;

5-chloro-2-(difluoromethyl)-N-((1r,4r)-4-((3-hydroxy-2-oxo-3-(3-(trifluoromethyl)phenyl)indolin-1-yl)methyl)cyclohexyl)nicotinamide;

5-chloro-2-(difluoromethyl)-N-((1r,4r)-4-((3-hydroxy-2-oxo-3-(3-(trifluoromethoxy)phenyl)indolin-1-yl)methyl)cyclohexyl)nicotinamide;

N-((1r,4r)-4-((3-(5-amino-3-methyl-1-(pyridin-2-yl)-1H-pyrazol-4-yl)-3-hydroxy-2-oxoindolin-1-yl)methyl)cyclohexyl)-5-chloro-2-(difluoromethyl)nicotinamide;

5-chloro-2-(difluoromethyl)-N-((1r,4r)-4-((3-(2,4-difluorophenyl)-3-hydroxy-2-oxoindolin-1-yl)methyl)cyclohexyl)nicotinamide;

5-chloro-2-(difluoromethyl)-N-((1r,4r)-4-((3-(2-fluoro-4-methoxyphenyl)-3-hydroxy-2-oxoindolin-1-yl)methyl)cyclohexyl)nicotinamide;

5-chloro-N-((1r,4r)-4-((3-(5-chloro-6-methoxypyridin-2-yl)-3-hydroxy-2-oxoindolin-1-yl)methyl)cyclohexyl)-2-(difluoromethyl)nicotinamide;

5-chloro-2-(difluoromethyl)-N-((1r,4r)-4-((3-hydroxy-2-oxo-3-(p-tolyl)indolin-1-yl)methyl)cyclohexyl)nicotinamide;

5-chloro-2-(difluoromethyl)-N-((1r,4r)-4-((3-hydroxy-3-(4-methylthiazol-2-yl)-2-oxoindolin-1-yl)methyl)cyclohexyl)nicotinamide;

5-chloro-2-(difluoromethyl)-N-((1r,4r)-4-((3-(2,5-difluorophenyl)-3-hydroxy-2-oxoindolin-1-yl)methyl)cyclohexyl)nicotinamide;

5-chloro-N-((1r,4r)-4-((3-(5-cyano-2-fluorophenyl)-3-hydroxy-2-oxoindolin-1-yl)methyl)cyclohexyl)-2-(difluoromethyl)nicotinamide;

5-chloro-2-(difluoromethyl)-N-((1r,4r)-4-((3-hydroxy-3-(1-hydroxy-2-phenylethyl)-2-oxoindolin-1-yl)methyl)cyclohexyl)nicotinamide;

5-chloro-2-(difluoromethyl)-N-((1r,4r)-4-((3-(2,6-difluorophenyl)-3-hydroxy-2-oxoindolin-1-yl)methyl)cyclohexyl)nicotinamide;

5-chloro-2-(difluoromethyl)-N-((1r,4r)-4-((3-(3-fluoro-2-methoxy-6-methylpyridin-4-yl)-3-hydroxy-2-oxoindolin-1-yl)methyl)cyclohexyl)nicotinamide;

5-chloro-2-(difluoromethyl)-N-((1r,4r)-4-((3-(2-fluoro-3-methylphenyl)-3-hydroxy-2-oxoindolin-1-yl)methyl)cyclohexyl)nicotinamide;

5-chloro-2-(difluoromethyl)-N-((1r,4r)-4-((3-(3-fluoro-2-methoxypyridin-4-yl)-3-hydroxy-2-oxoindolin-1-yl)methyl)cyclohexyl)nicotinamide;

5-chloro-N-((1r,4r)-4-((3-(2-chlorophenyl)-3-hydroxy-2-oxoindolin-1-yl)methyl)cyclohexyl)-2-(difluoromethyl)nicotinamide;

5-chloro-2-(difluoromethyl)-N-((1r,4r)-4-((3-(2-fluoro-3-methoxyphenyl)-3-hydroxy-2-oxoindolin-1-yl)methyl)cyclohexyl)nicotinamide;

5-chloro-N-((1r,4r)-4-((3-(3-chloro-2-fluorophenyl)-3-hydroxy-2-oxoindolin-1-yl)methyl)cyclohexyl)-2-(difluoromethyl)nicotinamide;

5-chloro-2-(difluoromethyl)-N-((1r,4r)-4-((3-(3,4-difluorophenyl)-3-hydroxy-2-oxoindolin-1-yl)methyl)cyclohexyl)nicotinamide;

5-chloro-2-(difluoromethyl)-N-((1r,4r)-4-((3-(3-(difluoromethyl)phenyl)-3-hydroxy-2-oxoindolin-1-yl)methyl)cyclohexyl)nicotinamide;

5-chloro-2-(difluoromethyl)-N-((1r,4r)-4-((3-(2-fluoro-3-(trifluoromethyl)phenyl)-3-hydroxy-2-oxoindolin-1-yl)methyl)cyclohexyl)nicotinamide;

5-chloro-N-((1r,4r)-4-((3-(3-cyano-2-fluorophenyl)-3-hydroxy-2-oxoindolin-1-yl)methyl)cyclohexyl)-2-(difluoromethyl)nicotinamide;

5-chloro-N-((1r,4r)-4-((3-(3-(1,1-difluoroethyl)phenyl)-3-hydroxy-2-oxoindolin-1-yl)methyl)cyclohexyl)-2-(difluoromethyl)nicotinamide;

5-chloro-2-(difluoromethyl)-N-((1r,4r)-4-((3-hydroxy-3-(3-(methylthio)phenyl)-2-oxoindolin-1-yl)methyl)cyclohexyl)nicotinamide;

5-chloro-2-(difluoromethyl)-N-((1r,4r)-4-((3-(2-fluoro-5-methoxyphenyl)-3-hydroxy-2-oxoindolin-1-yl)methyl)cyclohexyl)nicotinamide;

5-chloro-2-(difluoromethyl)-N-((1r,4r)-4-((3-(3-fluoro-4-methoxypyridin-2-yl)-3-hydroxy-2-oxoindolin-1-yl)methyl)cyclohexyl)nicotinamide;

5-chloro-2-(difluoromethyl)-N-((1r,4r)-4-((3-hydroxy-2-oxo-3-(quinolin-2-yl)indolin-1-yl)methyl)cyclohexyl)nicotinamide;

5-chloro-2-(difluoromethyl)-N-((1r,4r)-4-((3-hydroxy-3-(isoquinolin-1-yl)-2-oxoindolin-1-yl)methyl)cyclohexyl)nicotinamide;

5-chloro-2-(difluoromethyl)-N-((1r,4r)-4-((7-fluoro-3-(5-fluoropyridin-2-yl)-3-hydroxy-2-oxoindolin-1-yl)methyl)cyclohexyl)nicotinamide;

5-chloro-2-(difluoromethyl)-N-((1r,4r)-4-((6-fluoro-3-(5-fluoropyridin-2-yl)-3-hydroxy-2-oxoindolin-1-yl)methyl)cyclohexyl)nicotinamide;

5-chloro-2-(difluoromethyl)-N-((1r,4r)-4-((5-fluoro-3-(5-fluoropyridin-2-yl)-3-hydroxy-2-oxoindolin-1-yl)methyl)cyclohexyl)nicotinamide;

5-chloro-2-(difluoromethyl)-N-((1r,4r)-4-((4-fluoro-3-(5-fluoropyridin-2-yl)-3-hydroxy-2-oxoindolin-1-yl)methyl)cyclohexyl)nicotinamide;

5-chloro-2-(difluoromethyl)-N-((1r,4r)-4-((7-fluoro-3-(2-fluorophenyl)-3-hydroxy-2-oxoindolin-1-yl)methyl)cyclohexyl)nicotinamide;

5-chloro-2-(difluoromethyl)-N-((1r,4r)-4-((6-fluoro-3-(2-fluorophenyl)-3-hydroxy-2-oxoindolin-1-yl)methyl)cyclohexyl)nicotinamide;

5-chloro-2-(difluoromethyl)-N-((1r,4r)-4-((7-fluoro-3-(3-fluoropyridin-4-yl)-3-hydroxy-2-oxoindolin-1-yl)methyl)cyclohexyl)nicotinamide;

5-chloro-2-(difluoromethyl)-N-((1r,4r)-4-((6-fluoro-3-(3-fluoropyridin-4-yl)-3-hydroxy-2-oxoindolin-1-yl)methyl)cyclohexyl)nicotinamide;

5-chloro-2-(difluoromethyl)-N-((1r,4r)-4-((5-fluoro-3-(3-fluoropyridin-4-yl)-3-hydroxy-2-oxoindolin-1-yl)methyl)cyclohexyl)nicotinamide;

5-chloro-2-(difluoromethyl)-N-((1r,4r)-4-((4-fluoro-3-(3-fluoropyridin-4-yl)-3-hydroxy-2-oxoindolin-1-yl)methyl)cyclohexyl)nicotinamide;

5-chloro-2-(difluoromethyl)-N-((1r,4r)-4-((3-(5-fluoropyridin-2-yl)-3-hydroxy-2-oxo-6-(trifluoromethyl)indolin-1-yl)methyl)cyclohexyl)nicotinamide;

5-chloro-2-(difluoromethyl)-N-((1r,4r)-4-((3-(5-fluoropyridin-2-yl)-3-hydroxy-2-oxo-6-(trifluoromethoxy)indolin-1-yl)methyl)cyclohexyl)nicotinamide;

5-chloro-2-(difluoromethyl)-N-((1r,4r)-4-((3-(2-fluorophenyl)-3-hydroxy-2-oxo-6-(trifluoromethyl)indolin-1-yl)methyl)cyclohexyl)nicotinamide;

5-chloro-2-(difluoromethyl)-N-((1r,4r)-4-((3-hydroxy-2-oxo-3-(thiophen-2-yl)indolin-1-yl)methyl)cyclohexyl)nicotinamide;

5-chloro-2-(difluoromethyl)-N-((1r,4r)-4-((3-hydroxy-2-oxo-3-(thiophen-3-yl)indolin-1-yl)methyl)cyclohexyl)nicotinamide;

5-chloro-2-(difluoromethyl)-N-((1r,4r)-4-((5-fluoro-3-(2-fluorophenyl)-3-hydroxy-2-oxoindolin-1-yl)methyl)cyclohexyl)nicotinamide;

5-chloro-2-(difluoromethyl)-N-((1r,4r)-4-((3-(2-fluorophenyl)-3-hydroxy-2-oxo-2,3-dihydro-1H-pyrrolo[2,3-b]pyridin-1-yl)methyl)cyclohexyl)nicotinamide;

5-chloro-2-(difluoromethyl)-N-((1r,4r)-4-((3-(3-fluorothiophen-2-yl)-3-hydroxy-2-oxoindolin-1-yl)methyl)cyclohexyl)nicotinamide;

5-chloro-2-(difluoromethyl)-N-((1r,4r)-4-((3-hydroxy-3-(4-methoxythiophen-2-yl)-2-oxoindolin-1-yl)methyl)cyclohexyl)nicotinamide;
N-((1r,4r)-4-((3-(benzo[d]thiazol-2-yl)-3-hydroxy-2-oxoindolin-1-yl)methyl)cyclohexyl)-5-chloro-2-(difluoromethyl)nicotinamide;
5-chloro-2-(difluoromethyl)-N-((1r,4r)-4-((3-(4-fluorothiophen-2-yl)-3-hydroxy-2-oxoindolin-1-yl)methyl)cyclohexyl)nicotinamide;
5-chloro-2-(difluoromethyl)-N-((1r,4r)-4-((3-hydroxy-3-(5-methoxythiophen-2-yl)-2-oxoindolin-1-yl)methyl)cyclohexyl)nicotinamide;
5-chloro-N-((1r,4r)-4-((3-(5-chlorothiophen-2-yl)-3-hydroxy-2-oxoindolin-1-yl)methyl)cyclohexyl)-2-(difluoromethyl)nicotinamide;
5-chloro-2-(difluoromethyl)-N-((1r,4r)-4-((3-(3-fluoropyridin-4-yl)-3-hydroxy-2-oxo-2,3-dihydro-1H-pyrrolo[2,3-b]pyridin-1-yl)methyl)cyclohexyl)nicotinamide;
5-chloro-N-((1r,4r)-4-((6-fluoro-3-(2-fluorophenyl)-3-hydroxy-2-oxoindolin-1-yl)methyl)cyclohexyl)-2-methylnicotinamide;
5-chloro-N-((1r,4r)-4-((5-fluoro-3-(2-fluorophenyl)-3-hydroxy-2-oxoindolin-1-yl)methyl)cyclohexyl)-2-methylnicotinamide;
5-chloro-2-(difluoromethyl)-N-((1r,4r)-4-((3-(2-fluorophenyl)-3-hydroxy-2-oxo-2,3-dihydro-1H-pyrrolo[3,2-c]pyridin-1-yl)methyl)cyclohexyl)nicotinamide;
5-chloro-2-(difluoromethyl)-N-((1r,4r)-4-((3-(2-fluorophenyl)-3-hydroxy-6-methoxy-2-oxoindolin-1-yl)methyl)cyclohexyl)nicotinamide;
5-chloro-2-(difluoromethyl)-N-((1r,4r)-4-((3-(3-fluoropyridin-4-yl)-3-hydroxy-6-methoxy-2-oxoindolin-1-yl)methyl)cyclohexyl)nicotinamide;
5-chloro-2-(difluoromethyl)-N-((1r,4r)-4-((3-(2-fluorophenyl)-3-hydroxy-5-methoxy-2-oxoindolin-1-yl)methyl)cyclohexyl)nicotinamide;
5-chloro-2-(difluoromethyl)-N-((1r,4r)-4-((3-(2-fluorophenyl)-3-hydroxy-7-methoxy-2-oxoindolin-1-yl)methyl)cyclohexyl)nicotinamide;
5-chloro-2-(difluoromethyl)-N-((1r,4r)-4-((3-(3-fluoropyridin-4-yl)-3-hydroxy-7-methoxy-2-oxoindolin-1-yl)methyl)cyclohexyl)nicotinamide;
5-chloro-2-(difluoromethyl)-N-((1r,4r)-4-((3-(furan-3-yl)-3-hydroxy-2-oxoindolin-1-yl)methyl)cyclohexyl)nicotinamide;
5-chloro-N-((1r,4r)-4-((3-hydroxy-3-(3-methoxyphenyl)-2-oxoindolin-1-yl)methyl)cyclohexyl)-2-(trifluoromethyl)nicotinamide;
5-chloro-N-((1r,4r)-4-((3-(5-chloropyridin-2-yl)-3-hydroxy-2-oxoindolin-1-yl)methyl)cyclohexyl)-2-(trifluoromethyl)nicotinamide;
5-chloro-N-((1r,4r)-4-((3-(2,3-difluorophenyl)-3-hydroxy-2-oxoindolin-1-yl)methyl)cyclohexyl)-2-(trifluoromethyl)nicotinamide;
5-chloro-2-(difluoromethyl)-N-((1r,4r)-4-((3-(3,5-dimethoxyphenyl)-3-hydroxy-2-oxoindolin-1-yl)methyl)cyclohexyl)nicotinamide;
5-chloro-2-(difluoromethyl)-N-((1r,4r)-4-((6-fluoro-3-(5-fluoro-2-methoxypyridin-4-yl)-3-hydroxy-2-oxoindolin-1-yl)methyl)cyclohexyl)nicotinamide;
5-chloro-2-(difluoromethyl)-N-((1r,4r)-4-((3-(2,3-difluorophenyl)-6-fluoro-3-hydroxy-2-oxoindolin-1-yl)methyl)cyclohexyl)nicotinamide;
5-chloro-N-((1r,4r)-4-((3-(3-chloro-2-fluorophenyl)-6-fluoro-3-hydroxy-2-oxoindolin-1-yl)methyl)cyclohexyl)-2-(difluoromethyl)nicotinamide;
5-chloro-2-(difluoromethyl)-N-((1r,4r)-4-((3-(2,5-difluorophenyl)-6-fluoro-3-hydroxy-2-oxoindolin-1-yl)methyl)cyclohexyl)nicotinamide;
5-chloro-N-((1r,4r)-4-((3-(5-chloropyridin-2-yl)-6-fluoro-3-hydroxy-2-oxoindolin-1-yl)methyl)cyclohexyl)-2-(difluoromethyl)nicotinamide;
5-chloro-2-(difluoromethyl)-N-((1r,4r)-4-((3-(2-fluorophenyl)-3-hydroxy-4-methoxy-2-oxoindolin-1-yl)methyl)cyclohexyl)nicotinamide;
5-chloro-2-(difluoromethyl)-N-((1r,4r)-4-((3-(2,3-difluorophenyl)-3-hydroxy-2-oxo-2,3-dihydro-1H-pyrrolo[2,3-b]pyridin-1-yl)methyl)cyclohexyl)nicotinamide;
5-chloro-2-(difluoromethyl)-N-((1r,4r)-4-((3-(2,5-difluorophenyl)-3-hydroxy-2-oxo-2,3-dihydro-1H-pyrrolo[2,3-b]pyridin-1-yl)methyl)cyclohexyl)nicotinamide;
5-chloro-2-(difluoromethyl)-N-((1r,4r)-4-((3-(2,3-difluorophenyl)-5-fluoro-3-hydroxy-2-oxoindolin-1-yl)methyl)cyclohexyl)nicotinamide;
5-chloro-2-(difluoromethyl)-N-((1r,4r)-4-((5-fluoro-3-(5-fluoro-2-methoxypyridin-4-yl)-3-hydroxy-2-oxoindolin-1-yl)methyl)cyclohexyl)nicotinamide;
5-chloro-N-((1r,4r)-4-((3-(5-chloropyridin-2-yl)-5-fluoro-3-hydroxy-2-oxoindolin-1-yl)methyl)cyclohexyl)-2-(difluoromethyl)nicotinamide;
5-chloro-2-(difluoromethyl)-N-((1r,4r)-4-((3-(2,5-difluorophenyl)-5-fluoro-3-hydroxy-2-oxoindolin-1-yl)methyl)cyclohexyl)nicotinamide;
5-chloro-N-((1r,4r)-4-((3-(2,5-difluorophenyl)-3-hydroxy-2-oxoindolin-1-yl)methyl)cyclohexyl)-2-methylnicotinamide;
5-chloro-N-((1r,4r)-4-((3-(2-fluoro-5-methoxyphenyl)-3-hydroxy-2-oxoindolin-1-yl)methyl)cyclohexyl)-2-methylnicotinamide;
5-chloro-N-((1r,4r)-4-((3-(2-fluoro-5-(trifluoromethyl)phenyl)-3-hydroxy-2-oxoindolin-1-yl)methyl)cyclohexyl)-2-methylnicotinamide;
5-chloro-2-(difluoromethyl)-N-((1r,4r)-4-((3-hydroxy-3-(5-methylthiophen-3-yl)-2-oxoindolin-1-yl)methyl)cyclohexyl)nicotinamide;
5-chloro-N-((1r,4r)-4-((3-(5-chlorothiophen-3-yl)-3-hydroxy-2-oxoindolin-1-yl)methyl)cyclohexyl)-2-(difluoromethyl)nicotinamide;
5-chloro-N-((1r,4r)-4-((3-hydroxy-2-oxo-3-(2,3,5-trifluorophenyl)indolin-1-yl)methyl)cyclohexyl)-2-methylnicotinamide;
5-chloro-2-(difluoromethyl)-N-((1r,4r)-4-((3-hydroxy-2-oxo-3-(2,3,5-trifluorophenyl)indolin-1-yl)methyl)cyclohexyl)nicotinamide;
5-chloro-N-((1r,4r)-4-((3-(5-chloro-2-fluorophenyl)-3-hydroxy-2-oxoindolin-1-yl)methyl)cyclohexyl)-2-(difluoromethyl)nicotinamide;
5-chloro-2-(difluoromethyl)-N-((1r,4r)-4-((3-hydroxy-2-oxo-3-(2,3,4-trifluorophenyl)indolin-1-yl)methyl)cyclohexyl)nicotinamide;
5-chloro-2-(difluoromethyl)-N-((1r,4r)-4-((3-(2-fluoro-5-(trifluoromethyl)phenyl)-3-hydroxy-2-oxoindolin-1-yl)methyl)cyclohexyl)nicotinamide;
5-chloro-N-((1r,4r)-4-((3-(5-chloro-2-fluorophenyl)-3-hydroxy-2-oxoindolin-1-yl)methyl)cyclohexyl)-2-methylnicotinamide;
5-chloro-N-((1r,4r)-4-((3-hydroxy-2-oxo-3-(2,3,4-trifluorophenyl)indolin-1-yl)methyl)cyclohexyl)-2-methylnicotinamide;
5-chloro-N-((1r,4r)-4-((3-(2,3-difluoro-4-methoxyphenyl)-3-hydroxy-2-oxoindolin-1-yl)methyl)cyclohexyl)-2-methylnicotinamide;

5-chloro-N-((1r,4r)-4-((3-(5-chloropyridin-2-yl)-4-fluoro-3-hydroxy-2-oxoindolin-1-yl)methyl)cyclohexyl)-2-(difluoromethyl)nicotinamide;

5-chloro-N-((1r,4r)-4-((7-chloro-3-(2-fluorophenyl)-3-hydroxy-2-oxoindolin-1-yl)methyl)cyclohexyl)-2-(difluoromethyl)nicotinamide;

5-chloro-2-(difluoromethyl)-N-((1r,4r)-4-((3-(2-fluorophenyl)-3-hydroxy-5-methyl-2-oxoindolin-1-yl)methyl)cyclohexyl)nicotinamide;

5-chloro-N-((1r,4r)-4-((3-(2,3-difluorophenyl)-6-fluoro-3-hydroxy-2-oxoindolin-1-yl)methyl)cyclohexyl)-2-methylnicotinamide;

5-chloro-N-((1r,4r)-4-((6-fluoro-3-(5-fluoro-2-methoxypyridin-4-yl)-3-hydroxy-2-oxoindolin-1-yl)methyl)cyclohexyl)-2-methylnicotinamide;

5-chloro-N-((1r,4r)-4-((3-(5-chloropyridin-2-yl)-6-fluoro-3-hydroxy-2-oxoindolin-1-yl)methyl)cyclohexyl)-2-methylnicotinamide;

5-chloro-N-((1r,4r)-4-((3-(2-fluorophenyl)-3-hydroxy-6-methoxy-2-oxoindolin-1-yl)methyl)cyclohexyl)-2-methylnicotinamide;

5-chloro-2-(difluoromethyl)-N-((1r,4r)-4-((3-(5-fluoropyridin-2-yl)-3-hydroxy-6-methyl-2-oxoindolin-1-yl)methyl)cyclohexyl)nicotinamide;

5-chloro-2-(difluoromethyl)-N-((1r,4r)-4-((3-(2-fluorophenyl)-3-hydroxy-6-methyl-2-oxoindolin-1-yl)methyl)cyclohexyl)nicotinamide;

5-chloro-2-(difluoromethyl)-N-((1r,4r)-4-((3-(3-fluoropyridin-4-yl)-3-hydroxy-6-methyl-2-oxoindolin-1-yl)methyl)cyclohexyl)nicotinamide;

5-chloro-N-((1r,4r)-4-((3-(2,5-difluorophenyl)-3-hydroxy-2-oxoindolin-1-yl)methyl)cyclohexyl)-2-methylbenzamide;

N-((1r,4r)-4-((3-(2,5-difluorophenyl)-3-hydroxy-2-oxoindolin-1-yl)methyl)cyclohexyl)-2-methyl-2H-indazole-3-carboxamide;

5-chloro-N-((1r,4r)-4-((3-(2,5-difluorophenyl)-3-hydroxy-2-oxoindolin-1-yl)methyl)cyclohexyl)-2-(trifluoromethoxy)benzamide;

5-chloro-N-((1r,4r)-4-((3-(2,3-difluoro-4-methoxyphenyl)-3-hydroxy-2-oxoindolin-1-yl)methyl)cyclohexyl)-2-(difluoromethyl)nicotinamide;

5-chloro-2-(cyclobutylamino)-N-((1r,4r)-4-((3-(2,5-difluorophenyl)-3-hydroxy-2-oxoindolin-1-yl)methyl)cyclohexyl)nicotinamide;

5-chloro-2-(difluoromethyl)-N-((1r,4r)-4-((6-fluoro-3-(3-fluoro-2-methoxypyridin-4-yl)-3-hydroxy-2-oxoindolin-1-yl)methyl)cyclohexyl)nicotinamide;

5-chloro-2-(difluoromethyl)-N-((1r,4r)-4-((6-fluoro-3-(2-fluoro-5-methoxyphenyl)-3-hydroxy-2-oxoindolin-1-yl)methyl)cyclohexyl)nicotinamide;

5-chloro-N-((1r,4r)-4-((3-(5-chloropyridin-2-yl)-3-hydroxy-4-methoxy-2-oxoindolin-1-yl)methyl)cyclohexyl)-2-(difluoromethyl)nicotinamide;

5-chloro-2-(difluoromethyl)-N-((1r,4r)-4-((3-(2,3-difluorophenyl)-3-hydroxy-4-methoxy-2-oxoindolin-1-yl)methyl)cyclohexyl)nicotinamide;

5-chloro-N-((1r,4r)-4-((3-(2,3-difluorophenyl)-3-hydroxy-2-oxo-2,3-dihydro-1H-pyrrolo[2,3-b]pyridin-1-yl)methyl)cyclohexyl)-2-methylnicotinamide;

5-chloro-N-((1r,4r)-4-((3-(5-chloropyridin-2-yl)-5-fluoro-3-hydroxy-2-oxoindolin-1-yl)methyl)cyclohexyl)-2-methylnicotinamide;

5-chloro-N-((1r,4r)-4-((5-fluoro-3-(5-fluoro-2-methoxypyridin-4-yl)-3-hydroxy-2-oxoindolin-1-yl)methyl)cyclohexyl)-2-methylnicotinamide;

5-chloro-N-((1r,4r)-4-((3-(2,3-difluorophenyl)-5-fluoro-3-hydroxy-2-oxoindolin-1-yl)methyl)cyclohexyl)-2-methylnicotinamide;

5-chloro-N-((1r,4r)-4-((3-(5-cyano-2-fluorophenyl)-3-hydroxy-2-oxoindolin-1-yl)methyl)cyclohexyl)-2-(trifluoromethyl)nicotinamide;

5-chloro-N-((1r,4r)-4-((3-(2-fluoro-4-methoxyphenyl)-3-hydroxy-2-oxoindolin-1-yl)methyl)cyclohexyl)-2-(trifluoromethyl)nicotinamide;

5-chloro-N-((1r,4r)-4-((3-(5-fluoro-2-methoxypyridin-4-yl)-3-hydroxy-2-oxoindolin-1-yl)methyl)cyclohexyl)-2-(trifluoromethyl)nicotinamide;

5-chloro-N-((1r,4r)-4-((3-(2,3-difluorophenyl)-3-hydroxy-2-oxoindolin-1-yl)methyl)cyclohexyl)-2-methylbenzamide;

2,5-dichloro-N-((1r,4r)-4-((3-(2,3-difluorophenyl)-3-hydroxy-2-oxoindolin-1-yl)methyl)cyclohexyl)nicotinamide;

5-chloro-2-(difluoromethyl)-N-((1r,4r)-4-((5-fluoro-3-(2-fluoro-5-methoxyphenyl)-3-hydroxy-2-oxoindolin-1-yl)methyl)cyclohexyl)nicotinamide;

5-chloro-2-(difluoromethyl)-N-((1r,4r)-4-((5-fluoro-3-(3-fluoro-2-methoxypyridin-4-yl)-3-hydroxy-2-oxoindolin-1-yl)methyl)cyclohexyl)nicotinamide;

5-chloro-N-((1r,4r)-4-((6-chloro-3-(2-fluorophenyl)-3-hydroxy-2-oxoindolin-1-yl)methyl)cyclohexyl)-2-(difluoromethyl)nicotinamide;

5-chloro-2-(cyclopropylamino)-N-((1r,4r)-4-((3-(2,3-difluorophenyl)-3-hydroxy-2-oxoindolin-1-yl)methyl)cyclohexyl)nicotinamide;

5-chloro-N-((1r,4r)-4-((3-(5-cyano-2,3-difluorophenyl)-3-hydroxy-2-oxoindolin-1-yl)methyl)cyclohexyl)-2-methylnicotinamide;

5-chloro-N-((1r,4r)-4-((3-(2,3-difluorophenyl)-3-hydroxy-2-oxoindolin-1-yl)methyl)cyclohexyl)-2-methylnicotinamide;

5-chloro-2-(difluoromethyl)-N-((1r,4r)-4-((3-(5-fluoropyridin-2-yl)-3-hydroxy-7-methyl-2-oxoindolin-1-yl)methyl)cyclohexyl)nicotinamide;

5-chloro-2-(difluoromethyl)-N-((1r,4r)-4-((3-(2-fluorophenyl)-3-hydroxy-7-methyl-2-oxoindolin-1-yl)methyl)cyclohexyl)nicotinamide;

5-chloro-2-(difluoromethyl)-N-((1r,4r)-4-((3-(3-fluoropyridin-4-yl)-3-hydroxy-7-methyl-2-oxoindolin-1-yl)methyl)cyclohexyl)nicotinamide;

5-chloro-N-((1r,4r)-4-((4,6-difluoro-3-(2-fluorophenyl)-3-hydroxy-2-oxoindolin-1-yl)methyl)cyclohexyl)-2-(difluoromethyl)nicotinamide;

5-chloro-2-(difluoromethyl)-N-((1r,4r)-4-((3-(5-fluoropyridin-2-yl)-3-hydroxy-4-methyl-2-oxoindolin-1-yl)methyl)cyclohexyl)nicotinamide;

5-chloro-2-(difluoromethyl)-N-((1r,4r)-4-((3-(2-fluorophenyl)-3-hydroxy-4-methyl-2-oxoindolin-1-yl)methyl)cyclohexyl)nicotinamide;

5-chloro-2-(difluoromethyl)-N-((1r,4r)-4-((3-(3-fluoropyridin-4-yl)-3-hydroxy-4-methyl-2-oxoindolin-1-yl)methyl)cyclohexyl)nicotinamide;

5-chloro-N-((1r,4r)-4-((7-fluoro-3-(2-fluorophenyl)-3-hydroxy-2-oxoindolin-1-yl)methyl)cyclohexyl)-2-methylnicotinamide;

5-chloro-N-((1r,4r)-4-((4-fluoro-3-(5-fluoropyridin-2-yl)-3-hydroxy-2-oxoindolin-1-yl)methyl)cyclohexyl)-2-(trifluoromethyl)nicotinamide;

5-chloro-N-((1r,4r)-4-((3-(5-chloropyridin-2-yl)-4-fluoro-3-hydroxy-2-oxoindolin-1-yl)methyl)cyclohexyl)-2-(trifluoromethyl)nicotinamide;

5-chloro-N-((1r,4r)-4-((3-(5-fluoropyridin-2-yl)-3-hydroxy-2-oxoindolin-1-yl)methyl)cyclohexyl)-2-(trifluoromethyl)nicotinamide;

5-chloro-N-((1r,4r)-4-((3-(2-fluoro-5-methoxyphenyl)-3-hydroxy-2-oxoindolin-1-yl)methyl)cyclohexyl)-2-(trifluoromethyl)nicotinamide;

5-chloro-N-((1r,4r)-4-((3-(3-chloro-2-fluorophenyl)-3-hydroxy-2-oxoindolin-1-yl)methyl)cyclohexyl)-2-(trifluoromethyl)nicotinamide;

5-chloro-N-((1r,4r)-4-((3-hydroxy-2-oxo-3-phenylindolin-1-yl)methyl)cyclohexyl)-2-(trifluoromethyl)nicotinamide;

5-chloro-N-((1r,4r)-4-((3-(2,5-difluorophenyl)-3-hydroxy-2-oxoindolin-1-yl)methyl)cyclohexyl)-2-(trifluoromethyl)nicotinamide;

5-chloro-2-(difluoromethyl)-N-((1r,4r)-4-((4-fluoro-3-(2-fluoro-5-methoxyphenyl)-3-hydroxy-2-oxoindolin-1-yl)methyl)cyclohexyl)nicotinamide;

5-chloro-N-((1r,4r)-4-((3-(3-chloro-2-fluorophenyl)-4-fluoro-3-hydroxy-2-oxoindolin-1-yl)methyl)cyclohexyl)-2-(difluoromethyl)nicotinamide;

5-chloro-2-(difluoromethyl)-N-((1r,4r)-4-((4-fluoro-3-(2-fluorophenyl)-3-hydroxy-2-oxoindolin-1-yl)methyl)cyclohexyl)nicotinamide; and 5-chloro-2-(difluoromethyl)-N-((1r,4r)-4-((3-(2,3-difluorophenyl)-4-fluoro-3-hydroxy-2-oxoindolin-1-yl)methyl)cyclohexyl)nicotinamide;

or a pharmaceutically acceptable salt thereof or a prodrug thereof.

8. The compound according to claim 7, which is selected from the group consisting of:

5-chloro-2-(difluoromethyl)-N-((1r,4r)-4-((3-hydroxy-3-(4-methoxyphenyl)-2-oxoindolin-1-yl)methyl)cyclohexyl)nicotinamide;

5-chloro-2-(difluoromethyl)-N-((1r,4r)-4-((3-hydroxy-2-oxo-3-phenylindolin-1-yl)methyl)cyclohexyl)nicotinamide;

5-chloro-2-(difluoromethyl)-N-((1r,4r)-4-((3-(3-fluoropyridin-4-yl)-3-hydroxy-2-oxoindolin-1-yl)methyl)cyclohexyl)nicotinamide;

5-chloro-N-((1r,4r)-4-((3-(5-chloropyridin-2-yl)-3-hydroxy-2-oxoindolin-1-yl)methyl)cyclohexyl)-2-(difluoromethyl)nicotinamide;

5-chloro-2-(difluoromethyl)-N-((1r,4r)-4-((3-(4-fluorophenyl)-3-hydroxy-2-oxoindolin-1-yl)methyl)cyclohexyl)nicotinamide;

5-chloro-2-(difluoromethyl)-N-((1r,4r)-4-((3-(5-fluoropyridin-2-yl)-3-hydroxy-2-oxoindolin-1-yl)methyl)cyclohexyl)nicotinamide;

5-chloro-2-(difluoromethyl)-N-((1r,4r)-4-((3-(3-fluorophenyl)-3-hydroxy-2-oxoindolin-1-yl)methyl)cyclohexyl)nicotinamide;

5-chloro-2-(difluoromethyl)-N-((1r,4r)-4-((3-(5-fluoro-2-methoxypyridin-4-yl)-3-hydroxy-2-oxoindolin-1-yl)methyl)cyclohexyl)nicotinamide;

5-chloro-N-((1r,4r)-4-((6-chloro-3-hydroxy-2-oxo-3-phenylindolin-1-yl)methyl)cyclohexyl)-2-(difluoromethyl)nicotinamide;

5-chloro-2-(difluoromethyl)-N-((1r,4r)-4-((3-(2-fluorophenyl)-3-hydroxy-2-oxoindolin-1-yl)methyl)cyclohexyl)nicotinamide;

5-chloro-2-(difluoromethyl)-N-((1r,4r)-4-((3-(2,3-difluorophenyl)-3-hydroxy-2-oxoindolin-1-yl)methyl)cyclohexyl)nicotinamide;

5-chloro-2-(difluoromethyl)-N-((1r,4r)-4-((3-hydroxy-3-(3-methoxyphenyl)-2-oxoindolin-1-yl)methyl)cyclohexyl)nicotinamide;

5-chloro-N-((1r,4r)-4-((3-(3-chlorophenyl)-3-hydroxy-2-oxoindolin-1-yl)methyl)cyclohexyl)-2-(difluoromethyl)nicotinamide;

5-chloro-2-(difluoromethyl)-N-((1r,4r)-4-((3-hydroxy-2-oxo-3-(m-tolyl)indolin-1-yl)methyl)cyclohexyl)nicotinamide;

5-chloro-2-(difluoromethyl)-N-((1r,4r)-4-((3-(2,4-difluorophenyl)-3-hydroxy-2-oxoindolin-1-yl)methyl)cyclohexyl)nicotinamide;

5-chloro-2-(difluoromethyl)-N-((1r,4r)-4-((3-(2-fluoro-4-methoxyphenyl)-3-hydroxy-2-oxoindolin-1-yl)methyl)cyclohexyl)nicotinamide;

5-chloro-2-(difluoromethyl)-N-((1r,4r)-4-((3-hydroxy-2-oxo-3-(p-tolyl)indolin-1-yl)methyl)cyclohexyl)nicotinamide;

5-chloro-2-(difluoromethyl)-N-((1r,4r)-4-((3-(2,5-difluorophenyl)-3-hydroxy-2-oxoindolin-1-yl)methyl)cyclohexyl)nicotinamide;

5-chloro-N-((1r,4r)-4-((3-(5-cyano-2-fluorophenyl)-3-hydroxy-2-oxoindolin-1-yl)methyl)cyclohexyl)-2-(difluoromethyl)nicotinamide;

5-chloro-2-(difluoromethyl)-N-((1r,4r)-4-((3-(2-fluoro-3-methylphenyl)-3-hydroxy-2-oxoindolin-1-yl)methyl)cyclohexyl)nicotinamide;

5-chloro-2-(difluoromethyl)-N-((1r,4r)-4-((3-(2-fluoro-3-methoxyphenyl)-3-hydroxy-2-oxoindolin-1-yl)methyl)cyclohexyl)nicotinamide;

5-chloro-N-((1r,4r)-4-((3-(3-chloro-2-fluorophenyl)-3-hydroxy-2-oxoindolin-1-yl)methyl)cyclohexyl)-2-(difluoromethyl)nicotinamide;

5-chloro-2-(difluoromethyl)-N-((1r,4r)-4-((3-(2-fluoro-5-methoxyphenyl)-3-hydroxy-2-oxoindolin-1-yl)methyl)cyclohexyl)nicotinamide;

5-chloro-2-(difluoromethyl)-N-((1r,4r)-4-((6-fluoro-3-(5-fluoropyridin-2-yl)-3-hydroxy-2-oxoindolin-1-yl)methyl)cyclohexyl)nicotinamide;

5-chloro-2-(difluoromethyl)-N-((1r,4r)-4-((7-fluoro-3-(2-fluorophenyl)-3-hydroxy-2-oxoindolin-1-yl)methyl)cyclohexyl)nicotinamide;

5-chloro-2-(difluoromethyl)-N-((1r,4r)-4-((6-fluoro-3-(2-fluorophenyl)-3-hydroxy-2-oxoindolin-1-yl)methyl)cyclohexyl)nicotinamide;

5-chloro-2-(difluoromethyl)-N-((1r,4r)-4-((6-fluoro-3-(3-fluoropyridin-4-yl)-3-hydroxy-2-oxoindolin-1-yl)methyl)cyclohexyl)nicotinamide;

5-chloro-2-(difluoromethyl)-N-((1r,4r)-4-((3-hydroxy-2-oxo-3-(thiophen-3-yl)indolin-1-yl)methyl)cyclohexyl)nicotinamide;

5-chloro-2-(difluoromethyl)-N-((1r,4r)-4-((5-fluoro-3-(2-fluorophenyl)-3-hydroxy-2-oxoindolin-1-yl)methyl)cyclohexyl)nicotinamide;

5-chloro-2-(difluoromethyl)-N-((1r,4r)-4-((3-(2-fluorophenyl)-3-hydroxy-2-oxo-2,3-dihydro-1H-pyrrolo[2,3-b]pyridin-1-yl)methyl)cyclohexyl)nicotinamide;

5-chloro-2-(difluoromethyl)-N-((1r,4r)-4-((3-(3-fluorothiophen-2-yl)-3-hydroxy-2-oxoindolin-1-yl)methyl)cyclohexyl)nicotinamide;

5-chloro-2-(difluoromethyl)-N-((1r,4r)-4-((3-(4-fluorothiophen-2-yl)-3-hydroxy-2-oxoindolin-1-yl)methyl)cyclohexyl)nicotinamide;

5-chloro-2-(difluoromethyl)-N-((1r,4r)-4-((3-hydroxy-3-(5-methoxythiophen-2-yl)-2-oxoindolin-1-yl)methyl)cyclohexyl)nicotinamide;

5-chloro-2-(difluoromethyl)-N-((1r,4r)-4-((3-(2-fluorophenyl)-3-hydroxy-6-methoxy-2-oxoindolin-1-yl)methyl)cyclohexyl)nicotinamide;

5-chloro-N-((1r,4r)-4-((3-(2,3-difluorophenyl)-3-hydroxy-2-oxoindolin-1-yl)methyl)cyclohexyl)-2-(trifluoromethyl)nicotinamide;

5-chloro-2-(difluoromethyl)-N-((1r,4r)-4-((6-fluoro-3-(5-fluoro-2-methoxypyridin-4-yl)-3-hydroxy-2-oxoindolin-1-yl)methyl)cyclohexyl)nicotinamide;

5-chloro-2-(difluoromethyl)-N-((1r,4r)-4-((3-(2,3-difluorophenyl)-6-fluoro-3-hydroxy-2-oxoindolin-1-yl)methyl)cyclohexyl)nicotinamide;

5-chloro-N-((1r,4r)-4-((3-(3-chloro-2-fluorophenyl)-6-fluoro-3-hydroxy-2-oxoindolin-1-yl)methyl)cyclohexyl)-2-(difluoromethyl)nicotinamide;

5-chloro-2-(difluoromethyl)-N-((1r,4r)-4-((3-(2,5-difluorophenyl)-6-fluoro-3-hydroxy-2-oxoindolin-1-yl)methyl)cyclohexyl)nicotinamide;

5-chloro-N-((1r,4r)-4-((3-(5-chloropyridin-2-yl)-6-fluoro-3-hydroxy-2-oxoindolin-1-yl)methyl)cyclohexyl)-2-(difluoromethyl)nicotinamide;

5-chloro-2-(difluoromethyl)-N-((1r,4r)-4-((3-(2,3-difluorophenyl)-5-fluoro-3-hydroxy-2-oxoindolin-1-yl)methyl)cyclohexyl)nicotinamide;

5-chloro-2-(difluoromethyl)-N-((1r,4r)-4-((5-fluoro-3-(5-fluoro-2-methoxypyridin-4-yl)-3-hydroxy-2-oxoindolin-1-yl)methyl)cyclohexyl)nicotinamide;

5-chloro-N-((1r,4r)-4-((3-(5-chloropyridin-2-yl)-5-fluoro-3-hydroxy-2-oxoindolin-1-yl)methyl)cyclohexyl)-2-(difluoromethyl)nicotinamide;

5-chloro-N-((1r,4r)-4-((3-(2-fluoro-5-methoxyphenyl)-3-hydroxy-2-oxoindolin-1-yl)methyl)cyclohexyl)-2-methylnicotinamide;

5-chloro-2-(difluoromethyl)-N-((1r,4r)-4-((3-hydroxy-3-(5-methylthiophen-3-yl)-2-oxoindolin-1-yl)methyl)cyclohexyl)nicotinamide;

5-chloro-N-((1r,4r)-4-((3-hydroxy-2-oxo-3-(2,3,5-trifluorophenyl)indolin-1-yl)methyl)cyclohexyl)-2-methylnicotinamide;

5-chloro-2-(difluoromethyl)-N-((1r,4r)-4-((3-hydroxy-2-oxo-3-(2,3,5-trifluorophenyl)indolin-1-yl)methyl)cyclohexyl)nicotinamide;

5-chloro-2-(difluoromethyl)-N-((1r,4r)-4-((3-hydroxy-2-oxo-3-(2,3,4-trifluorophenyl)indolin-1-yl)methyl)cyclohexyl)nicotinamide;

5-chloro-N-((1r,4r)-4-((3-(2,3-difluoro-4-methoxyphenyl)-3-hydroxy-2-oxoindolin-1-yl)methyl)cyclohexyl)-2-methylnicotinamide;

5-chloro-N-((1r,4r)-4-((3-(5-chloropyridin-2-yl)-4-fluoro-3-hydroxy-2-oxoindolin-1-yl)methyl)cyclohexyl)-2-(difluoromethyl)nicotinamide;

5-chloro-N-((1r,4r)-4-((3-(2,3-difluorophenyl)-6-fluoro-3-hydroxy-2-oxoindolin-1-yl)methyl)cyclohexyl)-2-methylnicotinamide;

5-chloro-2-(difluoromethyl)-N-((1r,4r)-4-((3-(2-fluorophenyl)-3-hydroxy-6-methyl-2-oxoindolin-1-yl)methyl)cyclohexyl)nicotinamide;

5-chloro-2-(difluoromethyl)-N-((1r,4r)-4-((3-(3-fluoropyridin-4-yl)-3-hydroxy-6-methyl-2-oxoindolin-1-yl)methyl)cyclohexyl)nicotinamide;

5-chloro-N-((1r,4r)-4-((3-(2,3-difluoro-4-methoxyphenyl)-3-hydroxy-2-oxoindolin-1-yl)methyl)cyclohexyl)-2-(difluoromethyl)nicotinamide;

5-chloro-2-(difluoromethyl)-N-((1r,4r)-4-((6-fluoro-3-(3-fluoro-2-methoxypyridin-4-yl)-3-hydroxy-2-oxoindolin-1-yl)methyl)cyclohexyl)nicotinamide;

5-chloro-2-(difluoromethyl)-N-((1r,4r)-4-((6-fluoro-3-(2-fluoro-5-methoxyphenyl)-3-hydroxy-2-oxoindolin-1-yl)methyl)cyclohexyl)nicotinamide;

5-chloro-2-(difluoromethyl)-N-((1r,4r)-4-((3-(2,3-difluorophenyl)-3-hydroxy-4-methoxy-2-oxoindolin-1-yl)methyl)cyclohexyl)nicotinamide;

5-chloro-N-((1r,4r)-4-((3-(2,3-difluorophenyl)-5-fluoro-3-hydroxy-2-oxoindolin-1-yl)methyl)cyclohexyl)-2-methylnicotinamide;

5-chloro-N-((1r,4r)-4-((3-(2-fluoro-4-methoxyphenyl)-3-hydroxy-2-oxoindolin-1-yl)methyl)cyclohexyl)-2-(trifluoromethyl)nicotinamide;

2,5-dichloro-N-((1r,4r)-4-((3-(2,3-difluorophenyl)-3-hydroxy-2-oxoindolin-1-yl)methyl)cyclohexyl)nicotinamide;

5-chloro-2-(difluoromethyl)-N-((1r,4r)-4-((5-fluoro-3-(2-fluoro-5-methoxyphenyl)-3-hydroxy-2-oxoindolin-1-yl)methyl)cyclohexyl)nicotinamide;

5-chloro-N-((1r,4r)-4-((6-chloro-3-(2-fluorophenyl)-3-hydroxy-2-oxoindolin-1-yl)methyl)cyclohexyl)-2-(difluoromethyl)nicotinamide;

5-chloro-N-((1r,4r)-4-((3-(2,3-difluorophenyl)-3-hydroxy-2-oxoindolin-1-yl)methyl)cyclohexyl)-2-methylnicotinamide;

5-chloro-N-((1r,4r)-4-((4,6-difluoro-3-(2-fluorophenyl)-3-hydroxy-2-oxoindolin-1-yl)methyl)cyclohexyl)-2-(difluoromethyl)nicotinamide;

5-chloro-2-(difluoromethyl)-N-((1r,4r)-4-((4-fluoro-3-(5-fluoropyridin-2-yl)-3-hydroxy-2-oxoindolin-1-yl)methyl)cyclohexyl)nicotinamide;

5-chloro-2-(difluoromethyl)-N-((1r,4r)-4-((3-(5-fluoropyridin-2-yl)-3-hydroxy-4-methyl-2-oxoindolin-1-yl)methyl)cyclohexyl)nicotinamide;

5-chloro-2-(difluoromethyl)-N-((1r,4r)-4-((3-(2-fluorophenyl)-3-hydroxy-4-methyl-2-oxoindolin-1-yl)methyl)cyclohexyl)nicotinamide;

5-chloro-N-((1r,4r)-4-((3-(2-fluoro-5-methoxyphenyl)-3-hydroxy-2-oxoindolin-1-yl)methyl)cyclohexyl)-2-(trifluoromethyl)nicotinamide;

5-chloro-2-(difluoromethyl)-N-((1r,4r)-4-((4-fluoro-3-(2-fluoro-5-methoxyphenyl)-3-hydroxy-2-oxoindolin-1-yl)methyl)cyclohexyl)nicotinamide;

5-chloro-N-((1r,4r)-4-((3-(3-chloro-2-fluorophenyl)-4-fluoro-3-hydroxy-2-oxoindolin-1-yl)methyl)cyclohexyl)-2-(difluoromethyl)nicotinamide;

5-chloro-2-(difluoromethyl)-N-((1r,4r)-4-((4-fluoro-3-(2-fluorophenyl)-3-hydroxy-2-oxoindolin-1-yl)methyl)cyclohexyl)nicotinamide; and 5-chloro-2-(difluoromethyl)-N-((1r,4r)-4-((3-(2,3-difluorophenyl)-4-fluoro-3-hydroxy-2-oxoindolin-1-yl)methyl)cyclohexyl)nicotinamide;

or a pharmaceutically acceptable salt thereof or a prodrug thereof.

9. A method for the treatment of a condition or disorder in which CRHR2 is involved, in an animal, including a human, which comprises administering to the animal in need of such treatment a therapeutically effective amount of a compound or a prodrug thereof or a pharmaceutically acceptable salt thereof, according to claim 1.

10. The method according to claim 9, wherein said condition or disorder is selected from the group consisting of: gastrointestinal disorders, major depressive disorders, schizophrenic disorders, neurodegenerative diseases, pain, dysfunction of appetite and food intake, sleep disorders, cognitive disorders, tolerance to and dependence on a number of substances, inflammation, fertility problems, sexual dysfunctions and pre-term birth and non-inflammatory urogenital disorders, allergic disorders, mast cell activation disorders, Cushing's syndrome, emesis, gastrointestinal disorders, neurotoxic injury, loss of hair, heart disease, and combinations thereof.

11. The method according to claim 10, wherein the heart disease is selected from the group consisting of: acute and chronic heart failure, cardiovascular disease, hyper tension, myocardial infarction, coronary artery disease, and abdominal aortic aneurysm.

12. A pharmaceutical composition comprising a compound or a pharmaceutically acceptable salt thereof or a prodrug thereof, according to claim 1, and a pharmaceutically acceptable carrier.

13. The pharmaceutical composition according to claim 12, further comprising another pharmacologically active agent.

14. A process for preparing a pharmaceutical composition, wherein the process comprises mixing a compound according to claim 1 or a pharmaceutically acceptable salt thereof or a prodrug thereof and a pharmaceutically acceptable carrier or excipient.

\* \* \* \* \*